(12) United States Patent
Lai

(10) Patent No.: US 11,952,419 B2
(45) Date of Patent: Apr. 9, 2024

(54) REAGENTS AND METHODS FOR TREATING CANCER AND AUTOIMMUNE DISEASE

(71) Applicant: UNIVERSITY OF CONNECTICUT, Farmington, CT (US)

(72) Inventor: Laijun Lai, Farmington, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 480 days.

(21) Appl. No.: 17/057,429

(22) PCT Filed: Jul. 8, 2019

(86) PCT No.: PCT/US2019/040759
§ 371 (c)(1),
(2) Date: Nov. 20, 2020

(87) PCT Pub. No.: WO2020/014097
PCT Pub. Date: Jan. 16, 2020

(65) Prior Publication Data
US 2021/0206849 A1 Jul. 8, 2021

Related U.S. Application Data

(60) Provisional application No. 62/696,142, filed on Jul. 10, 2018.

(51) Int. Cl.
| | | |
|---|---|---|
| *C07K 16/28* | (2006.01) | |
| *A61K 38/00* | (2006.01) | |
| *A61K 39/00* | (2006.01) | |
| *A61P 35/00* | (2006.01) | |
| *A61P 37/00* | (2006.01) | |
| *C07K 14/705* | (2006.01) | |

(52) U.S. Cl.
CPC .......... *C07K 16/2803* (2013.01); *A61P 35/00* (2018.01); *A61P 37/00* (2018.01); *C07K 14/70503* (2013.01); *A61K 38/00* (2013.01); *A61K 2039/507* (2013.01)

(58) Field of Classification Search
CPC .......... C07K 16/2803; C07K 14/70503; A61P 35/00; A61P 37/00; A61K 38/00; A61K 2039/507
See application file for complete search history.

(56) References Cited

U.S. PATENT DOCUMENTS 5,595,756 A * 1/1997 Bally .................... A61K 9/1272
264/4.1

FOREIGN PATENT DOCUMENTS

| WO | 2009/051957 | 4/2009 | | |
|---|---|---|---|---|
| WO | WO-2015051159 A1 * | 4/2015 | ......... | A61K 49/0004 |
| WO | WO-2017044895 A2 * | 3/2017 | ............. | A61K 39/12 |

OTHER PUBLICATIONS

Kussie, A Single Engineered Amino Acid Substitution Changes Antibody Fine Specificity, 1994, Journal of Immunology, pp. 146-152 (Year: 1994).*
Sela-Culang, The structural basis of antibody-antigen recognition, 2013, Frontiers in Immunology, vol. 4, Article 302, pp. 1-13 (Year: 2013).*
Simhadri et al., CD300c is an Activating Receptor Expressed on Human Monocytes, 2013, Journal of Innate Immunity, vol. 5, pp. 389-400 (Year: 2013).*
Shen et al., Proinflammatory Cytokines Block Growth of Breast Cancer Cells by Impairing Signals from a Growth Factor Receptor, 2002, Cancer Research, vol. 62, pp. 4746-4756 (Year: 2003).*
Cooper et al., The Development and Causes of Cancer, 2000, The Cell: A Molecular Approach, 2nd edition (Year: 2000).*
Heppner and Miller, Tumor heterogeneity: biological implications and therapeutic consequences, 1983, Cancer Metastasis Reviews, vol. 2, pp. 5-23 (Year: 1983).*
Venkateswara R Simhadri et al., Journal of Innate Immunity, vol. 5, No. 4, pp. 389-400, published on Apr. 6, 2013.
The International Search Report (ISR) with Written Opinion for PCT/US2019/040759 dated Dec. 5, 2019, pp. 1-24.
Borrego, Francisco "The CD388 molecules: an emerging family of regulators of the irrmune system" Blood (2013) vol. 121(11), pp. 1951-1968.
Choi, Seung-Chul et al. "Cutting Edge: X AA Mouse CD300f (CMRF-35-Like Molecule-1) Recognizes Outer Membrane-Exposed Phosphatidylserine and Can Promote Phagocytosis" The Journal of Immunology (2011) vol. 187(7), pp. 3483-3487.
Clark, Georgina J. et al. "Novel human CD4+T lymphocyte subpopulations defined by CD300ajc molecule expression" Journal of Leukocyte Biology (2007) vol. 82(5), pp. 1126-1135.
Martinez-Barriocanal, Agueda et al. "CD300 heterocomplexes, a new and family-restricted mechanism for myeloid cell signaling regulation." The Journal of Biological Chemistry (2010) vol. 285(53), pp. 41781-41794.
Hart, D.N.J. et al. "319: CD300a and CD300c on Plasmacytoid Dendritic Cells are Down-Regulated by TLR7 and TLR9 Ligand Induced Type I Interferon" Biology of Blood and Marrow Transplantation (2008) vol. 14 (2), p. 118.
Abeler-Dorner L, Swamy M, Williams G, Hayday AC, Bas A. Butyrophilins: an emerging family of immune regulators. Trends Immunol, 2012;33:34-41.

(Continued)

*Primary Examiner* — Adam Weidner
*Assistant Examiner* — Brittney E Donoghue
(74) *Attorney, Agent, or Firm* — MCDONNELL BOEHNEN HULBERT & BERGHOFF LLP

(57) ABSTRACT

Disclosed herein are methods for treating cancer by administering to a subject having cancer antibodies against one or more of CD300c, BTN5 (Erythroid membrane-associated protein), TAPBPL (antigen processing (TAP) binding protein like protein), Skint8 (selection and upkeep of intraepithelial T cells 8 protein), and CD300f. Also disclosed herein are methods for treating autoimmune diseases by administering to a subject having an autoimmune disease an IgV domain, or a nucleic acid encoding an IgV domain, from one or more of CD300c, BTN5, TAPBPL, SkintS, and CD300f. Also disclosed herein are antibodies against CD300c and TAPBPL, and fusion proteins that can be used in the methods for treating autoimmune disease.

19 Claims, 31 Drawing Sheets

Specification includes a Sequence Listing.

(56) References Cited

OTHER PUBLICATIONS

Afrache H, Gouret P, Ainouche S, Pontarotti P, Olive D. The butyrophilin (BTN) gene family: from milk fat to the regulation of the immune response. Immunogenetics, 2012;64:781-94.
Ammann JU, Cooke A, Trowsdale J. Butyrophilin Btn2a2 inhibits TCR activation and phosphatidylinositol 3-kinase/Akt pathway signaling and induces Foxp3 expression in T lymphocytes. J Immunol, 2013; 190:5030-6.
Anderson MS, Bluestone JA. The NOD mouse: a model of immune dysregulation. Annu Rev Immunol, 2005;23:447-85.
Arnett HA, Escobar SS, Gonzalez-Suarez E, Budelsky AL, Steffen LA, Boiani N et al. BTNL2, a butyrophilin/B7-like molecule, is a negative costimulatory molecule modulated in intestinal inflammation. J Immunol, 2007;178:1523-33.
Arnett HA, Escobar SS, Viney JL. Regulation of costimulation in the era of butyrophilins. Cytokine, 2009;46:370-5.
Arnett HA, Viney JL. Immune modulation by butyrophilins. Nat Rev Immunol, 2014;14:559-69.
Brandt CS, Baratin M, Yi EC, Kennedy J, Gao Z, Fox B et al. The B7 family member B7-H6 is a tumor cell ligand for the activating natural killer cell receptor NKp30 in humans. J Exp Med, 2009;206:1495-503.
Brown EJ, Frazier WA. Integrin-associated protein (CD47) and its ligands. Trends Cell Biol, 2001;11:130-5.
Chapoval AI Ni J, Lau JS, Wilcox RA, Flies DB, Liu D et al. B7-H3: a costimulatory molecule for T cell activation and IFN-gamma production. Nat Immunol, 2001;2:269-74.
Chen QR, Hu Y, Yan C, Buetow K, Meerzaman D. Systematic genetic analysis identifies Cis-eQTL target genes associated with glioblastoma patient survival. PloS one, 2014;9:e105393.
Compte E, Pontarotti P, Collette Y, Lopez M, Olive D. Frontline: Characterization of BT3 molecules belonging to the B7 family expressed on immune cells. European journal of immunology, 2004;34:2089-99.
Cubillos-Ruiz JR, Martinez D, Scarlett UK, Rutkowski MR, Nesbeth YC, Camposeco-Jacobs AL et al. CD277 is a negative co-stimulatory molecule universally expressed by ovarian cancer microenvironmental cells. Oncotarget, 2010;1:329-38.
Dong H, Zhu G, Tamada K, Chen L. B7-H1, a third member of the B7 family, co-stimulates T-cell proliferation and interleukin-10 secretion. Nat Med, 1999;5:1365-9.
Du Pasquier L. The phylogenetic origin of antigen-specific receptors. Curr Top Microbiol Immunol, 2000;248:160-85.
Evans DM, Spencer CC, Pointon JJ, Su Z, Harvey D, Kochan G et al. Interaction between ERAP1 and HLA-B27 in ankylosing spondylitis implicates peptide handling in the mechanism for HLA-B27 in disease susceptibility. Nat Genet, 2011;43:761-7.
Freeman GJ, Gray GS, Gimmi CD, Lombard DB, Zhou LJ, White M et al. Structure, expression, and T cell costimulatory activity of the murine homologue of the human B lymphocyte activation antigen B7. J Exp Med, 1991;174:625-31.
Freeman GJ, Gribben JG, Boussiotis VA, Ng JW, Restivo VA, Jr., Lombard LA et al. Cloning of B7-2: a CTLA-4 counter-receptor that costimulates human T cell proliferation. Science (New York, NY), 1993;262:909-11.
Freeman GJ, Long AJ, Iwai Y, Bourque K, Chernova T, Nishimura H et al. Engagement of the PD-1 immunoinhibitory receptor by a novel B7 family member leads to negative regulation of lymphocyte activation. J Exp Med, 2000;192:1027-34.
Gordon SR, Maute RL, Dulken BW, Hutter G, George BM, McCracken MN et al. PD-1 expression by tumour-associated macrophages inhibits phagocytosis and tumour immunity. Nature, 2017;545:495-9.
Guo Y, Wang AY. Novel Immune Check-Point Regulators in Tolerance Maintenance. Front Immunol, 2015;6:421.
Hermann C, Trowsdale J, Boyle LH. TAPBPL: a new player in the MHC class I presentation pathway. Tissue Antigens, 2015;85:155-66.
Hofmeyer KA, Ray A, Zang X. The contrasting role of B7-H3. Proceedings of the National Academy of Sciences of the United States of America, 2008;105:10277-8.
Jin J, Goldschneider I, Lai L. In vivo administration of the recombinant IL-7/hepatocyte growth factor beta hybrid cytokine efficiently restores thymopoiesis and naive T cell generation in lethally irradiated mice after syngeneic bone marrow transplantation. Journal of immunology (Baltimore, Md : 1950), 2011;186:1915-22.
Lai L, Zhang M, Goldschneider I. Recombinant IL-7/HGFbeta efficiently induces transplantable murine hematopoietic stem cells. J Clin Invest, 2012;122:3552-62.
Lai L, Zhang M, Song Y, Rood D. Recombinant IL-7/HGFbeta Hybrid Cytokine Enhances T Cell Recovery in Mice Following Allogeneic Bone Marrow Transplantation. PloS one, 2013;8:e82998.
Latchman Y, Wood CR, Chernova T, Chaudhary D, Borde M, Chernova I et al. PD-L2 is a second ligand for PD-1 and inhibits T cell activation. Nat Immunol, 2001;2:261-8.
Ling V, Wu PW, Finnerty HF, Bean KM, Spaulding V, Fouser LA et al. Cutting edge: identification of GL50, a novel B7-like protein that functionally binds to ICOS receptor. Journal of immunology (Baltimore, Md : 1950), 2000; 164:1653-7.
Linsley PS, Peach R, Gladstone P, Bajorath J. Extending the B7 (CD80) gene family. Protein Sci, 1994;3:1341-3.
Mana P, Goodyear M, Bernard C, Tomioka R, Freire-Garabal M, Linares D. Tolerance induction by molecular mimicry: prevention and suppression of experimental autoimmune encephalomyelitis with the milk protein butyrophilin. Int Immunol, 2004;16:489-99.
Morozov GI, Zhao H, Mage MG, Boyd LF, Jiang J, Dolan MA et al. Interaction of TAPBPL, a tapasin homolog, with MHC-I molecules promotes peptide editing. Proceedings of the National Academy of Sciences of the United States of America, 2016;113:E1006-15.
Nguyen T, Liu XK, Zhang Y, Dong C. BTNL2, a butyrophilin-like molecule that functions to inhibit T cell activation. J Immunol, 2006;176:7354-60.
Oldenborg PA, Zheleznyak A, Fang YF, Lagenaur CF, Gresham HD, Lindberg FP. Role of CD47 as a marker of self on red blood cells. Science (New York, NY), 2000;288:2051-4.
Palakodeti A, Sandstrom A, Sundaresan L, Harly C, Nedellec S, Olive D et al. The molecular basis for modulation of human Vgamma9Vdelta2 T cell responses by CD277/butyrophilin-3 (BTN3A)-specific antibodies. J Biol Chem, 2012;287:32780-90.
Pineda-Torra I, Gage M, de Juan A, Pello OM. Isolation, Culture, and Polarization of Murine Bone Marrow-Derived and Peritoneal Macrophages. Methods in molecular biology (Clifton, NJ), 2015;1339:101-9.
Podojil JR, Liu LN, Marshall SA, Chiang MY, Goings GE, Chen L et al. B7-H4Ig inhibits mouse and human T-cell function and treats EAE via IL-10/Treg-dependent mechanisms. J Autoimmun, 2013;44:71-81.
Prasad DV, Richards S, Mai XM, Dong C. B7S1, a novel B7 family member that negatively regulates T cell activation. Immunity, 2003;18:863-73.
Prasad DVR, Nguyen T, Li Z, Yang Y, Duong J, Wang Y et al. Murine B7-H3 Is a Negative Regulator of T Cells. The Journal of Immunology, 2004;173:2500-6.
Rhodes DA, Reith W, Trowsdale J. Regulation of Immunity by Butyrophilins. Annu Rev Immunol, 2016;34:151-72.
Sakaguchi S, Yamaguchi T, Nomura T, Ono M. Regulatory T cells and immune tolerance. Cell, 2008;133:775-87.
Sica GL, Choi IH, Zhu G, Tamada K, Wang SD, Tamura H et al. B7-H4, a molecule of the B7 family, negatively regulates T cell immunity. Immunity, 2003; 18:849-61.
Smith IA, Knezevic BR, Ammann JU, Rhodes DA, Aw D, Palmer DB et al. BTN1A1, the mammary gland butyrophilin, and BTN2A2 are both inhibitors of T cell activation. Journal of immunology (Baltimore, Md : 1950), 2010;184:3514-25.
Song Y, Su M, Panchatsharam P, Rood D, Lai L. c-Met signalling is required for efficient postnatal thymic regeneration and repair. Immunology, 2015;144:245-53.
Stefferl A, Schubart A, Storch M, Amini A, Mather I, Lassmann H et al. Butyrophilin, a milk protein, modulates the encephalitogenic T cell response to myelin oligodendrocyte glycoprotein in experi-

(56) References Cited

OTHER PUBLICATIONS mental autoimmune encephalomyelitis. Journal of immunology (Baltimore, Md : 1950), 2000;165:2859-65.

Su M, Song Y, He Z, Hu R, Rood D, Lai L. Administration of embryonic stem cell-derived thymic epithelial progenitors expressing MOG induces antigen-specific tolerance and ameliorates experimental autoimmune encephalomyelitis. J Autoimmun, 2015;58:36-47.

Su YY, Gordon CT, Ye TZ, Perkins AC, Chui DH. Human ERMAP: an erythroid adhesion/receptor transmembrane protein. Blood cells, molecules & diseases, 2001;27:938-49.

Swallow MM, Wallin JJ, Sha WC. B7h, a novel costimulatory homolog of B7.1 and B7.2, is induced by TNFalpha. Immunity, 1999;11:423-32.

Swanson RM, Gavin MA, Escobar SS, Rottman JB, Lipsky BP, Dube S et al. Butyrophilin-like 2 modulates B7 costimulation to induce Foxp3 expression and regulatory T cell development in mature T cells. J Immunol, 2013;190:2027-35.

Teng MS, Stephens R, Du Pasquier L, Freeman T, Lindquist JA, Trowsdale J. A human TAPBP (TAPASIN)-related gene, TAPBP-R. European journal of immunology, 2002;32:1059-68.

Tseng SY, Otsuji M, Gorski K, Huang X, Slansky JE, Pai SI et al. B7-DC, a new dendritic cell molecule with potent costimulatory properties for T cells. J Exp Med, 2001;193:839-46.

Wang S, Zhu G, Chapoval AI, Dong H, Tamada K, Ni J et al. Costimulation of T cells by B7-H2, a B7-like molecule that binds ICOS. Blood, 2000;96:2808-13.

Weiskopf K, Weissman IL. Macrophages are critical effectors of antibody therapies for cancer. mAbs, 2015;7:303-10.

Xu H, Foltz L, Sha Y, Madlansacay MR, Cain C, Lindemann G et al. Cloning and characterization of human erythroid membrane-associated protein, human ERMAP. Genomics, 2001;76:2-4.

Yamashiro H, Yoshizaki S, Tadaki T, Egawa K, Seo N. Stimulation of human butyrophilin 3 molecules results in negative regulation of cellular immunity. J Leukoc Biol, 2010;88:757-67.

Yamazaki T, Goya I, Graf D, Craig S, Martin-Orozco N, Dong C. A butyrophilin family member critically inhibits T cell activation. J Immunol, 2010;185:5907-14.

Yan Y, Su M, Song Y, Tang Y, Tian C, Rood D et al. Tbx1 Modulates Endodermal and Mesodermal Differentiation from Mouse Induced Pluripotent Stem cells. Stem cells and development, 2014.

Yang Y, Liu XK, Nguyen T, Bishop C, Graf D, Dong C. Characterization of B7S3 as a novel negative regulator of T cells. Journal of immunology (Baltimore, Md : 1950), 2007;178:3661-7.

Ye TZ, Gordon CT, Lai YH, Fujiwara Y, Peters LL, Perkins AC et al. Ermap, a gene coding for a novel erythroid specific adhesion/receptor membrane protein. Gene, 2000;242:337-45.

Yoshinaga SK, Whoriskey JS, Khare SD, Sarmiento U, Guo J, Horan T et al. T-cell co-stimulation through B7RP-1 and ICOS. Nature, 1999;402:827-32.

Zang X, Loke P, Kim J, Murphy K, Waitz R, Allison JP. B7x: a widely expressed B7 family member that inhibits T cell activation. Proceedings of the National Academy of Sciences of the United States of America, 2003;100:10388-92.

Zhang X, Schwartz JC, Almo SC, Nathenson SG. Crystal structure of the receptor-binding domain of human B7-2: insights into organization and signaling. Proceedings of the National Academy of Sciences of the United States of America, 2003;100:2586-91.

Zhao R, Chinai JM, Buhl S, Scandiuzzi L, Ray A, Jeon H et al. HHLA2 is a member of the B7 family and inhibits human CD4 and CD8 T-cell function. Proceedings of the National Academy of Sciences of the United States of America, 2013;110:9879-84.

Zhu Y, Yao S, Iliopoulou BP, Han X, Augustine MM, Xu H et al. B7-H5 costimulates human T cells via CD28H. Nature communications, 2013;4:2043.

* cited by examiner

SEQUENCE LISTING

```
<160> NUMBER OF SEQ ID NOS: 29

<210> SEQ ID NO 1
<211> LENGTH: 228
<212> TYPE: PRT
<213> ORGANISM: Artificial Sequence
<220> FEATURE:
<223> OTHER INFORMATION: Synthetic polypeptide

<400> SEQUENCE: 1

Met Ile Pro Arg Val Ile Arg Leu Trp Leu Pro Ser Ala Leu Phe Leu
1               5                   10                  15

Ser Gln Val Pro Gly Cys Val Pro Leu His Gly Pro Ser Thr Ile Thr
            20                  25                  30

Gly Thr Val Gly Lys Ser Leu Ser Val Ser Cys Gln Tyr Glu Glu Lys
        35                  40                  45

Phe Lys Thr Lys Asp Lys Phe Trp Cys Arg Gly Ser Leu Lys Val Leu
    50                  55                  60

Cys Lys Asp Ile Val Lys Thr Ser Ser Glu Glu Val Arg Asn Gly
65                  70                  75                  80

Arg Val Thr Ile Arg Asp His Pro Asp Asn Leu Thr Phe Thr Val Thr
                85                  90                  95

Tyr Glu Ser Leu Thr Leu Glu Asp Ala Asp Thr Tyr Met Cys Ala Val
            100                 105                 110

Asp Ile Ser Leu Phe Asp Gly Ser Leu Gly Phe Asp Lys Tyr Phe Lys
        115                 120                 125

Ile Glu Leu Ser Val Val Pro Ser Glu Asp Pro Val Thr Gly Ser Ser
    130                 135                 140

Leu Glu Ser Gly Arg Asp Ile Leu Glu Ser Pro Thr Ser Ser Val Gly
145                 150                 155                 160

His Thr His Pro Ser Val Thr Thr Asp Asp Thr Ile Pro Thr Pro Cys
                165                 170                 175

Pro Gln Pro Arg Ser Leu Arg Ser Ser Leu Tyr Phe Arg Val Leu Val
            180                 185                 190
```

-continued

Ser Leu Lys Leu Phe Leu Phe Leu Ser Met Leu Gly Ala Val Leu Trp
        195                 200                 205

Val Asn Arg Pro Gln Lys Cys Ser Gly Gly Ser Thr Gln Pro Cys
    210                 215                 220

Tyr Glu Asn Gln
225

<210> SEQ ID NO 2
<211> LENGTH: 224
<212> TYPE: PRT
<213> ORGANISM: Artificial Sequence
<220> FEATURE:
<223> OTHER INFORMATION: Synthetic polypeptide

<400> SEQUENCE: 2

Met Thr Ala Arg Ala Trp Ala Ser Trp Arg Ser Ser Ala Leu Leu Leu
1               5                   10                  15

Leu Leu Val Pro Gly Tyr Phe Pro Leu Ser His Pro Met Thr Val Ala
            20                  25                  30

Gly Pro Val Gly Gly Ser Leu Ser Val Gln Cys Arg Tyr Glu Lys Glu
        35                  40                  45

His Arg Thr Leu Asn Lys Phe Trp Cys Arg Pro Gln Ile Leu Arg
    50                  55                  60

Cys Asp Lys Ile Val Glu Thr Lys Gly Ser Ala Gly Lys Arg Asn Gly
65                  70                  75                  80

Arg Val Ser Ile Arg Asp Ser Pro Ala Asn Leu Ser Phe Thr Val Thr
                85                  90                  95

Leu Glu Asn Leu Thr Glu Glu Asp Ala Gly Thr Tyr Trp Cys Gly Val
            100                 105                 110

Asp Thr Pro Trp Leu Arg Asp Phe His Asp Pro Ile Val Glu Val Glu
        115                 120                 125

Val Ser Val Phe Pro Ala Gly Thr Thr Thr Ala Ser Ser Pro Gln Ser
    130                 135                 140

Ser Met Gly Thr Ser Gly Pro Pro Thr Lys Leu Pro Val His Thr Trp
145                 150                 155                 160

Pro Ser Val Thr Arg Lys Asp Ser Pro Glu Pro Ser Pro His Pro Gly
                165                 170                 175

Ser Leu Phe Ser Asn Val Arg Phe Leu Leu Leu Val Leu Leu Glu Leu
            180                 185                 190

Pro Leu Leu Leu Ser Met Leu Gly Ala Val Leu Trp Val Asn Arg Pro
        195                 200                 205

Gln Arg Ser Ser Arg Ser Arg Gln Asn Trp Pro Lys Gly Glu Asn Gln
    210                 215                 220

<210> SEQ ID NO 3
<211> LENGTH: 592
<212> TYPE: PRT
<213> ORGANISM: Artificial Sequence
<220> FEATURE:
<223> OTHER INFORMATION: Synthetic polypeptide

<400> SEQUENCE: 3

Met Leu Lys Arg Leu Lys Lys His Val Val Ala Trp Lys Met Cys Val
1               5                   10                  15

Met Pro His Ser Arg Lys Met Ser Val His Met Glu Arg Pro Ser Pro
            20                  25                  30

Cys Gly Ser Trp Leu Val Gly Cys Leu Phe Thr Ile Ala Val Phe Gln
        35                  40                  45

-continued

```
Pro Pro Val Gln Val Leu Gly Asp Ala Gly Lys Val Tyr Ile Ala Pro
     50                  55                  60

Leu Arg Asp Thr Ala Asn Leu Pro Cys Pro Leu Phe Leu Trp Pro Asn
 65                  70                  75                  80

Met Val Leu Ser Glu Met Arg Trp Tyr Arg Pro Gly His Leu Pro Arg
                 85                  90                  95

Thr Gln Ala Val His Val Phe Arg Asp Gly Gln Asp Arg Asp Glu Asp
                100                 105                 110

Leu Met Pro Glu Tyr Lys Gly Arg Thr Ala Leu Val Arg Asp Ala His
            115                 120                 125

Lys Glu Ser Tyr Ile Leu Gln Ile Ser Asn Val Arg Leu Glu Asp Arg
130                 135                 140

Gly Leu Tyr Gln Cys Gln Val Trp Val Gly Asn Ser Ser Arg Glu Asp
145                 150                 155                 160

Asn Val Thr Leu Gln Val Ala Val Leu Gly Ser Asp Pro Tyr Ile His
                165                 170                 175

Val Lys Gly Tyr Asp Ala Gly Trp Ile Glu Leu Leu Cys Gln Ser Val
            180                 185                 190

Gly Trp Phe Pro Lys Pro Trp Thr Glu Trp Arg Asp Thr Thr Gly Arg
        195                 200                 205

Ala Leu Leu Ser Leu Ser Glu Val His Ser Leu Asp Glu Asn Gly Leu
210                 215                 220

Phe Arg Thr Ala Val Ser Ser Arg Ile Arg Asp Asn Ala Leu Gly Asn
225                 230                 235                 240

Val Ser Cys Thr Ile His Asn Glu Ala Leu Gly Gln Glu Lys Thr Thr
                245                 250                 255

Ala Met Ile Ile Gly Ala Pro Glu Arg Gly Ser Leu Ser Ser Pro Ala
            260                 265                 270

Val Ala Leu Ser Val Val Leu Pro Val Leu Gly Leu Leu Ile Leu Leu
        275                 280                 285

Gly Ile Trp Leu Ile Cys Lys Gln Lys Lys Ser Lys Glu Lys Leu Leu
290                 295                 300

Tyr Glu Gln Ala Met Glu Val Glu Asn Leu Leu Glu Asp His Ala Lys
305                 310                 315                 320

Glu Lys Gly Arg Leu His Lys Ala Leu Lys Lys Leu Arg Ser Glu Leu
                325                 330                 335

Lys Leu Lys Arg Ala Ala Ala Asn Ala Gly Trp Arg Arg Ala Arg Leu
            340                 345                 350

His Phe Val Ala Val Thr Leu Asp Pro Asp Thr Ala His Pro Lys Leu
        355                 360                 365

Ile Leu Ser Glu Asp Arg Arg Cys Val Arg Leu Gly Asp Arg Lys Arg
370                 375                 380

Pro Val Pro Asp Asn Pro Glu Arg Phe Asp Phe Val Val Ser Val Leu
385                 390                 395                 400

Gly Ser Glu Tyr Phe Thr Thr Gly Cys His Tyr Trp Glu Val Tyr Val
                405                 410                 415

Gly Glu Lys Thr Lys Trp Ile Leu Gly Val Cys Ser Glu Ser Val Ser
            420                 425                 430

Arg Lys Gly Lys Val Thr Ala Ser Pro Ala Asn Gly His Trp Leu Val
        435                 440                 445

Arg Gln Ser Arg Gly Asn Glu Tyr Glu Ala Leu Thr Ser Pro Gln Thr
450                 455                 460
```

```
Ser Phe Arg Leu Lys Glu Ser Pro Lys Cys Val Gly Ile Phe Leu Asp
465                 470                 475                 480

Tyr Glu Ala Gly Ile Ile Ser Phe Tyr Asn Val Thr Asp Lys Ser His
            485                 490                 495

Ile Phe Thr Phe Thr His Ser Phe Ser Ser Pro Leu Arg Pro Phe Phe
                500                 505                 510

Glu Pro Cys Leu His Asp Glu Gly Lys Asn Thr Ala Pro Leu Ile Ile
            515                 520                 525

Cys Thr Glu Leu Gln Lys Ser Glu Glu Ser Ile Val Pro Lys Gln Glu
            530                 535                 540

Gly Lys Asp Arg Ala Asn Gly Asp Val Ser Leu Lys Met Asn Pro Ser
545                 550                 555                 560

Leu Leu Ser Pro Gln Gly Ser Glu Leu Phe Leu Leu Asn Asp Thr Trp
                565                 570                 575

Pro Ser Asn Leu Gly Pro Ala Leu Lys Gly Leu Lys Val Pro Ser Leu
                580                 585                 590

<210> SEQ ID NO 4
<211> LENGTH: 475
<212> TYPE: PRT
<213> ORGANISM: Artificial Sequence
<220> FEATURE:
<223> OTHER INFORMATION: Synthetic polypeptide

<400> SEQUENCE: 4

Met Glu Met Ala Ser Ser Ala Gly Ser Trp Leu Ser Gly Cys Leu Ile
1               5                   10                  15

Pro Leu Val Phe Leu Arg Leu Ser His Val Ser Gly His Ala Gly
                20                  25                  30

Asp Ala Gly Lys Phe His Val Ala Leu Leu Gly Gly Thr Ala Glu Leu
            35                  40                  45

Leu Cys Pro Leu Ser Leu Trp Pro Gly Thr Val Pro Lys Glu Val Arg
50                  55                  60

Trp Leu Arg Ser Pro Phe Pro Gln Arg Ser Gln Ala Val His Ile Phe
65                  70                  75                  80

Arg Asp Gly Lys Asp Gln Asp Glu Asp Leu Met Pro Glu Tyr Lys Gly
                85                  90                  95

Arg Thr Val Leu Val Arg Asp Ala Gln Glu Gly Ser Val Thr Leu Gln
                100                 105                 110

Ile Leu Asp Val Arg Leu Glu Asp Gln Gly Ser Tyr Arg Cys Leu Ile
            115                 120                 125

Gln Val Gly Asn Leu Ser Lys Glu Asp Thr Val Ile Leu Gln Val Ala
130                 135                 140

Ala Pro Ser Val Gly Ser Leu Ser Pro Ser Ala Val Ala Leu Ala Val
145                 150                 155                 160

Ile Leu Pro Val Leu Val Leu Leu Ile Met Val Cys Leu Cys Leu Ile
                165                 170                 175

Trp Lys Gln Arg Arg Ala Lys Glu Lys Leu Leu Tyr Glu His Val Thr
            180                 185                 190

Glu Val Asp Asn Leu Leu Ser Asp His Ala Lys Glu Lys Gly Lys Leu
            195                 200                 205

His Lys Ala Val Lys Lys Leu Arg Ser Glu Leu Lys Leu Lys Arg Ala
        210                 215                 220

Ala Ala Asn Ser Gly Trp Arg Arg Ala Arg Leu His Phe Val Ala Val
225                 230                 235                 240
```

Thr Leu Asp Pro Asp Thr Ala His Pro Lys Leu Ile Leu Ser Glu Asp
            245                 250                 255

Gln Arg Cys Val Arg Leu Gly Asp Arg Arg Gln Pro Val Pro Asp Asn
        260                 265                 270

Pro Gln Arg Phe Asp Phe Val Val Ser Ile Leu Gly Ser Glu Tyr Phe
    275                 280                 285

Thr Thr Gly Cys His Tyr Trp Glu Val Tyr Val Gly Asp Lys Thr Lys
290                 295                 300

Trp Ile Leu Gly Val Cys Ser Glu Ser Val Ser Arg Lys Gly Lys Val
305                 310                 315                 320

Thr Ala Ser Pro Ala Asn Gly His Trp Leu Leu Arg Gln Ser Arg Gly
            325                 330                 335

Asn Glu Tyr Glu Ala Leu Thr Ser Pro Gln Thr Ser Phe Arg Leu Lys
        340                 345                 350

Glu Pro Pro Arg Cys Val Gly Ile Phe Leu Asp Tyr Glu Ala Gly Val
    355                 360                 365

Ile Ser Phe Tyr Asn Val Thr Asn Lys Ser His Ile Phe Thr Phe Thr
370                 375                 380

His Asn Phe Ser Gly Pro Leu Arg Pro Phe Phe Glu Pro Cys Leu His
385                 390                 395                 400

Asp Gly Gly Lys Asn Thr Ala Pro Leu Val Ile Cys Ser Glu Leu His
            405                 410                 415

Lys Ser Glu Glu Ser Ile Val Pro Arg Pro Glu Gly Lys Gly His Ala
        420                 425                 430

Asn Gly Asp Val Ser Leu Lys Val Asn Ser Ser Leu Leu Pro Pro Lys
    435                 440                 445

Ala Pro Glu Leu Lys Asp Ile Ile Leu Ser Leu Pro Pro Asp Leu Gly
450                 455                 460

Pro Ala Leu Gln Glu Leu Lys Ala Pro Ser Phe
465                 470                 475

<210> SEQ ID NO 5
<211> LENGTH: 451
<212> TYPE: PRT
<213> ORGANISM: Artificial Sequence
<220> FEATURE:
<223> OTHER INFORMATION: Synthetic polypeptide

<400> SEQUENCE: 5

Met Gly Leu Glu Pro Ser Trp Tyr Leu Leu Cys Leu Ala Val Ser
1               5                   10                  15

Gly Ala Ala Gly Thr Asp Pro Pro Thr Ala Pro Thr Thr Ala Glu Arg
            20                  25                  30

Gln Arg Gln Pro Thr Asp Ile Ile Leu Asp Cys Phe Leu Val Thr Glu
        35                  40                  45

Asp Arg His Arg Gly Ala Phe Ala Ser Ser Gly Asp Arg Glu Arg Ala
    50                  55                  60

Leu Leu Val Leu Lys Gln Val Pro Val Leu Asp Asp Gly Ser Leu Glu
65                  70                  75                  80

Gly Ile Thr Asp Phe Gln Gly Ser Thr Glu Thr Lys Gln Asp Ser Pro
                85                  90                  95

Val Ile Phe Glu Ala Ser Val Asp Leu Val Gln Ile Pro Gln Ala Glu
            100                 105                 110

Ala Leu Leu His Ala Asp Cys Ser Gly Lys Ala Val Thr Cys Glu Ile
        115                 120                 125

Ser Lys Tyr Phe Leu Gln Ala Arg Gln Glu Ala Thr Phe Glu Lys Ala
    130                 135                 140

His Trp Phe Ile Ser Asn Met Gln Val Ser Arg Gly Gly Pro Ser Val
145                 150                 155                 160

Ser Met Val Met Lys Thr Leu Arg Asp Ala Glu Val Gly Ala Val Arg
                165                 170                 175

His Pro Thr Leu Asn Leu Pro Leu Ser Ala Gln Gly Thr Val Lys Thr
            180                 185                 190

Gln Val Glu Phe Gln Val Thr Ser Glu Thr Gln Thr Leu Asn His Leu
        195                 200                 205

Leu Gly Ser Ser Val Ser Leu His Cys Ser Phe Ser Met Ala Pro Gly
    210                 215                 220

Leu Asp Leu Thr Gly Val Glu Trp Arg Leu Gln His Lys Gly Ser Gly
225                 230                 235                 240

Gln Leu Val Tyr Ser Trp Lys Thr Gly Gln Gly Gln Ala Lys Arg Lys
                245                 250                 255

Gly Ala Thr Leu Glu Pro Glu Leu Leu Arg Ala Gly Asn Ala Ser
            260                 265                 270

Leu Thr Leu Pro Asn Leu Thr Leu Lys Asp Glu Gly Asn Tyr Ile Cys
        275                 280                 285

Gln Ile Ser Thr Ser Leu Tyr Gln Ala Gln Gln Ile Met Pro Leu Asn
    290                 295                 300

Ile Leu Ala Pro Pro Lys Ile Gln Leu His Leu Ala Asn Lys Asp Pro
305                 310                 315                 320

Leu Pro Ser Leu Val Cys Ser Ile Ala Gly Tyr Tyr Pro Leu Asp Val
                325                 330                 335

Gly Val Thr Trp Ile Arg Glu Glu Leu Gly Gly Ile Pro Ala Gln Val
            340                 345                 350

Ser Gly Ala Ser Phe Ser Ser Leu Arg Gln Ser Thr Met Gly Thr Tyr
        355                 360                 365

Ser Ile Ser Ser Thr Val Met Ala Asp Pro Gly Pro Thr Gly Ala Thr
    370                 375                 380

Tyr Thr Cys Gln Val Ala His Val Ser Leu Glu Glu Pro Leu Thr Thr
385                 390                 395                 400

Ser Met Arg Val Leu Pro Asn Pro Glu Gln Arg Gly Thr Leu Gly Val
                405                 410                 415

Ile Phe Ala Ser Ile Ile Phe Leu Ser Ala Leu Leu Leu Phe Leu Gly
            420                 425                 430

Leu His Arg Gln Gln Ala Ser Ser Ser Arg Ser Thr Arg Pro Met Arg
        435                 440                 445

His Ser Gly
    450

<210> SEQ ID NO 6
<211> LENGTH: 468
<212> TYPE: PRT
<213> ORGANISM: Artificial Sequence
<220> FEATURE:
<223> OTHER INFORMATION: Synthetic polypeptide

<400> SEQUENCE: 6

Met Gly Thr Gln Glu Gly Trp Cys Leu Leu Leu Cys Leu Ala Leu Ser
1               5                   10                  15

Gly Ala Ala Glu Thr Lys Pro His Pro Ala Glu Gly Gln Trp Arg Ala
            20                  25                  30

-continued

```
Val Asp Val Val Leu Asp Cys Phe Leu Ala Lys Asp Gly Ala His Arg
         35                  40                  45
Gly Ala Leu Ala Ser Ser Glu Asp Arg Ala Arg Ala Ser Leu Val Leu
 50                  55                  60
Lys Gln Val Pro Val Leu Asp Asp Gly Ser Leu Glu Asp Phe Thr Asp
 65                  70                  75                  80
Phe Gln Gly Gly Thr Leu Ala Gln Asp Pro Pro Ile Ile Phe Glu
                 85                  90                  95
Ala Ser Val Asp Leu Val Gln Ile Pro Gln Ala Glu Ala Leu Leu His
             100                 105                 110
Ala Asp Cys Ser Gly Lys Glu Val Thr Cys Glu Ile Ser Arg Tyr Phe
             115                 120                 125
Leu Gln Met Thr Glu Thr Thr Val Lys Thr Ala Ala Trp Phe Met Ala
 130                 135                 140
Asn Met Gln Val Ser Gly Gly Pro Ser Ile Ser Leu Val Met Lys
145                 150                 155                 160
Thr Pro Arg Val Thr Lys Asn Glu Ala Leu Trp His Pro Thr Leu Asn
                 165                 170                 175
Leu Pro Leu Ser Pro Gln Gly Thr Val Arg Thr Ala Val Glu Phe Gln
             180                 185                 190
Val Met Thr Gln Thr Gln Ser Leu Ser Phe Leu Leu Gly Ser Ser Ala
             195                 200                 205
Ser Leu Asp Cys Gly Phe Ser Met Ala Pro Gly Leu Asp Leu Ile Ser
             210                 215                 220
Val Glu Trp Arg Leu Gln His Lys Gly Arg Gly Gln Leu Val Tyr Ser
225                 230                 235                 240
Trp Thr Ala Gly Gln Gly Gln Ala Val Arg Lys Gly Ala Thr Leu Glu
                 245                 250                 255
Pro Ala Gln Leu Gly Met Ala Arg Asp Ala Ser Leu Thr Leu Pro Gly
             260                 265                 270
Leu Thr Ile Gln Asp Glu Gly Thr Tyr Ile Cys Gln Ile Thr Thr Ser
             275                 280                 285
Leu Tyr Arg Ala Gln Gln Ile Ile Gln Leu Asn Ile Gln Ala Ser Pro
 290                 295                 300
Lys Val Arg Leu Ser Leu Ala Asn Glu Ala Leu Leu Pro Thr Leu Ile
305                 310                 315                 320
Cys Asp Ile Ala Gly Tyr Tyr Pro Leu Asp Val Val Thr Trp Thr
                 325                 330                 335
Arg Glu Glu Leu Gly Gly Ser Pro Ala Gln Val Ser Gly Ala Ser Phe
             340                 345                 350
Ser Ser Leu Arg Gln Ser Val Ala Gly Thr Tyr Ser Ile Ser Ser Ser
             355                 360                 365
Leu Thr Ala Glu Pro Gly Ser Ala Gly Ala Thr Tyr Thr Cys Gln Val
             370                 375                 380
Thr His Ile Ser Leu Glu Glu Pro Leu Gly Ala Ser Thr Gln Val Val
385                 390                 395                 400
Pro Pro Glu Arg Arg Thr Ala Leu Gly Val Ile Phe Ala Ser Ser Leu
                 405                 410                 415
Phe Leu Leu Ala Leu Met Phe Leu Gly Leu Gln Arg Arg Gln Ala Pro
             420                 425                 430
Thr Gly Leu Gly Leu Leu Gln Ala Glu Arg Trp Glu Thr Thr Ser Cys
             435                 440                 445
```

```
Ala Asp Thr Gln Ser Ser His Leu His Glu Asp Arg Thr Ala Arg Val
450                 455                 460

Ser Gln Pro Ser
465

<210> SEQ ID NO 7
<211> LENGTH: 398
<212> TYPE: PRT
<213> ORGANISM: Artificial Sequence
<220> FEATURE:
<223> OTHER INFORMATION: Synthetic polypeptide

<400> SEQUENCE: 7

Met Met Lys Pro Glu Phe Ser His Phe Gly Phe Cys Val Tyr Phe
1               5                   10                  15

Leu Phe Leu Gln Val Met Ala Ser Ser Glu Lys Leu Arg Val Thr Thr
                20                  25                  30

Pro Thr Arg His Leu Leu Ala Arg Val Gly Gln Ala Glu Leu Ser
            35                  40                  45

Cys Gln Val Ile Pro Pro His Ser Val Met His Met Glu Val Arg Trp
        50                  55                  60

Phe Arg Ser Gly His Ser Gln Pro Val Tyr Leu Tyr Arg Gly Gly His
65                  70                  75                  80

Lys Met Ser Glu Glu Ala Ala Pro Glu Tyr Ala Asn Arg Thr Glu Phe
                85                  90                  95

Val Lys Glu Ala Ile Gly Glu Gly Lys Val Ser Leu Arg Ile Tyr Asn
                100                 105                 110

Ile Asn Ile Leu Asp Asp Gly Pro Tyr Gln Cys Ser Phe Asn Asp Ser
            115                 120                 125

Gly Phe Ile Asp Val Ala Ile Met Asn Leu Asn Val Thr Ala Val Gly
130                 135                 140

Leu Glu Thr Glu Ile His Val Gln Ala Pro Asp Ala Asp Gly Val Met
145                 150                 155                 160

Val Glu Cys Asn Thr Gly Gly Trp Phe Pro Arg Pro Gln Met Glu Trp
                165                 170                 175

Arg Asp Ser Lys Gly Ala Thr Leu Pro His Ser Leu Lys Ser Tyr Ser
            180                 185                 190

Gln Asp Glu Ala Arg Phe Phe His Met Lys Met Thr Leu Leu Leu Thr
        195                 200                 205

Asn Met Ser His Gly Ser Ile Ile Cys Cys Ile Ser Asn Pro Val Thr
    210                 215                 220

Gly Glu Glu Lys Gln Thr Ser Ile Ile Leu Ala Asn Glu Leu Phe Asn
225                 230                 235                 240

Gln Asp Tyr Leu Trp Val Gly Ile Phe Pro Phe Ser Val Leu Ser Leu
                245                 250                 255

Ile Leu Phe Gly Val Leu Pro Phe Ile Asn Ser Phe Phe Arg Ser Gln
                260                 265                 270

Gly Cys Ala Ser Gly Cys Leu Ser Lys Cys Leu Pro Val Val Thr Ser
            275                 280                 285

Trp Pro Val Gln Ile Val His Phe Leu Val Cys Ser Gly Val Leu Phe
        290                 295                 300

Ala Val Tyr Leu Pro His Arg Tyr Arg Val Ser Leu Ser Asp Pro Gln
305                 310                 315                 320

Phe Pro Leu Tyr Asn Asn Trp Ile Thr Glu Leu Leu Ile Val Ile Leu
                325                 330                 335
```

```
Phe Leu Thr Ile Cys Phe Val Leu Pro Ile Thr Val Leu Leu Ile
            340                 345                 350
Lys Leu Ser Pro Thr Cys Leu Ala Lys Trp Glu Lys Asn Lys Asp Asp
        355                 360                 365
Ile Met Asp Ser Gln Leu Gly Leu Gly Lys Ala Arg Glu Ala Ser Thr
370                 375                 380
Leu Tyr Glu Glu Gln Ser Arg Lys Ser Trp Glu Gln Glu Lys
385                 390                 395
```

<210> SEQ ID NO 8
<211> LENGTH: 290
<212> TYPE: PRT
<213> ORGANISM: Artificial Sequence
<220> FEATURE:
<223> OTHER INFORMATION: Synthetic polypeptide

<400> SEQUENCE: 8

```
Met Pro Leu Leu Thr Leu Tyr Leu Leu Leu Phe Trp Leu Ser Gly Tyr
1               5                   10                  15
Ser Ile Val Thr Gln Ile Thr Gly Pro Thr Thr Val Asn Gly Leu Glu
                20                  25                  30
Arg Gly Ser Leu Thr Val Gln Cys Val Tyr Arg Ser Gly Trp Glu Thr
            35                  40                  45
Tyr Leu Lys Trp Trp Cys Arg Gly Ala Ile Trp Arg Asp Cys Lys Ile
50                  55                  60
Leu Val Lys Thr Ser Gly Ser Glu Gln Glu Val Lys Arg Asp Arg Val
65                  70                  75                  80
Ser Ile Lys Asp Asn Gln Lys Asn Arg Thr Phe Thr Val Thr Met Glu
                85                  90                  95
Asp Leu Met Lys Thr Asp Ala Asp Thr Tyr Trp Cys Gly Ile Glu Lys
            100                 105                 110
Thr Gly Asn Asp Leu Gly Val Thr Val Gln Val Thr Ile Asp Pro Ala
        115                 120                 125
Pro Val Thr Gln Glu Glu Thr Ser Ser Pro Thr Leu Thr Gly His
130                 135                 140
His Leu Asp Asn Arg His Lys Leu Leu Lys Leu Ser Val Leu Leu Pro
145                 150                 155                 160
Leu Ile Phe Thr Ile Leu Leu Leu Leu Val Ala Ala Ser Leu Leu
                165                 170                 175
Ala Trp Arg Met Met Lys Tyr Gln Gln Lys Ala Ala Gly Met Ser Pro
            180                 185                 190
Glu Gln Val Leu Gln Pro Leu Glu Gly Asp Leu Cys Tyr Ala Asp Leu
        195                 200                 205
Thr Leu Gln Leu Ala Gly Thr Ser Pro Gln Lys Ala Thr Thr Lys Leu
    210                 215                 220
Ser Ser Ala Gln Val Asp Gln Val Glu Val Glu Tyr Val Thr Met Ala
225                 230                 235                 240
Ser Leu Pro Lys Glu Asp Ile Ser Tyr Ala Ser Leu Thr Leu Gly Ala
                245                 250                 255
Glu Asp Gln Glu Pro Thr Tyr Cys Asn Met Gly His Leu Ser Ser His
            260                 265                 270
Leu Pro Gly Arg Gly Pro Glu Glu Pro Thr Glu Tyr Ser Thr Ile Ser
        275                 280                 285
Arg Pro
    290
```

```
<210> SEQ ID NO 9
<211> LENGTH: 368
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(136)
<223> OTHER INFORMATION: human CD300F
<220> FEATURE:
<221> NAME/KEY: MISC_FEATURE
<222> LOCATION: (137)..(368)
<223> OTHER INFORMATION: Ig domain

<400> SEQUENCE: 9

Thr Gln Ile Thr Gly Pro Thr Thr Val Asn Gly Leu Glu Arg Gly Ser
1               5                   10                  15

Leu Thr Val Gln Cys Val Tyr Arg Ser Gly Trp Glu Thr Tyr Leu Lys
            20                  25                  30

Trp Trp Cys Arg Gly Ala Ile Trp Arg Asp Cys Lys Ile Leu Val Lys
        35                  40                  45

Thr Ser Gly Ser Glu Gln Glu Val Lys Arg Asp Arg Val Ser Ile Lys
    50                  55                  60

Asp Asn Gln Lys Asn Arg Thr Phe Thr Val Thr Met Glu Asp Leu Met
65                  70                  75                  80

Lys Thr Asp Ala Asp Thr Tyr Trp Cys Gly Ile Glu Lys Thr Gly Asn
                85                  90                  95

Asp Leu Gly Val Thr Val Gln Val Thr Ile Asp Pro Ala Pro Val Thr
            100                 105                 110

Gln Glu Glu Thr Ser Ser Ser Pro Thr Leu Thr Gly His His Leu Asp
        115                 120                 125

Asn Arg His Lys Leu Leu Lys Leu Pro Arg Gly Pro Thr Ile Lys Pro
    130                 135                 140

Cys Pro Pro Cys Lys Cys Pro Ala Pro Asn Leu Leu Gly Gly Pro Ser
145                 150                 155                 160

Val Phe Ile Phe Pro Pro Lys Ile Lys Asp Val Leu Met Ile Ser Leu
                165                 170                 175

Ser Pro Ile Val Thr Cys Val Val Asp Val Ser Glu Asp Asp Pro
            180                 185                 190

Asp Val Gln Ile Ser Trp Phe Val Asn Asn Val Glu Val His Thr Ala
        195                 200                 205

Gln Thr Gln Thr His Arg Glu Asp Tyr Asn Ser Thr Leu Arg Val Val
    210                 215                 220

Ser Ala Leu Pro Ile Gln His Gln Asp Trp Met Ser Gly Lys Glu Phe
225                 230                 235                 240

Lys Cys Lys Val Asn Asn Lys Asp Leu Pro Ala Pro Ile Glu Arg Thr
                245                 250                 255

Ile Ser Lys Pro Lys Gly Ser Val Arg Ala Pro Gln Val Tyr Val Leu
            260                 265                 270

Pro Pro Pro Glu Glu Glu Met Thr Lys Lys Gln Val Thr Leu Thr Cys
        275                 280                 285

Met Val Thr Asp Phe Met Pro Glu Asp Ile Tyr Val Glu Trp Thr Asn
    290                 295                 300

Asn Gly Lys Thr Glu Leu Asn Tyr Lys Asn Thr Glu Pro Val Leu Asp
305                 310                 315                 320

Ser Asp Gly Ser Tyr Phe Met Tyr Ser Lys Leu Arg Val Glu Lys Lys
                325                 330                 335
```

```
Asn Trp Val Glu Arg Asn Ser Tyr Ser Cys Ser Val His Glu Gly
            340                 345                 350

Leu His Asn His His Thr Thr Lys Ser Phe Ser Arg Thr Pro Gly Lys
        355                 360                 365

<210> SEQ ID NO 10
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 10

Ile Tyr Gly Met Asn
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 11

Trp Ile Asn Thr Tyr Thr
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 12

Ala Arg Ser Arg Phe Ala Tyr
1               5

<210> SEQ ID NO 13
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 13

Lys Ala Ser Gln Asn Val Gly Thr Asn Val Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 14

Ser Ala Ser Tyr Arg Tyr Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic polypeptide
```

<400> SEQUENCE: 15

Gln Gln Tyr Asn Ser Tyr Pro Leu Thr
1               5

<210> SEQ ID NO 16
<211> LENGTH: 114
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(30)
<223> OTHER INFORMATION: FWR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FWR2
<220> FEATURE:
<221> NAME/KEY: MISC_FEATURE
<222> LOCATION: (50)..(55)
<223> OTHER INFORMATION: CDR2
<220> FEATURE:
<221> NAME/KEY: MISC_FEATURE
<222> LOCATION: (56)..(96)
<223> OTHER INFORMATION: FWR3
<220> FEATURE:
<221> NAME/KEY: MISC_FEATURE
<222> LOCATION: (97)..(103)
<223> OTHER INFORMATION: CDR3

<400> SEQUENCE: 16

Gln Ile Gln Leu Val Gln Ser Gly Pro Glu Leu Arg Lys Pro Gly Glu
1               5                   10                  15

Thr Val Lys Ile Ser Cys Lys Ala Ser Gly Tyr Thr Phe Thr Ile Tyr
                20                  25                  30

Gly Met Asn Trp Met Lys Gln Ala Pro Gly Lys Gly Leu Lys Trp Met
            35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Phe
65                  70                  75                  80

Leu Gln Ile Asn Asn Leu Thr Asn Glu Asp Thr Ala Thr Tyr Phe Cys
                85                  90                  95

Ala Arg Ser Arg Phe Ala Tyr Trp Gly Gln Gly Thr Leu Val Thr Val
            100                 105                 110

Ser Ala

<210> SEQ ID NO 17
<211> LENGTH: 107
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(23)
<223> OTHER INFORMATION: FWR1
<220> FEATURE:
<221> NAME/KEY: MISC_FEATURE
<222> LOCATION: (24)..(34)
<223> OTHER INFORMATION: CDR1

-continued

```
<220> FEATURE:
<221> NAME/KEY: MISC_FEATURE
<222> LOCATION: (35)..(49)
<223> OTHER INFORMATION: FWR2
<220> FEATURE:
<221> NAME/KEY: MISC_FEATURE
<222> LOCATION: (50)..(56)
<223> OTHER INFORMATION: CDR2
<220> FEATURE:
<221> NAME/KEY: MISC_FEATURE
<222> LOCATION: (57)..(88)
<223> OTHER INFORMATION: FWR3
<220> FEATURE:
<221> NAME/KEY: MISC_FEATURE
<222> LOCATION: (89)..(97)
<223> OTHER INFORMATION: CDR3

<400> SEQUENCE: 17

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Arg Ser Gly Thr Asp Phe Thr Leu Thr Ile Ser Asn Val Gln Ser
65                  70                  75                  80

Glu Asp Leu Ala Glu Tyr Val Cys Gln Gln Tyr Asn Ser Tyr Pro Leu
                85                  90                  95

Thr Phe Gly Ala Gly Thr Lys Leu Glu Leu Lys
            100                 105

<210> SEQ ID NO 18
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 18

Gly Tyr Phe Trp His
1               5

<210> SEQ ID NO 19
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 19

Tyr Ile Ser Tyr Ser Gly Thr Thr Asn Tyr Asn Pro Ser Leu Lys Asn
1               5                   10                  15

<210> SEQ ID NO 20
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 20

Asp Asp Trp Asp Trp Phe Ala Tyr
1               5
```

```
<210> SEQ ID NO 21
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 21

Ser Ala Ser Ser Ser Val Asn Tyr Met His
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 22

Asp Thr Ser Lys Leu Ala Ser
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 23

Phe Gln Gly Ser Gly Tyr Pro Leu Thr
1               5

<210> SEQ ID NO 24
<211> LENGTH: 117
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(31)
<223> OTHER INFORMATION: FWR1
<220> FEATURE:
<221> NAME/KEY: MISC_FEATURE
<222> LOCATION: (32)..(36)
<223> OTHER INFORMATION: CDR1
<220> FEATURE:
<221> NAME/KEY: MISC_FEATURE
<222> LOCATION: (37)..(50)
<223> OTHER INFORMATION: FWR2
<220> FEATURE:
<221> NAME/KEY: MISC_FEATURE
<222> LOCATION: (51)..(66)
<223> OTHER INFORMATION: CDR2
<220> FEATURE:
<221> NAME/KEY: MISC_FEATURE
<222> LOCATION: (67)..(98)
<223> OTHER INFORMATION: FWR3
<220> FEATURE:
<221> NAME/KEY: MISC_FEATURE
<222> LOCATION: (99)..(106)
<223> OTHER INFORMATION: CDR3

<400> SEQUENCE: 24

Asp Val Gln Leu Gln Glu Ser Gly Pro Gly Leu Val Lys Pro Ser Gln
1               5                   10                  15

Thr Leu Ser Leu Thr Cys Ser Val Thr Gly Tyr Ser Leu Thr Ser Gly
            20                  25                  30
```

```
Tyr Phe Trp His Trp Ile Arg Gln Phe Pro Gly Asn Lys Leu Glu Trp
             35                  40                  45

Met Gly Tyr Ile Ser Tyr Ser Gly Thr Thr Asn Tyr Asn Pro Ser Leu
 50                  55                  60

Lys Asn Arg Ile Ser Ile Thr His Asp Ser Ser Lys Asn Gln Phe Phe
 65                  70                  75                  80

Leu Asn Leu Asn Ser Val Thr Ala Glu Asp Thr Ala Thr Tyr Phe Cys
                 85                  90                  95

Ala Gly Asp Asp Trp Asp Trp Phe Ala Tyr Trp Gly Gln Gly Thr Leu
                100                 105                 110

Val Thr Val Ser Ala
            115

<210> SEQ ID NO 25
<211> LENGTH: 106
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(23)
<223> OTHER INFORMATION: FWR1
<220> FEATURE:
<221> NAME/KEY: MISC_FEATURE
<222> LOCATION: (24)..(33)
<223> OTHER INFORMATION: CDR1
<220> FEATURE:
<221> NAME/KEY: MISC_FEATURE
<222> LOCATION: (34)..(48)
<223> OTHER INFORMATION: FWR2
<220> FEATURE:
<221> NAME/KEY: MISC_FEATURE
<222> LOCATION: (49)..(55)
<223> OTHER INFORMATION: CDR2
<220> FEATURE:
<221> NAME/KEY: MISC_FEATURE
<222> LOCATION: (56)..(87)
<223> OTHER INFORMATION: FWR3
<220> FEATURE:
<221> NAME/KEY: MISC_FEATURE
<222> LOCATION: (88)..(96)
<223> OTHER INFORMATION: CDR3

<400> SEQUENCE: 25

Glu Asn Val Leu Thr Gln Ser Pro Ala Ile Met Ser Ala Ser Pro Gly
 1               5                  10                  15

Glu Lys Val Thr Met Thr Cys Ser Ala Ser Ser Val Asn Tyr Met
             20                  25                  30

His Trp Tyr Gln Gln Lys Ser Ser Thr Ser Pro Lys Leu Trp Ile Tyr
             35                  40                  45

Asp Thr Ser Lys Leu Ala Ser Gly Val Pro Gly Arg Phe Ser Gly Ser
 50                  55                  60

Gly Ser Gly Asn Ser Tyr Ser Leu Thr Ile Ser Ser Met Glu Ala Glu
 65                  70                  75                  80

Asp Val Ala Thr Tyr Tyr Cys Phe Gln Gly Ser Gly Tyr Pro Leu Thr
                 85                  90                  95

Phe Gly Ser Gly Thr Lys Leu Glu Ile Lys
            100                 105

<210> SEQ ID NO 26
<211> LENGTH: 387
<212> TYPE: PRT
<213> ORGANISM: Artificial Sequence
```

```
<220> FEATURE:
<223> OTHER INFORMATION: Synthetic polypeptide
<220> FEATURE:
<221> NAME/KEY: MISC_FEATURE
<222> LOCATION: (1)..(155)
<223> OTHER INFORMATION: human CD300c
<220> FEATURE:
<221> NAME/KEY: MISC_FEATURE
<222> LOCATION: (156)..(387)
<223> OTHER INFORMATION: Ig domain

<400> SEQUENCE: 26
```

| | | | | | | | | | | | | | | |
|---|---|---|---|---|---|---|---|---|---|---|---|---|---|---|
| Met | Thr | Val | Ala | Gly | Pro | Val | Gly | Gly | Ser | Leu | Ser | Val | Gln | Cys | Arg |
| 1 | | | | 5 | | | | | 10 | | | | | 15 | |

Tyr Glu Lys Glu His Arg Thr Leu Asn Lys Phe Trp Cys Arg Pro Pro
          20                  25                  30

Gln Ile Leu Arg Cys Asp Lys Ile Val Glu Thr Lys Gly Ser Ala Gly
             35                  40                  45

Lys Arg Asn Gly Arg Val Ser Ile Arg Asp Ser Pro Ala Asn Leu Ser
 50                  55                  60

Phe Thr Val Thr Leu Glu Asn Leu Thr Glu Glu Asp Ala Gly Thr Tyr
 65                  70                  75                  80

Trp Cys Gly Val Asp Thr Pro Trp Leu Arg Asp Phe His Asp Pro Ile
                 85                  90                  95

Val Glu Val Glu Val Ser Val Phe Pro Ala Gly Thr Thr Thr Ala Ser
             100                 105                 110

Ser Pro Gln Ser Ser Met Gly Thr Ser Gly Pro Pro Thr Lys Leu Pro
             115                 120                 125

Val His Thr Trp Pro Ser Val Thr Arg Lys Asp Ser Pro Glu Pro Ser
 130                 135                 140

Pro His Pro Gly Ser Leu Phe Ser Asn Val Arg Pro Arg Gly Pro Thr
145                 150                 155                 160

Ile Lys Pro Cys Pro Pro Cys Lys Cys Pro Ala Pro Asn Leu Leu Gly
                 165                 170                 175

Gly Pro Ser Val Phe Ile Phe Pro Pro Lys Ile Lys Asp Val Leu Met
             180                 185                 190

Ile Ser Leu Ser Pro Ile Val Thr Cys Val Val Val Asp Val Ser Glu
             195                 200                 205

Asp Asp Pro Asp Val Gln Ile Ser Trp Phe Val Asn Asn Val Glu Val
 210                 215                 220

His Thr Ala Gln Thr Gln Thr His Arg Glu Asp Tyr Asn Ser Thr Leu
225                 230                 235                 240

Arg Val Val Ser Ala Leu Pro Ile Gln His Gln Asp Trp Met Ser Gly
                 245                 250                 255

Lys Glu Phe Lys Cys Lys Val Asn Asn Lys Asp Leu Pro Ala Pro Ile
             260                 265                 270

Glu Arg Thr Ile Ser Lys Pro Lys Gly Ser Val Arg Ala Pro Gln Val
             275                 280                 285

Tyr Val Leu Pro Pro Pro Glu Glu Glu Met Thr Lys Lys Gln Val Thr
             290                 295                 300

Leu Thr Cys Met Val Thr Asp Phe Met Pro Glu Asp Ile Tyr Val Glu
305                 310                 315                 320

Trp Thr Asn Asn Gly Lys Thr Glu Leu Asn Tyr Lys Asn Thr Glu Pro
                 325                 330                 335

Val Leu Asp Ser Asp Gly Ser Tyr Phe Met Tyr Ser Lys Leu Arg Val
             340                 345                 350

```
Glu Lys Lys Asn Trp Val Glu Arg Asn Ser Tyr Ser Cys Ser Val Val
            355                 360                 365

His Glu Gly Leu His Asn His His Thr Thr Lys Ser Phe Ser Arg Thr
370                 375                 380

Pro Gly Lys
385

<210> SEQ ID NO 27
<211> LENGTH: 348
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(116)
<223> OTHER INFORMATION: human BTN5
<220> FEATURE:
<221> NAME/KEY: MISC_FEATURE
<222> LOCATION: (117)..(348)
<223> OTHER INFORMATION: Ig domain

<400> SEQUENCE: 27

His Ala Gly Asp Ala Gly Lys Phe His Val Ala Leu Leu Gly Gly Thr
1               5                   10                  15

Ala Glu Leu Leu Cys Pro Leu Ser Leu Trp Pro Gly Thr Val Pro Lys
            20                  25                  30

Glu Val Arg Trp Leu Arg Ser Pro Phe Pro Gln Arg Ser Gln Ala Val
        35                  40                  45

His Ile Phe Arg Asp Gly Lys Asp Gln Asp Glu Asp Leu Met Pro Glu
    50                  55                  60

Tyr Lys Gly Arg Thr Val Leu Val Arg Asp Ala Gln Glu Gly Ser Val
65                  70                  75                  80

Thr Leu Gln Ile Leu Asp Val Arg Leu Glu Asp Gln Gly Ser Tyr Arg
                85                  90                  95

Cys Leu Ile Gln Val Gly Asn Leu Ser Lys Glu Asp Thr Val Ile Leu
            100                 105                 110

Gln Val Ala Ala Pro Arg Gly Pro Thr Ile Lys Pro Cys Pro Pro Cys
        115                 120                 125

Lys Cys Pro Ala Pro Asn Leu Leu Gly Gly Pro Ser Val Phe Ile Phe
    130                 135                 140

Pro Pro Lys Ile Lys Asp Val Leu Met Ile Ser Leu Ser Pro Ile Val
145                 150                 155                 160

Thr Cys Val Val Val Asp Val Ser Glu Asp Asp Pro Asp Val Gln Ile
                165                 170                 175

Ser Trp Phe Val Asn Asn Val Glu Val His Thr Ala Gln Thr Gln Thr
            180                 185                 190

His Arg Glu Asp Tyr Asn Ser Thr Leu Arg Val Val Ser Ala Leu Pro
        195                 200                 205

Ile Gln His Gln Asp Trp Met Ser Gly Lys Glu Phe Lys Cys Lys Val
    210                 215                 220

Asn Asn Lys Asp Leu Pro Ala Pro Ile Glu Arg Thr Ile Ser Lys Pro
225                 230                 235                 240

Lys Gly Ser Val Arg Ala Pro Gln Val Tyr Val Leu Pro Pro Pro Glu
                245                 250                 255

Glu Glu Met Thr Lys Lys Gln Val Thr Leu Thr Cys Met Val Thr Asp
            260                 265                 270
```

```
Phe Met Pro Glu Asp Ile Tyr Val Glu Trp Thr Asn Asn Gly Lys Thr
            275                 280                 285

Glu Leu Asn Tyr Lys Asn Thr Glu Pro Val Leu Asp Ser Asp Gly Ser
        290                 295                 300

Tyr Phe Met Tyr Ser Lys Leu Arg Val Glu Lys Lys Asn Trp Val Glu
305                 310                 315                 320

Arg Asn Ser Tyr Ser Cys Ser Val Val His Glu Gly Leu His Asn His
                325                 330                 335

His Thr Thr Lys Ser Phe Ser Arg Thr Pro Gly Lys
            340                 345

<210> SEQ ID NO 28
<211> LENGTH: 617
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(385)
<223> OTHER INFORMATION: human TAPBL
<220> FEATURE:
<221> NAME/KEY: MISC_FEATURE
<222> LOCATION: (386)..(617)
<223> OTHER INFORMATION: Ig domain

<400> SEQUENCE: 28

Lys Pro His Pro Ala Glu Gly Gln Trp Arg Ala Val Asp Val Val Leu
1               5                   10                  15

Asp Cys Phe Leu Ala Lys Asp Gly Ala His Arg Gly Ala Leu Ala Ser
            20                  25                  30

Ser Glu Asp Arg Ala Arg Ala Ser Leu Val Leu Lys Gln Val Pro Val
        35                  40                  45

Leu Asp Asp Gly Ser Leu Glu Asp Phe Thr Asp Phe Gln Gly Gly Thr
    50                  55                  60

Leu Ala Gln Asp Asp Pro Pro Ile Ile Phe Glu Ala Ser Val Asp Leu
65                  70                  75                  80

Val Gln Ile Pro Gln Ala Glu Ala Leu Leu His Ala Asp Cys Ser Gly
                85                  90                  95

Lys Glu Val Thr Cys Glu Ile Ser Arg Tyr Phe Leu Gln Met Thr Glu
            100                 105                 110

Thr Thr Val Lys Thr Ala Ala Trp Phe Met Ala Asn Met Gln Val Ser
        115                 120                 125

Gly Gly Gly Pro Ser Ile Ser Leu Val Met Lys Thr Pro Arg Val Thr
    130                 135                 140

Lys Asn Glu Ala Leu Trp His Pro Thr Leu Asn Leu Pro Leu Ser Pro
145                 150                 155                 160

Gln Gly Thr Val Arg Thr Ala Val Glu Phe Gln Val Met Thr Gln Thr
                165                 170                 175

Gln Ser Leu Ser Phe Leu Leu Gly Ser Ser Ala Ser Leu Asp Cys Gly
            180                 185                 190

Phe Ser Met Ala Pro Gly Leu Asp Leu Ile Ser Val Glu Trp Arg Leu
        195                 200                 205

Gln His Lys Gly Arg Gly Gln Leu Val Tyr Ser Trp Thr Ala Gly Gln
    210                 215                 220

Gly Gln Ala Val Arg Lys Gly Ala Thr Leu Glu Pro Ala Gln Leu Gly
225                 230                 235                 240
```

Met Ala Arg Asp Ala Ser Leu Thr Leu Pro Gly Leu Thr Ile Gln Asp
                    245                 250                 255

Glu Gly Thr Tyr Ile Cys Gln Ile Thr Thr Ser Leu Tyr Arg Ala Gln
            260                 265                 270

Gln Ile Ile Gln Leu Asn Ile Gln Ala Ser Pro Lys Val Arg Leu Ser
        275                 280                 285

Leu Ala Asn Glu Ala Leu Leu Pro Thr Leu Ile Cys Asp Ile Ala Gly
    290                 295                 300

Tyr Tyr Pro Leu Asp Val Val Thr Trp Thr Arg Glu Glu Leu Gly
305                 310                 315                 320

Gly Ser Pro Ala Gln Val Ser Gly Ala Ser Phe Ser Ser Leu Arg Gln
                325                 330                 335

Ser Val Ala Gly Thr Tyr Ser Ile Ser Ser Ser Leu Thr Ala Glu Pro
            340                 345                 350

Gly Ser Ala Gly Ala Thr Tyr Thr Cys Gln Val Thr His Ile Ser Leu
        355                 360                 365

Glu Glu Pro Leu Gly Ala Ser Thr Gln Val Val Pro Pro Glu Arg Arg
    370                 375                 380

Thr Pro Arg Gly Pro Thr Ile Lys Pro Cys Pro Pro Cys Lys Cys Pro
385                 390                 395                 400

Ala Pro Asn Leu Leu Gly Gly Pro Ser Val Phe Ile Phe Pro Pro Lys
                405                 410                 415

Ile Lys Asp Val Leu Met Ile Ser Leu Ser Pro Ile Val Thr Cys Val
            420                 425                 430

Val Val Asp Val Ser Glu Asp Asp Pro Asp Val Gln Ile Ser Trp Phe
        435                 440                 445

Val Asn Asn Val Glu Val His Thr Ala Gln Thr Gln Thr His Arg Glu
    450                 455                 460

Asp Tyr Asn Ser Thr Leu Arg Val Val Ser Ala Leu Pro Ile Gln His
465                 470                 475                 480

Gln Asp Trp Met Ser Gly Lys Glu Phe Lys Cys Lys Val Asn Asn Lys
                485                 490                 495

Asp Leu Pro Ala Pro Ile Glu Arg Thr Ile Ser Lys Pro Lys Gly Ser
            500                 505                 510

Val Arg Ala Pro Gln Val Tyr Val Leu Pro Pro Pro Glu Glu Glu Met
        515                 520                 525

Thr Lys Lys Gln Val Thr Leu Thr Cys Met Val Thr Asp Phe Met Pro
    530                 535                 540

Glu Asp Ile Tyr Val Glu Trp Thr Asn Asn Gly Lys Thr Glu Leu Asn
545                 550                 555                 560

Tyr Lys Asn Thr Glu Pro Val Leu Asp Ser Asp Gly Ser Tyr Phe Met
                565                 570                 575

Tyr Ser Lys Leu Arg Val Glu Lys Lys Asn Trp Val Glu Arg Asn Ser
            580                 585                 590

Tyr Ser Cys Ser Val Val His Glu Gly Leu His Asn His His Thr Thr
        595                 600                 605

Lys Ser Phe Ser Arg Thr Pro Gly Lys
    610                 615

<210> SEQ ID NO 29
<211> LENGTH: 440
<212> TYPE: PRT
<213> ORGANISM: Artificial Sequence
<220> FEATURE:
<223> OTHER INFORMATION: Synthetic polypeptide

```
<220> FEATURE:
<221> NAME/KEY: MISC_FEATURE
<222> LOCATION: (1)..(208)
<223> OTHER INFORMATION: mouse Skint8
<220> FEATURE:
<221> NAME/KEY: MISC_FEATURE
<222> LOCATION: (209)..(440)
<223> OTHER INFORMATION: Ig domain

<400> SEQUENCE: 29
```

Glu Lys Leu Arg Val Thr Thr Pro Thr Arg His Leu Leu Ala Arg Val
1               5                   10                  15

Gly Gly Gln Ala Glu Leu Ser Cys Gln Val Ile Pro Pro His Ser Val
            20                  25                  30

Met His Met Glu Val Arg Trp Phe Arg Ser Gly His Ser Gln Pro Val
        35                  40                  45

Tyr Leu Tyr Arg Gly Gly His Lys Met Ser Glu Ala Ala Pro Glu
    50                  55                  60

Tyr Ala Asn Arg Thr Glu Phe Val Lys Glu Ala Ile Gly Glu Gly Lys
65                  70                  75                  80

Val Ser Leu Arg Ile Tyr Asn Ile Asn Ile Leu Asp Asp Gly Pro Tyr
                85                  90                  95

Gln Cys Ser Phe Asn Asp Ser Gly Phe Ile Asp Val Ala Ile Met Asn
            100                 105                 110

Leu Asn Val Thr Ala Val Gly Leu Glu Thr Glu Ile His Val Gln Ala
        115                 120                 125

Pro Asp Ala Asp Gly Val Met Val Glu Cys Asn Thr Gly Gly Trp Phe
    130                 135                 140

Pro Arg Pro Gln Met Glu Trp Arg Asp Ser Lys Gly Ala Thr Leu Pro
145                 150                 155                 160

His Ser Leu Lys Ser Tyr Ser Gln Asp Glu Ala Arg Phe Phe His Met
                165                 170                 175

Lys Met Thr Leu Leu Leu Thr Asn Met Ser His Gly Ser Ile Ile Cys
            180                 185                 190

Cys Ile Ser Asn Pro Val Thr Gly Glu Glu Lys Gln Thr Ser Ile Ile
        195                 200                 205

Pro Arg Gly Pro Thr Ile Lys Pro Cys Pro Pro Cys Lys Cys Pro Ala
    210                 215                 220

Pro Asn Leu Leu Gly Gly Pro Ser Val Phe Ile Phe Pro Pro Lys Ile
225                 230                 235                 240

Lys Asp Val Leu Met Ile Ser Leu Ser Pro Ile Val Thr Cys Val Val
                245                 250                 255

Val Asp Val Ser Glu Asp Asp Pro Asp Val Gln Ile Ser Trp Phe Val
            260                 265                 270

Asn Asn Val Glu Val His Thr Ala Gln Thr Gln Thr His Arg Glu Asp
        275                 280                 285

Tyr Asn Ser Thr Leu Arg Val Val Ser Ala Leu Pro Ile Gln His Gln
    290                 295                 300

Asp Trp Met Ser Gly Lys Glu Phe Lys Cys Lys Val Asn Asn Lys Asp
305                 310                 315                 320

Leu Pro Ala Pro Ile Glu Arg Thr Ile Ser Lys Pro Lys Gly Ser Val
                325                 330                 335

Arg Ala Pro Gln Val Tyr Val Leu Pro Pro Pro Glu Glu Met Thr
            340                 345                 350

Lys Lys Gln Val Thr Leu Thr Cys Met Val Thr Asp Phe Met Pro Glu
        355                 360                 365

```
Asp Ile Tyr Val Glu Trp Thr Asn Asn Gly Lys Thr Glu Leu Asn Tyr
    370                 375                 380

Lys Asn Thr Glu Pro Val Leu Asp Ser Asp Gly Ser Tyr Phe Met Tyr
385                 390                 395                 400

Ser Lys Leu Arg Val Glu Lys Lys Asn Trp Val Glu Arg Asn Ser Tyr
                405                 410                 415

Ser Cys Ser Val Val His Glu Gly Leu His Asn His His Thr Thr Lys
                420             425                 430

Ser Phe Ser Arg Thr Pro Gly Lys
        435             440
```

REAGENTS AND METHODS FOR TREATING CANCER AND AUTOIMMUNE DISEASE

CROSS REFERENCE

This application is a U.S. national phase of International Application No. PCT/US2019/040759, filed on Jul. 8, 2019, which claims priority to U.S. Provisional Application No. 62/696,142, filed Jul. 10, 2018, both of which are incorporated by reference herein in their entirety.

STATEMENT OF GOVERNMENT SUPPORT

This invention was made with government support under Grant #AI123131 awarded by the National Institutes of Health. The government has certain rights in the invention.

BACKGROUND

T cell immune responses are tightly controlled by co-stimulatory and co-inhibitory molecules. The co-stimulatory molecules contribute to the development of immune responses against cancers and foreign pathogens, while the co-inhibitory molecules are critical for peripheral tolerance to avoid autoimmunity, GVHD and transplant rejection.

SUMMARY

In one aspect, the disclosure provides methods for treating cancer, comprising administering to a subject in need thereof an antibody that selectively binds to a protein selected from the group consisting of CD300c, BTN5 (Erythroid membrane-associated protein), TAPBPL (antigen processing (TAP) binding protein like protein), Skint8 (selection and upkeep of intraepithelial T cells 8 protein), and/or CD300f in an amount effective to treat the cancer. In various embodiments, the antibody selectively binds to an extracellular domain (ECD) of CD300c, BTN5, TAPBPL, Skint8, and/or CD300f. In other embodiments, the antibody selectively binds to an IgV domain of CD300c, BTN5, TAPBPL, Skint8, and/or CD300f.

In another aspect, the disclosure provides an isolated anti-human CD300c antibody, or fragment thereof, comprising 1, 2, 3, 4, 5, or all 6 complementarity determining regions (CDRs) selected from the group consisting of:

Heavy chain CDR1 (H-CDR1) comprising the amino acid sequence at least 80%, 85%, 90%, 95%, or 100% identical to the amino acid sequence IYGMN (SEQ ID NO:10);

Heavy chain CDR2 (H-CDR2) comprising the amino acid sequence at least 80%, 85%, 90%, 95%, or 100% identical to the amino acid sequence WINTYT (SEQ ID NO:11);

Heavy chain CDR3 (H-CDR3) comprising the amino acid sequence at least 80%, 85%, 90%, 95%, or 100% identical to the amino acid sequence ARSRFAY (SEQ ID NO:12).

Light chain CDR1 (L-CDR1) comprising the amino acid sequence at least 80%, 85%, 90%, 95%, or 100% identical to the amino acid sequence KASQNVGTNVA (SEQ ID NO:13);

Light chain CDR2 (L-CDR2) comprising the amino acid sequence at least 80%, 85%, 90% 95%, or 100% identical to the amino acid sequence SASYRYS (SEQ ID NO:14); and Light chain CDR3 (L-CDR3) comprising the amino acid sequence at least 80%, 85%, 90%, 95%, or 100% identical to the amino acid sequence QQYNSYPLT (SEQ ID NO:15).

In one embodiment, the isolated anti-human CD300c antibody, or fragment thereof, comprises
(a) a heavy chain comprising the amino acid sequence having at least 60%, 65%, 70%, 75%, 80%, 85%, 90%, 91%, 92%, 93%, 94%, 95%, 96%, 97%, 98%, 99%, or 100% identity along the full length of the amino acid sequence of SEQ ID NO:16; and/or
(b) a light chain comprising the amino acid sequence having at least 60%, 65%, 70%, 75%, 80%, 85%, 90%, 91%, 92%, 93%, 94%, 95%, 96%, 97%, 98%, 99%, or 100% identity along the full length of the amino acid sequence of SEQ ID NO:17.

In a further aspect, the disclosure provides an isolated anti-human TAPBPL antibody, or fragment thereof, comprising 1, 2, 3, 4, 5, or all 6 complementarity determining regions (CDRs) selected from the group consisting of:

Heavy chain CDR1 (H-CDR1) comprising the amino acid sequence at least 80% a, 85%, 90%, 95%, or 100% identical to the amino acid sequence GYFWH (SEQ ID NO:18);

Heavy chain CDR2 (H-CDR2) comprising the amino acid sequence at least 80%, 85%, 90%, 95%, or 100% identical to the amino acid sequence YISYSGTTNYNPSLKN (SEQ ID NO:19);

Heavy chain CDR3 (H-CDR3) comprising the amino acid sequence at least 80%, 85%, 90%, 95%, or 100% identical to the amino acid sequence DDWDVFAY (SEQ ID NO:20);

Light chain CDR1 (L-CDR1) comprising the amino acid sequence at least 80%, 85%, 90%, 95%, or 100% identical to the amino acid sequence SASSSVNYMH (SEQ ID NO:21);

Light chain CDR2 (L-CDR2) comprising the amino acid sequence at least 80%, 85%, 90% 95%, or 100% identical to the amino acid sequence DTSKLAS (SEQ ID NO:22); and Light chain CDR3 (L-CDR3) comprising the amino acid sequence at least 80% 85%, 90%, 95%, or 100% identical to the amino acid sequence FQGSGYPLT (SEQ ID NO:23).

In one embodiment, the isolated anti-human TAPBPL antibody, or fragment thereof, comprises a heavy chain comprising the amino acid sequence having at least 60%, 65%, 70%, 75%, 80%, 85%, 90%, 91%, 92%, 93%, 94%, 95%, 96%, 97%, 98%, 99%, or 100% identity along the full length of the amino acid sequence of SEQ ID NO:24: and/or
(b) a light comprising the amino acid sequence having at least 60%, 65%, 70%, 75%, 80%, 85%, 90%, 91%, 92%, 93%, 94%, 95%, 96%, 97%, 98%, 99%, or 100% identity along the full length of the amino acid sequence of SEQ ID NO:25.

In various embodiments, the antibody comprises a monoclonal antibody, or fragment thereof; the antibody comprises a humanized antibody, or fragment thereof; the antibody or fragment thereof further comprises a detectable label; and/or the isolated antibody or fragment thereof further comprises a therapeutic agent, including but not limited to a chemotherapeutic, conjugated to the antibody or fragment thereof.

In one aspect, the disclosure provides a method for treating an autoimmune disorder, comprising administering to a subject in need thereof an amount effective to treat the autoimmune disorder of one or more of:

(a) an IgV domain from a protein selected from the group consisting of CD300c, BTN5, TAPBPL, Skint8, and CD300f; and/or
(b) an expression vector comprising a promoter operatively linked to a nucleic acid sequence encoding a protein selected from the group consisting of CD300c, BTN5, TAPBPL, Skint8, and CD300f. In one embodiment, the autoimmune disease is selected from the group consisting of multiple sclerosis, type I diabetes, arthritis including but not limited to rheumatoid arthritis, systemic lupus erythematosus, Crohn's disease, scleroderma, sarcoidosis, ulcerative colitis, ankylosing spondylitis, autoimmune hepatitis, autoimmune myocarditis, dermatomyositis, Graves' disease, Sjogren's syndrome, and vitiligo, and other autoimmune diseases. In a further embodiment, the method further comprises administering to the subject an amount effective of an immune regulator to stimulate T cell function, including but not limited to anti-CD3 antibodies.

In another aspect, the disclosure provides a fusion molecule comprising
(a) a first polypeptide comprising an IgV domain from a protein selected from the group consisting of CD300c, BTN5, TAPBPL, Skint8, and CD300f, and
(b) a heterologous molecule.

In one embodiment, the first polypeptide does not include any portion of CD300c, BTN5, TAPBPL, Skint8, or CD300f outside of the ECM domain. In another embodiment, the heterologous molecule comprises a second polypeptide selected from the group consisting of a constant region of an immunoglobulin or a fragment thereof (including but not limited to CH1, CH2, and/or CH3; and Fc regions from immunoglobulins, including but not limited to native IgG1, IgG2, or IgG4). In another embodiment, the heterologous molecule comprises an organic molecule of interest.

In another aspect, the disclosure provides nucleic acids encoding the fusion molecule, wherein the heterologous molecule is a second polypeptide, or the antibodies of the disclosure. In other aspects, the disclosure provides expression vectors comprising the nucleic acids operatively linked to a promoter, and recombinant host cell comprising the nucleic acid and/or expression vectors.

Immunohistochemical analysis of hCD300c expression in normal and tumor human tissues by immunohistochemistry using an anti-hCD300c Ab. The data are representative of 3 independent experiments.

Figure 5:
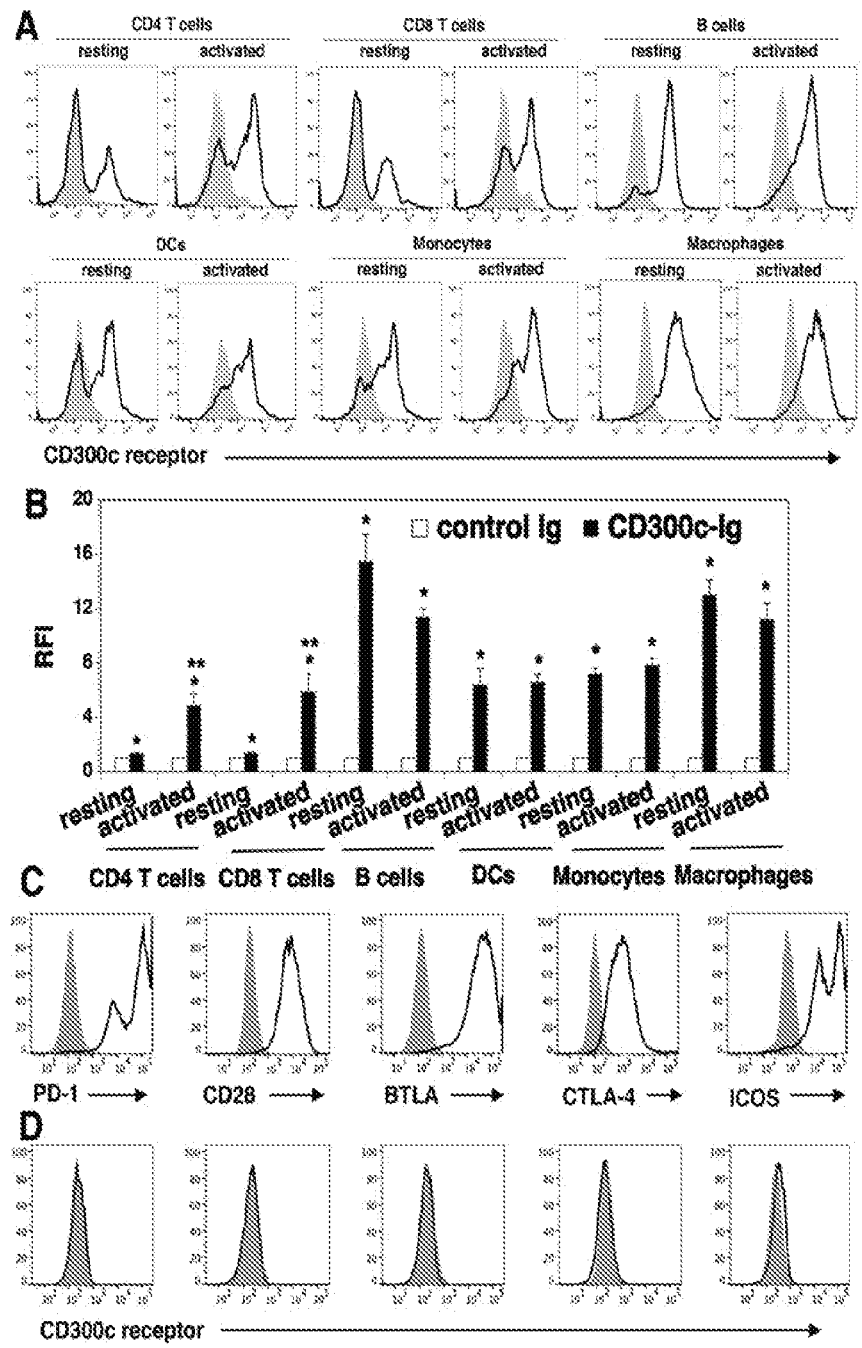

FIG. 5. The expression pattern of the putative mCD300c2 counter-receptor. (A. B) Murine resting and activated immune cells were harvested or generated as in FIG. 5A. The cells were stained with biotinylated mCD300c2-Ig (open histograms) or control Ig (shaded histograms), followed by streptavidin-PE. The binding of mCD300c2 to its putative receptor on immune cells was determined by flow cytometry. (A) Representative flow cytometric profiles and (B) statistical analysis showing the binding of mCD300c2-Ig or control Ig to resting and activated immune cells. (B) Data are presented as relative fluorescence intensity (RFI) for cell binding of mCD300c2-Ig versus control Ig. The data were pooled from 3 independent experiments. (A, B) *P<0.05 compared with control Ig. **P<0.05 compared with resting cells. (C. D) HEK-293 cells were transfected with an expression vector containing the mouse CD28, CTLA-4, PD-1, BTLA, or ICOS gene. The transfected cells were stained with (C) antibodies against the respective CD28, CTLA-4, PD-1, BTLA, or ICOS protein (open histograms) or isotype Ab (shaded histograms), or (D) biotinylated mCD300c2-Ig (open histograms) or control Ig protein (shaded histograms), and analyzed by flow cytometry. Representative flow cytometric profiles showing the binding of (A, D) mCD300c-Ig or control Ig, or (C) indicated antibodies to (A) resting and activated immune cells, or (C, D) transfected HEK-293 cells.

Figure 6:
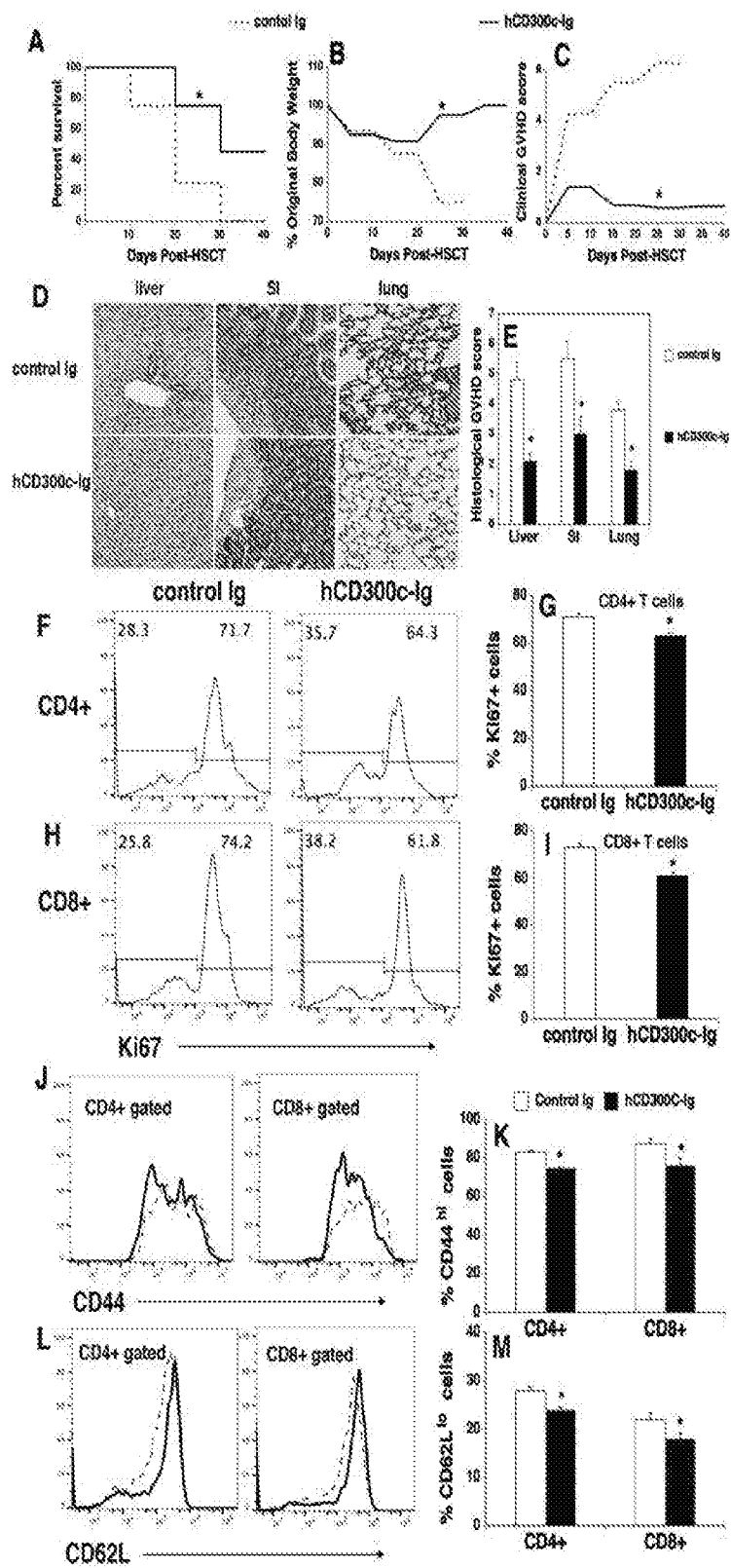

FIG. 6. hCD300c-Ig ameliorates GVHD in mice. Lethally irradiated BALB/c recipients were injected i.v. with $5\times10^6$ BM and $2.5\times10^6$ spleen cells from C57BL/6 mice at day 0 and i.p. with 20 μg hCD300c-Ig, or control Ig every 3 days for 6 times. (A-C) Recipients were monitored for (A) survival, (B) weight change, and (C) clinical GVHD. (D, E) In separate experiments, recipients given 20 μg hCD300c-Ig or control Ig at 3-day intervals from days 0-12 were euthanized 2 weeks after BMT. (D, E) The liver, SI and lung were analyzed for histologic damage. (D) Representative photomicrographs (the magnification was X200), and (E) mean±SD of histopathology scores. (F-M) hCD300c-Ig inhibits T-cell proliferation and activation in response to alloantigens in vivo. Lethally irradiated BALB/c mice were injected i.v. with $5\times10^6$ BM $1\times10^6$ splenic cells from C57BL/6 mice. The recipients were injected i.v. on day 0 and i.p. on day 2 with 20 μg hCD300c-Ig, or control Ig. On Day 4 post-transplant, the percentage of (F-I) Ki67$^+$, (J, K) CD44$^{hi}$, and (L, M) CD62L$^{lo}$ cells in donor T cells (H2$^{b+}$ CD4$^+$, or H2$^{b+}$CD8$^+$) of the spleens were examined by flow cytometry. (F, H, J, L) Representative flow cytometric profiles and (G, I, K, M) statistical data are shown. (J. L) Dash lines: control Ig; solid lines: hCD300c. Pooled data from 2 separate experiments are represented; with 5-6 mice per group in each experiment. *P<0.05 compared with control Ig-treated mice.

Figure 7:
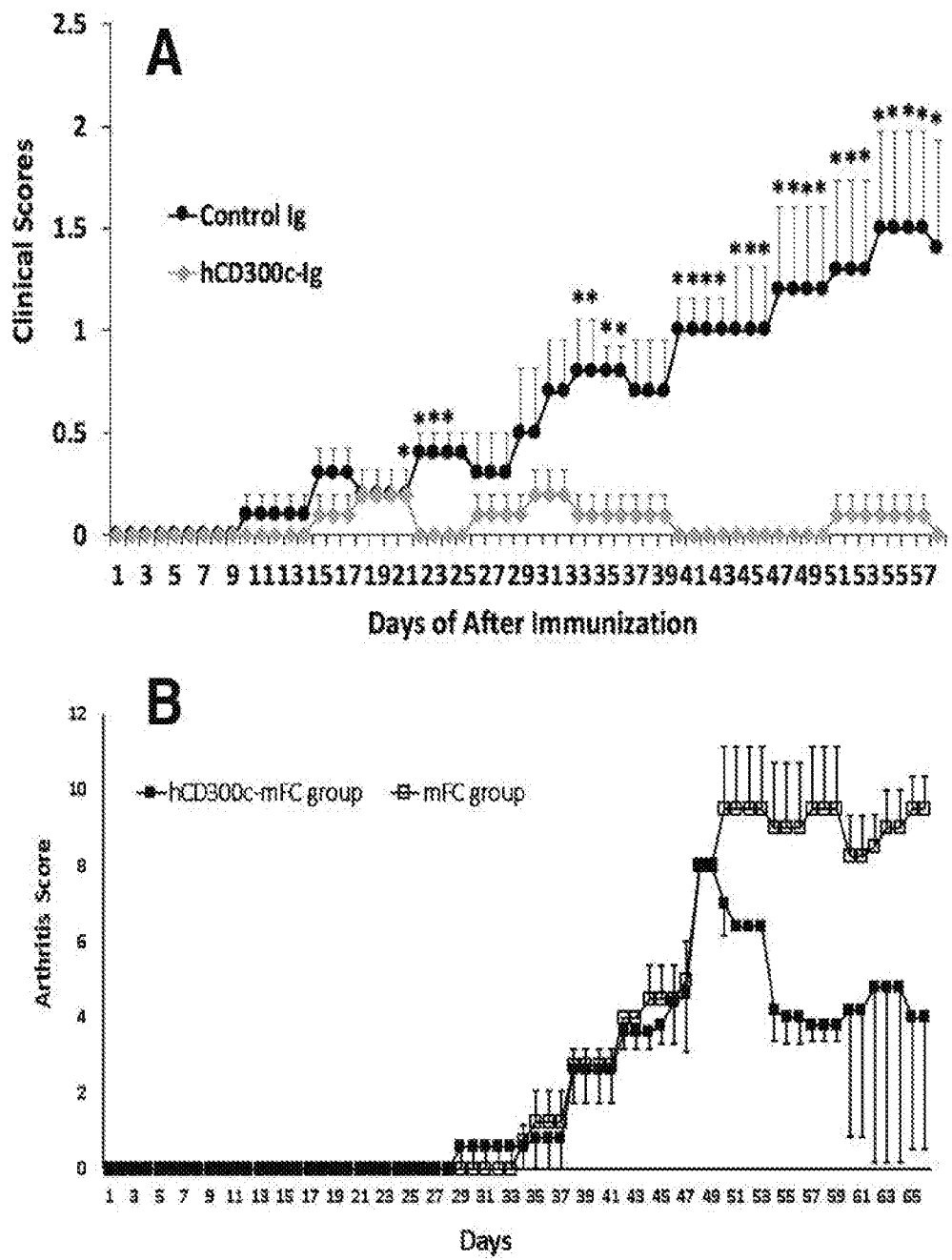

FIG. 7: hCD300c-Ig attenuates autoimmune diseases EAE and CIA in mice. (A) C57BL/6 mice were immunized with 200 μg MOG35-55 emulsified in CFA and 500 ng of purified *Bordetella pertussis* toxin. The mice were injected i.p. with 25 μg hCD300c-Ig or control Ig protein 3 times per week for 5 weeks. EAE development was monitored. (B) DBA/1 mice were injected s.c. with the emulsion of CII in CFA on day 0. On day 14, the mice will receive a booster injection of the CII/IFA emulsion. When CIA symptom occurred (day 48), the mice were injected i.p. with 25 μg hCD300c-Ig, or control Ig once every 3 days for 6 times. The CIA clinical scores were measured over time. Mean clinical scores are shown.

Figure 8:
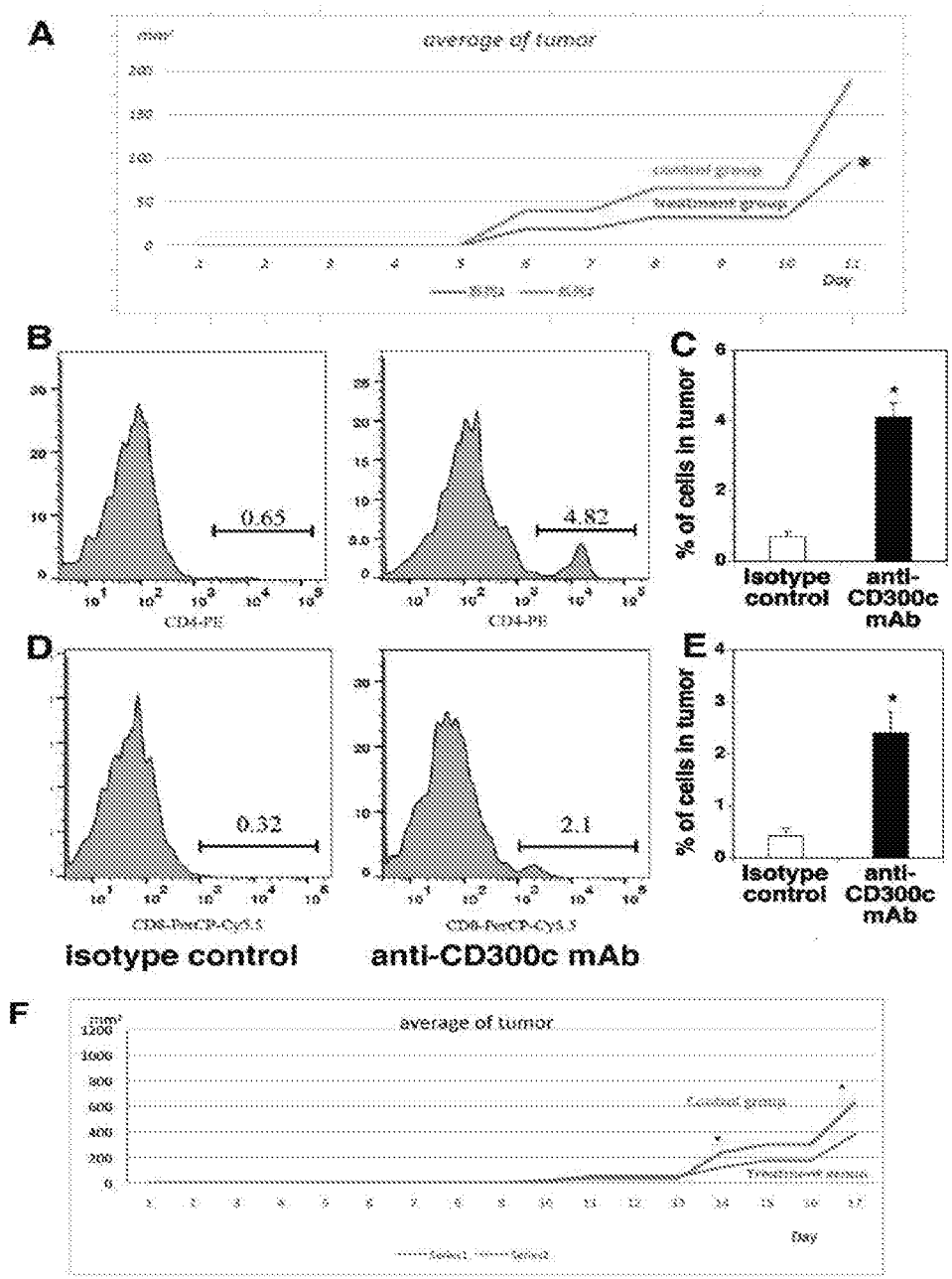

FIG. 8. In vivo administration of anti-hCD300c mAb inhibits local growth of melanoma and colon cancer. (A-E) BALB/c mice were injected s.c. with $2\times10^5$ CT-26 colon cancer cells, followed by injections with anti-hCD300c mAb or isotype antibody control into the tumor injection site 3 times each week. Tumor sizes were measured over time. (A) The mean tumor volume (mm$^3$)+S.D. at the indicated time points are shown. (B-E) At the end of studies, the mice were euthanized and the colon tumors were removed. Single-cell suspensions from the tumors were analyzed by flow cytometry for the percentages of (B, C) CD4$^+$ and (D, E) CD8$^+$ T cells. (F) C57BL/6 mice were injected s.c. with $1\times10^5$ B16F10 melanoma cells followed by intratumoral injections with anti-hCD300c mAb or isotype antibody control three times a week. Tumor sizes were measured over time.

Figure 9:
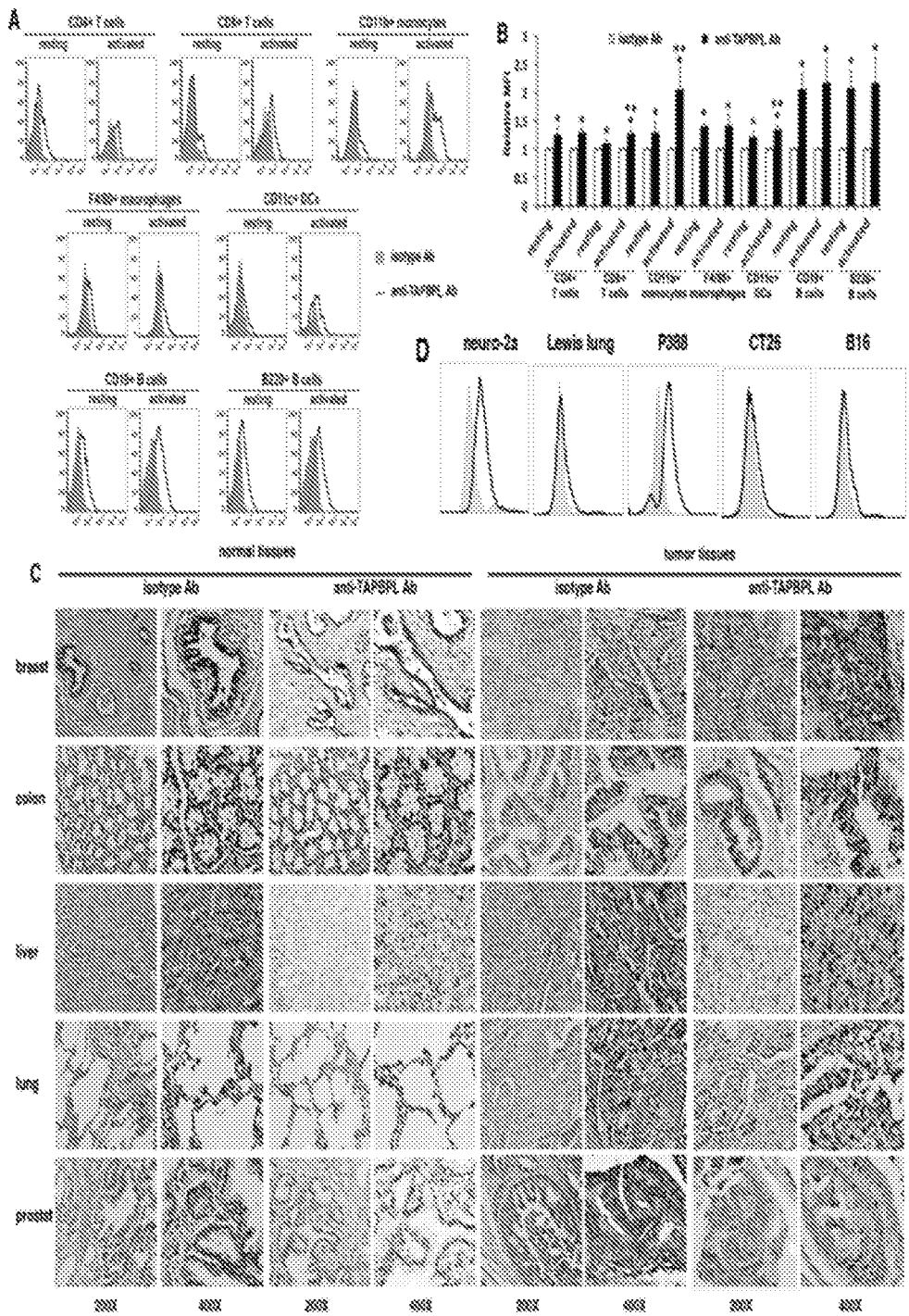

FIG. 9. The expression patterns of TAPBPL protein. (A, B) Analysis of TAPBPL protein expression on immune cells. Splenocytes from C57BL/6 mice were freshly harvested and analyzed for TAPBPL protein expression on resting immune cells. To obtain activated T cells, the splenocytes were incubated with anti-CD3 (1 μg/ml) and anti-CD28 (0.5 μg/ml) antibodies for 3 days. To obtain activated B cells, DCs, monocytes and macrophages, the splenocytes were incubated with LPS (10 μg/ml) for 3 days. The resting and activated immune cells were stained with anti-TAPBPL or isotype antibody (Ab), as well as anti-CD4, CD8, CD11b, F4/80, CD11c, B220 or CD19 antibody to identify immune cells. (A) Representative flow cytometric profiles and (B) statistical analysis showing the expression of TAPBPL protein on resting and activated immune cells. (C) Determination of TAPBPL protein expression in normal and tumor human tissues by immunohistochemistry using anti-TAPBPL or isotype Ab. (D) Analysis of TAPBPL protein expression on neuro-2a, Lewis lung, P388, CT26, and B16 cancer cell lines by flow cytometry. The data are representative of 3 independent experiments. (B) *P<0.05 compared with isotype Ab. **P<0.05 compared with resting cells.

Figure 10:
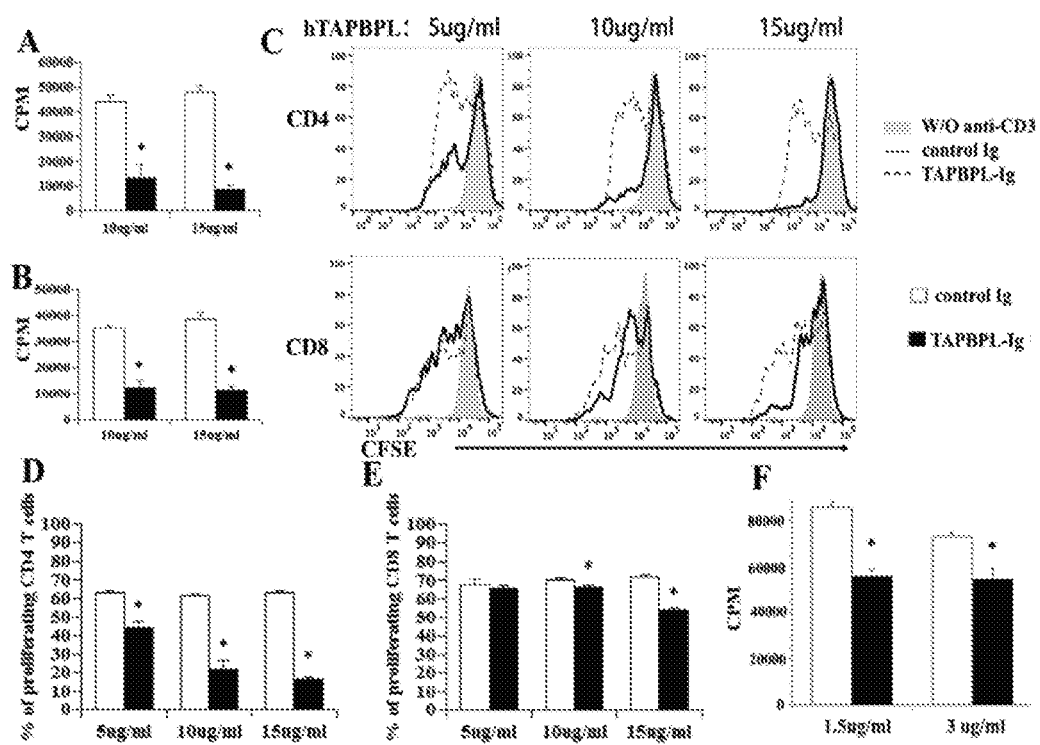

FIG. 10. The effects of hTAPBPL-Ig protein on T cell proliferation in vitro. (A, B) T cells were purified from splenocytes of C57BL/6 mice by magnetic separation. The cells were cultured on plates pre-coated with (A) anti-CD3 antibody (1 μg/ml) or (B) anti-CD3 (1 μg/ml) and anti-CD28 (0.5 μg/ml) antibodies in the presence of graded doses of hTAPBPL-Ig (10 and 15 μg/ml) or equimolar amounts of control Ig (3.75 and 5.63 μg/ml) for 3 days. [$^3$H] thymidine (1 μCi/well) was added to the cultures 12 hours before harvest. T cell proliferation was measured by [$^3$H] thymidine incorporation. (C-E) Splenic cells were labelled with CFSE and cultured in 96-well plates that were precoated with anti-CD3 antibody and hTAPBPL-Ig or control Ig for 3 days as in FIG. 3A. The cells were analyzed for CFSE levels by CD4$^+$ and CD8$^+$ T cells. (C) Representative flow cytometric analysis of CFSE distribution of CD4$^+$ and CD8$^+$ T cells, and (D, E) statistical analysis of (D) CD4 and (E) CD8 T cell proliferation. (F) Purified human T cells were cultured with plate-bound anti-human CD3 antibody (1 μg/ml) in the presence of graded doses of hTAPBPL-Ig (1.5 and 3 μg/ml) or control Ig protein (1.5 and 3 μg/ml) for 3 days. Cell proliferation was measured by [$^3$H] thymidine incorporation. The data are expressed as mean±SD and representative of 3 independent experiments. *P<0.05 compared with control Ig.

Figure 11:
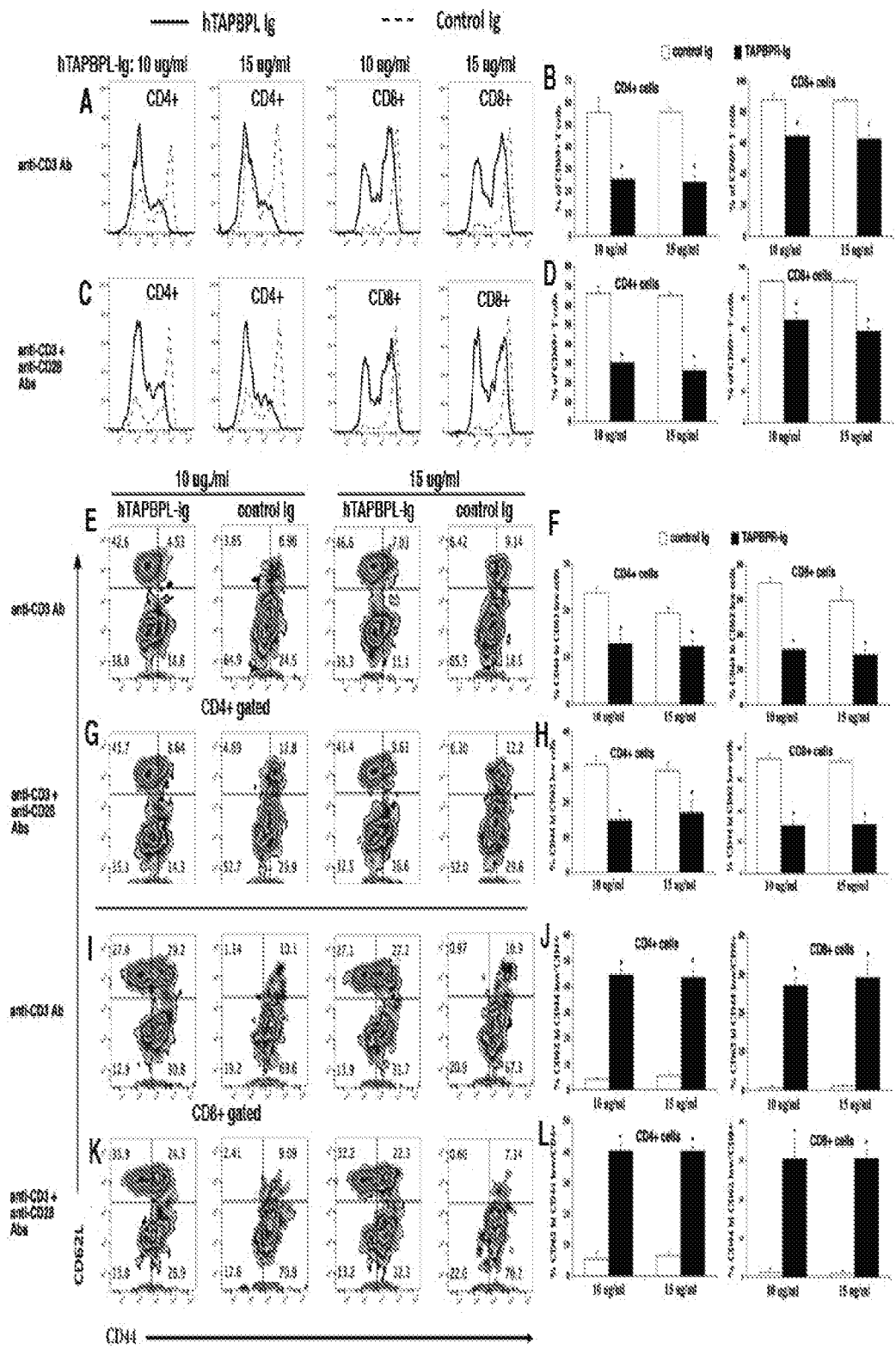

FIG. 11. The effects of hTAPBPL-Ig protein on T cell activation in vitro. Splenic cells from C57BL/6 mice were cultured with (A, B, E, F, I, J) anti-CD3 antibody (1 μg/ml) or (C. D. G H, K, L) anti-CD3 (1 μg/ml) and anti-CD28 (0.5 μg/ml) antibodies in the presence of graded doses of hTAPBPL-Ig (10 and 15 μg/ml) or equimolar amounts of control Ig (3.75 and 5.63 μg/ml) for (A-D) 1 day or (E-L) 3 days. The cells were analyzed for the percentages of (A-D) CD69$^+$, (E-I, K) CD44hCD62L$^{lo}$ and (E, G, 1-L) CD44$^{lo}$CD62L$^{hi}$ cells in CD4 and CD8 T cells. (A, C, E, G, I, K) Representative flow cytometric and (B, D, F, H, J, L) statistical analyses of the percentages of CD69$^+$, CD44$^{hi}$CD62L$^{lo}$ and CD44$^{lo}$CD62L$^{hi}$ cells in CD4 and CD8 T cells. The data are expressed as mean±SD and representative of 3 independent experiments. *P<0.05 compared with control Ig.

Figure 12:
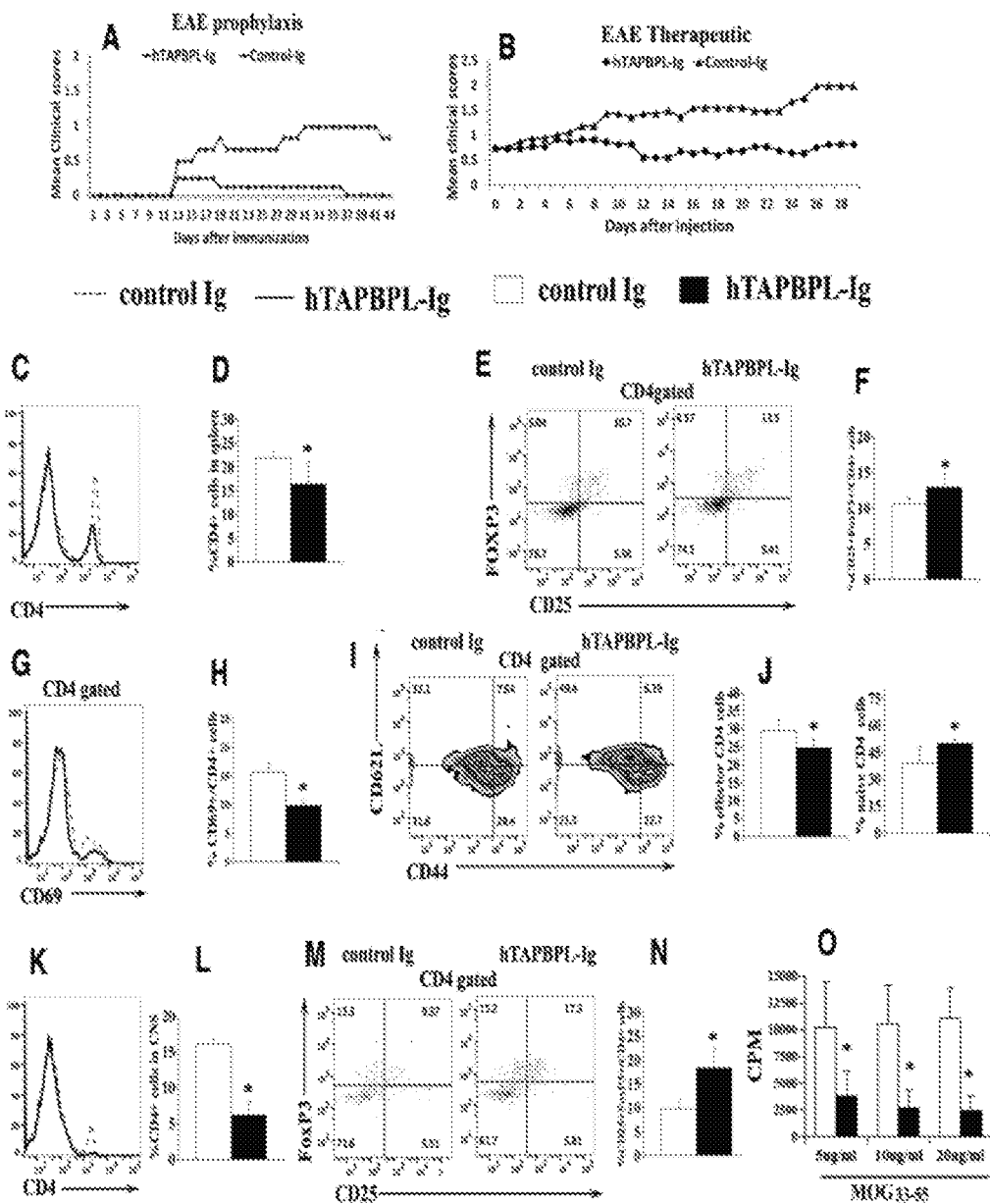

FIG. 12: hTAPBPL-Ig attenuates autoimmune disease EAE in mice. C57BL/6 mice were immunized with 200 μg MOG35-55 emulsified in CFA and 500 ng of purified *Bordetella pertussis* toxin. (A) Mice were injected i.p. with 25 μg hTAPBPL-Ig or control Ig protein 3 times per week from day 0. Mean clinical scores. (B-O) When EAE symptoms occurred, the mice were injected i.p. with 25 μg hTAPBPL-Ig or control Ig protein 3 times per week. (B) Mean clinical scores (C-O) At the end of the study, spleens were harvested and analyzed for (C and D) CD4$^+$ T cells. (E and F) CD4$^+$CD25$^+$FoxP3$^+$ Tregs, (G and H) CD69 expression by CD4$^+$ T cells, and (I, J) CD4$^+$CD44$^{hi}$ CD62L$^{lo}$ effector memory and CD4$^+$CD44$^{lo}$CD62L$^{hi}$ nave T cells. (K-N) The CNS-infiltrating (K and L) CD4$^+$ T cells and (M and N) CD4$^+$CD25$^+$FoxP3$^+$ Tregs were analyzed. (O) Splenocytes were cultured with graded doses of MOG$_{35-55}$ for 72 hours. [$^3$H] thymidine (1 μCi/well) was added to the cultures 12 hours before harvest. T cell proliferation was measured by [$^3$H] Thymidine incorporation. The data are expressed as mean SD and representative of 3 independent experiments with n=8/group. *P<0.05 compared with control Ig.

Figure 13:
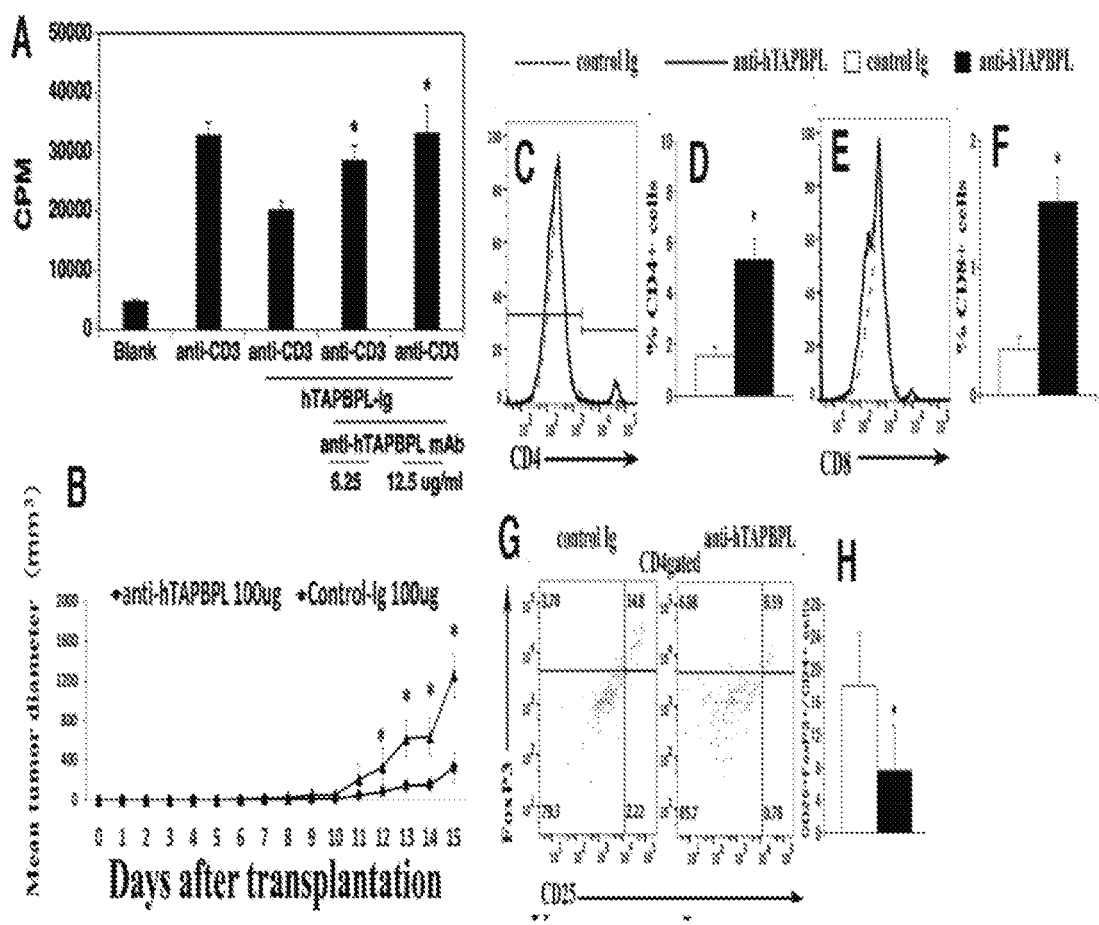

FIG. 13. Anti-hTAPBPL mAb inhibits tumor growth in vivo. (A) Anti-hTAPBPL mAb (clone 54) neutralize the proliferation inhibitory of hTAPBPL-Ig on T cells in vitro. (B-H) DBA/2J mice were injected s.c. with 1×10$^5$ P388 leukemia cells followed by injection with anti-hTAPBPL mAb (100 μg) or control-Ig (100 μg) 3 times per week. (B) Tumors size was measured over time. The mean tumor diameter (mm$^3$)±S.D. at the indicated time points are shown. (C-H) At the end of the studies, tumors were harvested. Single-cell suspension of the tumors was analyzed for the percentage of (C, D) CD4$^+$ T cells, (E, F) CD8$^+$ T cells, and (G and H) CD4$^+$CD25$^+$FoxP3 Tregs by flow cytometry. The data are expressed as mean±SD and representative of 2 independent experiments with similar results. *P<0.05 compared with isotype antibody.

Figure 14:
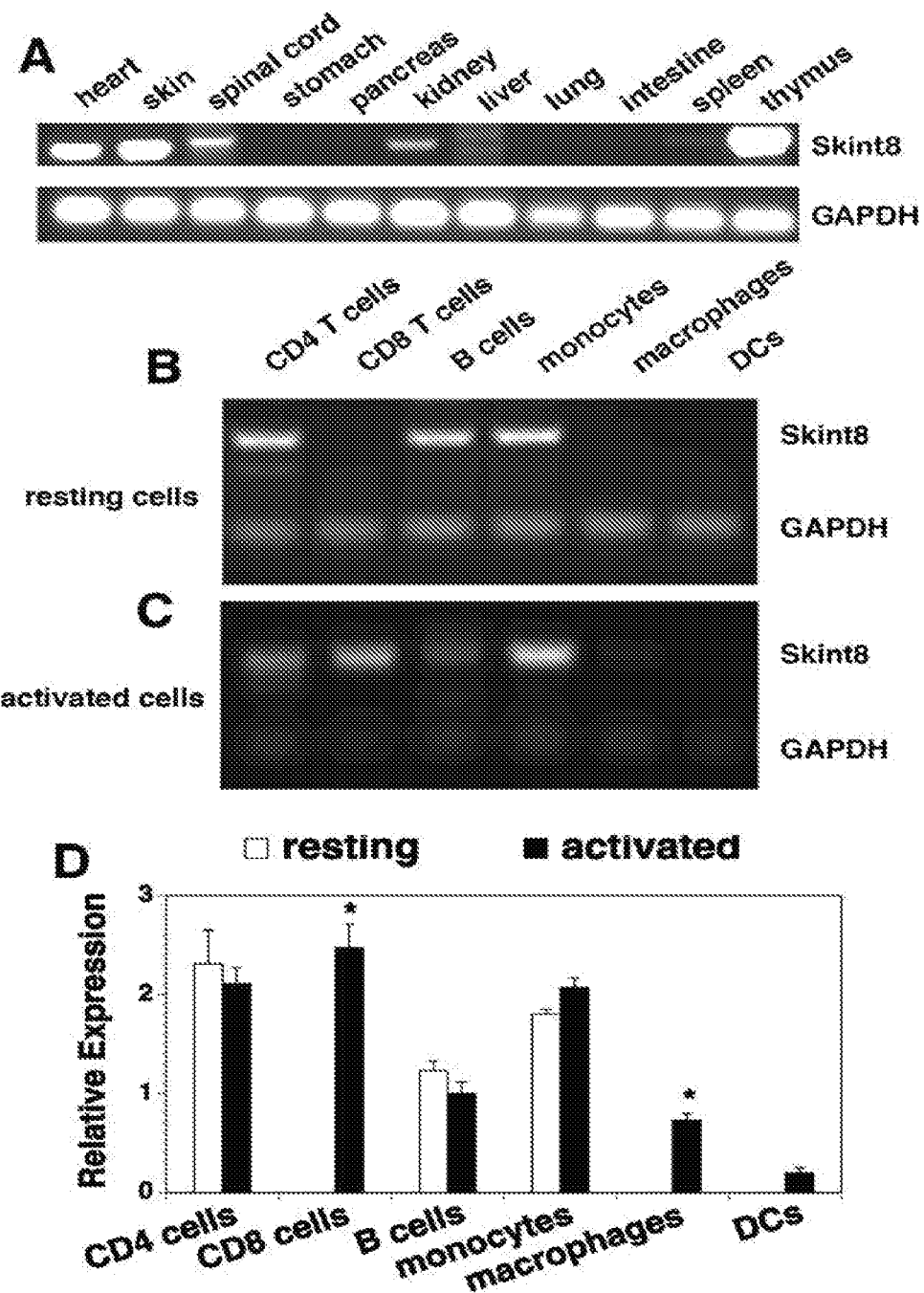

FIG. 14. The expression pattern of Skint8 mRNA in tissues and immune cells. (A) RNA was isolated from indicated tissues of C57BL/6 mice. The expression of Skint8 mRNA was determined by RT-PCR. GAPDH was used as a loading control. (B) CD4$^+$ and CD8$^+$ T cells, B220 B cells, CD11b$^+$ monocytes, F4/80 macrophages, and CD11c$^+$ DCs were magnetically isolated from splenocytes. (C) To activate T cells, purified CD4$^+$ or CD8$^+$ T cells were incubated with anti-CD3 (1 μg/ml) and anti-CD28 (0.5 μg/ml) antibodies for 3 days. To activate B cells, monocytes, macrophages, or DCs, the purified immune cells were incubated with LPS (10 μg/ml) for 3 days. RNA was isolated from the (B) resting and (C) activated immune cells. The expression of Skint8 mRNA was determined by RT-PCR. (D) The expression of Skint8 mRNA was determined by qRT-PCR. Each column was normalized with GAPDH. *P<0.05 compared with resting cells. The data are representative of 3 independent experiments.

Figure 15:
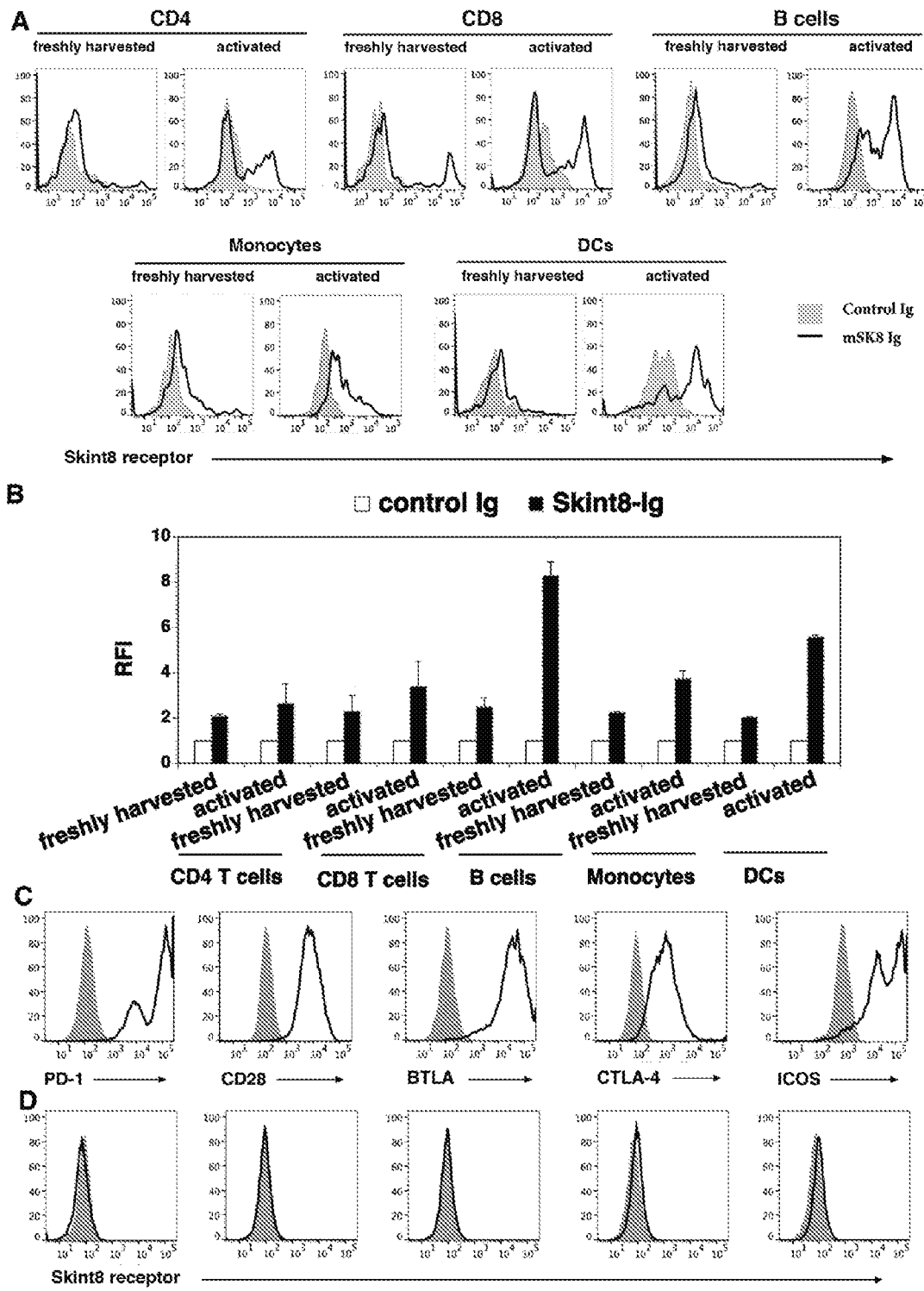

FIG. 15. The expression pattern of the Skint8 putative receptor. (A, B) Spleen cells were harvested from C57BL/6 mice. To obtain activated T cells, the spleen cells were incubated with anti-CD3 (1 μg/ml) and anti-CD28 (0.5 μg/ml) antibodies for 3 days. To obtain activated B cells, monocytes and DCs, the spleen cells were incubated with LPS (10 μg/ml) for 3 days. The freshly harvested and activated immune cells were stained with biotinylated Skint8-Ig or control Ig, followed by streptavidin-PE, as well as anti-CD4, CD8, B220, CD11b, or CD11c antibodies to identify the immune cells. (A) Representative flow cytometric profiles and (B) Statistical analysis showing the binding of Skint8-Ig or control Ig to freshly harvested and activated immune cells. (B) Data are presented as relative fluorescence intensity (RFI) for cell binding of Skint8-Ig versus control Ig. (C) HEK-293 cells were transfected with an expression vector containing the murine PD-, CD28, BTLA, CTLA-4, or ICOS gene and screened for cells stably expressing each gene. The transfected cells were stained with antibody against the respective PD-1, CD28, BTLA, CTLA-4, or ICOS protein (open histograms) or isotype antibody (shaded histograms). Representative flow cytometric profiles showing the expression of each receptor. (D) PD-, CD28, BTLA, CTLA-4, or ICOS gene-transfected HEK-293 cells were stained with biotinylated Skint8-Ig or control Ig, followed by streptavidin-PE. Representative flow cytometric profiles showing the binding of Skint8-Ig (open histograms) or control Ig protein (shaded histograms) to the transfected cells. The data are representative of 3 independent experiments.

Figure 16:
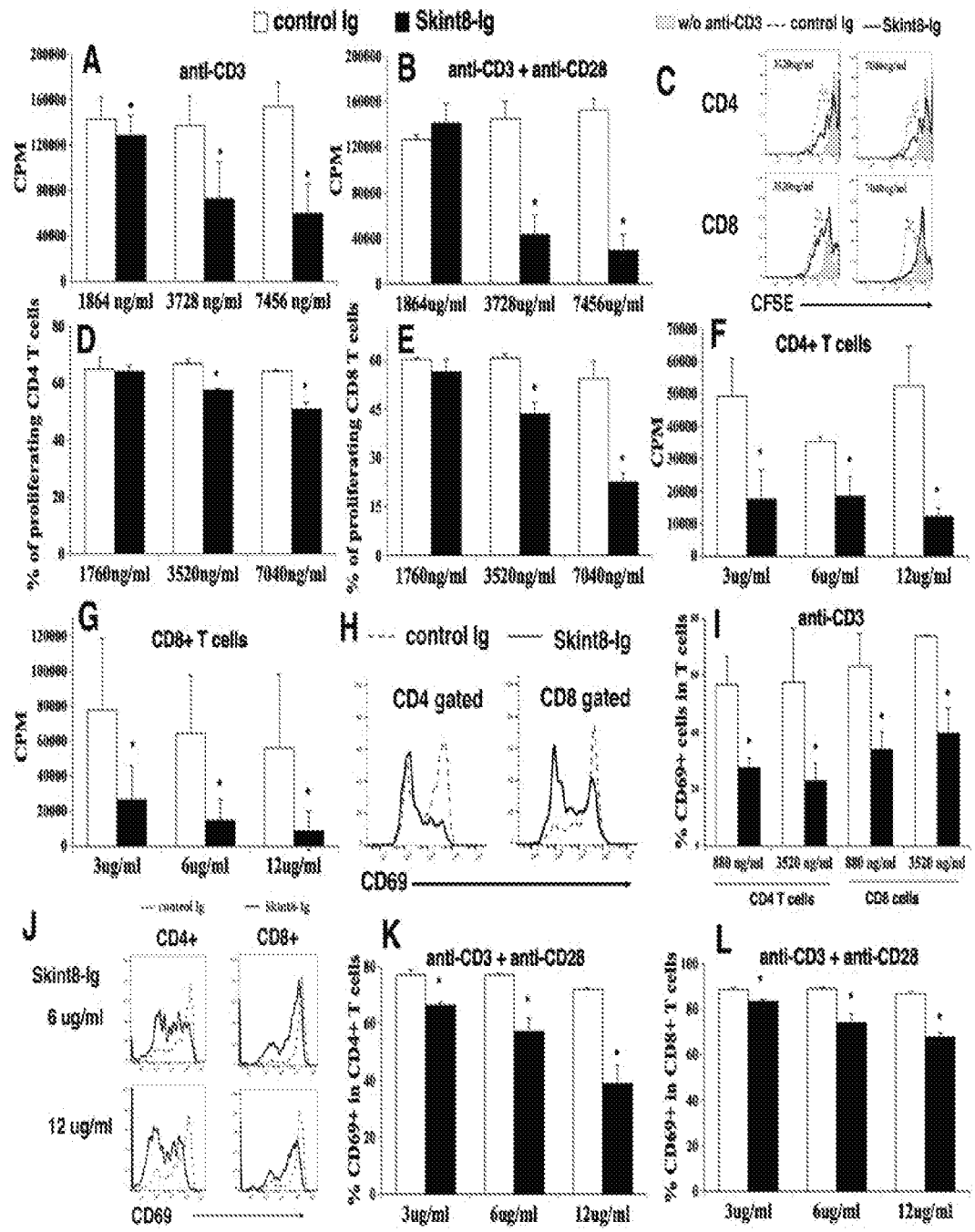

FIG. 16. The effects of Skint8-Ig protein on T cell proliferation and activation in vitro. (A) T cells were purified from spleen cells of C57BL/6 mice by magnetic separation. The cells were cultured on plates pre-coated with (A) anti-CD3 antibody (1 μg/ml) and graded doses of Skint8-Ig (1840, 3728, 7456 ng/ml) or equimolar amounts of control Ig (990, 1980, 3960 ng/ml) protein, or (B) anti-CD3 (1 μg/ml) and anti-CD28 (0.5 μg/ml) antibodies in the presence of Skint8-Ig or equimolar amount of control Ig for 3 days. [$^3$H]thymidine (1 μCi/well) was added to the cultures 12 hours before harvest. T cell proliferation was measured by [$^3$H] thymidine incorporation. (C-E) Spleen cells were labelled with CFSE and cultured in anti-CD3 antibody precoated 96-well plates in the presence of indicated doses of Skint8-Ig or control Ig for 3 days. The cells were analyzed for CFSE levels by CD4$^+$ and CD8$^+$ T cells. (C) Representative flow cytometric analysis of CFSE distribution of CD4$^+$ and CD8$^+$ T cells, and (D, E) statistical analysis of T cell proliferation. (F, G) Purified CD4$^+$ or CD8$^+$ T cells were cultured with anti-CD3 antibody and graded doses of Skint8-Ig or equimolar amounts of control Ig protein for 3 days. T cell proliferation was measured by [$^3$H] thymidine incorporation as in (A). (H-L) Spleen cells were cultured with (H, I) anti-CD3 antibody or (J-L) anti-CD3 and anti-CD28 antibodies in the presence of Skint8-Ig or control Ig. The cells were analyzed for the expression of CD69 24 hours later. (H, J) Representative flow cytometric profiles, and (I, K, L) statistical analyses of the percentages of CD69$^+$ cells in CD4$^+$ or CD8$^+$ T cells. The data are expressed as mean±SD and representative of 3 independent experiments. *P<0.05 compared with control Ig.

Figure 17:
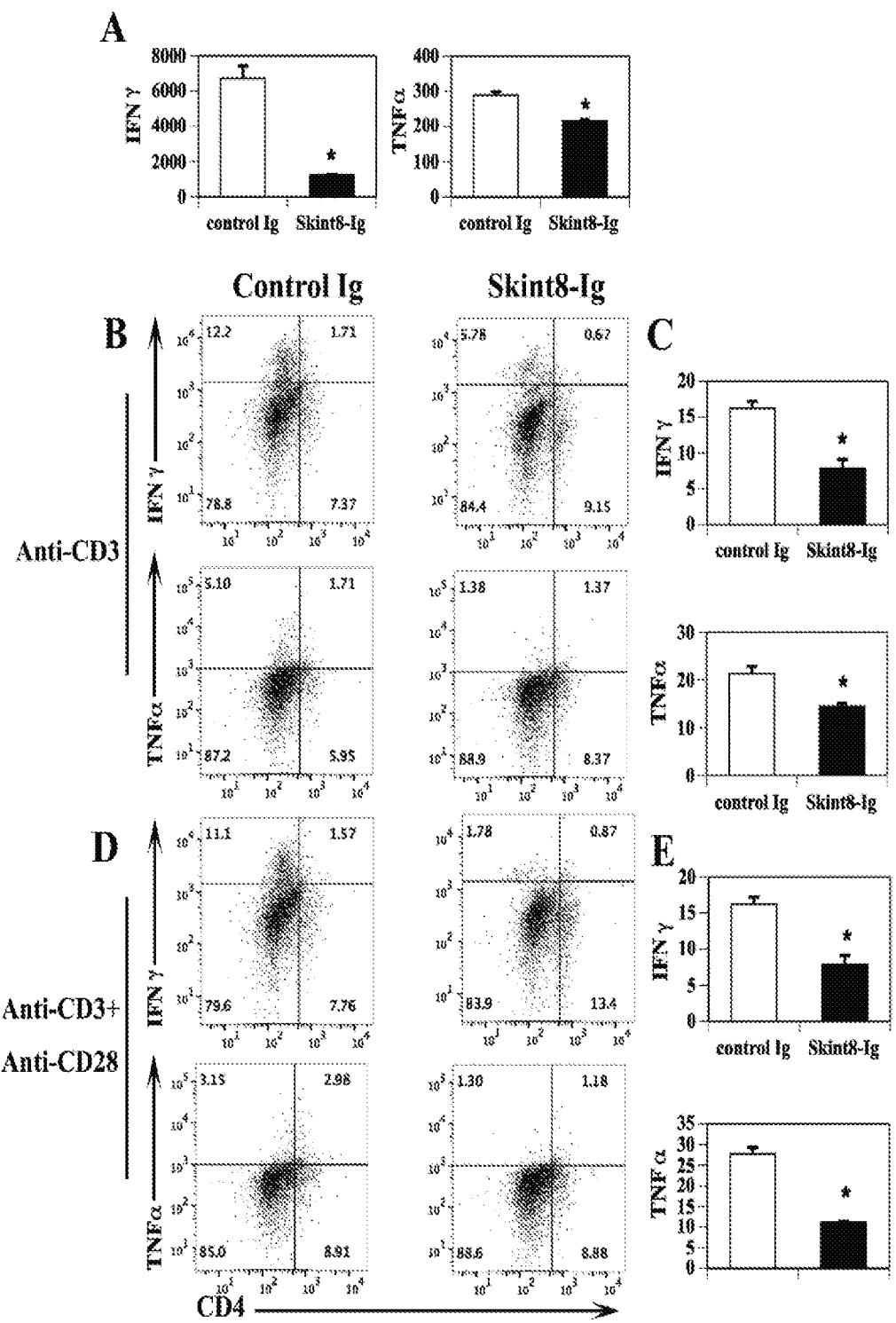

FIG. 17. The effects of Skint8-Ig protein on cytokine production from T cells in vitro. Purified murine T cells were cultured with plate-bound (A-C) anti-CD3 antibody (1

µg/ml) in the presence of Skint8-Ig (3728 ng/ml) or equimolar amount of control Ig (1980 ng/ml), or (D, E) anti-CD3 (µg/ml) and anti-CD28 (0.5 µg/ml) antibodies in the presence of Skint8-Ig (6 µg/ml) or equimolar amount of control Ig for 3 days. (A) The levels of IFN, and TNFα, (pg/ml) in the supernatant were measured by ELISA kits. (B-E) The T cells were stimulated with phorbol myristate acetate and ionomycin 4 hours before harvesting, and then stained with antibodies against CD4, IFNγ, and TNFα. The percentages of the cytokine positive cells in CD4$^+$ T cells were determined by flow cytometry. (B, D) Representative flow cytometric profiles, and (C. E) statistical analyses of the percentages of cytokines in CD4$^+$ T cells. The data are expressed as mean±SD and representative of 3 independent experiments. *P<0.05 compared with control Ig.

Figure 18:
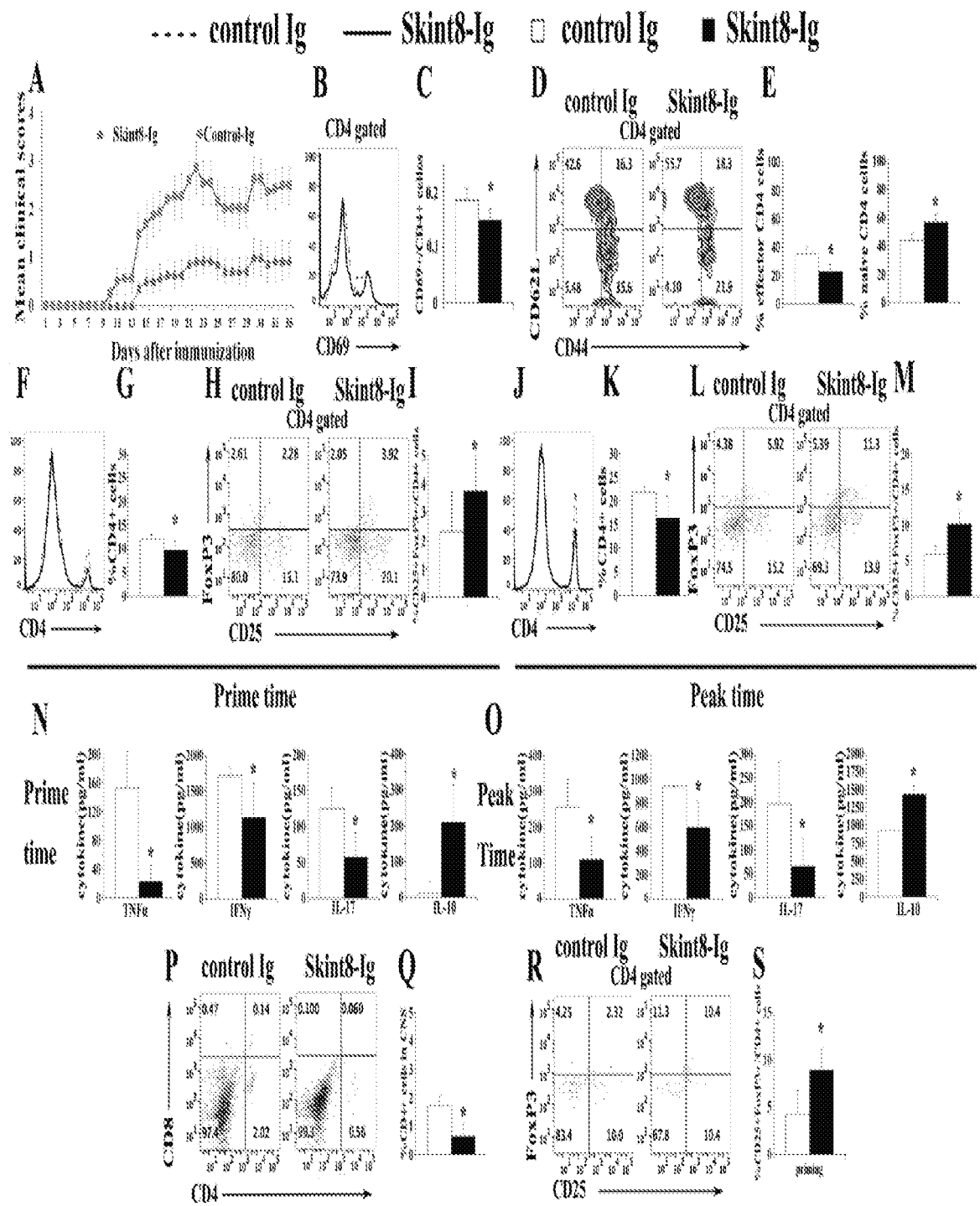

FIG. 18. Skint8-Ig attenuates EAE in mice. C57BL/6 mice were immunized with 200 µg MOG$_{50-55}$ emulsified in CFA and 500 ng of purified Bordetella pertussis toxin. The mice were injected i.p. with 25 µg Skint8-Ig or control Ig protein 3 times per week from day 0. EAE development was monitored. (A) Mean clinical scores, (B-E) Thirty five days after immunization, spleens were harvested and analyzed for (B. C) CD69 expression by CD4 T cells, and (D, E) CD44$^{lo}$CD62L$^{hi}$ naïve and CD44$^{hi}$CD62L$^{lo}$ effector memory CD4 T cells. (F-S) In separate experiments, groups of EAE mice were sacrificed at (F-I, N) prime time (day 10) or (J-M, O, P-S) peak time (day 22) of EAE. (F, G, J, K) The percentage of CD4$^+$ T cells in the spleen, and (H, I, L, M) the percentage of CD4$^+$CD25$^+$Foxp3$^+$Tregs in CD4$^+$ T cells were examined. (N, O) The splenic CD4$^+$ T cells were stimulated with MOG (20 µg/ml) in vitro for 3 days; the supernatant was analyzed for the production of the indicated cytokines by ELISA. (P-S) The CNS infiltrating (P. Q) CD4$^+$ T cells and (R, S) CD4$^+$CD25$^+$Foxp3$^+$ Tregs were analyzed. The data are pooled from 2 independent experiments (n=8 for Skint8-Ig or control Ig groups each). *P<0.05 compared with control Ig-treated mice.

Figure 19:
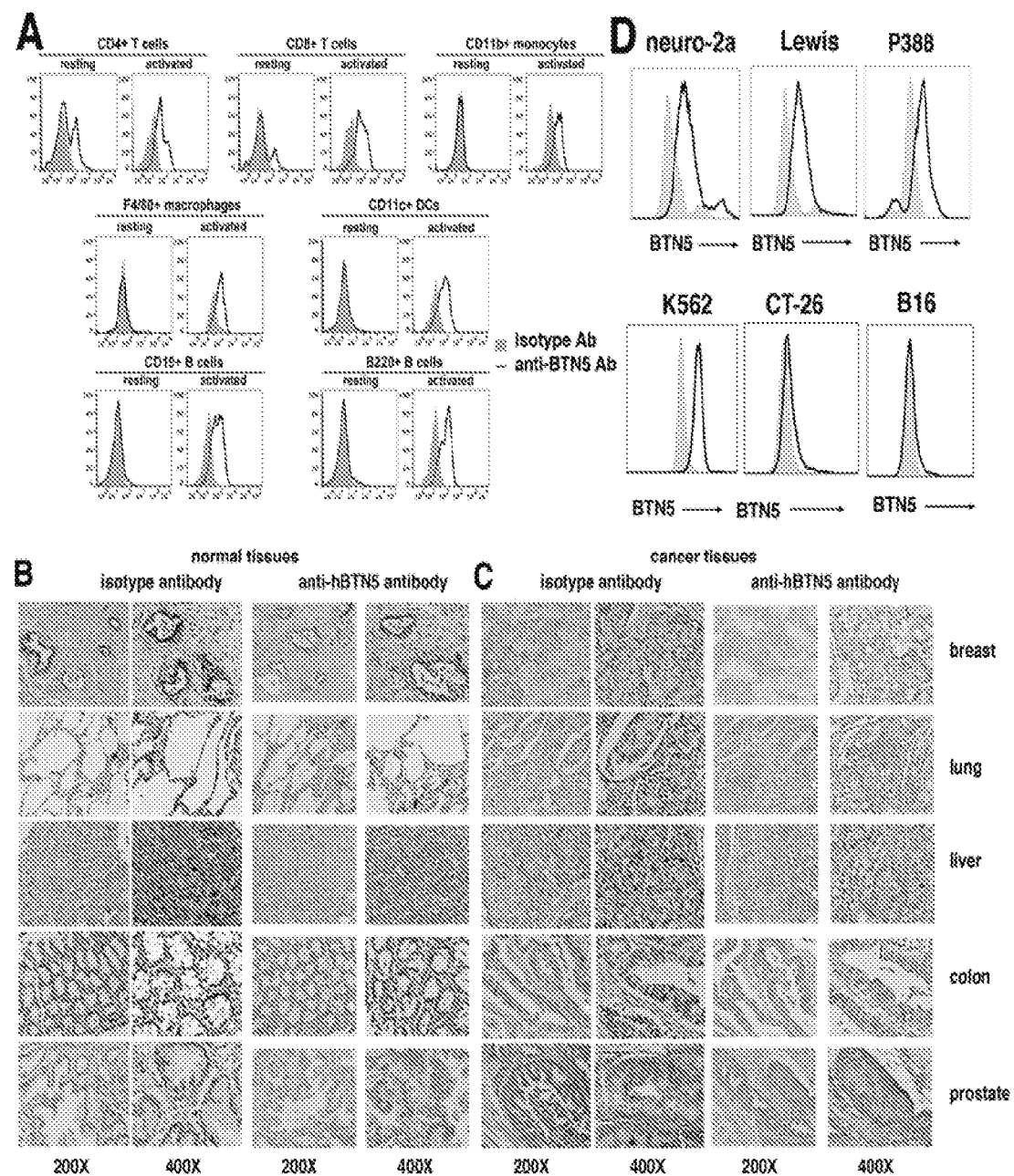

FIG. 19. The expression pattern of BTN5 protein. (A) Analysis of mBTN5 protein expression on immune cells. Splenocytes from C57BL/6 mice were freshly harvested and analyzed for mBTN5 protein expression on resting immune cells. To obtain activated B cells, DCs, monocytes and macrophages, splenocytes were incubated with LPS (10 µg/ml) for 3 days. To obtain activated T cells, splenocytes were incubated with anti-CD3 antibody (1 µg/ml) and anti-CD28 antibody (0.5 µg/ml) for 3 days. The resting and activated immune cells were stained with anti-BTN5 or isotype antibody, as well as anti-CD4, CD8, B220, CD11c, or CD11b antibody to identify immune cells. Representative flow cytometric profiles showing the expression of mBTN5 protein on resting and activated immune cells. (B, C) Determination of hBTN5 protein expression in human (B) normal and (C) cancer tissues by immunohistochemistry. (D) Analysis of BTN5 protein expression on neuro-2a, Lewis lung, P388, K562, CT26, and B16 tumor cell lines by flow cytometry. The data are representative of 3 independent experiments.

Figure 20:
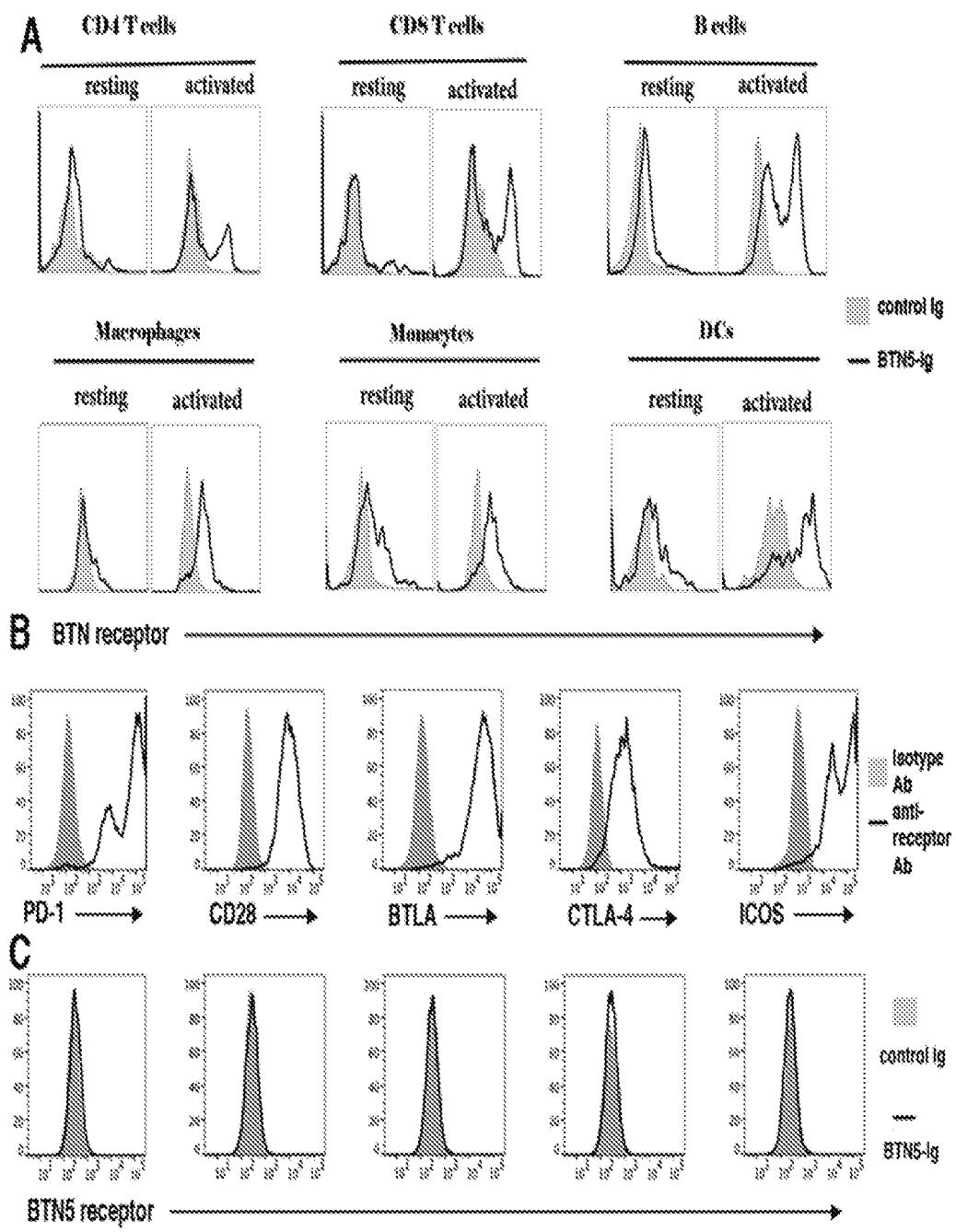

FIG. 20. The expression pattern of the mBTN5 putative receptor. (A) Splenocytes from C57BL/6 mice were freshly harvested and analyzed for resting immune cells. For T cell activation, splenocytes were incubated with anti-CD3 (1 µg/ml) and anti-CD28 (0.5 µg/ml) antibodies for 3 days. For the activation of B cells, DCs and monocytes, splenocytes were incubated with LPS (10 µg/ml) for 3 days. The resting and active immune cells were stained with anti-CD4, CD8, B220, CD11c, or CD11b antibodies, and biotinylated mBTN5-Ig or control Ig, followed by streptavidin-PE. Representative flow cytometric profiles showing the binding of mBTN5-Ig or control Ig to resting and activated immune cells. (B, C) HEK-293 cells were transfected with an expression vector containing murine PD-1, CD28, BTLA, CTLA-4, or ICOS gene. The transfected cells were stained with (B) antibodies against the respective PD-1, CD28, BTLA, CTLA-4, or ICOS protein, (C) biotinylated mBTN5-Ig or control Ig, followed by streptavidin-PE. Representative flow cytometric profiles showing the binding of (B) the antibodies or (C) mBTN5-Ig to the transfected cells. Representative of 3 independent experiments.

Figure 21:
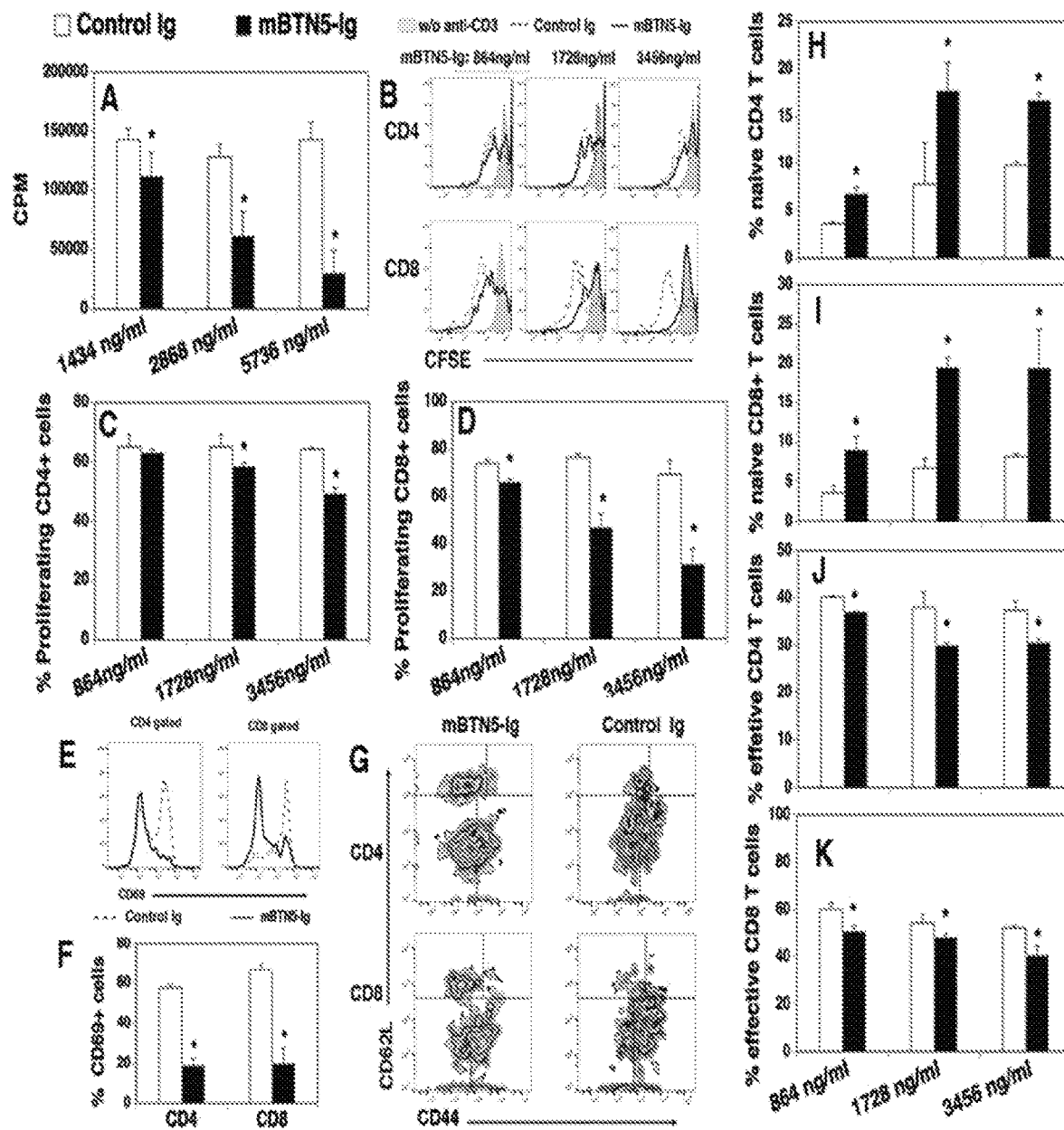

FIG. 21. The effects of mBTN5-Ig protein on murine T cell proliferation and activation in vitro. (A) T cells were purified from splenocytes of C57BL/6 mice by magnetic separation. The cells were cultured on plates pre-coated with anti-CD3 antibody (1 µg/ml) and indicated doses of mBTN5-Ig or control Ig for 3 days. [$^3$H] thymidine (1 µCi/well) was added to the cultures 12 hours before harvest. T cell proliferation was measured by [$^3$H]thymidine incorporation. Results are expressed as counts per minute (CPM). (B-D) Splenic cells from C57BL/6 mice were labelled with CFSE and cultured in 96-well plates that were precoated with anti-CD3 antibody and indicated doses of mBTN5-Ig or control Ig for 3 days. The cells were analyzed for CFSE levels by CD4$^+$ and CD8$^+$ T cells. (B) Representative flow cytometric analysis of CFSE distribution of CD4$^+$ and CD8$^+$ T cells, and (C, D) statistical analysis of the percentages of proliferating CD4 and CD8 T cells. (E-K) Splenic cells were cultured with anti-CD3 antibody in the presence of mBTN5-Ig or control Ig (1728 ng/ml). The cells were analyzed for the expression of (E, F) CD69 24 hours later, (G-K) and the expression of CD44 and CD62L 72 hours later. (E, G) Representative flow cytometric and (F. H-K) statistical analyses of the percentages of (F) CD69$^+$, (H, I) CD44$^{lo}$CD62L$^{hi}$ naïve CD4 and CD8 T cells and (J, K) CD44$^{hi}$CD62L$^{lo}$ effective memory CD4 and CD8 T cells. The data are expressed as mean±SD and representative of 3 independent experiments. *P<0.05 compared with control Ig.

Figure 22:
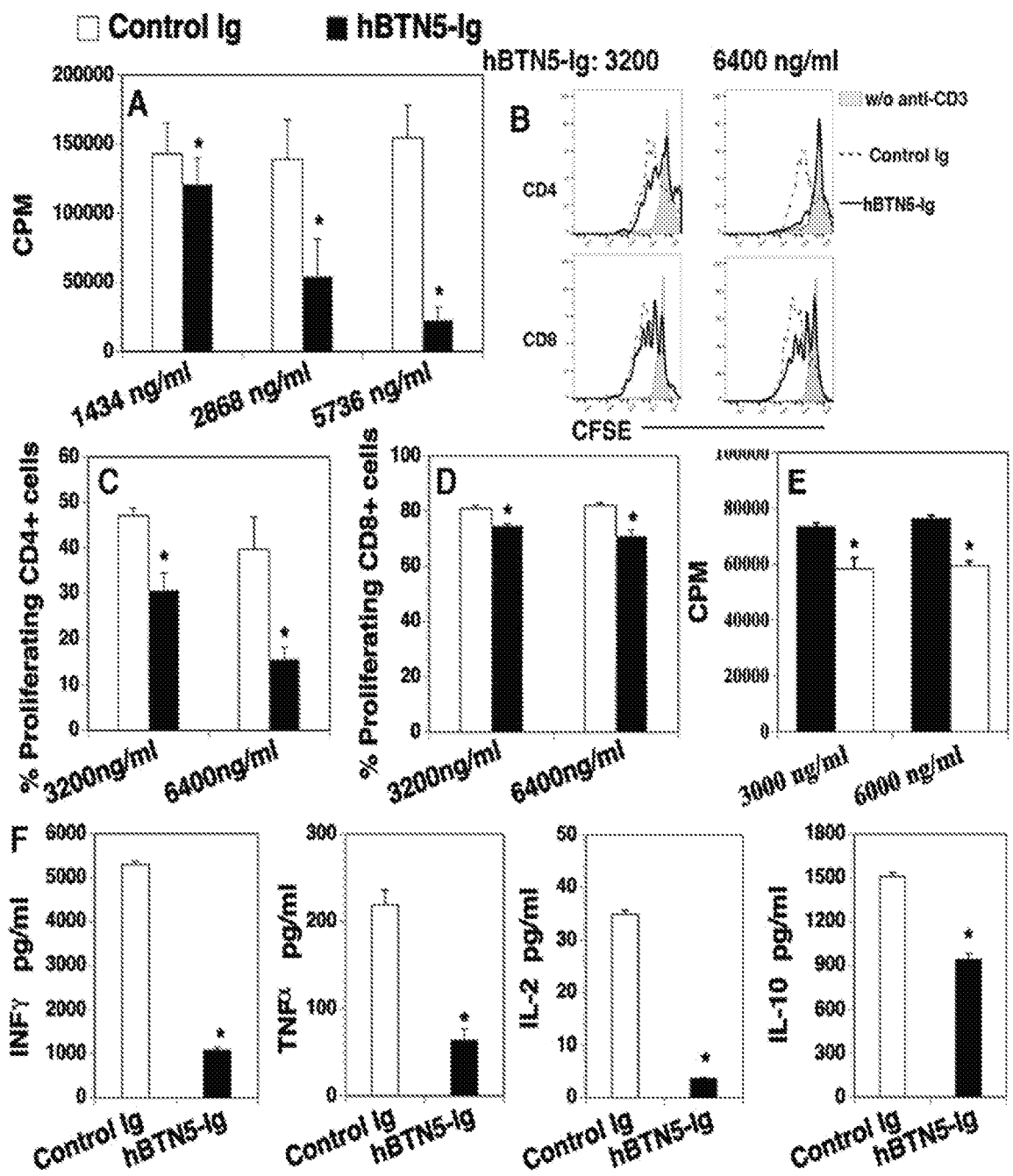

FIG. 22. The effects of hBTN5-Ig protein on murine and human T cells in vitro. (A) T cells were purified from splenocytes of C57BL/6 mice and cultured on plates pre-coated with anti-CD3 antibody (1 µg/ml) and indicated doses of hBTN5-Ig or control Ig for 3 days. [$^3$H] thymidine (1 µCi/well) was added to the cultures 12 hours before harvest, and T cell proliferation was measured by [$^3$H] thymidine incorporation. (B-D) Murine splenic cells were labelled with CFSE and cultured in 96-well plates that were precoated with anti-CD3 antibody and indicated doses of hBTN5-Ig or control Ig for 3 days. The cells were analyzed for CFSE levels by CD4$^+$ and CD8$^+$ T cells. (B) Representative flow cytometric analysis of CFSE distribution of CD4$^+$ and CD8$^+$ T cells, and (C, D) statistical analysis of CD4$^+$ and CD8$^+$ T cell proliferation. (E) Purified human T cells were cultured with plate-bound anti-human CD3 antibody (1 µg/ml) in the presence of indicated doses of hBTN5-Ig protein or control Ig protein for 3 days. Cell proliferation was measured by [$^3$H] thymidine incorporation. (F) hBTN5-Ig protein suppresses cytokine production from T cells. Purified murine T cells were cultured with plate-bound anti-CD3 antibody (1 µg/ml) in the presence of 6.4 µg/ml hBTN5-Ig protein or control Ig protein for 3 days. The levels of IFNγ, TNFα, IL-2, and IL-10 in the supernatant were measured by ELISA kits. The data are expressed as mean±SD and representative of 3 independent experiments. *P<0.05 compared with control Ig.

Figure 23:
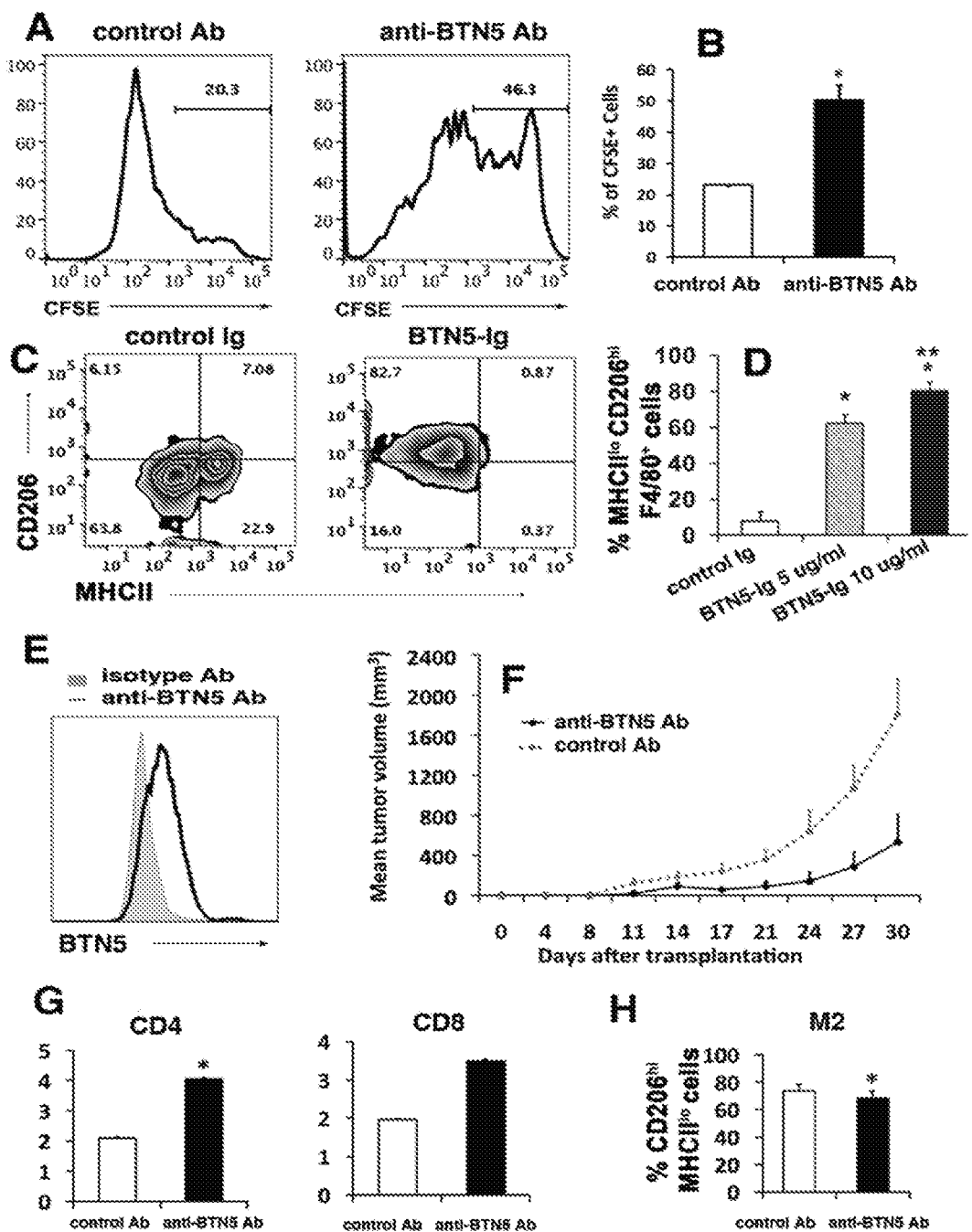

FIG. 23. The effects of hBTN5 on macrophage function and differentiation in vitro and tumor growth in vivo. (A, B) Macrophages were generated from BM of C57BL/6 mice. K562 cancer cells were labeled with CFSE and cultured with the macrophages in the presence of anti-hBTN5 or control antibody (10 μg/ml) for 2 hours. (A) Representative flow cytometric profiles and (B) statistical data showing the percentages of CFSE$^+$ cells in F4/80$^+$ macrophages. (C, D) M0 macrophages were induced to differentiate into M2 in the presence of hBTN5 or control Ig (5 or 10 μg/ml). (C) Representative flow cytometric profiles and (D) statistical data the percentages of CD206$^{hi}$MHC II$^{lo}$ M2 macrophages in F4/80$^+$ cells. (E) CT-26 colon cancer cells were transfected with an expression vector containing the full-length hBTN5 gene and screened for the cancer cells that stably expressed BTN5. A representative flow cytometric profile showing the expression of hBTN5 protein on the cell surface. (F-H) BALB/c mice were injected s.c. with 2×10$^5$ hBTN5-transfected CT-26 cells. When the tumors were palpable, the mice were injected intratumorally with anti-hBTN5 or control polyclonal antibody (25 μl) twice each week from days 10-28 after tumor inoculation. (F) The mean tumor volume (mm$^3$)±S.D. at the indicated time points are shown. (G. H) Thirty days after CT26 cell inoculation, the mice were euthanized and the tumors were removed. Single-cell suspensions from the tumors were analyzed by flow cytometry for (G) CD4$^+$ and CD8$^+$ T cells; and (H) M2 macrophages. *P<0.05 compared with control group. The data are representative of 2 independent experiments with 4-6 mice per group.

Figure 24:
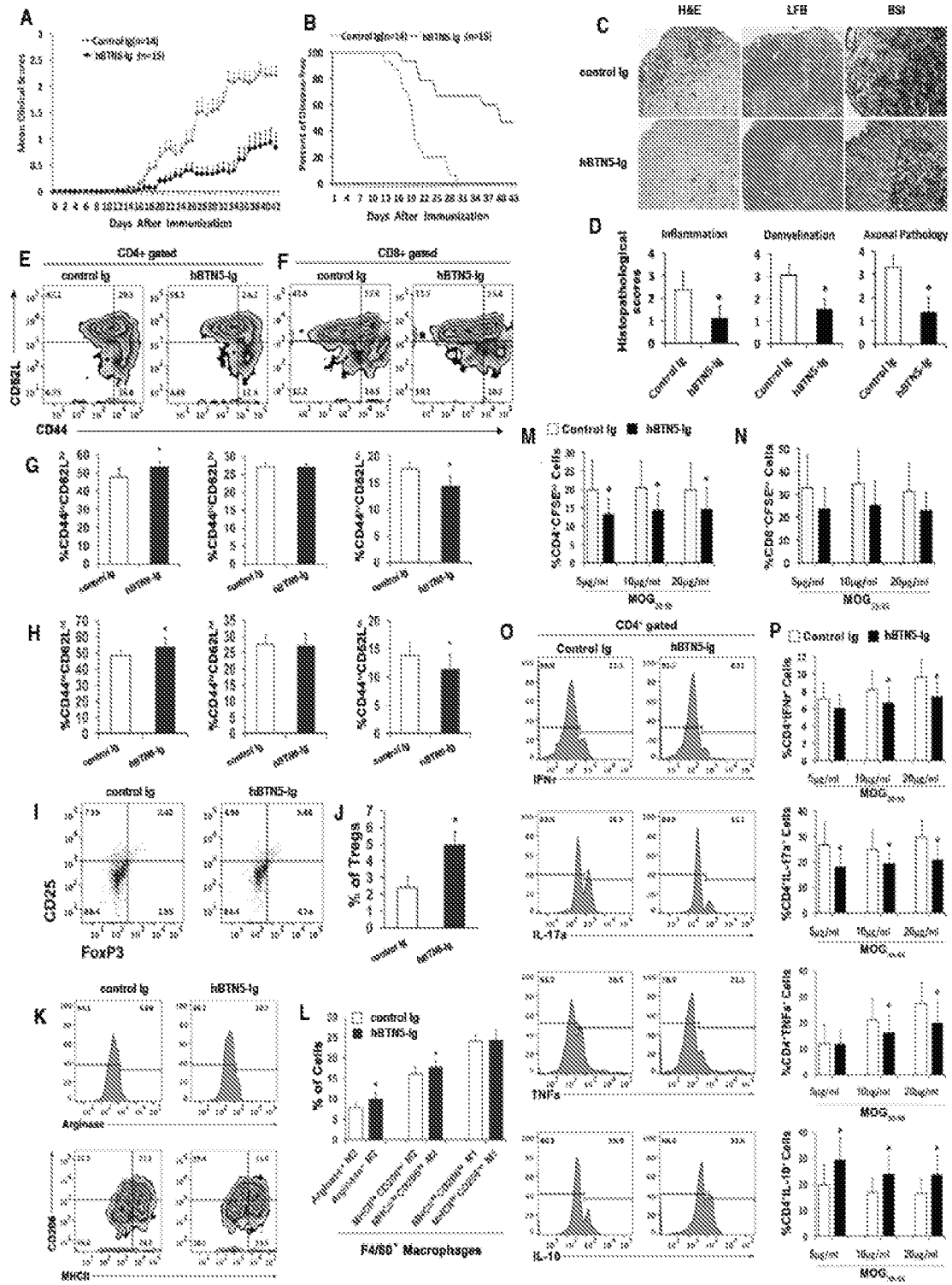

FIG. 24: hBTN5-Ig attenuates autoimmune disease EAE in mice. C57BL/6 mice were immunized with 200 μg MOG$_{35-55}$ emulsified in CFA and 500 ng of purified *Bordetella pertussis* toxin. The mice were injected i.p. with 25 μg/ml hBTN5-Ig or control Ig protein 3 times per week for 5 weeks. EAE development was monitored for 42 days. (A) Mean clinical scores, and (B) a Kaplan-Meier plot of the proportion of disease-free mice are shown. (C-P) Forty two days after immunization, spinal cords and spleens were harvested. (C, D) Histological sections of the spinal cords were stained with H&E, LFB and BSI. (C) Representative stained histological sections (the magnification was 200×), and (D) histological scores are shown. (E-H) The splenocytes were analyzed for CD44$^{hi}$CD62L$^{hi}$ naïve, CD44$^{hi}$CD62L$^{lo}$ effective memory, and CD44$^{hi}$CD62L$^{hi}$ central memory (G) CD4 and (H) CD8 T cells; (I, J) CD4$^+$CD25$^+$FoxP3$^+$ Tregs; and (K, L) arginase$^+$ and CD206$^{hi}$MHC$^{lo}$ M2, as well as CD206$^{lo}$MHC$^{hi}$ M1 macrophages. (M, N) Splenocytes were labelled with CFSE and stimulated with varying doses of pMOG$_{35-55}$ in vitro. CFSE dilution was analyzed 3 days later to determine CD4$^+$ and CD8$^+$ T cell proliferative responses. (O, P) Splenocytes were stimulated with pMOG$_{35-55}$ in vitro for 3 days. The cells were analyzed for the percentages of cytokine-producing cells by flow cytometry. The data are expressed as mean±SD and representative of 3 independent experiments. *P<0.05 compared with control Ig-treated mice.

Figure 25:
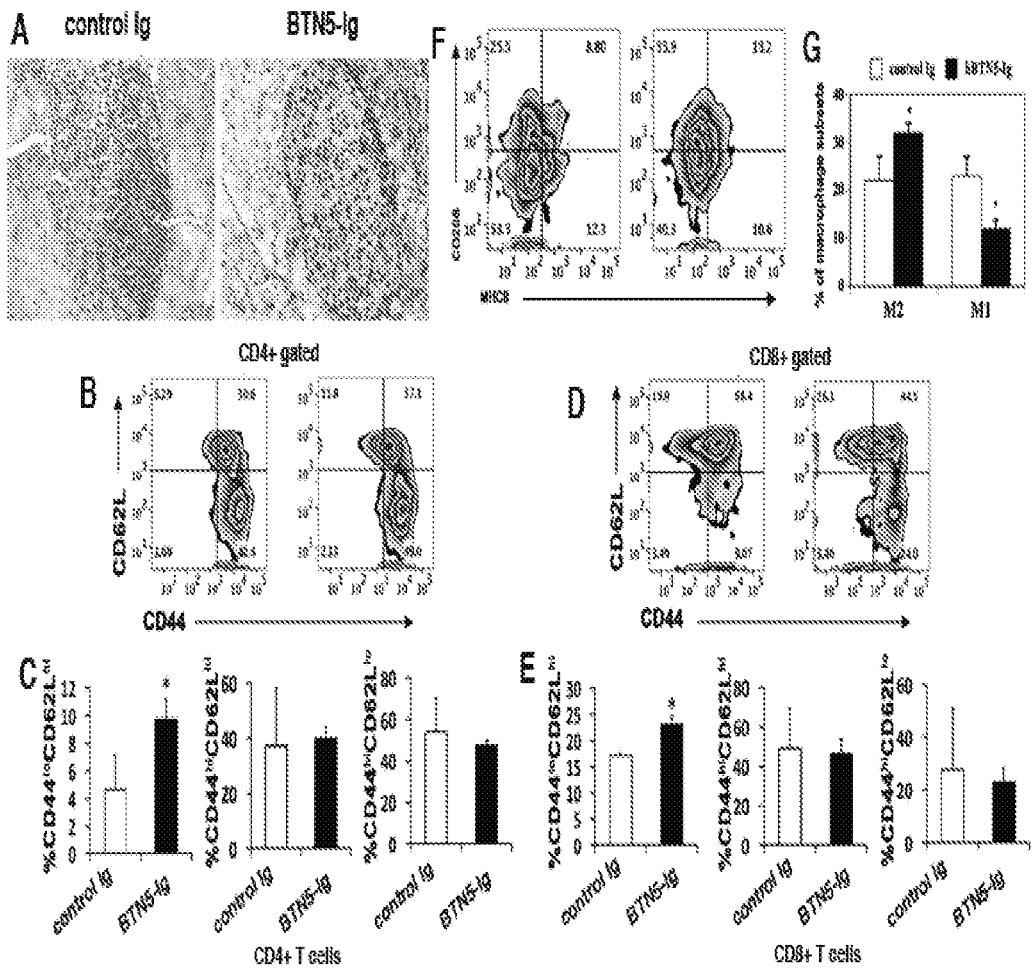

FIG. 25: hBTN5-Ig treatment ameliorates T1D in mice. 22 week-old female NOD mice were injected i.p. with 30 μg hBTN5-Ig or control Ig protein at 2-day intervals for 3 weeks. At week 30, the mice were euthanized. (A) The pancreases were stained with hematoxylin and eosin (H&E). Representative sections (200×). (B-G) the spleens were analyzed for (B-E) T cell and (F, G) macrophage subsets. (B, D, F) Representative flow cytometric profiles and (C, E, G) statistical analysis of (B-E) CD44$^{lo}$CD62L$^{hi}$ naïve, CD44$^{hi}$CD62L$^{lo}$ effective memory, and CD44$^{hi}$CD62L$^{hi}$ central memory CD4 and CD8 T cells, as well as (F, G) CD206$^{hi}$MHC$^{lo}$ M2 and CD206$^{lo}$MHC$^{hi}$ M1 macrophages. The data are expressed as mean±SD and representative of 2 independent experiments per group. *P<0.05 compared with control Ig-treated mice.

Figure 26:
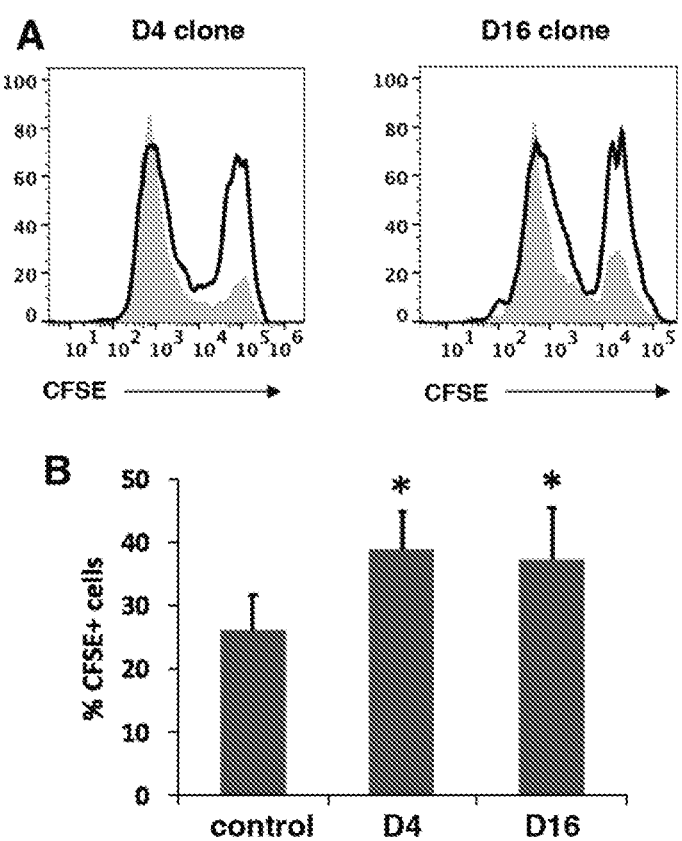

FIG. 26. Anti-hBTN-5 mAbs enhance macrophage-mediated phagocytosis of cancer cells in vitro. Macrophages were generated from BM of C57BL/6 mice. K562 cancer cells were labeled with CFSE and cultured with the macrophages in the presence of anti-hBTN5 mAbs (clones D4 and D16) for 2 hours. (A) Representative flow cytometric profiles (anti-hBTN5 mAbs: open histograms; control mAbs: shaded histograms) and (B) statistical data of the percentages of CFSE cells in F4/80$^+$ macrophages. The data are expressed as mean±SD and pooled from 3 independent experiments. *P<0.05 compared with control mAbs.

Figure 27:
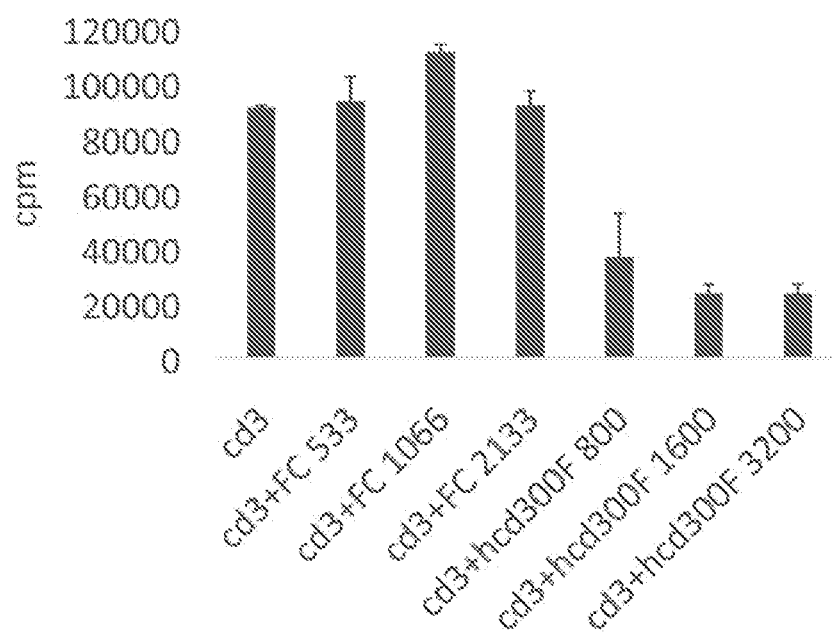

FIG. 27. CD300f-Ig protein inhibits lymphocyte proliferation in vitro. Splenocytes from C57BL/6 mice were cultured with plate-bound anti-CD3 antibody (1 μg/ml) in the presence of graded doses of CD300f-Ig protein (800, 1600, and 3200 ng/ml) or equimolar amounts of control Ig protein for 3 days. Cell proliferation was measured by [$^3$H]thymidine incorporation. The data are expressed as mean±SD and representative of 3 independent experiments.

Figures 28A, 28B:
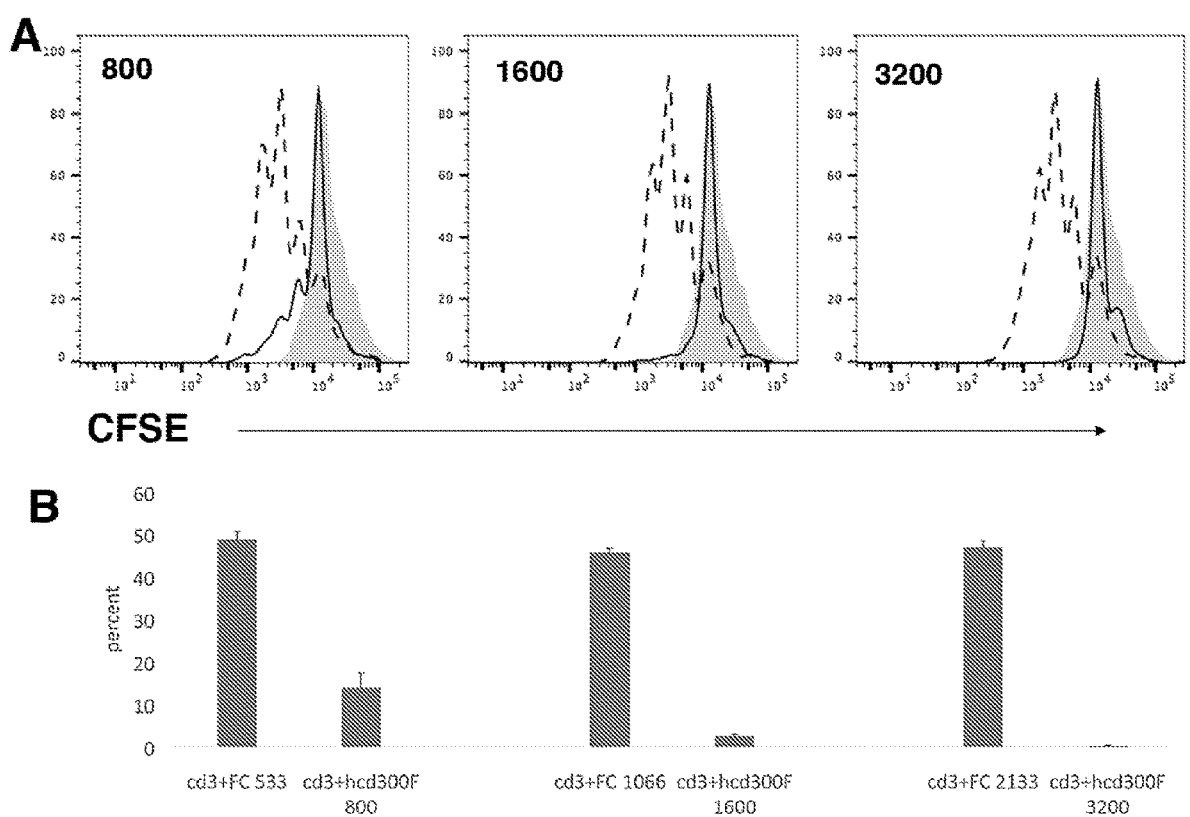
Figures 28C, 28D:
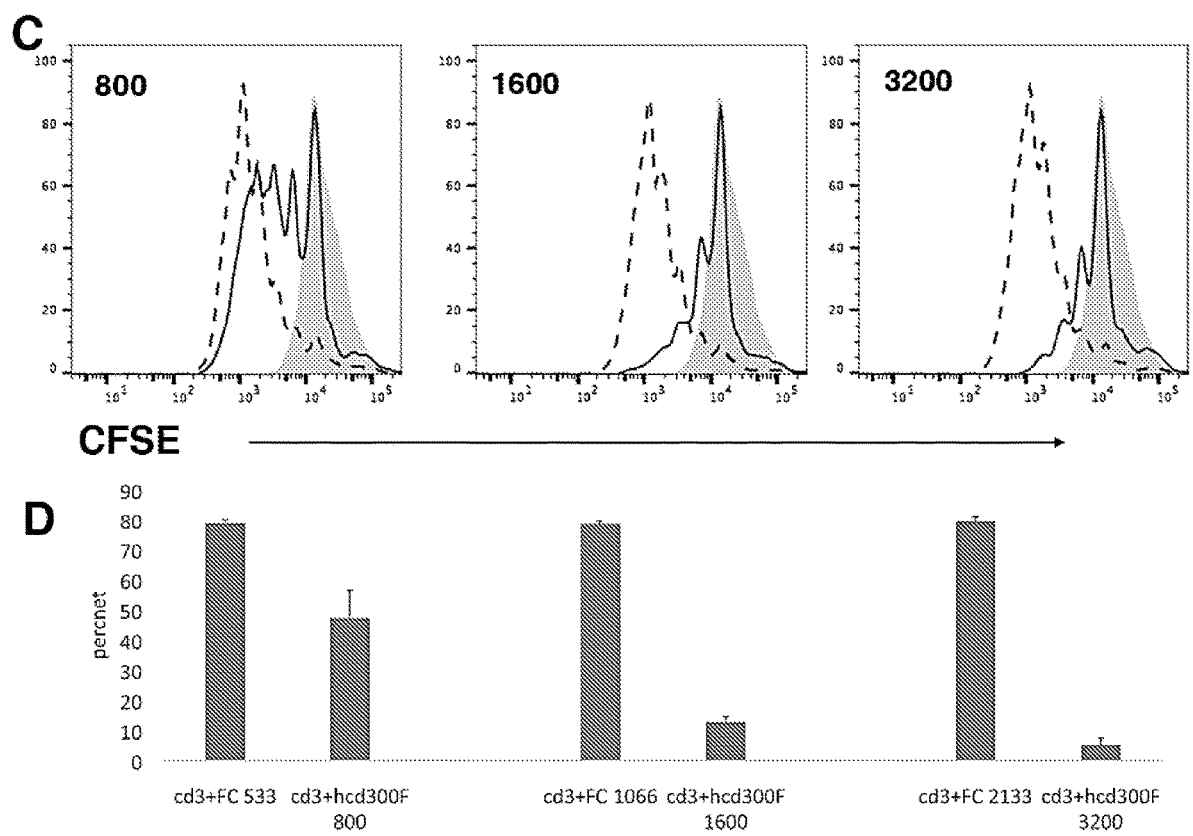

FIG. 28. CD300f-Ig protein inhibits T cell proliferation in vitro. Splenocytes from C57BL/6 mice were labelled with CFSE and cultured with anti-CD3 antibody (μg/ml) in the presence of graded doses of CD300f-Ig protein (800, 1600, and 3200 ng/ml) or equimolar amounts of control Ig protein for 3 days. The cells were stained with anti-CD4 and CD8 antibodies, and analyzed for CFSE levels by CD4$^+$ and CD8$^+$ T cells. (A. C) Representative flow cytometric profiles, and (B, D) statistical analysis of CFSE$^{lo}$ proliferating (A, B) CD4$^+$ and (C, D) CD8$^+$ T cells. (B, D) The data are expressed as mean±SD and representative of 3 independent experiments.

Figures 29A, 29B:
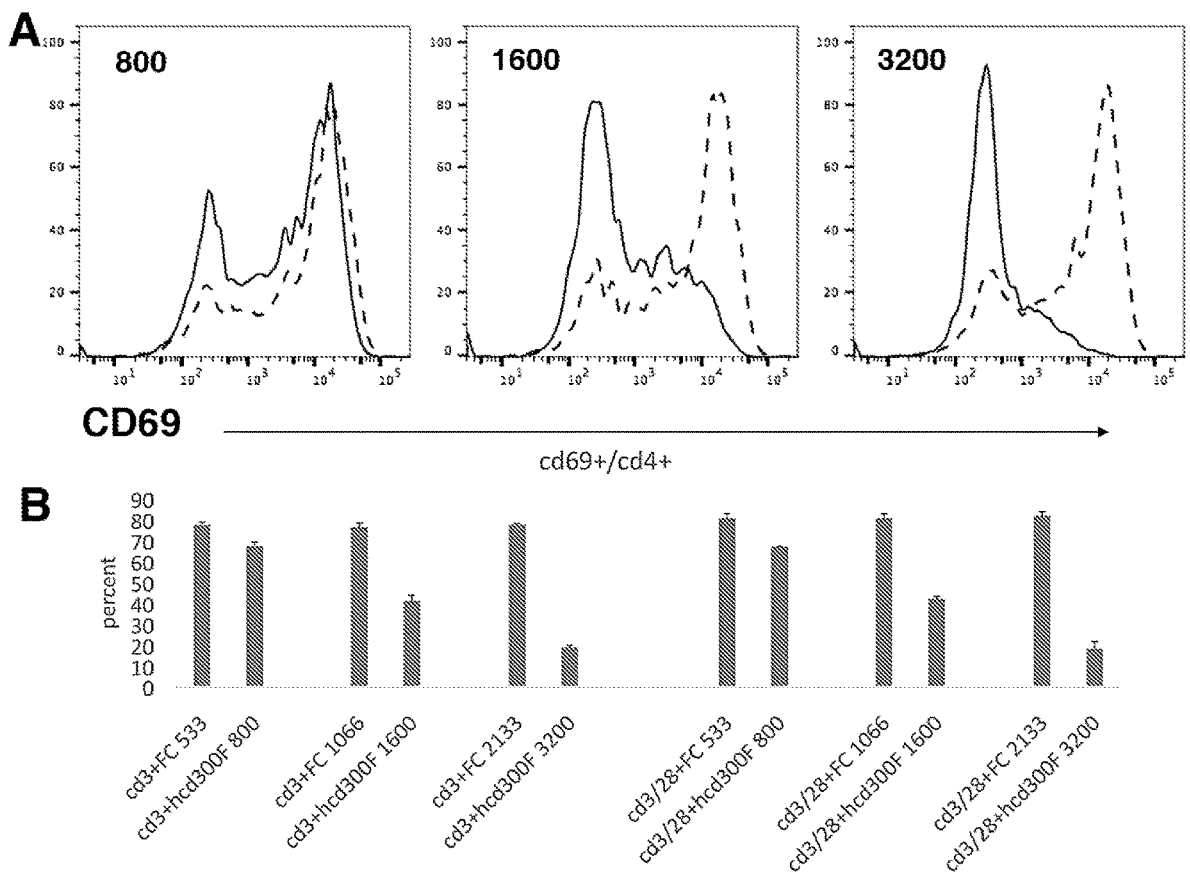
Figures 29C, 29D:
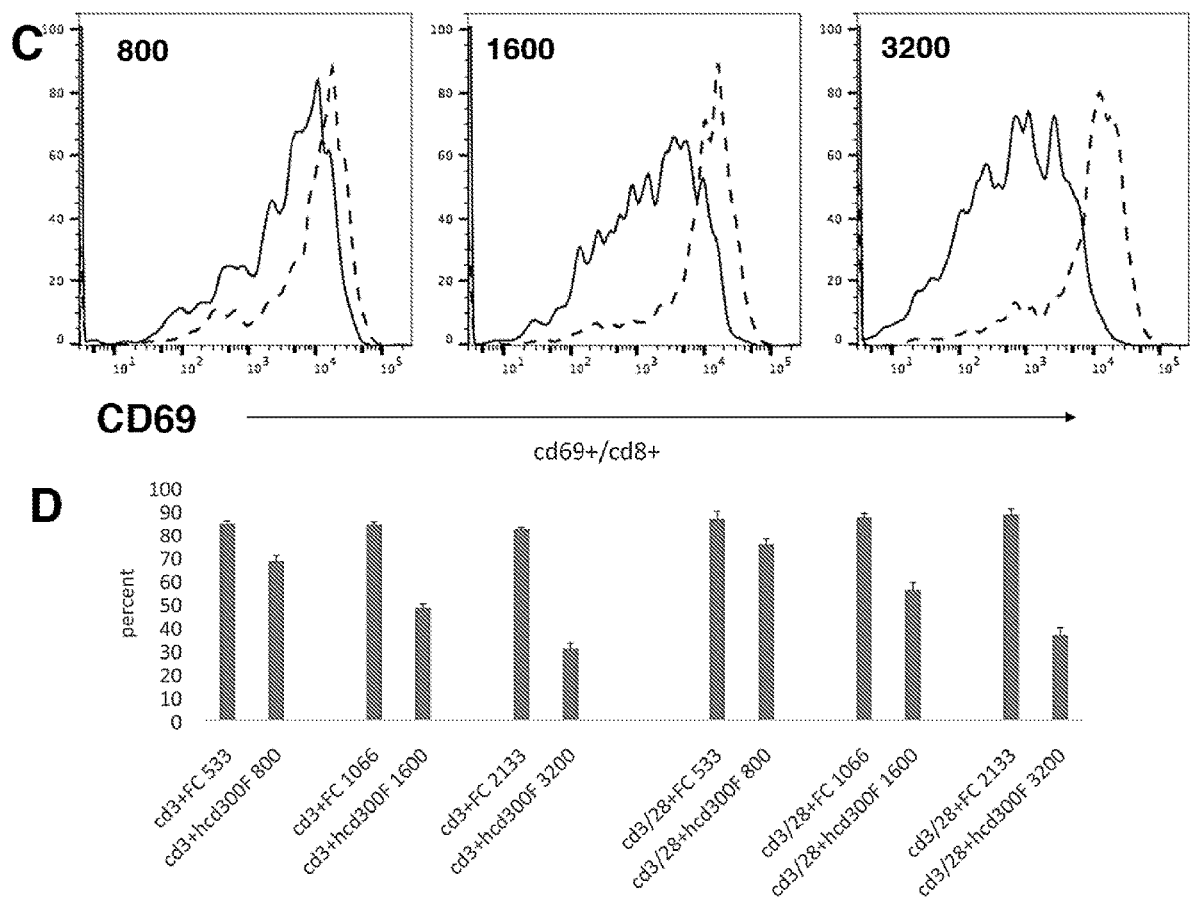

FIG. 29. CD300f-Ig protein inhibits T cell activation in vitro. Splenocytes from C57BL/6 mice were cultured with plate-bound anti-CD3 antibody (1 μg/ml), or anti-CD3 antibody (1 μg/ml) and (B) anti-CD28 antibody (0.5 μg/ml) in the presence of graded doses of CD300f-Ig protein (800, 1600, and 3200 ng/ml) or equimolar amounts of control Ig protein. The cells were analyzed for the expression of CD69 by (A, B) CD4$^+$ and (C, D) CD8$^+$ T cells 24 hours later. (B, D) The data are expressed as mean±SD and representative of 3 independent experiments.

DETAILED DESCRIPTION

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural or singular number, respectively. Additionally, the words "herein," "above" and "below" and words of similar import, when used in this application, shall refer to this application as a whole and not to any particular portions of this application.

As used herein, the amino acid residues are abbreviated as follows: alanine (Ala: A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

All embodiments of any aspect of the invention can be used in combination, unless the context clearly dictates otherwise.

In a first aspect, the disclosure provides methods for treating cancer, comprising administering to a subject in need thereof an antibody that selectively binds to a protein selected from the group consisting of CD300c, BTN5 (Erythroid membrane-associated protein), TAPBPL (antigen processing (TAP) binding protein like protein), Skint8 (selection and upkeep of intraepithelial T cells 8 protein), and/or CD300f in an amount effective to treat the cancer. The methods may be used to treat any suitable cancer. In various non-limiting embodiments, the cancer may be selected from the group consisting of breast cancer, lung cancer, colon cancer, prostate cancer, leukemia, neuroblastoma, liver, lymphoma, cervical cancer, ovarian cancer, gastric cancer, and esophageal cancer, etc.

Tumor progression is often accompanied by profound immune suppression that interferes with an effective antitumor response and tumor elimination. In contrast, graft-versus-host disease (GVHD) and autoimmune diseases, such as type 1 diabetes (T D), arthritis, including but not limited to rheumatoid arthritis (RA), and multiple sclerosis (MS), arise when the immune system actively targets and destroys self-tissues. In order to elicit protective immunity to cancer and infection, and to prevent an overactive immune system, immune responses need to be tightly controlled by immune cell stimulatory and inhibitory molecules. Many cancers protect themselves from the immune system by producing inhibitory molecules to inhibit T cell function.

As disclosed in the examples herein, the inventors have identified CD300c, BTN5, TAPBPL, Skint8, and CD300f as targets for treating cancer, and as therapeutics for treating autoimmune disease.

As used herein, the term "treat," "treatment," or "treating," means to reverse, alleviate, ameliorate, inhibit, slow down or stop the progression or severity of a symptom or condition of the disorder being treated. The term "treating" includes reducing or alleviating at least one adverse effect or symptom of a condition. Treatment is generally "effective" if one or more symptoms are reduced. Alternatively, treatment is "effective" if the progression of a condition is reduced or halted. That is, "treatment" may include not just the improvement of symptoms, but also a cessation or slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of a tumor, malignancy, or autoimmune disease; delay or slowing of tumor growth and/or metastasis or autoimmune disease effects, and an increased lifespan as compared to that expected in the absence of treatment.

As used herein, the term "administering," refers to the placement of a therapeutic into a subject by a method or route deemed appropriate. The therapeutic can be administered by any appropriate route which results in an effective treatment in the subject including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. Dosage regimens can be adjusted to provide the optimum desired response (e.g., a therapeutic response). A suitable dosage range may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight. The therapeutic can be delivered in a single bolus, or may be administered more than once (e.g., 2, 3, 4, 5, or more times) as determined by an attending physician.

As used herein, the phrase "amount effective" or "the like refers to an amount that provides a therapeutic benefit in the treatment, of cancer or autoimmune disease. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "antibody" refers to binding proteins having at least one antigen-binding domain and includes monoclonal antibodies fragments and/or variants thereof including recombinant polypeptides, fusion proteins, and immunoconjugates. Thus, the terms "antibody," "antibody fragment," and "antibody variant" are used interchangeably herein. Examples of antibody fragments of the invention include, but are not limited to, the Fab fragment, consisting of VL, VH, CL and CHI domains; the Fc fragment, consisting of the VH and CHI domains; the Fv fragment consisting of the VL and VH; the dAb fragment consisting of a VH domain; isolated CDR regions: F(ab')$_2$ a bivalent fragment comprising two linked Fab fragments; and single chain Fv molecules (scFv). The antibodies provided herein may be generated from any species including, but not limited to, mouse, rat, rabbit, primate, llama and human. The antibodies may be chimeric, humanized, or fully human antibodies. In one specific embodiment, the antibody is a monoclonal antibody. In other specific embodiments, the antibody may be the anti-CD300c and/or anti-TAPBPL antibodies disclosed and claimed herein.

As used herein, selective binding or specific binding means the antibody specifically bound to its target antigen is not displaced by a non-similar competitor and preferentially recognizes its target antigen in a complex mixture of proteins and/or macromolecules. Antibodies and fragments thereof that are selective for the target antigens described herein bind the target antigen with greater affinity (i.e., a lower binding affinity Kd value) than any other target. In non-limiting embodiments, the antibodies and fragments or variants thereof may have a binding affinity Kd value for target antigen in the range of about 0.01 nM to about 500 nM, about 0.02 nM to about 250 nM, about 0.02 to about 200 nM, about 0.05 to about 100 nM, about 0.05 to about 50 nM. The antibodies and fragments thereof may have a binding affinity Kd value for target antigen of about 500 nM, about 250 nM, about 200 nM, about 150 nM, about 100 nM, about 75 nM, about 50 nM, about 25 nM, about 10 nM, about nM, about 1 nM, about 500 pM, about 250 pM, about 100 pM, about 50 pM, or about 10 pM. The antibodies and fragments thereof may have a binding affinity Kd value for target antigen of about 100 nM or less, about 75 nM or less, about 50 nM or less, about 10 nM or less, about 1 nM or less, about 500 pM or less, or about 100 pM or less.

In one embodiment, the antibody selectively binds to an extracellular domain (ECD) of CD300c, including but not limited to an ECD of human CD300c within amino acid residues 21-138. In another embodiment, the antibody selectively binds to an IgV domain of CD300c, including but not limited to an IgV domain of human Cd300c within amino acid residues 20-135. Exemplary Cd300c sequences are shown below:

```
Mouse CD300c2 amino acid sequences (ECM region:
22-187, IgV: 24-116); the IgV domain is predicted
from aa20-28 to aa112-140:
                                       (SEQ ID NO: 01)
MIPRVIRLWLPSALFLSQVPGCVPLHGPSTITGTVGKSLSVSCQYEEKFK

TKDKFWCRGSLKVLCKDIVKTSSSEEVRNGRVTIRDHPDNLTFTVTYESL

TLEDADTYMCAVDISLFDGSLGFDKYFKIELSVVPSEDPVTGSSLESGRD

ILESPTSSVGHTHPSVTTDDTIPTPCPQPRSLRSSLYFRVLVSLKLFLFL

SMLGAVLWVNRPQKCSGGSSTQPCYENQ

Human CD300c amino acid sequences (ECM region:
21-183, IgV: 22-128); the IgV domain is predicted
from aa20-28 to aa114-135:
                                       (SEQ ID NO: 02)
   1 MTARAWASWR SSALLLLLVP GYFPLSHPMT VAGPVGGSLS
     VQCRYEKEHR TLNKFWCRPP

61 QILRCDKIVE TKGSAGKRNG RVSIRDSPAN LSFTVTLENL
     TEEDAGTYWC GVDTPWLRDE

121 HDPIVEVEVS VFPAGTTTAS SPQSSMGTSG PPTKLPVHTW
     PSVTRKDSPE PSPHPGSLES

181 NVRFLLLVLL ELPLLLSMLG AVLWVNRPQR SSRSRQNWPK
     GENQ
```

In one embodiment, the antibody selectively binds to an extracellular domain of PP21DNA BTN5, including but not limited to an ECD of human BTN5 within amino acid residues 30-155. In another embodiment, the antibody selective binds to an IgV domain of BTN5, including but not limited to an IgV domain of human BTN within amino acid residues 17-150. Exemplary BTN5 sequences are shown below:

```
Mouse BTN5 amino acid sequences (Signal peptides:
1-47; ECM region: 48-271, IgV: 49-165); the IgV
domain is predicted from amino acid (aa) 49-68
to aa151-170.
                                       (SEQ ID NO: 03)
   1 MLKRLKKHVV AWKMCVMPHS RKMSVHMERP SPCGSWLVGC
     LFTIAVFQPP VQVLGDAGKV

61 YIAPLRDTAN LPCPLELWPN MVLSEMRWYR PGHLPRTQAV
     HVERDGQDRD EDLMPEYKGR

121 TALVRDAHKE SYILQISNVR LEDRGLYQCQ VWVGNSSRED
     NVTLQVAVLG SDPYTHVKGY

181 DAGWIELLCQ SVGWFPKPWT EWRDTTGRAL LSLSEVHSLD
     ENGLERTAVS SRIRDNALGN

241 VSCTIHNEAL GQEKTTAMII GAPERGSLSS PAVALSVVLP
     VLGLLILLGI WLICKQKKSK

301 EKLLYEQAME VENLLEDHAK EKGRLHKALK KLRSELKLKR
     AAANAGWRRA RLHFVAVTLD

361 PDTAHPKLIL SEDRRCVRLG DRKRPVPDNP ERFDFVVSVL
     GSEYFTTGCH YWEVYVGEKT

421 KWILGVCSES VSRKGKVTAS PANGHWLVRQ SRGNEYEALT
     SPQTSFRLKE SPKCVGIELD

481 YEAGIISFYN VTDKSHIFTF THSFSSPLRP FFEPCLHDEG
     KNTAPLIICT ELQKSEESIV

541 PKQEGKDRAN GDVSLKMNPS LLSPQGSELF LINDTWPSNL
     GPALKGLKVP SL

Human BTN5 amino acid sequences (ECM 30-155,
IgV: 30-144); the IgV domain is predicted from
aa17-45 to aa143-150:
                                       (SEQ ID NO: 04)
   1 MEMASSAGSW LSGCLIPLVF LRLSVHVSG HAGDAGKFHVA
     LLGGTAELLC PLSLWPGTVP

61 KEVRWLRSPF PQRSQAVHIF RDGKDQDEDL MPEYKGRTVL
     VRDAQEGSVT LQILDVRLED

121 QGSYRCLIQV GNLSKEDTVI LQVAAPSVGS LSPSAVALAV
     ILPVLVLLIM VCLCLIWKQR

181 RAKEKLLYEH VTEVDNLLSD HAKEKGKLHK AVKKLRSELK
     LKRAAANSGW RRARLHEVAV

241 TLDPDTAHPK LILSEDQRCV RLGDRRQPVP DNPQRFDEVV
     SILGSEYFTT GCHYWEVYVG

301 DKTKWILGVC SESVSRKGKV TASPANGHWL LRQSRGNEYE
     ALTSPQTSFR LKEPPRCVGI

361 FLDYEAGVIS FYNVINKSHI FTFTHNFSGP LRPFFEPCLH
     DGGKNTAPLV ICSELHKSEE

421 SIVPRPEGKG HANGDVSLKV NSSLLPPKAP ELKDIILSLP
     PDLGPALQEL KAPSF
```

In one embodiment, the antibody selectively binds to an extracellular domain of TAPBPL, including but not limited to an ECD of human TAPBPL within amino acid residues 19-405. In another embodiment, the antibody selective binds to an IgV domain of TAPBPL, including but not limited to an IgV domain of human TAPBPL within amino acid residues 181-300. Exemplary TAPBPL sequences are shown below:

```
Mouse TAPBPL amino acid sequences (ECM region:
21-412, IgV: 196-305); the IgV domain is
predicted from aa196-210 to aa301-306.
                                       (SEQ ID NO: 05)
   1 mglepswyll lclavsgaag tdpptaptta erqrqptdii
     ldcflvtedr hrgafassgd 61 rerallvikq vpvlddgsle gitdfqgste tkqdspvife
     asvdlvqipq aeallhadcs 121 gkavtceisk yflgarqeat fekahwfisn mqvsrggpsv
     smvmktlrda evgavrhptl 181 nlplsaqgtv ktqvefqvts etqtlnhllg ssvslhcsfs
     mapgldltgv ewrlqhkgsg 241 qlvyswktgq gqakrkgatl epeellragn asltlpnltl
     kdegnyicqi stslyqaqqi 301 mplnilappk iqlhlankdp lpslvcsiag yypldvgvtw
     ireelggipa qvsgasfssl 361 rqstmgtysi sstvmadpgp tgatytcqva hvsleepltt
     smrvipnpeq rgtlgvifas 421 iiflsalllf lglhrqqass srstrpmrhs g Human TAPBPL amino acid sequences (ECM region:
19-405, IgV: 198-300); the IgV domain is predicted
from aa181-198 to aa297-300:
                                       (SEQ ID NO: 06)
   1 mgtqegwcll lclalsgaae tkphpaegqw ravdvvldcf
     lakdgahrga lassedrara 61 slvlkqvpvl ddgsledftd fqggtlaqdd ppiifeasvd
     lvqipqaeal lhadcsgkev
```

In one embodiment, the antibody selective binds to an extracellular domain of Skint8, including but not limited to an ECD of mouse Skint8 within amino acid residues 26-233. In another embodiment, the antibody selective binds to an IgV domain of Skint8, including but not limited to an ECD of mouse Skint8 within amino acid residues 18-142. An exemplary Skint8 sequence is shown below:

```
Mouse Skint8 amino acid sequences (ECM region:
26-233, IgV: 29-140); the IgV domain is
predicted from aa18-35 to aa140-142:
                                        (SEQ ID NO: 07)
   1 mmkpefshff gfcvyflflq vmasseklrv ttptrhllar
     vgggaelscq vipphsvmhm 61 evrwfrsghs qpvylyrggh kmseeaapey anrtefvkea
     igegkvslri yninilddgp 121 yqcsfndsgf idvaimninv tavgleteih vqapdadgvm
     vecntggwfp rpqmewrdsk 181 gatlphalks ysqdearffh mkmtllltnm shgsiiccis
     npvtgeekqt siilanelfn 241 qdylwvgifp fsvlslilfg vlpfinsffr sqgcasgcls
     kclpvvtswp vqivhflvcs 301 gvlfavylph ryrvslsdpq fplynnwite llivilflti
     cfvlpitvll liklsptcla 361 kweknkddim dsqlglgkar eastlyeeqs rksweqek
```

In one embodiment, the antibody selective binds to an extracellular domain of CD300f including but not limited to an ECD of human CD300f within amino acid residues 20-155. In another embodiment, the antibody selective binds to an IgV domain of CD300f, including but not limited to an IgV domain of human CD300f within amino acid residues 2-140. An exemplary CD300f sequence is shown below:

```
Human CD300F amino acid sequences (ECM region:
20-155, IgV: 24-125); the IgV domain is predicted
from aa2-25 to aa125-140:
                                        (SEQ ID NO: 08)
   1 mplltlylll fwlsgysivt qitgpttyng lergsltvqc
     vyrsgwetyl kwwcrgaiwr 61 dckilvktsg seqevkrdrv sikdnqknrt ftvtmedlmk
     tdadtywcgi ektgndlgvt 121 vqvtidpapv tqeetssspt ltghhldnrh kllklsvllp
     liftillll vaasllawrm 181 mkyqqkaagm speqvlqple gdlcyadltl qlagtspqka
     ttklssaqvd qveveyvtma 241 slpkedisya sltlgaedqe ptycnmghls shlpgrgpee
     pteystisrp
```

In another aspect the disclosure provides isolated anti-human CD300c antibodies, or antigen binding fragments thereof, comprising 1, 2, 3, 4, 5, or all 6 complementarity determining regions (CDRs) selected from the group consisting of:

Heavy chain CDR1 (H-CDR1) comprising the amino acid sequence at least 80%, 85%, 90%, 95%, or 100% identical to the amino acid sequence IYGMN (SEQ ID NO:10);

Heavy chain CDR2 (H-CDR2) comprising the amino acid sequence at least 80%, 85%, 90%, 95%, or 100% identical to the amino acid sequence WINTYT (SEQ ID NO:11);

Heavy chain CDR3 (H-CDR3) comprising the amino acid sequence at least 80%, 85%, 90%, 95%, or 100% identical to the amino acid sequence ARSRFAY (SEQ ID NO:12).

Light chain CDR1 (L-CDR1) comprising the amino acid sequence at least 80%, 85%, 90%, 95%, or 100% identical to the amino acid sequence KASQNVGTNVA (SEQ ID NO:13);

Light chain CDR2 (L-CDR2) comprising the amino acid sequence at least 80%, 85%, 90%, 95%, or 100% identical to the amino acid sequence SASYRYS (SEQ ID NO:14); and Light chain CDR3 (L-CDR3) comprising the amino acid sequence at least 80%, 85%, 90% 95%, or 100% identical to the amino acid sequence QQYNSYPLT (SEQ ID NO:15).

As shown in the examples that follow, the disclosed antibodies are the first antibodies shown to have the ability to neutralize the inhibitory effects of CD300c on T cells. The sequences of these antibodies have been determined, including the complementarity determining regions (CDRs) disclosed herein. As will be understood by those of skill in the art, the CDRs are the key factor in antigen-binding selectivity, and thus other regions of the antibody amino acid sequence may be substantially modified. In a further embodiment, the anti-human CD300c antibody, or antigen-binding fragment thereof comprises:

(a) a heavy chain comprising the amino acid sequence having at least 60%, 65%, 70%, 75%, 80%, 85%, 90%, 91%, 92%, 93%, 94%, 95%, 96%, 97%, 98%, 99%, or 100% identity along the full length of the amino acid sequence of SEQ ID NO:16

(SEQ ID NO: 16; CDRs are highlighted)
QIQLVQSGPELRKPGETVKISCKASGYTFTIYGMNWMKQAPGKGLKWMG

WINTYTGEPTYADDFKGRFAFSLETSASTAFLQINNLTNEDTATYFC

ARSRFAYWGQGTLVTVSA;
and/or (b) a light chain comprising the amino acid sequence having at least 60%, 65%, 70%, 75%, 80%, 85%, 90%, 91%, 92% 0.93%, 94%, 95%, 96%, 97%, 98% 0.99%, or 100% identity along the full length of the amino acid sequence of SEQ ID NO:17.

(SEQ ID NO: 17; CDRs are highlighted)
DIVMTQSQKEMSTSVGDRVSVTCKASQNVGTNVAWYQQKPGQSPKALIY

SASYRYSGVPDRFTGSRSGTDFTLTISNVQSEDLAEYVCQQYNSYPLTF

GAGTKLELK.

In one embodiment, variability compared to the reference sequence is present only outside the CDRs.

In another aspect the disclosure provides isolated anti-human TAPBPL antibodies, or antigen binding fragments thereof, comprising 1, 2, 3, 4, 5, or all 6 complementarity determining regions (CDRs) selected from the group consisting of:

Heavy chain CDR1 (H-CDR1) comprising the amino acid sequence at least 80%, 85%, 90%, 95%, or 100% identical to the amino acid sequence GYFWH (SEQ ID NO:18);

Heavy chain CDR2 (H-CDR2) comprising the amino acid sequence at least 80%, 85%, 90%, 95%, or 100% identical to the amino acid sequence YISYSGTINYNPSLKN (SEQ ID NO:19);

Heavy chain CDR3 (H-CDR3) comprising the amino acid sequence at least 80%, 85%, 90%, 95%, or 100% identical to the amino acid sequence DDWDWFAY (SEQ ID NO:20);

Light chain CDR1 (L-CDR1) comprising the amino acid sequence at least 80%, 85%, 90%, 95%, or 100% identical to the amino acid sequence SASSSVNYMH (SEQ ID NO:21);

Light chain CDR2 (L-CDR2) comprising the amino acid sequence at least 80%, 85%, 90%, 95%, or 100% identical to the amino acid sequence DTSKLAS (SEQ ID NO:22); and Light chain CDR3 (L-CDR3) comprising the amino acid sequence at least 80%, 85%, 90% 95%, or 100% identical to the amino acid sequence FQGSGYPLT (SEQ ID NO:23).

As shown in the examples that follow, the disclosed antibodies are the first antibodies shown to have the ability to neutralize the inhibitory effects of TAPBPL on T cells. The sequences of these antibodies have been determined, including the complementarity determining regions (CDRs) disclosed herein. In a further embodiment, the anti-human TAPBPL antibody, or antigen-binding fragment thereof comprises:

(a) a heavy chain comprising the amino acid sequence having at least 60%, 65%, 70%, 75%, 80%, 85%, 90%, 91%, 92%, 93%, 94%, 95%, 96%, 97%, 98%, 99%, or 100% identity along the full length of the amino acid sequence of SEQ ID NO:24:

```
                  (SEQ ID NO:24; CDRs are highlighted)
DVQLQESGPGLVKPSQTLSLTCSVTGYSLTSGYFWHWIRQFPGNKLEWM

GYISYSGTTNYNPSLKNRISITHDSSKNQFELNLNSVTAEDTATYFCAG

DDWDWFAYWGQGTLVTVSA;
and/or
```

(b) a light chain comprising the amino acid sequence having at least 60%, 65%, 70%, 75%, 80%, 85%, 90%, 91%, 92%, 93%, 94%, 95%, 96%, 97%, 98%, 99%, or 100% identity along the full length of the amino acid sequence of SEQ ID NO:25).

```
                  (SEQ ID NO: 25; CDRs are highlighted)
ENVLTQSPAIMSASPGEKVTMTCSASSSVNYMHWYQQKSSTSPKLWIY

DTSKLASGVPGRFSGSGSGNSYSLTISSMEAEDVATYYCFQGSGYPLT

FGSGTKLEIK.
```

In one embodiment, variability compared to the reference sequence is present only outside the CDRs.

In one specific embodiment of these aspects, the antibody may be a monoclonal antibody or antigen-binding fragments thereof, and/or may be a humanized antibody or antigen-binding fragment thereof.

In some embodiments, the antibodies and fragments thereof (in the compositions or methods of the disclosure) are conjugated to one or more agents selected from the group including an additional therapeutic agent, such as a chemotherapeutic agent. A "chemotherapeutic agent" is a chemical compound useful in the treatment of cancer. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e. g., calicheamicin, especially calicheamicin gamma 11 and calicheamicin omega 11 (see, e.g., Agnew, Chem Intl. Ed. Engl., 33: 183-186 (1994)); dynemicin, including dynemicin A; bisphosphonates, such as clodronate; an esperamicin; as well as neocarzinostatin chromophor and related chromoprotein enediyne antibiotic chromophores), aclacinomysins, actinomycin, anthramycin, azaserine, blcomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; polysaccharide complex (JHS Natural Products. Eugene, Oreg.); razoxane;

rhizoxin; sizofiran; spirogermanium; tenuazonic acid; triaziquone; 2,2', 22"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel, ABRAXANE® Cremophor-free, albumin-engineered nanoparticle formulation of paclitaxel (American Pharmaceutical Partners, Schaumberg, Ill.), and doxetaxel; chloranbucil; gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluorometlhylomithinc (DMFO); rtinoids such as retinoic acid; capecitabine; and pharmaceutically acceptable salts, acids or derivatives of any of the above. Also included in the definition are proteasome inhibitors such as bortezomib (Velcade), BCL-2 inhibitors, AP antagonists (e.g. Smac mimics/xIAP and cIAP inhibitors such as certain peptides, pyridine compounds such as (S)—N-{6-benzo[1,3]dioxol-5-yl-1-[5-(4-fluoro-benzoyl)-pyridin-3-ylmethy-1]-2-oxo-1, 2-dihydro-pyridin-3-yl}-2-methylamino-propionamide, xIAP antisense). HDAC inhibitors (HDACI) and kinase inhibitors (Sorafenib).

In other embodiments, the antibodies and fragments thereof are linked to a detectable label, such as a radiolabel, an enzyme, a fluorescent label, a luminescent label, a bioluminescent label, a magnetic label, and/or biotin.

In some embodiments, the agent and/or detectable label is conjugated directly to the antibodies or fragments thereof. In other embodiments, the agent and/or detectable label is conjugated to the antibodies or fragments thereof via a linker. Suitable linkers include, but are not limited to, amino acid and polypeptide linkers disclosed herein. Linkers may be cleavable or non-cleavable.

In another aspect, the disclosure provides methods for treating an autoimmune disorder, comprising administering to a subject in need thereof an amount effective to treat the autoimmune disorder of one or more of:
 (a) an IgV domain from a protein selected from the group consisting of CD300c, BTN5 (Erythroid membrane-associated protein), TAPBPL (antigen processing (TAP) binding protein like protein). Skint8 (selection and upkeep of intraepithelial T cells 8 protein), and CD300f; and/or
 (b) an expression vector comprising a promoter operatively linked to a nucleic acid sequence encoding a protein selected from the group consisting of CD300c, BTN5 (Erythroid membrane-associated protein), TAPBPL (antigen processing (TAP) binding protein like protein), Skint8 (selection and upkeep of intraepithelial T cells 8 protein), and CD300f.

In one embodiment, the IgV domain comprises an IgV domain from CD300c. In another embodiment, the IgV domain comprises amino acids 28-114 of human CD300c. In a further embodiment, the IgV domain comprises amino acids 22-128 of human CD300c. In one embodiment, the method comprises administering the subject a polypeptide comprising, or an expression vector encoding, residues 21-183 of human CD300c. Exemplary CD300c sequences are SEQ ID NOs:1-2. In a further embodiment, the method comprises administering the subject a polypeptide comprising, or an expression vector encoding the amino acid sequence having at least 60%, 65%, 70%, 75%, 80%, 85%, 90%, 91%, 92%, 93%, 94%, 95%, 96%, 97%, 98%, 99%, or 100% identity along the full length of the amino acid sequence of SEQ ID NO:26.

```
Human CD300c-Ig fusion protein amino acid
sequences (hCD300c: lower case, Ig: upper):
                                          (SEQ ID NO: 26)
Mtvagpvggslsvqcryekehrtlnkfwcrppqilrcdkivetkgsagkr ngrvsirdspanlsftvtlenlteedagtywcgvdtpwlrdfhdpiveve vsvfpagtttasspqssmgtsgpptklpvhtwpsvtrkdspepsphpgsl fsnvrPRGPTIKPCPPCKCPAPNLLGGPSVFIFPPKIKDVLMISLSPIVT

CVVVDVSEDDPDVQISWFVNNVEVHTAQTQTHREDYNSTLRVVSALPIQH

QDWMSGKEFKCKVNNKDLPAPIERTISKPKGSVRAPQVYVLPPPEEEMTK

KQVTLTCMVTDFMPEDIYVEWTNNGKTELNYKNTEPVLDSDGSYFMYSKL

RVEKKNWVERNSYSCSVVHEGLHNHHTTKSFSRTPGK
```

In one embodiment, the IgV domain comprises an IgV domain from BTN5. In another embodiment, the IgV domain comprises amino acids 45-143 of human BTN5. In a further embodiment, the IgV domain comprises amino acids 30-144 of human BTN5. In one embodiment, the method comprises administering the subject a polypeptide comprising residues 30-155 of human BTN5 or an expression vector comprising a promoter operatively linked to a nucleic acid sequence encoding a polypeptide comprising residues 30-155 of human BTN5. Exemplary BTN5 amino acid sequences are provided in SEQ ID NOS: 3-4. In a further embodiment, the method comprises administering the subject a polypeptide comprising, or an expression vector encoding the amino acid sequence having at least 60%, 65%, 70%, 75%, 80%, 85%, 90%, 91%, 92%, 93%, 94%, 95%, 96%, 97%, 98%, 99%, or 100% identity along the full length of the amino acid sequence of SEQ ID NO:27.

```
Human BTN5-Ig fusion protein amino acid sequences
(hBTN5: lower case, Ig: upper):
                                          (SEQ ID NO: 27)
hagdagkfhvallggtaellcplslwpgtvpkevrwlrspfpqrsqavhi frdgkdqdedlmpeykgrtvlvrdaqegsvtlqildvrledqgsyrcliq vgnlskedtvilqvaaPRGPTIKPCPPCKCPAPNLLGGPSVFIFPPKIKD

VLMISLSPIVTCVVVDVSEDDPDVQISWFVNNVEVHTAQTQTHREDYNST

LRVVSALPIQHQDWMSGKEFKCKVNNKDLPAPIERTISKPKGSVRAPQVY

VLPPPEEEMTKKQVTLTCMVTDFMPEDIYVEWTNNGKTELNYKNTEPVLD

SDGSYFMYSKLRVEKKNWVERNSYSCSVVHEGLHNHHTTKSFSRTPGK
```

In one embodiment, the IgV domain comprises and IgV domain from TAPBPL. In another embodiment, the IgV domain comprises amino acids 198-297 of human TAPBPL. In a further embodiment, the IgV domain comprises amino acids 198-300 of human TAPBPL. In one embodiment, the method comprises administering the subject a polypeptide comprising, or an expression vector encoding, residues 19-405 of human TAPBPL. Exemplary TAPBPL amino acid sequences are provided in SEQ ID NOS: 5-6. In a further embodiment, the method comprises administering the subject a polypeptide comprising, or an expression vector encoding the amino acid sequence having at least 60%, 65%, 70%, 75%, 80%, 85%, 90%, 91%, 92%, 93%, 94%, 95%, 96%, 97%, 98%, 99%, or 100% identity along the full length of the amino acid sequence of SEQ ID NO:28.

```
Human TAPBPL-Ig fusion protein amino acid
sequences (hTAPBPL: lower case, Ig; upper case):
                                    (SEQ ID NO: 28)
Kphpaegqwravdvvldcflakdgahrgalassedraraslvlkqvpvld dgsledftdfqggtlaqddppiifeasvdlvqipqaeallhadcsgkevt ceisryflqmtettvktaawfmanmqvsgggpsislvmktprvtknealw hptlnlplspqgtvrtavefqvmtqtqslsfllgssasldcgfsmapgld lisvewrlqhkgrgqlvyswtagqgqavrkgatlepaqlgmardasltlp gltiqdegtyicqittslyraqqiiqlniqaspkvrlslaneallptlic diagyypldvvvtwtreelggspaqvsgasfsslrqsvagtysisssslta epgsagatytcqvthisleeplgastqvvpperrtPRGPTIKPCPPCKCP

APNLLGGPSVFIFPPKIKDVLMISLSPIVTCVVVDVSEDDPDVQISWFVN

NVEVHTAQTQTHREDYNSTLRVVSALPIQHQDWMSGKEFKCKVNNKDLPA

PIERTISKPKGSVRAPQVYVLPPPEEEMTKKQVTLTCMVTDFMPEDIYVE

WTNNGKTELNYKNTEPVLDSDGSYFMYSKLRVEKKNWVERNSYSCSVVHE

GLHNHHTTKSFSRTPGK
```

In one embodiment, the IgV domain comprises and IgV domain from Skint8. In another embodiment, the IgV domain comprises amino acids 35-140 of Skint8. In a further embodiment, the IgV domain comprises amino acids 29-140 of Skint8. In one embodiment, the method comprises administering the subject a polypeptide comprising, or an expression vector encoding residues 26-233 of Skint8. An exemplary Skint8 amino acid sequence is provided in SEQ ID NO:7. In a further embodiment, the method comprises administering the subject a polypeptide comprising, or an expression vector encoding the amino acid sequence having at least 60%, 65%, 70%, 75% 0.80%, 85%, 90% 0.91%, 92%, 93%, 94%, 95%, 96% 97%, 98%, 99%, or 100% identity along the full length of the amino acid sequence of SEQ ID NO:29

```
Mouse Skint8-Ig fusion protein amino acid
sequences (mouse Skint8: lower case, Ig:
upper case):
                                    (SEQ ID NO: 29)
eklrvttptrhllarvggqaelscqvipphsvmhmevrwfrsghsqpvyl yrgghkmseeaapeyanrtefvkeaigegkvslriyninilddgpyqcsf ndsgfidvaimnlnvtavgleteihvqapdadgvmvecntggwfprpqme wrdskgatlphslksysqdearffhmkmtllltnmshgsiiccisnpvtg eekqtsiiPRGPTIKPCPPCKCPAPNLLGGPSVFIFPPKIKDVLMISLSP

IVTCVVVDVSEDDPDVQISWFVNNVEVHTAQTQTHREDYNSTERVVSALP

IQHQDWMSGKEFKCKVNNKDLPAPIERTISKPKGSVRAPQVYVLPPPEEE

MTKKQVTLTCMVTDFMPEDIYVEWTNNGKTELNYKNTEPVLDSDGSYFMY

SKLRVEKKNWVERNSYSCSVVHEGLHNHHTTKSFSRTPGK
```

In one embodiment, the IgV domain comprises an IgV domain from CD300f. In another embodiment, the IgV domain comprises amino acids 2-140 of human CD300f. In a further embodiment, the IgV domain comprises amino acids 24-125 of human CD300f. In one embodiment, the method comprises administering the subject a polypeptide comprising, or an expression vector encoding, residues 20-155 of human CD300f. An exemplary CD300f amino acid sequence is provided in SEQ ID NO:8. In a further embodiment, the method comprises administering the subject a polypeptide comprising, or an expression vector encoding the amino acid sequence having at least 60%, 65%, 70%, 75%, 80%, 85%, 90%, 91%, 92%, 93%, 94%, 95%, 96%, 97%, 98%, 99%, or 100% identity along the full length of the amino acid sequence of SEQ ID NO:9

```
Human CD300F-Ig fusion protein amino acid
sequences (hCD300F: lower case, Ig: upper case):
                                    (SEQ ID NO: 09)
tqitgpttvnglergsltvqcvyrsgwetylkwwcrgaiwrdckilvkts gseqevkrdrvsikdnqknrtftvtmedlmktdadtywcgiektgndlgv tvqvtidpapvtqeetsssptltghhldnrhkllklPRGPTIKPCPPCKC

PAPNLLGGPSVFIFPPKIKDVLMISLSPIVTCVVVDVSEDDPDVQISWFV

NNVEVHTAQTQTHREDYNSTLRVVSALPIQHQDWMSGKEFKCKVNNKDLP

APIERTISKPKGSVRAPQVYVLPPPEEEMTKKQVTLTCMVTDFMPEDIYV

EWTNNGKTELNYKNTEPVLDSDGSYFMYSKLRVEKKNWVERNSYSCSVVH

EGLHNHHTTKSFSRTPGK
```

In all of these embodiments, the methods may be used to treat any suitable autoimmune disorder. In various non-limiting embodiments, the autoimmune disease may be selected from the group consisting of multiple sclerosis, type I diabetes, arthritis including but not limited to rheumatoid arthritis, systemic lupus erythematosus, Crohn's disease, scleroderma, sarcoidosis, ulcerative colitis, ankylosing spondylitis, autoimmune hepatitis, autoimmune myocarditis, dermatomyositis, Graves' disease, Sjogren's syndrome, and vitiligo, and other autoimmune diseases. In one embodiment, the methods further comprise administering to the subject an amount effective of an immune regulator to stimulate T cell function. Any suitable immune regulator may be used, including but not limited to anti-CD3 antibodies.

In another aspect, the disclosure provides fusion molecules comprising
(a) a first polypeptide comprising an IgV domain from a protein selected from the group consisting of CD300c, BTN5 (Erythroid membrane-associated protein), TAPBPL (antigen processing (TAP) binding protein like protein), Skint8 (selection and upkeep of intraepithelial T cells 8 protein), and CD300f and
(b) a heterologous molecule.

In one embodiment, the first polypeptide does not include any portion of CD300c, BTN5, TAPBPL, Skint8, or CD300f outside of the ECM domain. In another embodiment, the heterologous molecule comprises a second polypeptide selected from the group consisting of a constant region of an immunoglobulin or a fragment thereof (including but not limited to CH1, CH2, and/or CH3; Fe regions from immunoglobulins, including but not limited to native IgG1, IgG2, or IgG4). In this embodiment, the immunoglobulin or a fragment thereof adds functionality to the by, for example, helping target the first polypeptide to a cell type that has a cell surface receptor to which the immunoglobulin or a fragment thereof selectively binds. As a result, fusion molecules of this embodiment are particularly useful for therapeutic applications. As will be understood by those of skill in the art, any suitable immunoglobulin or a fragment thereof can be employed that targets a cell or tissue of interest. The immunoglobulin or a fragment thereof may be recombinantly expressed as part of the polypeptide. In another embodiment, the heterologous molecule comprises an organic molecule of interest.

The fusion molecules disclosed herein may be used, for example, in the methods of the invention. In a specific embodiment, a fusion molecule is a fusion protein comprising the first polypeptide and a second polypeptide sequence. In one embodiment, the second polypeptide is a constant region of an immunoglobulin or a fragment thereof (e.g., CH1, CH2, and/or CH3). In various non-limiting embodiments, Fc regions from immunoglobulins including but not limited to IgG1, IgG2, or IgG4 can be used to produce such a fusion protein. In various further embodiments, hybrid IgG1/IgG4 Fc domains can be used to produce such a fusion protein as can modified IgG1 Fc domains (e.g., IgG1 modified to improve binding to certain Fc gamma receptors; IgG1 modified to minimize effector function; IgG1 with altered/no glycan; and IgG1 with altered pH-dependent binding to FcRn) and modified IgG4 Fc domains (e.g., IgG4 modified to prevent binding to Fc gamma receptors and/or complement). In other embodiments, the first polypeptide may act as a targeting moiety to target a therapeutic second polypeptide to a cell or tissue target of interest; non-limiting embodiments of such therapeutic second polypeptides include but are not limited to interferon-γ, interferon-β, interferon-α, interleukin-2 ("IL-2"), interleukin-7 ("IL-7"), interleukin 9 ("IL-9"), interleukin-10 ("IL-10"), interleukin-12 ("IL-12"), interleukin-15 ("IL-15"), interleukin-23 ("IL-23"), granulocyte macrophage colony stimulating factor ("GM-CSF"), granulocyte colony stimulating factor ("G-CSF")), or growth factors.

In other embodiments, the fusion molecule is a fusion protein or a conjugate (such as via a linker) comprising the first polypeptide and an organic molecule of interest. In this embodiment, the first polypeptide may, for example, act as a targeting moiety to target the organic molecule to which it is fused or conjugated to particular organs or tissues (e.g., lymphoid organs or tissues). The attached appendices provide information regarding the organs and tissues expressing the first polypeptide. The organic molecule fused or conjugated to the first polypeptide may be a molecule that one skilled in the art is interested in targeting to a particular organ(s) or tissue(s) (e.g., a cytokine, drug, marker, etc.).

In one embodiment, the first polypeptide comprises an IgV domain from CD300c. In another embodiment, the IgV domain comprises amino acids 28-114 of human CD300c. In a further embodiment, the IgV domain comprises amino acids 22-128 of human CD300c. In one embodiment, the first polypeptide comprises residues 21-183 of human CD300c. Exemplary CD300c amino acid sequences are provided in SEQ ID NOs:1-2. In another embodiment, the fusion molecule comprises the amino acid sequence having at least 60%, 65%, 70%, 75%, 80%, 85%, 90%, 91%, 92%, 93%, 94%, 95% 96%, 97%, 98%, 99%, or 100% identity along the full length of the amino acid sequence of SEQ ID NO:26.

Human CD300c-Ig fusion protein amino acid
sequences (hCD300c: lower case, Ig: upper case):
(SEQ ID NO: 26)
Mtvagpvggslsvqcryekehrtlnkfwcrppqilrcdkivetkgsagkr ngrvsirdspanlsftvtlenlteedagtywcgvdtpwlrdfhdpiveve vsvfpagtttasspqssmgtsgpptklpvhtwpsvtrkdspepsphpgsl fsnvrPRGPTIKPCPPCKCPAPNLLGGPSVFIFPPKIKDVLMISLSPIVT -continued
CVVVDVSEDDPDVQISWFVNNVEVHTAQTQTHREDYNSTLRVVSALPIQH

QDWMSGKEFKCKVNNKDLPAPIERTISKPKGSVRAPQVYVLPPPEEEMTK

KQVTLTCMVTDFMPEDIYVEWTNNGKTELNYKNTEPVLDSDGSYFMYSKL

RVEKKNWVERNSYSCSVVREGLHNHHTTKSFSRTPGK

In one embodiment, the first polypeptide comprises an IgV domain from BTN5. In another embodiment, the IgV domain comprises amino acids 45-143 of human BTN5. In a further embodiment, the IgV domain comprises amino acids 30-144 of human BTN5. In one embodiment, the first polypeptide comprises residues 30-155 of human BTN5. Exemplary BTN5 amino acid sequences are provided in SEQ ID NOs:3-4. In another embodiment, the fusion molecule comprises the amino acid sequence having at least 60%, 65%, 70%, 75%, 80%, 85%, 90%, 91%, 92%, 93%, 94%, 95%, 96%, 97%, 98%, 99%, or 100% identity along the full length of the amino acid sequence of SEQ ID NO:27.

Human BTN5-Ig fusion protein amino acid sequences
(hBTN5: lower case, Ig: upper case):
(SEQ ID NO: 27)
hagdagkfhvallggtaellcplslwpgtvpkevrwlrspfpqrsqavhi frdgkdqdedlmpeykgrtvlvrdaqegsvtlqildvrledqgsyrcliq vgnlskedtvilqvaaPRGPTIKPCPPCKCPAPNLLGGPSVFIFPPKIKD

VLMISLSPIVTCVVVDVSEDDPDVQISWFVNNVEVHTAQTQTHREDYNST

LRVVSALPIQHQDWMSGKEFKCKVNNKDLPAPIERTISKPKGSVRAPQVY

VLPPPEEEMTKKQVTLTCMVTDFMPEDIYVEWTNNGKTELNYKNTEPVLD

SDGSYFMYSKLRVEKKNWVERNSYSCSVVHEGLHNHHTTKSFSRTPGK

In one embodiment, the first polypeptide comprises an IgV domain from TAPBPL, in another embodiment, the IgV domain comprises amino acids 198-297 of human TAPBPL. In a further embodiment, the IgV domain comprises amino acids 198-300 of human TAPBPL. In one embodiment, the first polypeptide comprises residues 19-405 of human TAPBPL. Exemplary TAPBPL amino acid sequences are provided in SEQ ID NO:5-6. In another embodiment, the fusion molecule comprises the amino acid sequence having at least 60%, 65%, 70%, 75%, 80%, 85%, 90%, 91%, 92%, 93%, 94%, 95%, 96%, 97%, 98%, 99%, or 100% identity along the full length of the amino acid sequence of SEQ NO:28.

Human TAPBPL-Ig fusion protein amino acid
sequences (hTAPBPL: lower case, Ig: upper case):
(SEQ ID NO: 28)
Kphpaegqwravdvvldcflakdgahrgalassedraraslvlkqvpvld dgsledftdfqggtlaqddppiifeasvdlvqipqaeallhadcsgkevt ceisryflqmtettvktaawfmanmqvsgggpsislvmktprvtknealw hptlnlplspqgtvrtavefqvmtqtqslsfllgssasldcgfsmapgld lisvewrlqhkgrgqlvyswtagqgqavrkgatlepaqlgmardasltlp gltiqdegtyicqittslyraqqiiqlniqaspkvrlslaneallptlic diagyypldvvvtwtreelggspaqvsgasfsslrqsvagtysisssita epgsagatytcqvthisleeplgastqvvpperrtPRGPTIKPCPPCKCP

APNLLGGPSVFIFPPKIKDVLMISLSPIVTCVVVDVSEDDPDVQISWFVN

-continued
NVEVHTAQTQTHREDYNSTLRVVSALPIQHQDWMSGKEFKCKVNNKDLPA

PIERTISKPKGSVRAPQVYVLPPPEEEMTKKQVTLTCMVTDFMPEDIYVE

WTNNGKTELNYKNTEPVLDSDGSYFMYSKLRVEKKNWVERNSYSCSVVHE

GLHNHHTTKSFSRTPGK

In one embodiment, the first polypeptide comprises an IgV domain from Skint8. In another embodiment, the IgV domain comprises amino acids 35-140 of Skint8. In a further embodiment, the IgV domain comprises amino acids 29-140 of Skint8. In one embodiment, the first polypeptide comprises residues 26-233 of Skint& An exemplary Skint8 amino acid sequence is provided in SEQ ID NO:7. In another embodiment, the fusion molecule comprises the amino acid sequence having at least 60%, 65%, 70%, 75%, 80%, 85%, 90%, 91%, 92%, 93%, 94%, 95%, 96%, 97%, 98%, 99%, or 100% identity along the full length of the amino acid sequence of SEQ NO:29.

```
Mouse Skint8-Ig fusion protein amino acid
sequences (lower case, Ig: upper case):
                                      (SEQ ID NO: 29)
eklrvttptrhllarvggqaelscqvipphsvmhmevrwfrsghsqpvyl yrgghkmseeaapeyanrtefvkeaigegkvslriyniniliddgpyqcsf ndsgfidvaimnlnvtavgleteihvgapdadgvmvecntggwfprpqme wrdskgatlphslksysqdearffhmkmtllltnmshgsiiccisnpvtg eekqtsiiPRGPTIKPCPPCKCPAPNLLGGPSVFIFPPKIKDVEMISLSP

IVTCVVVDVSEDDPDVQISWFVNNVEVHTAQTQTHREDYNSTLRVVSALP

IQHQDWMSGKEFKCKVNNKDLPAPIERTISKPKGSVRAPQVYVLPPPEEE

MTKKQVTLTCMVTDFMPEDIYVEWTNNGKTELNYKNTEPVLDSDGSYFMY

SKLRVEKKNWVERNSYSCSVVHEGLHNHHTTKSFSRTPGK
```

In one embodiment, the IgV domain comprises an IgV domain from CD300f. In another embodiment, the IgV domain comprises amino acids 2-140 of human CD300f. In a further embodiment, the IgV domain comprises amino acids 24-125 of human CD300f. In one embodiment, the first polypeptide comprises residues 20-155 of human CD300f. An exemplary CD300f amino acid sequence is provided in SEQ ID NO:8. In one embodiment, the fusion molecule comprises the amino acid sequence having at least 60%, 65%, 70%, 75%, 80%, 85%, 90%, 91%, 92%, 93%, 94%, 95%, 96%, 97%, 98%, 99%, or 100% identity along the full length of the amino acid sequence of SEQ ID NO:9.

```
Human CD300F-Ig fusion protein amino acid
sequences (hCD300F: lower case, Ig: upper case):
                                      (SEQ ID NO: 09)
tqitgpttvnglergsltvqcvyrsgwetylkwwcrgaiwrdckilvkts gseqevkrdrvsikdnqknrtftvtmedlmktdadtywcgiektgndlgv tvqvtidpapvtqeetsssptltghhldnrhkllklPRGPTIKPCPPCKC

PAPNLLGGPSVFIFPPKIKDVLMISLSPIVTCVVVDVSEDDPDVQISWFV

NNVEVHTAQTQTHREDYNSTLRVVSALPIQHQDWMSGKEFKCKVNNKDLP

APIERTISKPKGSVRAPQVYVLPPPEEEMTKKQVTLTCMVTDFMPEDIYV

EWTNNGKTELNYKNTEPVEDSDGSYFMYSKLRVEKKNWVERNSYSCSVVH

EGLHNHHTTKSFSRTPGK
```

As used throughout the present application, the term "polypeptide" is used in its broadest sense to refer to a sequence of subunit amino acids, whether naturally occurring or of synthetic origin. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may be linked to other compounds to promote an increased half-life in vivo, such as by PEGylation, HESylation, PASylation, or glycosylation. Such linkage can be covalent or non-covalent as is understood by those of skill in the art. The polypeptides may be linked to any other suitable linkers, including but not limited to any linkers that can be used for purification or detection (such as FLAG or His tags).

In another aspect, the present disclosure provides nucleic acids encoding the antibodies or fusion molecules in which the heterologous molecule is a polypeptide of any aspect or embodiment of the invention. The nucleic acid sequence may comprise RNA or DNA. Such nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the antibodies or fusion molecules disclosed herein.

In a further aspect, the present disclosure provides nucleic acid expression vectors comprising the nucleic acid of any embodiment of the disclosure operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the disclosure are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive. The expression vector must be replicable in the host organisms either as an episome or by integration into host chromosomal DNA. In one, the expression vector comprises a plasmid; in another embodiment a viral vector, including but not limited to adenoviral vectors or rAAV vectors.

In another aspect, the present disclosure provides recombinant host cells comprising the nucleic acid expression vectors of the disclosure. The host cells can be either prokaryotic or eukaryotic. The cells can be transiently or stably transfected or transduced. Such transfection and transduction of expression vectors into prokaryotic and eukaryotic cells can be accomplished via any suitable technique. A method of producing the antibodies or fusion molecules of the disclosure is also provided herein. The method comprises the steps of (a) culturing a host according to this aspect of the disclosure under conditions conducive to the expression of the antibodies or fusion molecules, and (b) optionally, recovering the expressed antibodies or fusion molecules. The expressed antibodies or fusion molecules can be recovered from the cell free extract, cell pellet, or recovered from the culture medium.

In a further aspect, the present disclosure provides pharmaceutical compositions, comprising the antibodies or fusion molecules, nucleic acids, nucleic acid expression vectors, or recombinant host cells, of any aspect or embodiment of the disclosure, and a pharmaceutically acceptable carrier. The pharmaceutical compositions of the disclosure can be used, for example, in the methods of the disclosure. The pharmaceutical composition may comprise in addition to the polypeptides, nucleic acids, etc. of the disclosure (a) a lyoprotectant; (b) a surfactant; (c) a bulking agent; (d) a tonicity adjusting agent; (e) a stabilizer; (f) a preservative and/or (g) a buffer.

In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The antibodies or fusion molecules, nucleic acids, etc. of the disclosure may be the sole active agent in the pharmaceutical composition, or the composition may further comprise one or more other active agents suitable for an intended use.

The pharmaceutical compositions described herein generally comprise a combination of a therapeutic described herein and a pharmaceutically acceptable carrier, diluent, or excipient. Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by any suitable route. In a preferred embodiment, the pharmaceutical compositions and formulations are designed for oral administration. Conventional pharmaceutical carriers, aqueous, powder or oily bases, thickeners and the like may be necessary or desirable.

The pharmaceutical compositions can be in any suitable form, including but not limited to tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Example 1. CD300c

In this example, we describe CD300c as a novel T cell co-inhibitory molecule that shares significant sequence homology with existing B7 family members. CD300c protein is expressed on professional antigen-presenting cells (APC), including B cells, monocytes, macrophages and dendritic cells (DCs). The putative CD300c counter-receptor is expressed on CD4 and CD8 T cells, and the expression levels are upregulated upon activation. Soluble human and mouse CD300c-Fc fusion proteins significantly inhibit the proliferation, activation, and cytokine production by CD4 and CD8 T cells in vitro.

Administration of CD300c-Fc protein attenuates graft-versus-host disease (GVHD) in mice, and autoimmune diseases including experimental autoimmune encephalomyclitis (EAE) and collagen-induced arthritis (CIA), animal models for human multiple sclerosis (MS) and rheumatoid arthritis (RA). Furthermore, anti-CD300 antibodies inhibit tumor growth in melanoma and colon cancer mouse models, which is related to the neutralization of the inhibitory activity of CD300c on T cells and other immune cells. Our results demonstrate that therapeutic interaction with the CD300c inhibitory pathway represents a new strategy to modulate T cell-mediated immunity for the treatment of GVHD and autoimmune disease, as well as cancer.

Materials and Methods

Cloning and Purification of hCD300c and mCD300c2

The extracellular domains of hCD300c (aa29-183) and mCD300c2 (aa22-193) were cloned and fused into a pCMV6-AC-FC-S expression vector containing the constant region of mouse IgG2a (ORIGENE). The vectors were transfected into HEK293F cells. The fusion proteins were purified for supernatant using Protein G Sepharose 4 Fast Flow™ according to the manufacturer's instructions (GE Healthcare). Purified proteins were verified by SDS-PAGE, Coomassie Staining and Western blot. Protein was quantified using the Pierce™ BCA Protein Assay Kit (Pierce, Rockford, Ill.). Control Ig (recombinant mouse IgG2a Fc protein) was purchased from BXCell (West Lebanon, NH).

SDS-PAGE and Western Blot

Purified CD300c-Ig was loaded on a 12% SDS-PAGE, and stained with Coomassie blue or transferred to a polyvinylidene fluoride membrane. The protein containing membrane was incubated with HRP conjugated anti-mouse IgG2 antibody, or anti-hCD300c antibody (Novus Biologicals, Littleton, Colo.) followed by HRP conjugated second antibody, and then developed with Super Signal®, West Pico chemiluminescent Substrate (Thermo Scientific).

Flow Cytometry Analysis

Single cell suspensions of organs were stained with the fluorochrome-conjugated antibodies protein as described [35; 36; 37; 38]. For intracellular staining, the cells were first permeabilized with a BD Cytofix/Cytopenn solution for 20 minutes at 4° C. Direct or indirect staining of fluorochrome-conjugated antibodies included: CD4, CD8, CD19, B220, CD11c, CD11b, F4/80, $H2^b$, Annexin V, Ki67, CD44, CD62L, CD69, CTLA-4, CD28, PD-1, BTLA, and ICOS and mCD300c2 (BioLegend, or BD Biosciences, San Jose, Calif., San Diego, Calif.). mCD300c2-Ig and hCD300c-Ig were biotinylated with sulfo-NHS-LC-Biotin (Pierce). The samples were analyzed on a FACSCalibur™ or LSR-Fortessa™ X-20 Cell Analyzer (BD Biosciences). Data analysis was done using FlowJo™ software (Ashland, Oreg.).

Limulus Amebocyte Lysate (LAL) Assay

The endotoxin level in the purified proteins was determined by the endpoint chromogenic LAL test according to the manufacturer's instructions (Lonza, Walkersville, Md.) [39].

In Vitro T Cell Proliferation Assays

Normal human peripheral blood $CD3^+$ Pan T Cells that were negatively isolated from mononuclear cells using an indirect immunomagnetic Pan-T labeling system were purchased from ALLCELLS, LLC (Alameda, Calif.). Murine $CD3^+$ T cells were purified from C57BL/6 mice by an immunomagnetic system (Miltenyi, Auburn, Calif.), and the purity of the cells was usually >95%. T cells were stimulated with anti-CD3 and/or anti-CD28 antibodies (Biolegend) in the presence of CD300c-Ig or control Ig. Proliferative response was assessed by pulsing the culture with 1 μCi of [$^3$H] thymidine (PerkinElmer, Inc., Downers Grove, Ill.) 12 hours before harvest. Incorporation of [$^3$H] thymidine was measured by liquid scintillation spectroscopy (PerkinElmer, Inc.). For carboxyfluorescein diacetate succinimidyl ester (CFSE) assay, splenocytes were labeled with CFSE (ThermoFisher Scientific) and stimulated with anti-CD3 in the presence of CD300c-Ig or control Ig. The cells were analyzed by flow cytometry.

Mice

Four-week-old female C57BL/6 and BALB/c mice were purchased from Jackson Laboratory. The mice were used in accordance with a protocol approved by the Institutional Animal Care and Use Committee of the University of Connecticut.

GVHD Model

BALB/c recipients received 900 cGy total body irradiation from a 137Cs source (Gammator-50 Gamma Irradiator; Radiation Machinery Corporation, Parsippany, N.J.). Two to four hours later, the mice were injected intravenously (i.v.) with BM and spleen cells from C57BL/6 mice. The recipients were injected i.p. with hCD300c-Ig, or control Ig. The severity of GVHD was evaluated with a clinical GVHD scoring system. In brief, GVHD recipients in coded cages were individually scored every week for five clinical parameters on a scale from 0 to 2: weight loss, posture, activity, fur texture and skin integrity. A clinical GVHD index was generated by summation of the five criteria scores (maximum index=10).

GVHD target organs were harvested for histopathological analysis. The organs were formalin-preserved, paraffin-embedded, sectioned and hematoxylin/eosin (H&E)-stained. Assessment of tissue damage was performed based on scoring systems previously described [40]. Briefly, liver GVHD was scored on the number of involved tracts and severity of liver cell necrosis; the maximum score is 10. Gut GVHD was scored on the basis of crypt apoptosis and lamina propria inflammation; the maximum score is 8. Lung GVHD was scored on the periluminal infiltrates, pneumonitis, and the severity of lung tissues involved; the maximum score is 9.

Induction and assessment of EAE

Mouse $MOG_{35-55}$ (GL Biochem, Shanghai, China) was emulsified in complete Freud's adjuvant (Sigma-Aldrich, St Louis, Mo., USA) supplemented with *Mycobacterium tuberculosis* H37Ra (Difco Laboratories. Detroit. Mich.). Mice were injected s.c. with the MOG at 4 points in the dorsal flank on day 0. The mice were also injected i.p. with 500 ng of purified *Bordetella pertussis* toxin (Sigma-Aldrich). The mice were injected i.p. with hCD300c-Ig, or control Ig, and observed for clinical scores based on the following scale: 0, normal; 0.5, partially limp tail; 1, paralyzed tail; 2, loss in coordinated movement, hind limb paresis; 2.5, one hind limb paralyzed; 3, both hind limbs paralyzed; 3.5, hind limbs paralyzed, weakness in forelimbs; 4, forelimbs paralyzed; 5, moribund or dead. As required by animal ethics, mice were euthanized beyond a clinical score of 4.

Induction and Assessment of Collagen-Induced Arthritis (CIA)

Type II collagen (CII) (2 mg/ml) was emulsified with an equal volume of complete Freund's adjuvant (CFA). DBA/l mice were injected s.c. 1 cm from the base of the tail with 50 ul of the emulsion on day 0. On day 14, the mice were receive a booster injection of the CII/incomplete Freund's adjuvant (IFA) emulsion s.c. around the base of the tail. When CIA symptom occurred, the mice were injected i.p. with hCD300c-Ig, or control Ig. The development of CIA was assessed over time. The clinical severity of arthritis in each paw was quantified according to a graded scale from 0 to 4 as follows: 0, no swelling; 1, swelling in one digit or mild edema; 2, moderate swelling affecting several digits; 3, severe swelling affecting most digits; and 4, the most severe swelling and/or ankyloses.

Generation of Anti-hCD300c Polyclonal and Monoclonal Antibodies

BALB/c mice were immunized with 100 sg hCD300c-Ig protein emulsified in complete Freund's adjuvant (CFA) on day 0 and boosted on day 14 and day 21 in the same protein quantity in incomplete Freund's adjuvant (IFA). The mice were boosted with 100 μg hCD300c-Ig without IFA 3 times (days 28, 29, and 30). On day 31, the serum that contain anti-CD300c polyclonal antibody was harvested.

To make anti-hCD300c monoclonal antibodies, the spleens were also harvested from the immunized mice on day 31. Single-cell suspension of the splenocytes were fused to X63-Ag8.653 myeloma cells to produce hybridomas. ELISA was performed to identify the hybridomas that could produce mAbs that reacted with hCD300c-Ig, but not with control Ig protein. These hybridoma clones were subcloned by limiting dilution. The anti-hCD300c mAbs were further screened for the ability to neutralize the inhibitory activity of hCD300c on T cell proliferation and activation. The anti-hCD300c mAbs were purified for supernatant of the hybridomas using Protein G Sepharose 4 Fast Flow according to the manufacturer's instructions (GE Healthcare).

Evaluation of Local Tumor Growth

Murine CT-26 colon cancer cells and B16F10 melanoma cells were obtained from the National Cancer Institute and ATCC. The cancer cells were injected s.c. into syngeneic BALB/c or C57BL/6 mice. Anti-hCD300c or control mAb was then injected into the tumor injection site. Tumor size (volume) was determined every other day by caliper measurements of the shortest (A) and longest (B) diameter, using the formula V=(A2B)/2.

Statistical Analysis

P-values were based on the two-sided Student's t test. A confidence level above 95% (p<0.05) was determined to be significant.

Results:

hCD300c Inhibits the Proliferation and Activation of Mouse and Human T Cells in Vitro To investigate whether CD300c protein can affect T cell function, we produced an hCD300c-Ig fusion protein by cloning the extracellular domain of the hCD300c gene into an expression vector containing the constant region of the mouse IgG2a. The expression vector was then transfected into human HEK-293 cells to produce hCD300c-Ig fusion protein that was then purified from the supernatant of the cells. A relatively high purity of hCD300c-g protein was obtained, as determined by Coomassie blue-stained SDS-PAGE. The identity of the fusion protein was verified by Western blot using anti-IgG2a antibody or anti-hCD300c antibody. The actual molecular weight (MW) of the hCD300c-Ig was higher than the predicted MW, suggesting that the recombinant protein was glycosylated. The endotoxin level was less than 0.01 EU/ml of 1 µg of purified protein.

We then determined whether hCD300c-Ig protein affected T cell proliferation. To do this, $CD3^+$ T cells were purified from splenocytes of C57BL/c mice, and cultured on plates pre-coated with anti-CD3 antibody in the presence of graded doses of hCD300-Ig (800, 1600, and 3200 ng/ml) for 3 days. Since the molecular weight of hCD300-Ig fusion protein is ~1.5-fold higher than that of control Ig protein, we used equimolar amounts of the control Ig as a control. T cell proliferation was measured by [$^3$H] thymidine incorporation. As shown in FIG. 1A, hCD300c-Ig inhibited anti-CD3-activated T cell proliferation in a dose-responsive manner, with ~32%, 72% and 78% inhibition by 800, 1600, and 3200 ng/ml hCD300c-Ig, respectively, as compared to equimolar amounts of control Ig. We also determined whether hCD300c could inhibit anti-CD3 and anti-CD28 antibody-activated T cell proliferation. Similarly, hCD300c-Ig reduced anti-CD3 and anti-CD28-activated T cell proliferation in a dose-dependent manner, although to a lesser extent than that with anti-CD3 activation only (FIG. 1B).

To confirm the effect on T cell proliferation and to determine whether hCD300c affects CD4 and/or CD8 T cells, we performed a carboxyfluorescein diacetate succinimidyl ester (CFSE) dilution assay. Murine splenocytes were labelled with CFSE, and then cultured with anti-CD3 antibody in the presence of graded doses of hCD300c-Ig or control Ig. T cell proliferation was measured by CFSE fluorescent dilution in CD4 and CD8 T cells. As shown in FIG. 1C-F, hCD300c-Ig inhibited anti-CD3-activated proliferation of both CD4 and CD8 T cells in a dose-dependent manner.

We next determined whether hCD300c-Ig affects the activation of T cells in vitro. CD69 is an early activation marker. After splenocytes were cultured with anti-CD3 antibody and hCD300c-Ig or control Ig, the expression of the CD69 on CD4 and CD8 T cells was analyzed 24 hours later. As shown in FIG. 1G-J, hCD300c-Ig at the dose of 3200 ng/ml significantly reduced the expression of CD69 on both CD4 and CD8 T cells. The results suggest that hCD300c also inhibits the activation of CD4 and CD8 T cells.

Having demonstrated that hCD300c-Ig inhibited murine T cells proliferation in vitro, we examined whether hCD300c-Ig affected human T cells. Purified human T cells were cultured with anti-CD3 antibody in the presence of graded doses of hCD300-Ig or control Ig, and T cell proliferation was measured by [$^3$H] thymidine incorporation. Similarly, hCD300c-Ig markedly inhibited human T cell proliferation with ~53% and 77% inhibition by 1500, and 3000 ng/ml hCD300c-g, respectively (FIG. 1K). Furthermore, hCD300c-Ig at both 1600 ng/ml and 3200 ng/ml doses significantly reduced the expression of CD69 on both human CD4 and CD8 T cells (FIG. 1L, M).

Taken together, our results indicate that hCD300c-Ig inhibits TCR-mediated proliferation and/or activation of both mouse and human T cells in vitro. hCD300c has similar inhibitory effects in both human and mouse primary T cells, suggesting that its binding partner and its conferred function on T cells may be conserved across species.

mCD300c2 Inhibits the Proliferation and Activation of Mouse T Cells In Vitro

Figure 2:
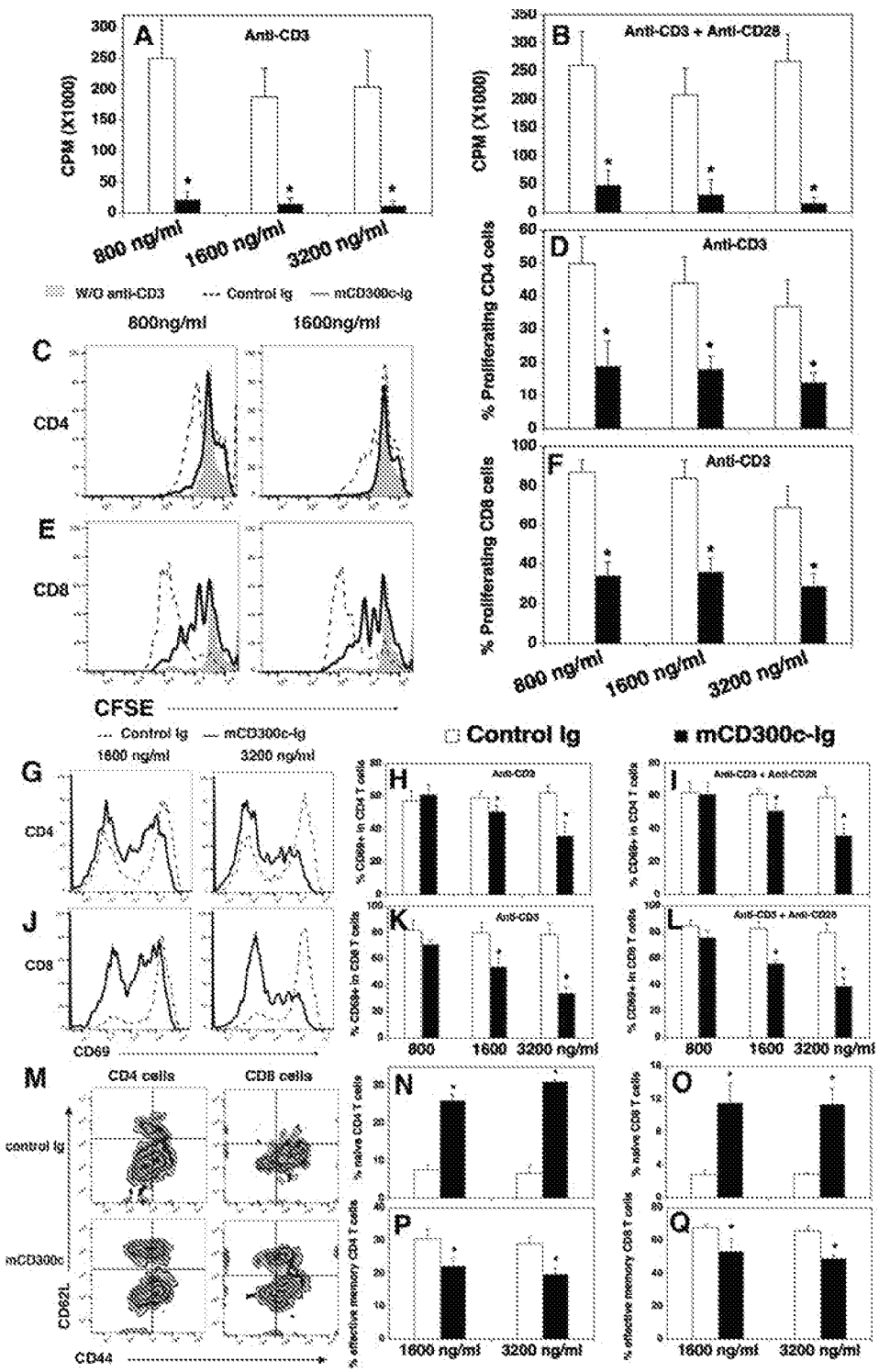
FIG. 2. The effects of mCD300c-Ig protein on the proliferation and activation of mouse T cells in vitro. (A, B) CD3$^+$ T cells were isolated from the spleen of C57BL/6 mice and cultured with (A, B) plate-bound anti-CD3 antibody (1 µg/ml) and (B) anti-CD28 antibody (0.5 µg/ml) in the presence of graded doses of mCD300c2-Ig protein (800, 1600, and 3200 ng/ml) or equimolar amounts of control Ig protein for 3 days. Cell proliferation was measured by [$^3$H] thymidine incorporation. (C-F) Mouse splenic cells were labelled with CFSE and cultured with anti-CD3 antibody (1 µg/ml) and graded doses of mCD300c2-Ig protein or control Ig protein as (A). The cells were then stained with anti-CD4 and CD8 antibodies and analyzed for CFSE levels by CD4$^+$ and CD8$^+$ T cells. (C, E) Representative flow cytometric analysis of CFSE distribution of CD4$^+$ or CD8$^+$ T cells. (D, F) statistical analysis of CFSE$^{lo}$ proliferating CD4$^+$ or CD8$^+$ T cells. (G-Q) Mouse splenic cells were cultured with (G-Q) anti-CD3 antibody and (1, L) anti-CD28 antibody in the presence of graded doses of mCD300c2-Ig or control Ig protein as (A, B). The cells were analyzed for the expression of (G-L) CD69 24 hours later, (M-Q) CD44 and CD62L 72 hours later. (G, J, M) Representative flow cytometric profiles, and (H, I, K, L, N-Q) statistical analyses of the percentages of CD69$^+$, CD44$^{low}$CD62L$^{hi}$ naïve, and CD44$^{hi}$CD62L$^{low}$ effector memory CD4 and CD8 T cells. The data were pooled from 3 independent experiments and expressed as mean±SD. *P<0.05 compared with control Ig.

We also produced a mCD300c2-g protein by fusing the extracellular domain of mCD300c2 to the mouse IgG2a constant region, and analyzed the effects of purified mCD300c2-Ig fusion protein on mouse T cell proliferation and activation in vitro. We found that mCD300c2-Ig markedly inhibited anti-CD3-induced T cell proliferation, with more than 90% inhibition by 800, 1600, or 3200 ng/ml of mCD300c2-Ig (FIG. 2A). mCD300c2-Ig also inhibited anti-CD3 and anti-CD28 antibody-induced T cell proliferation, with ~81%, 85% and 94% inhibition by 800, 1600, and 3200 ng/ml hCD300c-Ig, respectively (FIG. 2B). CFSE dilution assay confirmed that mCD300c2-Ig inhibited anti-CD3-induced proliferation of both $CD4^+$ and $CD8^+$ T cells (FIG. 2C-F).

Like hCD300c-Ig, mCD300c2-Ig significantly reduced the expression of CD69 on both $CD4^+$ and $CD8^+$ T cells induced by either anti-CD3 antibody, or anti-CD3 plus anti-CD28 antibodies, and the reduction was also in dose-dependent manner (FIG. 2G-L). To further confirm that mCD300c2-Ig inhibits T cell activation, we analyzed the expression of CD44 and CD62L by $CD4^+$ and $CD8^+$ T cells. It has been reported that naïve T cells are $CD44^{low}CD62L^{hi}$, while effective memory T cells are $CD44^{hi}CD62L^{low}$. As shown in FIG. 2M-Q, mCD300c2-Ig significantly increased the percentages of $CD44^{low}CD62L^{hi}$ naïve cells in anti-CD3-activated $CD4^+$ and $CD8^+$ T cells, but decreased the percentages of $CD44^{hi}CD62L^{low}$ effector memory T cells. The results further suggest that mCD300c2-g inhibits the activation of $CD4^+$ and $CD8^+$ T cells.

Collectively, our results indicate that both hCD300c-Ig and mCD300c2-g inhibit TCR-mediated proliferation and activation of both CD4 and CD8 T cells in vitro, providing further evidence that CD300c has T cell co-inhibitory properties.

mCD300c2 Inhibits Cytokine Production from T Cells

Figure 3:
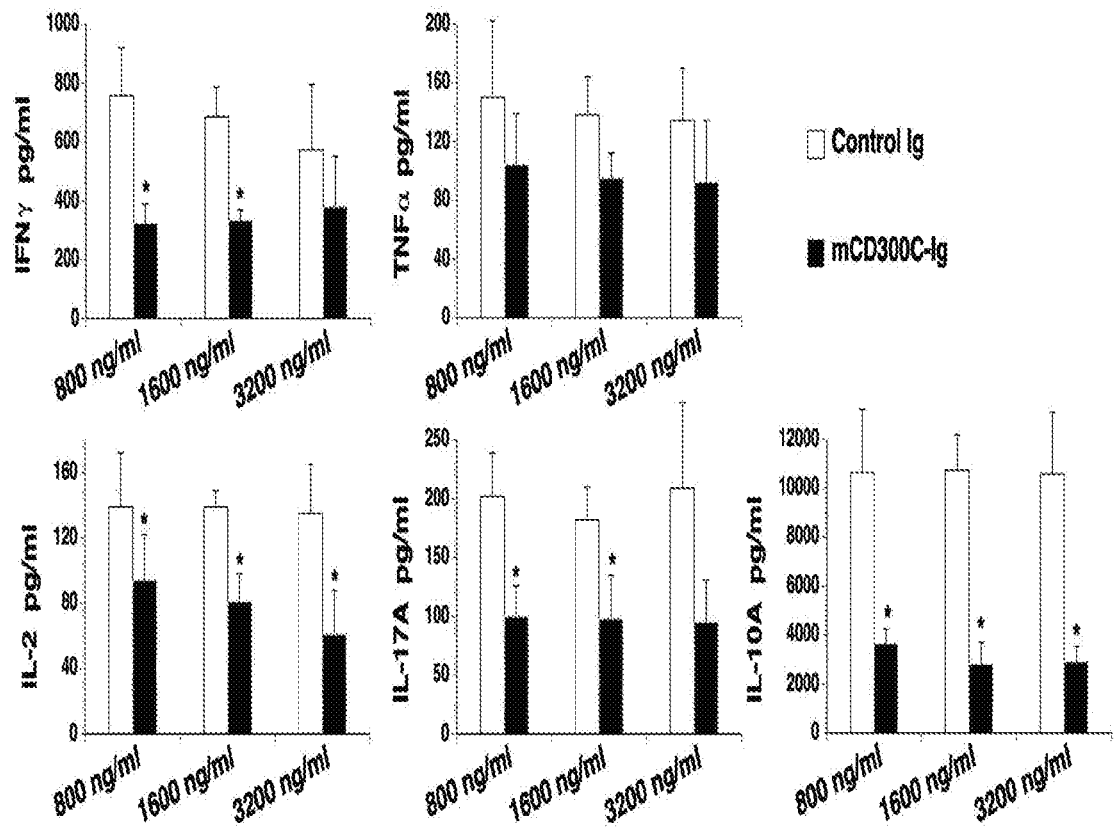
FIG. 3. mCD300c2 suppresses cytokine production from T cells. Purified murine T cells were cultured with plate-bound anti-CD3 antibody (1 µg/ml) in the presence of graded doses of mCD300c2-Ig protein or control Ig protein for 3 days as FIG. 3A. The levels of IFNγ, TNFα, IL-2, IL-17A and IL-10 in the supernatant were measured by ELISA kits. The data were pooled from 3 independent experiments and expressed as mean±SD. *P<0.05 compared with control Ig.

We then determined the effect of mCD300c2 on cytokine production from T cells in vitro. $CD3^+$ T cells were purified from the spleens of C57BL/6 mice and stimulated with anti-CD3 antibody in the presence of graded doses of mCD300c2-Ig or control Ig protein for 3 days. The contents of cytokines in the supernatants were measured by ELISA. As shown in FIG. 3, mCD300c2-Ig inhibited the production of IFNγ, IL-2, IL-17A and IL-10, but not TNFα. The results indicate that mCD300c2-Ig suppresses certain Th1/Th2/Th17 cytokine production by T cells induced by TCR signaling.

Figure 4:
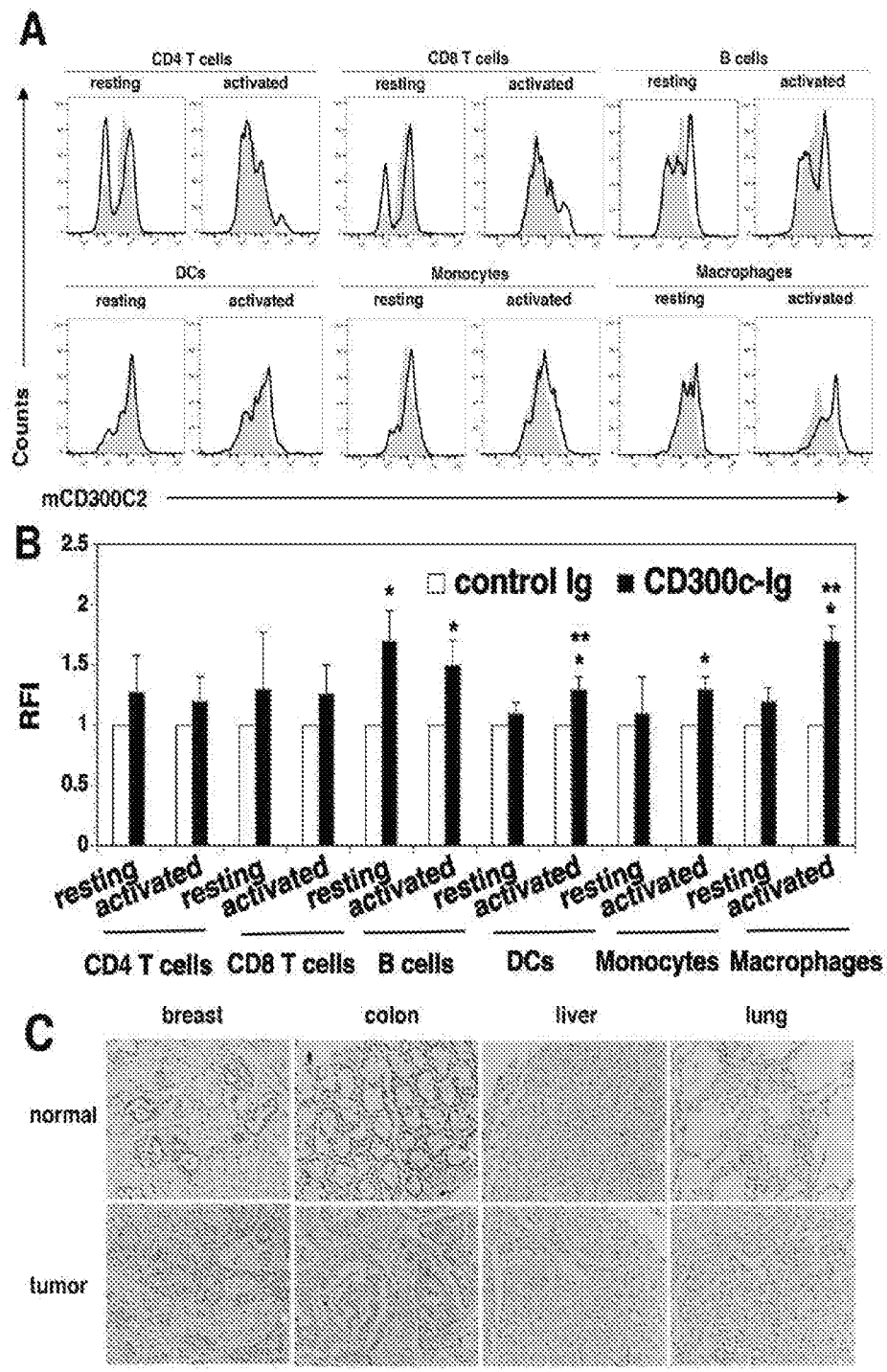
FIG. 4. Analysis of the expression of mCD300c2 on immune cells. Splenocytes from C57BL/6 mice were freshly harvested and used for resting immune cells. To initiate T cell activation, splenocytes were incubated with anti-CD3 (µg/ml) and anti-CD28 (0.5 µg/ml) antibodies for 3 days. For activated B cells, DCs, monocytes and macrophages, splenocytes were incubated with LPS (10 µg/ml) for 3 days. The resting and activated immune cells were stained with anti-mCD300c2 antibody (Ab) (open histograms) or isotype Ab (shaded histograms), as well as anti-CD4, CD8, B220, CD11c, CD11b, or F4/80 Ab to identify immune cells. (A) Representative flow cytometric profiles and (B) statistical analysis showing the expression of mCD300c2 on resting and activated immune cells. (B) The data were pooled from 3 independent experiments and presented as relative fluorescence intensity (RFI) for the expression of mCD300c2 on activated cells versus resting cells. *P<0.05 compared with isotype Ab. **P<0.05 compared with resting cells. (C)

The Expression Pattern of CD300c on Murine Immune Cells and in Normal and Human Tumor Tissues We analyzed cell surface expression of mCD300c2 protein on murine immune cells by flow cytometry using a monoclonal antibody against mCD300c2 (clone TX52). We found that resting splenic $CD4^+$ and $CD8^+$ T cells scarcely expressed mCD300c2 protein (FIG. 4A, B). After activation by anti-CD3 and anti-CD28 antibodies, a small percentage of activated $CD4^+$ and $CD8^+$ T cells expressed mCD300c2. We then examined the expression of mCD300c2 protein on other immune cells, and found that resting and activated $B220^+$ B cells. $CD11b^+$ monocytes and $F4/80^+$ macrophages expressed various levels of mCD300c2 (FIG. 4A, B). The expression level of mCD300c2 on macrophages was upregulated upon activation. In addition, although CD300c protein was scarcely expressed on resting $CD11c^+$ DCs, it was induced upon activation by LPS (FIG. 4A, B). These results indicate that CD300c is expressed on a variety of APCs.

We then determined the expression of hCD300c protein in normal and tumor human tissues by immunohistochemistry. As shown in FIG. 4C, hCD300c was weakly or not at all expressed in normal breast, colon, and liver tissues. The expression levels of hCD300c in breast, colon, and liver tumor tissues were higher than the respective normal tissues, whereas the expression levels of hCD300c in normal and tumor tissues of lung were similar (FIG. 4C). hCD300c protein was largely confined to the plasma membrane or cytoplasm of epithelial cells.

The Expression of the Putative CD300c Counter-Receptor

To determine the expression pattern of the CD300c counter-receptor, purified mCD300c2-Ig and control Ig proteins were biotinylated. Splenocytes from C57BL/c mice were stained with the biotinylated proteins, followed by streptavidin-PE. Flow cytometric analysis showed that mCD300c2-Ig bound to resting $CD4^+$ and $CD8^+$ T cells, and the binding was increased when $CD4^+$ and $CD8^+$ T cells were activated by anti-CD3 and anti-CD28 antibodies (FIG. 5A, B).

We also analyzed the expression of the CD300c counter-receptor on other immune cells. We found that mCD300c2-Ig bound to both resting and activated $B220^+$ B cells, $CD11c^+$ DCs, $CD11b^+$ monocytes and $G4/80^+$ macrophages (FIG. 5A, B). The expression levels of the putative mCD300c counter-receptor on these immune cells were not significantly changed upon activation by LPS.

To determine whether mCD300c binds to molecules previously identified as receptors of the known B7 family members, HEK-293 cells were transfected with an expression vector containing the mouse CD28. CTLA4, PD-1, BTLA or ICOS gene. The expression of these receptors on the transfected 293 cells was confirmed by flow cytometric analysis with the antibodies against the respective receptors (FIG. 5C). The binding of mCD300c to the transfected HEK-293 cells was then analyzed. As shown in FIG. 5D, mCD300c2 did not bind to the CD28, CTLA-4, PD-1, BTLA or COS transfected cells.

Taken together, our results indicate that the mCD300c2 counter-receptor is expressed on resting and activated CD4 and CD8 T cells, B cells, DCs, monocytes, and macrophages. The expression levels of the receptor on activated CD4 and CD8 T cells is upregulated. The mCD300c counter-receptor seems to be distinct from CD28, PD-1, CTLA-4, PD-1, or BTLA.

hCD300c-Ig Protein Ameliorates GVHD in Mice

Although bone marrow (BM) transplantation (BMT) has been widely used in the treatment of many diseases, GVHD remains a major complication after allogeneic BMT. Acute GVDH is primarily caused by T cells in donor transplants attacking recipient's tissues. We used a well-defined MHC-mismatched [C57BL/6 (H2b)→BALB/c (H2d)]GVHD mouse model to validate the effect of CD300c on T cells in vivo. BALB/c mice were lethally irradiated and injected i.v. with BM and splenic cells from allogeneic C57BL/6 mice. The recipients were then injected i.p. with hCD300c-Ig, or control Ig. The development of GVHD was monitored over time. As shown in FIG. 6A-C, control Ig-treated GVHD recipients revealed gradual body weight loss and all succumbed by day 35 after BMT. hCD300c-Ig treatment significantly reduced the mortality and morbidity of GVHD, with 45% of the mice still surviving at day 40 post transplantation (FIG. 6A-C). GVHD severity was confirmed by pathologic analysis, showing that pathology scores of the liver, small intestine (SI), and lung in hCD300c-Ig-treated recipients were significantly lower than those in control Ig-treated recipients (FIG. 6D, E). These data indicate that hCD300c-Ig treatment attenuates GVHD in vivo.

Figure 1:
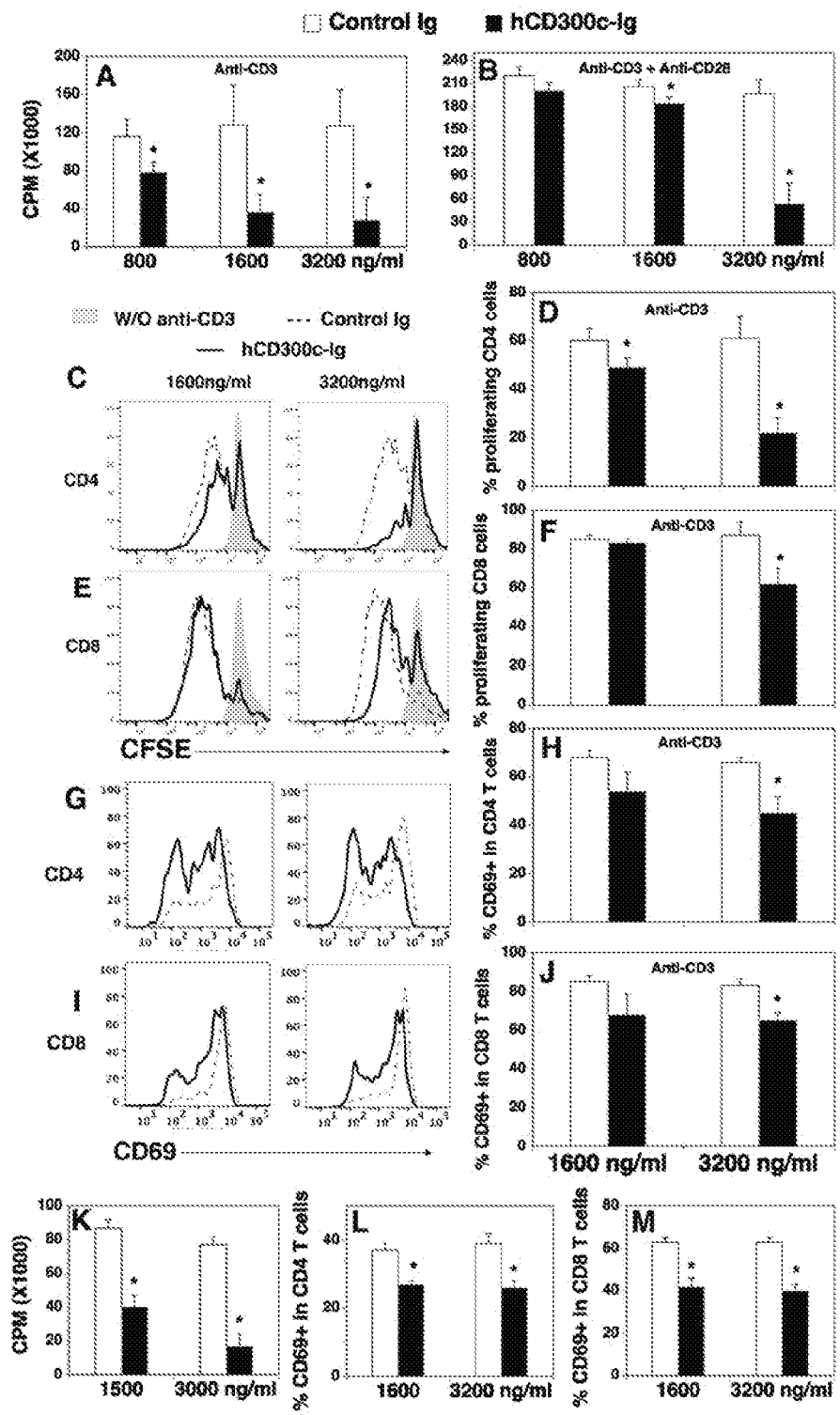
FIG. 1. The effects of hCD300c-Ig protein on the proliferation and activation of mouse and human T cells in vitro. (A, B) T cells were isolated from the spleen of C57BL/6 mice and cultured with (A, B) plate-bound anti-CD3 antibody (1 µg/ml) and (B) anti-CD28 antibody (0.5 µg/ml) in the presence of graded doses of hCD300c-Ig protein (800, 1600, and 3200 ng/ml) or equimolar amounts of control Ig protein for 3 days. Cell proliferation was measured by [$^3$H] thymidine incorporation. (C-F) Mouse splenic cells were labelled with CFSE and cultured with anti-CD3 antibody (1 µg/ml) and graded doses of hCD300c-Ig protein (1600, and 3200 ng/ml) or equimolar amounts of control Ig protein for 3 days. The cells were stained with anti-CD4 and CD8 antibodies, and analyzed for CFSE levels by CD4$^+$ and CD8$^+$ T cells. (C, E). Representative flow cytometric profiles, and (D, F) statistical analysis of CFSE$^{lo}$ proliferating CD4$^+$ or CD8$^+$ T cells. (G-J) Mouse splenic cells were cultured with anti-CD3 antibody and graded doses of hCD300c-Ig protein or control Ig protein as (C) for 24 hours. The cells were then analyzed for CD69 expression by CD4$^+$ and CD8$^+$ T cells. (G, I) Representative flow cytometric profiles, and (H, J) statistical analysis of CD69$^+$ cells in CD4$^+$ or CD8$^+$ T cells. (K) Purified human CD3$^+$ T cells were cultured with plate-bound anti-human CD3 antibody (1 µg/ml) in the presence of graded doses of hCD300c-Ig protein (1500, and 3000 ng/ml) or control Ig protein for 3 days. Cell proliferation was measured by [$^3$H] thymidine incorporation. (L, M) Purified human CD3$^+$ T cells were cultured with plate-bound anti-human CD3 antibody (1 µg/ml) in the presence of graded doses of hCD300c-Ig protein (1600, and 3200 ng/ml) or control Ig protein for 1 days. The cells were then analyzed for human CD69 expression by CD4$^+$ and CD8$^+$ T cells. The data were pooled from 3 independent experiments and expressed as mean±SD. *P<0.05 compared with control Ig.

We then analyzed T cell proliferation, survival, and activation in hCD300c-Ig- or control Ig-treated GVHD mice. Lethally irradiated BALB/c recipients were injected i.v. with BM and splenic cells from C57BL/6 mice. The mice were injected i.v. on day 0 and i.p. on day 2 with 20 μg hCD300c-Ig or control Ig protein. The recipients were euthanized and the spleens were harvested on day 4. We analyzed for the expression of Ki67, a cell marker of proliferation. As shown in FIG. 6F-1, the percentages of $Ki67^+$ cells in donor $CD4^+$ and $CD8^+$ T cells of hCD300c-Ig-treated recipients were significantly lower than those in control Ig-treated mice. We also analyzed the survival of donor $CD4^+$ and $CD8^+$ T cells, and found that the percentages of annexin $V^+$ $7\text{-ADD}^-$ apoptotic $CD4^+$ or $CD8^+$ T cells were not significantly different between hCD300c-Ig- and control Ig-treated groups (data not shown). We next examined the expression of activation markers by $CD4^+$ and $CD8^+$ T cells. Although the percentages of $CD69^+$ cells in donor $CD4^+$ and $CD8^+$ T cells were not significantly different between hCD300c-Ig- and control Ig-treated groups (data not shown), the percentages of $CD44^{hi}$ cells and $CD62L^{lo}$ cells in donor $CD4^+$ and $CD8^+$ T cells were significantly reduced in hCD300c-Ig-treated GVHD mice (FIG. 6J-M).

Taken together, our data indicate that hCD300c-Ig treatment attenuates GVHD, likely by inhibition of the proliferation and activation of donor T cells in response to alloantigen stimulation.

Administration of hCD300c-Ig Fusion Protein Ameliorates EAE and CIA in Mice

Since hCD300c-Ig fusion protein inhibits T cell proliferation, activation and cytokine production in vitro, we set out to investigate whether in vivo administration of hCD300c-Ig could ameliorate autoimmune diseases that are caused by an overactive immune system. Multiple sclerosis (MS) is an autoimmune disease of the central nervous system, and EAE is a common animal model for MS. To determine whether hCD300c-Ig attenuates EAE, C57BL/6 mice were immunized with pMOG peptide to induce EAE development. The mice were then treated with hCD300c-Ig or control Ig protein. As shown in FIG. 7A, hCD300c-Ig treatment reduced the mean clinical scores throughout the entire 57 day time course.

CIA is an animal model for human RA. We also determined the ability of hCD300c-Ig to treat CIA. Similarly.

hCD300c-Ig treatment reduced the mean clinical scores of CIA (FIG. 7B). Our data suggest that hCD300c-Ig treatment ameliorates autoimmune diseases including EAE and CIA.

Generation of Anti-hCD300c Monoclonal Antibodies (mAbs)

To generate anti-hCD300c mAbs, BALB/c mice (8-10 weeks of age) were immunized with hCD300c-Ig protein in complete Freund's adjuvant (CFA) on day 0 and boosted on day 14 and day 21 in the same protein quantity in incomplete Freund's adjuvant (IFA). The mice were boosted with hCD300c-Ig (no adjuvant, add 100 ml 1×PBS instead) three times three days in a row (days 28, 29, 30). The spleens were harvested from the mice on day 31. Single-cell suspension of the splenocytes were fused to X63-Ag8.653 myeloma cells to produce hybridomas. ELISA was performed to identify the hybridomas that could produce mAbs reacting with hCD300c-Ig but not with control Ig protein.

We then determined the ability of anti-hCD300c mAbs to neutralize the ability of hCD300c to inhibit the proliferation and activation of T cells. We found that an anti-hCD300c mAb (clone B47-1D2) significantly inhibited the proliferation and activation of T cells. The heavy and light chain amino acid sequences of the B47-1D2 anti-hCD300c mAb were as follows

```
Heavy chain (complementarity regions highlighted):
                                          (SEQ ID NO: 16)
QIQLVQSGPELRKPGETVKISCKASGYTFTIYGMNWMKQAPGKGLKWMG

WINTYTGEPTYADDFKGRFAFSLETSASTAFLQINNLINEDTATYFC

ARSRFAYWGQGTLVTVSA.

Light chain (complementarity regions highlighted):
                                          (SEQ ID NO: 17)
DIVMTQSQKFMSTSVGDRVSVTCKASQNVGTNVAWYQQKPGQSPKALIY

SASYRYSGVPDRFTGSRSGTDFTLTISNVQSEDLAEYVCQQYNSYPLTF

GAGTKLELK.
```

We then determined the ability of the anti-hCD300c mAb (clone B47-1D2) to inhibit tumor growth in mouse models. We found that the mAb significantly reduced colon cancer cell growth in a CT-26 mouse model (FIG. 8A). The antitumor activity of the anti-CD300c antibodies was related to increased infiltration of CD4+ and CD8+ T cells, NK cells and B cells, as well as enhanced activation of B cells and monocytes in the tumors (FIG. 8B-E, and data not shown). Similarly, the anti-CD300c mAb significantly inhibited melanoma cell growth in a B16/F16 melanoma model (FIG. 8F). Taken together, our data demonstrates that the anti-CD300c mAb can inhibit tumor growth in vivo.

Discussion

The present study describes CD300c as a novel T cell co-inhibitory molecule. CD300c protein is expressed on APCs and its counter-receptor is expressed on T cells. Functionally, CD300c-Ig protein inhibits the proliferation, activation and cytokine production of T cells.

Both human and mouse CD300c have only one IgV domain in the extracellular region. It has been reported that the interaction site in the Ig superfamily members is often mapped to the distal Ig domain, which would be the IgV domain in the CD300c.

We have shown that the mCD300c2 protein is expressed on the cell surface of a variety of APCs, including B cells, monocytes, macrophages and DCs. Our results demonstrate that the mCD300c3 counter-receptor is expressed on resting and activated CD4 and CD8 T cells, B cells, DCs, monocytes, and macrophages. The expression levels of the counter-receptor on activated CD4 and CD8 T cells is upregulated upon activation, while the expression levels of the mCD300c counter-receptor on resting and activated B cells, DCs, monocytes, and macrophages were not significantly different. mCD300c2 protein did not bind to CD28, PD-1, CTLA-4, PD-1, or BTLA-expressing cells, indicating that the mCD300c2 counter-receptor is distinct from known members of the CD28 receptor family.

The expression of CD300c protein on APCs and its counter-receptor on T cells suggests that CD300c affects T cells. Indeed, we have demonstrated that both hCD300c and mCD300c2 significantly inhibit the proliferation, activation, and/or cytokine production of CD4 and CD8 T cells in vitro.

We have also shown that hCD300c-Ig treatment attenuates acute GVHD in mice. To the best of our knowledge, this is the first report that CD300c is able to inhibit T cell function and treat GVHD. The effect of CD300c on GVHD is associated with the inhibition of T cell function in vivo. In agreement with the in vitro data, hCD300c-Ig inhibits T cell proliferation and activation in the GVHD model. However, although both mCD300c2-Ig and hCD300c-Ig inhibit the expression of CD69 in T cells in vitro, we did not observe that hCD300c-Ig treatment reduced CD69 expression by donor T cells in vivo. This inconsistency is most likely caused by time differences in analyzing this marker. CD69 is an early activation marker. We analyzed the expression of this marker 1 day after activation by anti-CD3 antibody or anti-CD3 and anti-CD28 antibodies in vitro, but 4 days after activation by allogeneic antigens in the GVHD model. hCD300c-Ig may inhibit the expression of CD69 in vivo at early time points, but this inhibition was not in effect 4 days later. This notion is supported by our results that hCD300c-Ig reduced the percentages of two other T cell activation markers CD44$^{hi}$ cells and CD62L$^{lo}$ cells, in CD4$^+$ and CD8$^+$ T cells in vitro 3 days (FIG. 2M-Q) and in vivo 4 days (FIG. 6J-M) after activation.

In summary, CD300c protein is expressed on APCs, and its counter-receptor is expressed on T cells. Soluble human or mouse CD300c-Ig fusion proteins significantly inhibit T cell proliferation, activation, and cytokine production in vitro. Administration of hCD300c-Ig protein attenuates GVHD and autoimmune diseases in mice. Anti-CD300c mAb inhibits tumor growth in vivo. Therefore, CD300c protein has can be used in the treatment of GVHD, autoimmune disease, and transplant rejection, as well as cancer. Abbreviations: APC, antigen-presenting cells; DCs, dendritic cells; GVHD, graft-versus-host disease, ICOSL, T cell co-stimulator ligand; Ig, immunoglobulin; CD300c-Ig, CD300c-IgG2a Fc; CFSE, carboxyfluorescein diacetate succinimidyl ester; human CD300c, hCD300c; mCD300c, mouse CD300c; CLM-6, CMRF-35-like molecule-6; LMIR2, leukocyte mono-Ig-like receptor 2. DIgR1, dendritic cell-derived Ig-like receptor 1; MAIR-II, myeloid-associated Ig-like receptor II; MW, molecular weight; BM, bone marrow; BMT, BM transplantation; SI, small intestine

REFERENCES

[1] G. J. Freeman, G. S. Gray, C. D. Gimmi, D. B. Lombard, L. J. Zhou, M. White, J. D. Fingeroth, J. G. Gribben, and L. M. Nadler, Structure, expression, and T cell costimulatory activity of the murine homologue of the human B lymphocyte activation antigen B7. J. Exp. Med. 174 (1991) 625-31.

[2] G. J. Freeman, J. G. Gribben, V. A. Boussiotis, J. W. Ng, V. A. Restivo, Jr., L. A. Lombard, G. S. Gray, and L. M.

Nadler, Cloning of B7-2; a CTLA-4 counter-receptor that costimulates human T cell proliferation. Science (New York, N. Y.) 262 (1993) 909-11.

[3] H. Dong, G. Zhu, K. Tamada, and L. Chen. B7-H1, a third member of the B7 family, co-stimulates T-cell proliferation and interleukin-10 secretion. Nat. Med. 5 (1999) 1365-9.

[4] G. J. Freeman, A. J. Long, Y. Iwai, K. Bourque, T. Chernova, H. Nishimura, L. J. Fitz, N. Malenkovich, T. Okazaki, M. C. Byrne, H. F. Horton, L. Fouser, L. Carter. V. Ling, M. R. Bowman, B. M. Carreno, M. Collins, C. R. Wood, and T. Honjo, Engagement of the PD-1 immunoinhibitory receptor by a novel B7 family member leads to negative regulation of lymphocyte activation. J. Exp. Med. 192 (2000) 1027-34.

[5] Y. Latchman, C. R Wood, T. Chernova, D. Chaudhary, M. Borde, I. Chemova, Y. Iwai, A. J. Long, J. A. Brown, R. Nunes, E. A. Greenfield, K. Bourque, V. A. Boussiotis, L. L. Carter, B. M. Carreno, N. Malenkovich, H. Nishimura, T. Okazaki, T. Honjo, A. H. Sharpe, and G. J. Freeman, PD-L2 is a second ligand for PD-1 and inhibits T cell activation. Nat. Immunol. 2 (2001) 261-8.

[6] S. Y. Tseng, M. Otsuji, K. Gorski, X. Huang, J. E. Slansky, S. I. Pai, A. Shalabi, T. Shin, D. M. Pardoll, and H. Tsuchiya. B7-DC, a new dendritic cell molecule with potent costimulatory properties for T cells. J. Exp. Med. 193 (2001)839-46.

[7] S. Wang, G. Zhu, A. I. Chapoval, H. Dong, K. Tamada, J. Ni, and L. Chen, Costimulation of T cells by B7-H2, a B7-like molecule that binds ICOS. Blood 96 (2000) 2808-13.

[8] V. Ling, P. W. Wu, H. F. Finnerty, K. M. Bean, V. Spaulding, L. A. Fouser, J. P. Leonard, S. E. Hunter, R. Zollner, J. L. Thomas, J. S. Miyashiro, K. A. Jacobs, and M. Collins. Cutting edge: identification of GL50, a novel B7-like protein that functionally binds to ICOS receptor. Journal of immunology (Baltimore, Md.: 1950) 164 (2000) 1653-7.

[9] M. M. Swallow. J. J. Wallin, and W. C. Sha, B7h, a novel costimulatory homolog of B7.1 and B7.2, is induced by TNFalpha. Immunity 11 (1999)423-32.

[10] S. K. Yoshinaga. J. S. Whoriskey, S. D. Khare, U. Sarmiento, J. Guo, T. Horan, G. Shih, M. Zhang, M. A. Coccia, T. Kohno, A. Tafuri-Bladt, D. Brankow, P. Campbell, D. Chang, L. Chiu, T. Dai, G. Duncan, G. S. Elliott, A. Hui, S. M. McCabe, S. Scully. A. Shahinian, C. L. Shaklee, G. Van, T. W. Mak, and G. Senaldi, T-cell co-stimulation through B7RP-1 and ICOS. Nature 402 (1999) 827-32.

[11] A. I. Chapoval, J. Ni, J. S. Lau, R. A. Wilcox, D. B. Flies, D. Liu, H. Dong, G. L. Sica, G. Zhu, K. Tamada, and L. Chen, B7-H3: a costimulatory molecule for T cell activation and IFN-gamma production. Nat. Immunol. 2 (2001) 269-74.

[12] D. V. Prasad, S. Richards, X. M. Mai, and C. Dong, B7S1, a novel B7 family member that negatively regulates T cell activation. Immunity 18 (2003)863-73, 1131 G. L. Sica I. H. Choi, G. Zhu, K. Tamada, S. D. Wang, H. Tamura, A. I. Chapoval, D. B. Flies, J. Bajorath, and L. Chen, B7-H4, a molecule of the B7 family, negatively regulates T cell immunity. Immunity 18 (2003) 849-61.

[14] X. Zang, P. Loke, J. Kim, K. Murphy, R. Waitz, and J. P. Allison, B7x: a widely expressed B7 family member that inhibits T cell activation. Proceedings of the National Academy of Sciences of the United States of America 100 (2003) 10388-92.

[15] R. Zhao, J. M. Chinai, S. Buhl, L. Scandiuzzi, A. Ray, H. Jeon. K. C. Ohaegbulam, K. Ghosh, A. Zhao, M. D. Scharff, and X. Zang, HHLA2 is a member of the B7 family and inhibits human CD4 and CD8 T-cell function. Proceedings of the National Academy of Sciences of the United States of America 110 (2013) 9879-84.

[16] Y. Zhu, S. Yao, B. P. Iliopoulou, X. Han, M. M. Augustine, H. Xu, R. T. Phennicie, S. J. Flies, M. Broadwater, W. Ruff, J. M. Taube, L. Zheng, L. Luo, G. Zhu, J. Chen, and L. Chen, B7-H5 costimulates human T cells via CD28H. Nature communications 4 (2013) 2043.

[17] C. S. Brandt, M. Baratin, E. C. Yi. J. Kennedy, Z. Gao, B. Fox, B. Haldeman, C. D. Ostrander, T. Kaifu, C. Chabannon, A. Moretta, R. West, W. Xu, E. Vivier, and S. D. Levin, The B7 family member B7-H6 is a tumor cell ligand for the activating natural killer cell receptor NKp30 in humans. J. Exp. Med. 206 (2009) 1495-503.

[18] G. J. Clark, B. Cooper, S. Fitzpatrick, B. J. Green, and D. N. Hart, The gene encoding the immunoregulatory signaling molecule CMRF-35A localized to human chromosome 17 in close proximity to other members of the CMRF-35 family. Tissue Antigens 57 (2001) 415-23.

[19] A. Daish, G. C. Starling, J. L. McKenzie, J. C. Nimmo, D. G. Jackson, and D. N. Hart, Expression of the CMRF-35 antigen, a new member of the immunoglobulin gene superfamily, is differentially regulated on leucocytes. Immunology 79 (1993)55-63.

[20] D. G. Jackson, D. N. Hart, G. Starling. and J. I. Bell, Molecular cloning of a novel member of the immunoglobulin gene superfamily homologous to the polymeric immunoglobulin receptor. European journal of immunology 22 (1992) 1157-63.

[21] F. Borrego, The CD300 molecules: an emerging family of regulators of the immune system. Blood 121 (2013) 1951-60.

[22] H. Kumagai, T. Oki, K. Tamitsu, S. Z. Feng, M. Ono, H. Nakajima, Y. C. Bao, Y. Kawakami, K. Nagayoshi, N. G. Copeland, D. J. Gilbert, N. A. Jenkins, T. Kawakami, and T. Kitamura. Identification and characterization of a new pair of immunoglobulin-like receptors LMIR1 and 2 derived from murine bone marrow-derived mast cells. Biochem. Biophys. Res. Commun. 307 (2003) 719-29.

[23] K. Luo, W. Zhang, L. Sui, N. Li, M. Zhang, X. Ma, L. Zhang, and X. Cao, DIgR1, a novel membrane receptor of the immunoglobulin gene superfamily, is preferentially expressed by antigen-presenting cells. Biochem. Biophys. Res. Commun. 287 (2001) 35-41.

[24] K. Yotsumoto, Y. Okoshi, K. Shibuya, S. Yamazaki, S. Tahara-Hanaoka. S. Honda, M. Osawa, A. Kuriwa, Y. Matsuda, D. G. Tenen, A. Iwama, H. Nakauchi, and A. Shibuya, Paired activating and inhibitory immunoglobulin-like receptors, MAIR-I and MAIR-II, regulate mast cell and macrophage activation. J. Exp. Med. 198 (2003) 223-33.

[25] D. H. Chung, M. B. Humphrey, M. C. Nakamura, D. G. Ginzinger, W. E. Seaman, and M. R. Daws, CMRF-35-like molecule-1, a novel mouse myeloid receptor, can inhibit osteoclast formation. Journal of immunology (Baltimore, Md.: 1950) 171 (2003) 6541-8.

[26] M. Dimitrova. O. Zenarruzabeitia. F. Borrego, and V. R. Simhadri, CD300c is uniquely expressed on CD56 bright Natural Killer Cells and differs from CD300a upon ligand recognition. Sci Rep 6 (2016) 23942.

[27] V. R. Simhadri, J. L. Mariano, A. Gil-Krzewska, Q. Zhou, and F. Borrego, CD300c is an activating receptor expressed on human monocytes. Journal of innate immunity 5 (2013) 389-400.

[28] C. Nakahashi, S. Tahara-Hanaoka, N. Totsuka, Y. Okoshi, T. Takai, N. Ohkohchi, S. Honda, K. Shibuya. and A. Shibuya, Dual assemblies of an activating immune receptor, MAIR-II, with ITAM-bearing adapters DAP12 and FcRgamma chain on peritoneal macrophages. Journal of immunology (Baltimore, Md.: 1950) 178 (2007) 765-70.

[29] T. Nakano-Yokomizo, S. Tahara-Hanaoka, C. Nakahashi-Oda, T. Nabekura, N. K. Tchao, M. Kadosaki, N. Totsuka, N. Kurita, K. Nakamagoe, A. Tamaoka, T. Takai, T. Yasui, H. Kikutani, S. Honda, K. Shibuya, L. L. Lanier, and A. Shibuya, The immunoreceptor adapter protein DAP12 suppresses B lymphocyte-driven adaptive immune responses. J. Exp. Med. 208 (2011) 1661-71.

[30] N. Totsuka, Y. G. Kim, K. Kanemaru, K. Niizuma, E. Umemoto, K. Nagai, S. Tahara-Hanaoka, C. Nakahasi-Oda, S. Honda, M. Miyasaka, K. Shibuya, and A. Shibuya, Toll-like receptor 4 and MAIR-II/CLM-4/LMIR2 immunoreceptor regulate VLA-4-mediated inflammatory monocyte migration. Nature communications 5 (2014) 4710.

[31] G. J. Clark, X. Ju, M. Azlan, C. Tate, Y. Ding, and D. N. Hart, The CD300 molecules regulate monocyte and dendritic cell functions. Immunobiology 214 (2009) 730-6.

[32] X. Ju, M. Zenke, D. N. Hart, and G. J. Clark, CD300a/c regulate type I interferon and TNF-alpha secretion by human plasmacytoid dendritic cells stimulated with TLR7 and TLR9 ligands. Blood 112 (2008) 1184-94.

[33] O. Zenarruzabeitia, J. Vitalle, I. Terren, A. Orrantia, I. Astigarraga, L. Dopazo, C. Gonzalez, L. Santos-Diez, C. Tutau, P. M. Gamboa, A. Bilbao. and F. Borrego, CD300c co-stimulates IgE-mediated basophils activation and its expression is increased in cow s milk allergy. J. Allergy Clin. Immunol. (2018).

[34] M. Takahashi, K. Izawa. J. Kashiwakura, Y. Yamanishi, Y. Enomoto, A. Kaitani, A. Maehara, M. Isobe, S. Ito, T. Matsukawa, F. Nakahara, T. Oki, M. Kajikawa, C. Ra, Y. Okayama, T. Kitamura, and J. Kitaura, Human CD300C delivers an Fc receptor-gamma-dependent activating signal in mast cells and monocytes and differs from CD300A in ligand recognition. J. Biol. Chem. 288 (2013) 7662-75.

[35] J. Jin, I. Goldschneider, and L. Lai, In vivo administration of the recombinant IL-7/hepatocyte growth factor beta hybrid cytokine efficiently restores thymopoiesis and naive T cell generation in lethally irradiated mice after syngeneic bone marrow transplantation. Journal of immunology (Baltimore, Md.: 1950) 186 (2011) 1915-22.

[36] L. Lai, M. Zhang, and 1. Goldschneider, Recombinant IL-7/HGFbeta efficiently induces transplantable murine hematopoietic stem cells. J. Clin. Invest. 122 (2012) 3552-62.

[37] L. Lai, M. Zhang, Y. Song, and D. Rood, Recombinant IL-7/HGFbeta Hybrid Cytokine Enhances T Cell Recovery in Mice Following Allogeneic Bone Marrow Transplantation. PloS one 8 (2013) e82998.

[38] Y. Song, M. Su, P. Panchatsharam, D. Rood, and L. Lai, c-Met signalling is required for efficient postnatal thymic regeneration and repair. Immunology 144 (2015) 245-53.

[39] Y. Song, Y. Liu. R. Hu, M. Su, D. Rood, and L. Lai, In vivo antitumor Activity of a Recombinant IL-7/IL-15 Hybrid Cytokine in Mice. Mol. Cancer Ther. (2016).

[40] R. Hu, Y. Liu, Y. Song, M. Su, X. Lu, D. Rood, and L. Lai, Recombinant IL-7/HGFbeta hybrid cytokine separates acute graft-versus-host-disease from graft-versus-tumour activity by altering donor T cell trafficking. Br. J. Haematol. 175 (2016)505-516.

[41] J. P. Cannon, M. O'Driscoll, and G. W. Litman, Specific lipid recognition is a general feature of CD300 and TREM molecules. Immunogenetics 64 (2012) 3947.

Example 2: TAPBPL

In this example, we identify a novel T cell co-inhibitory molecule TAPBPL/TAPBPR, whose amino acid sequence shares homolog with known B7 family members. TAPBPL protein is expressed on resting and activated T cells, B cells, monocytes and dendritic cells (DCs), as well as in tumor tissues. A soluble recombinant human TAPBPL-IgG Fc (hTAPBPL-Ig) fusion protein inhibits the proliferation and activation of CD4 and CD8 T cells in vitro. In vivo administration of hTAPBPL-Ig protein attenuates experimental autoimmune encephalomylitis (EAE) in mice. Furthermore, anti-TAPBPL antibody can neutralize the inhibitory activity of hTAPBPL-Ig on T cells, and inhibit tumor growth in a tumor animal model. Our results indicate that therapeutic intervention of the TAPBPL inhibitory pathway represents a new strategy to modulate T cell-mediated immunity for the treatment of cancer, infection, autoimmune disease, and transplant rejection.

TAPBPL is a member of the Ig superfamily [18-21]. The TAPBPL gene encodes a signal peptide in the N terminus, an extracellular region, a transmembrane domain, and an intracellular region. The B7 family members typically contain IgV and IgC domains in the extracellular portion. The extracellular region of TAPBPL also contains an IgV domain and an IgC domain. TAPBPL is highly conserved among vertebrates, and human and mouse TAPBPL proteins have 69% homology [19, 21].

TAPBPL Protein is Expressed on the Cell Surface of APCs and T Cells, and in Some Tumor Tissues We used a commercial available anti-TAPBPL monoclonal antibody (clone 5D7) to determine whether TAPBPL protein is expressed on APC and/or T cells. Although the antibody was raised against hTAPBPL, it cross-reacted with mTAPBPL (data not shown). As shown in FIGS. 9A and B. TAPBPL was expressed on the cell surface of $CD4^+$ and $CD8^+$ T cells at low levels. The expression level of TAPBPL on $CD8^+$ T cells was slightly increased upon activation by anti-CD3 and anti-CD28 antibodies. TAPBPL protein was also detected on APCs including $CD11b^+$ monocytes, $F4/80^+$ macrophages, $CD11c^+$ dendritic cells (DCs), and $B220^+$ or $CD19^+$ B cells.

The expression levels of TAPBPL on monocytes and DCs, but not on macrophages and B cells, were increased upon activation by LPS. The results suggest that TAPBPL protein is constitutively expressed on the cell surface of APCs and T cells, and the expression of TAPBPL is upregulated on monocytes, DCs cells, and CD8 T cells after activation.

We then determined the expression of TAPBPL protein in normal and tumor human tissues by immunohistochemistry. As shown in FIG. 9C, TAPBPL protein was detected in normal breast, colon, liver, lung and prostate tissues at low levels, as compared to isotype antibody staining. TAPBPL protein was expressed in liver, lung and prostate cancer tissues at medium to high levels (FIG. 9C). Therefore, the expression levels of TAPBPL in liver, lung and prostate cancer tissues was higher than the respective normal tissues. TAPBPL protein was largely located to the plasma membrane or cytoplasm of epithelial cells. We also examined TAPBPL protein expression on some cancer cell lines by flow cytometry. As shown in FIG. 9D, TAPBPL was expressed highly on the cell surface of murine neuro-2a neuroblastoma and P388 leukemia cells, and weakly expressed on murine Lewis Lung Carcinoma, CT-26 colon cancer and B16F10 melanoma cells. We have also found that TAPBPL is expressed on human K562 and HL60 leukemia cell lines (data not shown).

TAPBPL Inhibits T Cell Proliferation In Vitro

Since TAPBPL shares sequence homolog with the B7 family members and TAPBPL is expressed on APCs, we hypothesized that TAPBPL has regulatory roles on T cells. We produced an hTAPBPL-Ig fusion protein by cloning the extracellular domain of human TAPBPL into an expression vector containing the constant region of mouse IgG2a. The vector was transfected into HEK-293 cells to produce a recombinant hTAPBPL-Ig fusion protein. We then purified hTAPBPL-Ig protein from the supernatant of HEK-293 cells. A relative high purity of hTAPBPL-Ig fusion protein was obtained as shown by SDS-PAGE and confirmed by Western blot.

To determine whether TAPBPL-Ig protein affects T cell proliferation, CD3$^+$ T cells were purified from splenocytes of C57BL/c mice, and cultured on plates pre-coated with anti-CD3 antibody in the presence of graded doses of hTAPBPL-Ig for 3 days. Since the molecular weight of hTAPBPL-Ig is ~2.7-fold higher than that of control Ig, we used equimolar amounts of recombinant mouse IgG2a (control Ig) protein as a control. T cell proliferation was measured by [$^3$H] thymidine incorporation. As shown in FIG. 10A, TAPBPL-Ig inhibited anti-CD3-induced T cell proliferation in a dose-dependent manner, with ~70% and 81% inhibition in the presence of 10 and 15 µg/ml hTAPBPL-g, respectively, as compared to equimolar amounts of control Ig. We also determined whether hTAPBPL-Ig could inhibit anti-CD3 and anti-CD28 antibody-induced T cell proliferation. Similarly, hTAPBPL-Ig inhibited the T cell proliferation in a dose-dependent manner, with ~66% and 70% inhibition in the presence of 10 and 15 µg/ml hTAPBPL-Ig, respectively (FIG. 10B).

To confirm the inhibitory effect on T cell proliferation and to determine whether hTAPBPL-Ig inhibits CD4 and/or CD8 T cells, splenocytes were labelled with carboxyfluorescein diacetate succinimidyl ester (CFSE), and cultured with anti-CD3 antibody and graded doses of TAPBPL-Ig or equimolar amounts of control Ig. T cell proliferation was analyzed for CFSE fluorescent intensity in CD4$^+$ or CD8$^+$ T cells by flow cytometry. Consistent with results from the [$^3$H] thymidine incorporation assay, hTAPBPL-Ig inhibited anti-CD3-induced proliferation of both CD4$^+$ and CD8$^+$ T cells (FIG. 10C-E).

Having shown that hTAPBPL-Ig inhibits murine T cell proliferation in vitro, we next determined whether hTAPBPL-Ig also inhibits the proliferation of human T cells. Purified human T cells were cultured with anti-human CD3 antibody in the presence of graded doses of hTAPBPL-Ig or control Ig for 3 days. T cell proliferation was measured by [$^3$H] thymidine incorporation. As shown in FIG. 10F, hTAPBPL-Ig also significantly inhibited the proliferation of human T cells. When compared to the doses of hTAPBPL-Ig that have an effect on murine T cells, the doses for human T cells were lower (FIG. 10F vs A). Collectively, our results indicate that hTAPBPL-Ig can inhibit the proliferation of both mouse and human primary T cells.

TAPBPL Inhibits T Cell Activation In Vitro

We then determined whether hTAPBPL-Ig affects T cell activation in vitro. After splenocytes were cultured with anti-CD3 antibody and hTAPBPL-Ig or control Ig, T cells were analyzed for the expression of an early activation marker CD69 24 hours later. As shown in FIGS. 1A and B, TAPBPL-Ig reduced anti-CD3-activated CD69 expression on both CD4 and CD8 T cells. Similarly, the expression levels of CD69 on both CD4 and CD8 T cells activated by both anti-CD3 and anti-CD28 antibodies were also significantly decreased by TAPBPL-Ig (FIGS. 11C and D).

T cells can be divided into naïve (CD44$^{lo}$CD62L$^{hi}$) and effective memory (CD44$^{hi}$CD62 L$^{lo}$ T cells based on the expression levels of CD44 and CD62L. We next analyzed the effect of mBTN5-Ig on these T cell subsets. We found that the percentages of CD44$^{hi}$CD62L$^{lo}$ CD4 and CD8 effective memory T cells were significantly lower in the presence of hTAPBPL-Ig than those in the control group (FIG. 1E-I, K). In contrast, the percentages of CD44$^{lo}$CD62L$^{hi}$ CD4 and CD8 T naïve cells were significantly higher in the presence of hTAPBPL-Ig (FIG. 11E-G, I-L). The results further suggest that hTAPBPL-Ig inhibits the activation of CD4 and CD8 T cells. Taken together, our results indicate that hTAPBPL-Ig inhibits TCR-mediated proliferation and activation of both CD4 and CD8 T cells in vitro.

Administration of hTAPBPL-Ig Fusion Protein Ameliorates EAE in Mice

We then determined whether in vivo administration of hTAPBPL-Ig fusion protein could ameliorate multiple sclerosis (MS) that is an autoimmune disease of the central nervous system. EAE induced by autoantigen pMOG peptide is a well-established animal model for MS. C57BL/6 mice were injected with pMOG peptide to induce EAE. To determine whether hTAPBPL-Ig could prevent EAE development, mice were injected with 25 µg/ml hTAPBPL-Ig or control Ig protein beginning from the day that EAE was induced (day 0). EAE development was monitored over time. As shown in FIG. 12A, hTAPBPL-Ig significantly reduced the mean clinical scores throughout the entire 42-day time course. To determine whether hTAPBPL-Ig could treat established EAE, mice were injected with hTAPBPL-Ig or control Ig protein after the mice had developed EAE. hTAPBPL-Ig also significantly reduced the mean clinical scores in the treatment model (FIG. 12B). At end of the studies, the spleen and spinal cord were harvested from the mice. hTAPBPL-Ig-treated mice had decreased proportion of CD4$^+$ T cells and increased percentage of CD4$^+$CD25FoxP3$^+$Tregs in the spleen (FIG. 12C-F). CD4 T cell activation in hTAPBPL-Ig-treated mice was also significantly reduced, as indicated by reduced expression of CD69, decreased percentage of effector memory T cells, but increased percentage of naïve T cells (FIG. 12G-J). Furthermore, CNF-infiltrating CD4 T cells were decreased, but Tregs were increased. In addition, when the splenocytes from hTAPBPL-Ig-treated mice were stimulated with MOP in vitro, the cell proliferation was reduced, indicating that hTAPBPL inhibits antigen-specific proliferation.

Taken together, our results suggest that in vivo administration of hTAPBPL-Ig can prevent and treat EAE. This is associated with decreased proportion of CD4 T cells and increased Tregs in the spleen and CNS, and reduced activation of CD4 T cells.

Anti-hTAPBPL mAb Inhibits Tumor Growth In Vivo

Since TAPBPL is highly expressed in some tumor tissues and hTAPBPL-Ig inhibits T cell functions, we hypothesized that anti-TAPBPL antibody could block the inhibitory effect of TAPBPL, thereby enhancing antitumor immunity and inhibiting tumor growth in vivo. We produced anti-hTAPBPL mAbs by immunizing BALB/c mice with hTAPBPL-Ig protein.

The splenocytes were fused to X63-Ag8.653 myeloma cells to produce hybridomas. ELSA was performed to identify the clones of hybridomas that could produce antihTAPBPL mAbs reacting with hTAPBPL-Ig fusion protein but not with control Ig protein. We also screened the mAbs by determining their ability to neutralize the inhibitory activity of hTAPBPL on T cells in vitro. As shown in FIG. 13A, an anti-hTAPBPL mAb (clone 54) neutralized the inhibitory activity of hTAPBPL on T cell proliferation.

We then determined the ability of the mAb to treat cancer in a leukemia mouse model that was injected s.c. with P388 cells. Anti-hTAPBPL mAb at 25 and 50 μg doses inhibited tumor growth in the model although at some time points the differences did not reach statistical significance (data not shown). Anti-hTAPBPL mAb at 100 μg dose significantly inhibited tumor growth for most of time points (FIG. 13B). Analyses of tumor infiltrating lymphocytes show that anti-hTAPBPL mAb significantly increased the percentages of (FIG. 13C-F) CD4$^+$ and CD8$^+$ T cells, but decreased the percentage of CD4$^+$CD25$^+$FoxP3$^+$ Tregs (FIG. 13G, H). Together, our results suggest that the anti-TAPBPL mAb can inhibit tumor growth in vivo, which is related to neutralizing the inhibitory activity of TAPBPL on tumor infiltrating T cells.

```
Heavy chain:
                                       (SEQ ID NO: 24)
DVQLQESGPGLVKPSQTLSLTCSVTGYSLTSGYFWHWIRQFPGNKLEWMG

YISYSGTTNYNPSLKNRISITHDSSKNQFFLNLNSVTAEDTATYFCAG

DDWDWFAYWGQGTLVTVSA;

Light chain
                                       (SEQ ID NO: 25)
ENVLTQSPAIMSASPGEKVTMTCSASSSVNYMHWYQQKSSTSPKLWIY

DTSKLASGVPGRFSGSGSGNSYSLTISSMEAEDVATYYCFQGSGYPLT

FGSGTKLEIK
```

In summary, we described TAPBPL as a novel T cell co-inhibitory molecule. TAPBPL protein is expressed on APCs and in tumor tissues. TAPBPL-Ig fusion protein inhibits T cell proliferation and activation in vitro. In vivo administration of TAPBPL-Ig protein attenuates EAE. Anti-TAPBPL antibody inhibits tumor growth in a mouse model. Therefore, targeting the TAPBPL has can be used in the treatment of autoimmune diseases (such as MS) and transplant rejection, as well as cancer and infection.

Materials and Methods

Cloning and Purification of TAPBPL

The extracellular domains of hTAPBPL (aa22406) were cloned and fused into a pCMV6-AC-FC-S expression vector containing the constant region of mouse IgG2a (ORIGENE, Rockville, Md.). The vectors were transfected into HEK-293 cells. The fusion proteins were purified for the supernatant using Protein G Sepharose 4 Fast Flow according to the manufacturer's instructions (GE Healthcare). Purified proteins were verified by SDS-PAGE, Coomassie Staining and Western blot. Protein was quantified using the Pierce™ BCA Protein Assay Kit (Pierce, Rockford. Ill.). Control Ig (recombinant mouse IgG2a Fc protein) was purchased from BXCell (West Lebanon, NH).

Mice

C57BL/6 mice were purchased from Jackson Laboratory. The mice were used in accordance with protocols approved by the Institutional Animal Care and Use Committee of the University of Connecticut.

Flow Cytometry Analysis

Single cell suspensions of organs and tumors were stained with the fluorochrome-conjugated antibodies protein as described [24-27]. For intracellular staining, the cells were first permeabilized with a BD Cytofix/Cytoperm solution for 20 minutes at 4° C. Direct or indirect staining of fluorochrome-conjugated antibodies included: CD4, CD8, CD19, B220, CD11c, CD11b, F4/80, CD44, CD62L, CD69, CTLA-4, CD28, PD-1, BTLA, and ICOS (BioLegend, or BD Biosciences, San Jose, Calif., San Diego, Calif.). Anti-TAPBPL monoclonal antibodies were purchased from LifeSpan Biosciences, Inc (Seattle, Wash.). The samples were analyzed on a FACSCalibur or LSRFortessa™ X-20 Cell Analyzer (BD Biosciences). Data analysis was done using FlowJo™ software (Ashland, Oreg.).

Histopathology

Human Multiple Normal and Tumor Tissue Arrays were purchased from BioChain (Newark, Calif.). The tissues were subjected to antigen unmasking, and then incubated with anti-TAPBPL monoclonal antibody, followed by ImmPRESS™ 4VR Polymer HRP anti-mouse IgG reagent, and developed with peroxidase substrate solution (Vector Laboratories) according to the manufacturer's instructions.

In Vitro T Cell Assays

Normal human peripheral blood CD3$^+$ Pan T Cells that were negatively isolated from mononuclear cells using an indirect immunomagnetic Pan-T labeling system were purchased from ALLCELLS, LLC (Alameda, Calif.). Murine CD3$^+$ T cells were purified from C57BL/6 mice by an immunomagnetic system (Miltenyi, Auburn, Calif.), and the purity of the cells was usually >95%. T cells were stimulated with anti-CD3 and/or anti-CD28 (Biolegend) in the presence of hTAPBPL-Ig or control Ig. Proliferative response was assessed by pulsing the culture with 1 μCi of [$^3$H] thymidine (PerkinElmer, Inc., Downers Grove, Ill.) 12 hours before harvest. Incorporation of [$^3$H] thymidine was measured by liquid scintillation spectroscopy (PerkinElmer, Inc.). For the carboxyfluorescein diacetate succinimidyl ester (CFSE) assay, splenocytes were labeled with CFSE (ThermoFisher Scientific) and stimulated with anti-CD3 in the presence of hTAPBPL-Ig or control Ig. The cells were analyzed by flow cytometry.

Induction and Assessment of EAE

Mouse MOG35-55 (GL Biochem, Shanghai, China) was emulsified in complete Freud's adjuvant (Sigma-Aldrich, St Louis, Mo., USA) supplemented with *Mycobacterium tuberculosis* H37Ra (Difco Laboratories, Detroit, Mich.). Mice were injected s.c. with the MOG at 4 points in the dorsal flank on day 0. The mice were also injected i.p. with 500 ng of purified *Bordetella pertussis* toxin (Sigma-Aldrich). The mice were injected i.p. with hTAPBPL-Ig, or control Ig, and observed for clinical scores based on the following scale: 0, normal; 0.5, partially limp tail; 1, paralyzed tail; 2, loss in coordinated movement, hind limb paresis; 2.5, one hind limb paralyzed; 3, both hind limbs paralyzed; 3.5, hind limbs paralyzed, weakness in forelimbs; 4, forelimbs paralyzed; 5, moribund or dead. As required by animal ethics, mice were euthanized beyond a clinical score of 4.

Generation of hTAPBPL Monoclonal Antibodies (mAbs)

BALB/c mice were immunized with 50 μg hTAPBPL-Ig protein emulsified in complete Freund's adjuvant (CFA) on day 0 and boosted on day 14 and day 21 in the same protein quantity in incomplete Freund's adjuvant (IFA). The mice were boosted with 50 μg hTAPBPL-Ig without IFA 3 times (days 28, 29, and 30). On day 31, the spleens were harvested from the immunized mice. Single-cell suspension of the splenocytes were fused to X63-Ag8.653 myeloma cells to produce hybridomas. ELISA was performed to identify the hybridomas that could produce anti-hTAPBPL mAbs but not with control Ig protein. These hybridoma clones were further subcloned by limiting dilution. The anti-hTAPBPL mAbs were further screened for the ability to neutralize the inhibitory activity of hTAPBPL-Ig on T cell proliferation and activation. The anti-hTAPBPL mAbs were purified for supernatant of the hybridomas using Protein G Sepharose 4 Fast Flow according to the manufacturer's instructions (GE Healthcare).

Evaluation of Local Tumor Growth

Murine P388 leukemia cells were obtained from ATCC. The cancer cells were injected s.c. into syngeneic DBA/2a mice. Anti-hTAPBPL or control mAb was then injected into the tumor injection site. Tumor size (volume) was determined by caliper measurements of the shortest (A) and longest (B) diameter, using the formula V=(A2B)/2.

Statistical Analysis

P-values were based on the two-sided Student's t test. A confidence level above 95% (p<0.05) was determined to be significant.

REFERENCES

[1] Freeman G J, Gray G S, Gimmi C D, Lombard D B, Zhou L J, White M et al. Structure, expression, and T cell costimulatory activity of the murine homologue of the human B lymphocyte activation antigen B7. J Exp Med, 1991; 174:625-31.
[2] Freeman G J. Gribben J G. Boussiotis V A, Ng J W, Restivo V A, Jr., Lombard L A et al. Cloning of B7-2: a CTLA-4 counter-receptor that costimulates human T cell proliferation. Science (New York, N.Y.), 1993; 262:909-11.
[3] Dong H, Zhu G, Tamada K, Chen L. B7-H1, a third member of the B7 family, co-stimulates T-cell proliferation and interleukin-10 secretion. Nat Med, 1999; 5:1365-9.
[4] Freeman G J, Long A J, Iwai Y, Bourque K, Chernova T, Nishimura H et al. Engagement of the PD-1 immunoinhibitory receptor by a novel B7 family member leads to negative regulation of lymphocyte activation. J Exp Med, 2000:192:1027-34.
[5] Latchman Y, Wood C R. Chemova T. Chaudhary D, Borde M, Chemova I et al. PD-L2 is a second ligand for PD-1 and inhibits T cell activation. Nat Immunol, 2001; 2:261-8.
[6] Tseng S Y, Otsuji M, Gorski K, Huang X, Slansky J E, Pai S I et al. B7-DC, a new dendritic cell molecule with potent costimulatory properties for T cells. J Exp Med, 2001; 193:839-46.
[7] Wang S, Zhu G. Chapoval A I, Dong H, Tamada K, Ni J et al. Costimulation of T cells by B7-H2, a B7-like molecule that binds ICOS. Blood, 2000:96:2808-13.
[8] Ling V, Wu P W, Finnerty H F, Bean K M, Spaulding V, Fouser L A et al. Cutting edge: identification of GL50, a novel B7-like protein that functionally binds to ICOS receptor. Journal of immunology (Baltimore, Md.: 1950), 2000, 164:1653-7.
[9] Swallow M M, Wallin J J, Sha W C. B7h, a novel costimulatory homolog of B7.1 and B7.2, is induced by TNFalpha. Immunity, 1999; 11:423-32.
[10] Yoshinaga S K, Whoriskey J S, Khar S D, Sarmiento U, Guo J. Horan T et al. T-cell co-stimulation through B7RP-1 and ICOS. Nature, 1999:402:827-32.
[11] Chapoval A, Ni J, Lau J S, Wilcox R A, Flies D B, Liu D et al. B7-H3: a costimulatory molecule for T cell activation and IFN-gamma production. Nat Immunol, 2001; 2:269-74.
[12] Prasad D V. Richards S, Mai X M, Dong C. B7S1, a novel B7 family member that negatively regulates T cell activation. Immunity, 2003; 18:863-73.
[13] Sica G L, Choi I H, Zhu G, Tamada K, Wang S D, Tamura H et al. B7-H4, a molecule of the B7 family, negatively regulates T cell immunity. Immunity, 2003; 18:849-61.
[14] Zang X. Loke P. Kim J, Murphy K, Waitz R, Allison J P. B7x: a widely expressed B7 family member that inhibits T cell activation. Proceedings of the National Academy of Sciences of the United States of America, 2003; 100:10388-92.
[15] Zhao R, Chinai J M, Buhl S, Scandiuzzi L, Ray A. Jeon H et al. HHLA2 is a member of the B7 family and inhibits human CD4 and CD8 T-cell function. Proceedings of the National Academy of Sciences of the United States of America, 2013; 110:9879-84.
[16] Zhu Y, Yao S, Iliopoulou B P, Han X, Augustine M M, Xu H et al. B7-H5 costimulates human T cells via CD28H. Nature communications, 2013:4:2043.
[17] Brandt C S, Baratin M, Yi E C, Kennedy J, Gao Z. Fox B et al. The B7 family member B7-H6 is a tumor cell ligand for the activating natural killer cell receptor NKp30 in humans. J Exp Med, 2009; 206:1495-503.
[18] Du Pasquier L. The phylogenetic origin of antigen-specific receptors. Cuff Top Microbiol Immunol, 2000; 248:160-85.
[19] Hermann C, Trowsdale J, Boyle L H. TAPBPL: a new player in the MHC class I presentation pathway. Tissue Antigens, 2015; 85:155-66.
[20] Morozov G I, Zhao H, Mage M G, Boyd L F, Jiang J, Dolan M A et al. Interaction of TAPBPL, a tapasin homolog, with MHC-I molecules promotes peptide editing. Proceedings of the National Academy of Sciences of the United States of America, 2016; 113:E1006-15.
[21] Teng M S, Stephens R Du Pasquier L, Freeman T, Lindquist J A, Trowsdale J. A human TAPBP (TAPASIN)-related gene, TAPBP-R. European journal of immunology, 2002:32:1059-68.
[22] Chen Q R. Hu Y, Yan C, Buetow K, Meerzaman D. Systematic genetic analysis identifies Cis-eQTL target genes associated with glioblastoma patient survival. PloS one, 2014; 9:e105393.
[23] Evans D M, Spencer C C, Pointon J J, Su Z, Harvey D, Kochan G et al. Interaction between ERAP1 and HLA-B27 in ankylosing spondylitis implicates peptide handling in the mechanism for HLA-B27 in disease susceptibility. Nat Genet, 2011; 43:761-7.
[24] Jin J, Goldschneider I, Lai L. In vivo administration of the recombinant IL-7/hepatocyte growth factor beta hybrid cytokine efficiently restores thymopoiesis and naive T cell generation in lethally irradiated mice after syngeneic bone marrow transplantation. Journal of immunology (Baltimore, Md.: 1950), 2011; 186:1915-22.
[25] Lai L. Zhang M, Goldschneider I. Recombinant IL-7/HGFbeta efficiently induces transplantable murine hematopoietic stem cells. J Clin Invest, 2012; 122:3552-62.
[26] Lai L, Zhang M, Song Y, Rood D. Recombinant IL-7/HGFbeta Hybrid Cytokine Enhances T Cell Recovery in Mice Following Allogeneic Bone Marrow Transplantation. PloS one, 2013; 8:e82998.
[27] Song Y, Su M, Panchatsharam P, Rood D, Lai L. c-Met signalling is required for efficient postnatal thymic regeneration and repair. Immunology, 2015; 144:245-53.

Example 3. Skint8

In this example, we identify Skint8 as a new member of T cell co-inhibitory group, whose extracellular domains share significant homology with existing B7 family members. Skint8 mRNA is expressed in resting and activated B cells, monocytes, and CD4 T cells. The Skint8 putative receptor is expressed on activated CD4 and CD8 T cells, B cells, monocytes and dendritic cells (DCs). Recombinant Skint8-IgG Fc (Skint8-Ig) fusion protein inhibits T cell proliferation, activation, and cytokine production in vitro. In vivo administration of Skint8-Ig reduces T cell activation and ameliorates experimental autoimmune encephalomyelitis (EAE) in mice.

Results

The Expression Pattern of Skint8 mRNA

We first evaluated the expression of Skint8 mRNA in various tissues by using RT-PCR analysis. As shown in FIG. 14A, Skint8 mRNA was expressed in the heart, skin, spinal cord, kidney, spleen and thymus with the highest expression level in the thymus.

We then examined the expression of Skint8 mRNA in purified immune cells. We found that Skint8 was expressed in resting $CD4^+$ T cells, $B220^+$ B cells, and $CD11b^+$ monocytes, but not in resting $CD8^+$ T cells, $F4/80^+$ macrophages, and $CD11c^+$ DCs (FIG. 14B). The expression of Skint8 mRNA in $CD4^+$ T cells, $B220^+$ B cells, and $CD11b^+$ monocytes was not significantly altered upon activation (FIG. 14C). The expression of Skint8 mRNA was induced in $CD8^+$ T cells, and slightly upregulated in $F4/80^+$ macrophages upon activation (FIG. 14C). The data suggest that Skint8 transcript was constitutively expressed in CD4 T cells, B cells, and monocytes and induced in CD8 T cells and macrophages.

To confirm the expression of Skint8 mRNA in immune cells, we also performed real-time quantitative RT-PCR (qRT-PCR). The expression levels of Skint8 mRNA were not significantly different between resting and activated $CD4^+$ T cells, $B220^+$ B cells, and $CD11b^+$ monocytes. However, the expression of Skint8 mRNA was induced in $CD8^+$ T cells and $F4/80^+$ macrophages upon activation (FIG. 14D). The qRT-PCR data were consistent with the RT-PCR results.

The Putative Skint8 Receptor is Expressed on Activated T Cells, B Cells, Monocytes, and DCs In order to determine the expression pattern of the putative Skint8 receptor, we cloned and expressed Skint8-Ig fusion protein in which the extracellular domain of Skint8 was fused to the constant region of mouse IgG2a. Skint8-Ig fusion protein was purified from the expression system. A relatively high purity of Skint8-Ig protein was obtained, as determined by Coomassie blue-stained SDS-PAGE. The identity of the fusion protein was verified by Western blot using anti-IgG2a antibody. The actual molecular weight (MW) of the Skint8-Ig was higher than the predicted MW, suggesting that the recombinant protein was glycosylated.

Purified Skint8-Ig and control mouse IgG2a Fc (control Ig) proteins were then biotinylated. Spleen cells from C57BL/6 mice were stained with the biotinylated Skint8-Ig or control Ig, followed by streptavidin-PE. The binding of Skint8-Ig or control Ig to immune cells was analyzed by flow cytometry. As shown in FIGS. 15A and B, Skint8 bound to a small fraction of freshly harvested $CD4^+$ or $CD8^+$ T cells. It has been reported that naïve T cells are $CD44^{low}CD62L^{hi}$, while effective memory T cells are $CD44^{hi}CD62L^{low}$. We found that there were not $CD44^{low}CD62L^{hi}$ naïve T cells in the $CD4^+$ and $CD8^+$ T cells that bound to Skint8 (data not shown). In contrast, significant percentages of the freshly harvested $CD4^+$ and $CD8^+$ T cells that did bind to Skint8 were naïve T cells (data not shown). Our data indicate that resting $CD4^+$ and $CD8^+$ T cells did not express the putative Skint8 receptor. We also analyzed the binding of Skint8 to other immune cells and found that Skint8 bound weakly to freshly harvested $B220^+$ B cells, $CD11b^+$ monocytes, and $CD11c^+$ DCs.

We then determined the binding of Skint8 to activated immune cells. We activated $CD4^+$ and $CD8^+$ T cells by anti-CD3 and anti-CD28 antibodies. After the activation, there were few $CD44^{low}CD62L^{hi}$ naïve $CD4^+$ and $CD8^+$ T cells in the cultures (data not shown), confirming that the T cells were activated. The binding of Skint8 to $CD4^+$ and $CD8^+$ T cells was significantly increased upon the activation (FIG. 15A, B).

To determine whether the IgV- and IgC-like domains are required for Skint8 ligand binding, we produced Skint8 IgV-Ig and Skint8 IgC-Ig fusion proteins. We found that Skint8 IgV-Ig could bind to both activated $CD4^+$ and $CD8^+$ T cells, whereas Skint8 IgC-Ig did not (data not shown). The data suggest that the IgV-like domain is required for the Skint8 ligand binding.

We also analyzed the binding of Skint8 to other activated immune cells. After activation by LPS, the binding of Skint8 to activated B cells, monocytes and DCs was also significantly enhanced (FIG. 15A, B). Taken together, our data suggest that activated CD4 and CD8 T cells, B cells, monocytes and DCs express high levels of the putative Skint8 receptor, whereas the resting immune cells express the putative receptor at low levels or not at all.

To determine whether the putative Skint8 receptor is a known receptor for B7 family members, HEK-293 cells were transfected with an expression vector containing the murine PD-1, CD28, BTLA, CTLA-4, or ICOS gene. The expression of PD-1, CD28, BTLA, CTLA-4, and ICOS proteins on the transfected cells was confirmed by flow cytometric analysis with antibodies against the respective receptors (FIG. 15C). The binding of Skint8 to the transfected cells was then analyzed. As shown in FIG. 15D, Skint8 did not bind to the PD-1, CD28, BTLA, CTLA-4, or ICOS transfected cells. The data indicate that Skint8 binds to a receptor distinct from PD-1, CD28, BTLA, CTLA-4, or ICOS.

Skint8-Ig Fusion Protein Inhibits T Cell Proliferation and Activation In Vitro

The expression of the Skint8 putative receptor on T cells suggests that Skint8 may have an effect on T cell function. We first evaluated whether Skint8-Ig affected T cell proliferation in vitro. $CD3^+$ T cells were purified from spleen cells of C57BL/c mice, and cultured on plates pre-coated with or without anti-CD3 antibody in the presence of graded doses of Skint8-Ig for 3 days. Since Skint8-Ig has a 1.88-fold higher molecular weight than control Ig, we used equimolar amounts of Ig as a control. T cell proliferation was measured by [$^3$H] thymidine incorporation. Skint8-Ig did not affect the proliferation of T cells in the absence of anti-CD3 antibody stimulation (data not shown). However, Skint8-Ig inhibited anti-CD3-activated T cell proliferation in a dose-dependent manner, with ~10%, 47% and 61% inhibition in the presence of 1864, 3728, and 7456 ng/ml Skint8-Ig, respectively, as compared to equimolar amounts of control Ig (FIG. 16A). We then determined whether Skint8-Ig could inhibit anti-CD3 and anti-CD28 antibody-activated T cell proliferation. As shown in FIG. 16B, Skint8-Ig also reduced anti-CD3 and anti-CD28-activated T cell proliferation although Skint8-Ig at a low dose (1864 ng/ml) did not have the effect.

To confirm the inhibitory effect of Skint8-Ig on T cell proliferation and to determine whether Skint8-Ig inhibits CD4 and/or CD8 T cells, spleen cells were labelled with carboxyfluorescein diacetate succinimidyl ester (CFSE), and cultured with anti-CD3 antibody and equimolar amounts of Skint8-Ig or control Ig. T cell proliferation was assessed by CFSE intensity that is diluted with each cell division. As shown in FIG. 16C-E, Skint8-Ig inhibited anti-CD3-activated proliferation of CD4⁺ and CD8⁺ T cells. The inhibition was further confirmed by [³H] thymidine incorporation with purified CD4⁺ and CD8⁺ T cells (FIG. 16F, G).

We then determined whether Skint8-Ig affects T cell activation in vitro. Murine spleen cells were cultured with anti-CD3 antibody in the presence of Skint8-Ig or control Ig. The expression of CD69 that is an early marker of T cell activation was analyzed by flow cytometry 24 hours later. As shown in FIGS. 16H and I, the expression levels of CD69 on both CD4 and CD8 T cells were significantly reduced by Skint8-Ig. Similarly, Skint8-Ig at high doses also inhibited the expression levels of CD69 on anti-CD3 and CD28 antibody-activated CD4 and CD8 T cells (FIG. 16J-L). Collectively, our results suggest that Skint8-Ig inhibits TCR-mediated proliferation and activation of both CD4 and CD8 T cells in vitro.

Skint8-Ig Fusion Protein Inhibits Cytokine Production from T Cells In Vitro

We next examined whether Skint8-Ig affects cytokine production from T cells in vitro. Murine purified T cells were stimulated with anti-CD3 antibody in the presence of Skint8-Ig or control Ig protein for 3 days. The cytokines in the supernatants were measured by ELISA. As shown in FIG. 17A, Skint8-Ig inhibited the production of IFNγ and TNFα. The results suggest that Skint8-Ig can also inhibit TCR-mediated cytokine production from T cells in vitro.

We then used flow cytometry to determine whether Skint8-Ig inhibited Th1 cytokine production by CD4⁺ or CD8⁺ T cells. Skint8-Ig significantly inhibited the production of IFNγ and TNFα by anti-CD3-, or anti-CD3- and anti-CD28-stimulated CD4⁺ T cells (FIG. 17B-E). Skint8-Ig also significantly reduced the production of TNFα, but not IFNγ by anti-CD3- or anti-CD3 and CD28-stimulated CD8⁺ T cells (data not shown).

Administration of Skint8-Ig Fusion Protein Ameliorates EAE in Mice

Multiple sclerosis (MS) is an autoimmune disease of the central nervous system and is caused by an overactive immune system. EAE is a common animal model for MS. We determined whether in vivo administration of Skint8-Ig protein could ameliorate EAE. C57BL/6 mice were induced for EAE and injected with Skint8-Ig or control Ig protein. As shown in FIG. 18A, hBTN5-Ig treatment delayed EAE onset, and reduced the mean clinical scores throughout the entire 35 day time course.

Since EAE is primarily mediated by CD4 T cells, we analyzed CD4 T cell activation in the mice. Skint8-Ig reduced the expression of CD69 by CD4⁺ T cells (FIG. 18B, C). In addition, Skint8-Ig increased the percentages of CD44$^{lo}$CD62L$^{hi}$ naïve CD4 T cells, but decreased the percentages of CD44$^{hi}$CD62L$^{lo}$ effector memory CD4 T cells (FIG. 18D. E).

We also examined the percentages of CD4⁺ T cells and CD4⁺CD25⁺Foxp3⁺ regulatory T cells (Tregs) in the spleen at both prime (day 10) and peak (day 22) times. The percentages of CD4⁺ T cells in Skint8-Ig-treated mice were decreased, whereas those of Tregs were increased at both time points (FIG. 18F-M). We then analyzed antigen-specific T cell responses. After MOG in vitro stimulation, the production of TNFα, IFNγ, and IL-17 was decreased, whereas that of IL-10 was increased by splenic CD4⁺ T cells in Skint8-Ig-treated EAE mice (FIG. 18N, O). Similar trends were also observed in the draining lymph nodes (data not shown). In addition, we found that the percentage of the CNS infiltrating CD4 T cells was decreased, whereas that of CD4⁺CD25⁺Foxp3⁺ Tregs was increased in Skint8-Ig-treated EAE mice (FIG. 18P-S).

Taken together, our results indicate that in vivo administration of Skint8-Ig ameliorates EAE in mice. This is related to reduced CD4 T cell activation, and a decreased proportion of CD4 T cells and an increased percentage of Tregs in the lymphoid organs and CNS. Furthermore, Skint8-Ig inhibits antigen-specific T cell responses.

Discussion

In this example we characterize a novel T cell inhibitory molecule Skint8 that shares ~20% identity in the extracellular region with several existing members of the B7 family. Like B7 family molecules, the extracellular region of Skint8 contains one IgV-like and one IgC-like domain. Although Skint8 has a higher sequence identity with the BTN molecules than with the B7 members, unlike most of BTN members, Skint8 does not have the intracellular B30.2 domain. Therefore, Skint8 appear to be a novel member of the extended B7 family or a B7 family-related molecule.

We analyzed its expression in purified immune cells and found that Skint8 mRNA was expressed in purified CD4 T cells, B cells and monocytes. The expression levels of Skint8 mRNA in these immune cells were not significantly altered upon activation of these cells. The constitutive expression of Skint8 transcript in APCs including B cells and monocytes is in accordance with its functions in regulating T cell proliferation and/or activation.

The Skint8 putative receptor is not expressed on resting CD4 and CD8 T cells, but is induced upon activation by anti-CD3 and anti-CD28 antibodies. This expression pattern is similar to the receptors for other BTN and BTNL proteins, such as BTN1A1, BTN2A2, BTNL2, BTNL1 and BTN3 (24, 26, 29, 31), as well as some B7 family molecules, such as ICOSL, PDL1/PDL2, B7-H3, B7-H4 (11, 13). Skint8 protein did not bind the PD-1, CD28, BTLA, CTLA-4, or ICOS gene transfected cells, suggesting that the putative Skint8 receptor is distinct from the receptors for the known B7 family ligands.

The expression of the Skint8 putative receptor on activated T cells indicates that Skint8 may affect T cells that have already been activated and provides a negative signal that limits the effector phase, akin to the activity of PD-L1. Indeed, we have demonstrated that Skint8-Ig protein inhibits anti-CD3 or anti-CD3 plus anti-CD28-induced proliferation, activation and cytokine production from T cells. Furthermore, in vivo administration of Skint8-Ig inhibits T cell activation and attenuates EAE in mice. In addition to the expression on activated T cells, the Skint8 putative receptor is expressed on activated B cells, DCs and monocytes.

In summary, we have identified Skint8 as a novel T cell inhibitory molecule. Skint8 mRNA is expressed on APCs, and the Skint8 putative receptor is expressed on activated T cells, and APCs. Skint8-Ig fusion protein inhibits the proliferation, activation, and cytokine production of T cells in vitro and ameliorates EAE in vivo, and thus is a target for regulation of immune responses, which has implications for the treatment of many immune-associated diseases.

Materials and Methods Bioinformatics Analysis of Skint8.

Sequence alignment of the extracellular domains of Skint8 and existing B7 family members was analyzed via the Clustal W™ program in MacVector™ 16.0.5 (MacVector, Inc.). Phylogenic tree analysis was also performed via the Clustal W® program in MacVector™.

Cloning and Purification of Skint8

The IgV- and IgC-like domains in the extracellular region of Skint8 (aa 26-233) were cloned and fused into a pCMV6-AC-FC-S expression vector containing the constant region of mouse IgG2a (ORIGENE, Rockville, Md.). Separately, the IgV-like domain (aa 26-142) or IgC-like domain (aa 159-233) alone was cloned and fused into the vector. The vectors were transfected into HEK-293 cells. The fusion proteins were purified from the supernatant using Protein G Sepharose 4 Fast Flow according to the manufacturer's instructions (GE Healthcare). Purified proteins were verified by SDS-PAGE, Coomassie Staining and Western blot. Proteins were quantified using the Pierce™ BCA Protein Assay Kit (Pierce, Rockford, Ill.). Control Ig (recombinant mouse IgG2a Fc protein) was purchased from BXCell (West Lebanon, NH).

Mice

Four-week-old female C57BL/6 mice were purchased from Jackson Laboratory. The mice were used in accordance with protocols approved by the Institutional Animal Care and Use Committee of the University of Connecticut.

RT-PCR and qRT-PCR

Total RNA from cells was isolated from tissues or cells, and cDNA was synthesized as described (37). Equal amounts of cDNAs were used for RT-PCR. PCR products were viewed after running through an agarose gel. qRT-PCRs were performed with the Power SYBR green mastermix (Applied Biosystems, UK) using the 7500 real-time PCR system (Applied Biosystems, UK).

Flow Cytometry Analysis

Single cell suspensions of organs were stained with the fluorochrome-conjugated antibodies protein as described (38-41). Direct or indirect staining of fluorochrome-conjugated antibodies included: CD4, CD8, B220, CD11c, CD11b, F4/80, CD69, CD44, CD62L, IFNγ, TNFα, IL-2, IL-10, CD28, CTLA-4, PD-1, BTLA, and ICOS (BioLegend, or BD Biosciences, San Jose, Calif., San Diego, Calif.). Skint8-g, Skint8 IgV-Ig or Skint8 IgC-Ig proteins were biotinylated with sulfo-NHS-LC-Biotin (Pierce) and detected by streptavidin-PE. The samples were analyzed on a FACSCalibur or LSRFortessa X-20 Cell Analyzer (BD Biosciences). Data analysis was done using FlowJo software (Ashland, Oreg.).

In Vitro T Cell Assays

Murine CD3$^+$, CD4$^+$ or CD8$^+$ T cells were purified from C57BL/6 mice by an immunomagnetic system (Miltenyi, Auburn, Calif.), and the purity of the cells was usually >95%. T cells were stimulated with anti-CD3 antibody, or anti-CD3 and anti-CD28 antibodies (Biolegend) in the presence of Skint8-Ig or control Ig. Proliferative response was assessed by pulsing the culture with 1 μCi of [$^3$H] thymidine (PerkinElmer, Inc., Downers Grove, Ill.) 12 hours before harvest. [$^3$H] thymidine incorporation was measured by liquid scintillation spectroscopy (PerkinElmer, Inc.). For the carboxyfluorescein diacetate succinimidyl ester (CFSE) assay, splenocytes were labeled with CFSE (ThermoFisher Scientific, Grand Island, N.Y.) and stimulated with anti-CD3 in the presence of Skint8-Ig or control Ig. The cells were analyzed by flow cytometry.

ELISA

The concentration of cytokines IFNγ, TNFα, IL-2, and IL-10 was determined by its respective ELISA Kit (Biolegend) according to the manufacturer's instructions.

Induction and Assessment of EAE

Mouse MOG35-55 (GL Biochem, Shanghai, China) was emulsified in complete Freud's adjuvant (Sigma-Aldrich, St Louis, Mo., USA) supplemented with *Mycobacterium tuberculosis* H37Ra (Difco Laboratories, Detroit, Mich.). Mice were injected s.c. with the MOG in the dorsal flank on day 0. The mice were also injected i.p. with 500 ng of purified *Bordetella pertussis* toxin (Sigma-Aldrich). The mice were then observed for clinical scores based on the following scale: 0, normal; 0.5, partially limp tail; 1, paralyzed tail; 2, loss in coordinated movement, hind limb paresis; 2.5, one hind limb paralyzed; 3, both hind limbs paralyzed; 3.5, hind limbs paralyzed, weakness in forelimbs; 4, forelimbs paralyzed; 5, moribund or dead. As required by animal ethics, mice were euthanized beyond a clinical score of 4.

Statistical Analysis

P-values were based on the two-sided Student's t test. A confidence level above 95% (p<0.05) was determined to be significant.

REFERENCES

1. Freeman, G. J., G. S. Gray, C. D. Gimmi, D. B. Lombard, L. J. Zhou, M. White, J. D. Fingeroth, J. G. Gribben, and L. M. Nadler. 1991. Structure, expression, and T cell costimulatory activity of the murine homologue of the human B lymphocyte activation antigen B7. *J Exp. Med.* 174: 625-631.
2. Freeman, G. J., J. G. Gribben, V. A. Boussiotis, J. W. Ng, V. A. Restivo, Jr., L. A. Lombard, G. S. Gray, and L. M. Nadler. 1993. Cloning of B7-2: a CTLA-4 counter-receptor that costimulates human T cell proliferation. *Science* (New York. N.Y.) 262: 909-911.
3. Dong, H., G. Zhu, K. Tamada, and L. Chen. 1999. B7-H1, a third member of the B7 family, co-stimulates T-cell proliferation and interleukin-10 secretion. *Nat. Med.* 5: 1365-1369.
4. Freeman, G. J., A. J. Long, Y. Iwai, K. Bourque, T. Chernova, H. Nishimura, L. J. Fitz, N. Malenkovich, T. Okazaki, M. C. Byme, H. F. Horton, L. Fouser, L. Carter, V. Ling, M. R. Bowman, B. M. Carreno, M. Collins, C. R. Wood, and T. Honjo. 2000. Engagement of the PD-1 immunoinhibitory receptor by a novel B7 family member leads to negative regulation of lymphocyte activation. *J. Exp. Med.* 192: 1027-1034.
5. Latchman, Y., C. R. Wood, T. Chemova, D. Chaudhary, M. Borde, I. Chemova, Y. Iwai, J. Long, J. A. Brown, R. Nunes, E. A. Greenfield, K. Bourque, V. A. Boussiotis, L. L. Carter, B. M. Carreno, N. Malenkovich, H. Nishimura, T. Okazaki, T. Honjo, A. H. Sharpe. and G. J. Freeman. 2001. PD-L2 is a second ligand for PD-1 and inhibits T cell activation. *Nat. Immunol.* 2: 261-268.
6. Tseng, S. Y., M. Otsuji, K. Gorski, X. Huang, J. E. Slansky, S. I. Pai, A. Shalabi, T. Shin, D. M. Pardoll, and H. Tsuchiya. 2001. B7-DC, a new dendritic cell molecule with potent costimulatory properties for T cells. *J. Exp. Med.* 193: 839-846.
7. Wang, S., G. Zhu, A. I. Chapoval, H. Dong, K. Tamada, J. Ni, and L. Chen. 2000. Costimulation of T cells by B7-H2, a B7-like molecule that binds ICOS. *Blood* 96: 2808-2813.
8. Ling, V., P. W. Wu, H. F. Finnerty, K. M. Bean, V. Spaulding, L. A. Fouser, J. P. Leonard. S. E. Hunter. R. Zollner, J. L. Thomas. J. S. Miyashiro, K. A. Jacobs, and M. Collins. 2000. Cutting edge: identification of GL50, a novel B7-like protein that functionally binds to ICOS receptor. *Journal of immunology* (Baltimore. Md.: 1950) 164: 1653-1657.
9. Swallow, M. M., J. J. Wallin, and W. C. Sha. 1999. B7h, a novel costimulatory homolog of B7.1 and B7.2, is induced by TNFalpha. *Immunity,* 11: 423-432.

10. Yoshinaga, S. K., J. S. Whoriskey, S. D. Khare, U. Sarmiento, J. Guo, T. Horan, G. Shih, M. Zhang, M. A. Coccia, T. Kohno, A. Tafuri-Bladt, D. Brankow, P. Campbell, D. Chang. L. Chiu, T. Dai, G. Duncan, G. S. Elliott, A. Hui. S. M. McCabe, S. Scully. A. Shahinian, C. L. Shaklee, G. Van, T. W. Mak, and G. Senaldi. 1999. T-cell co-stimulation through B7RP-1 and ICOS. *Nature* 402: 827-832.
11. Chapoval, A. I., J. Ni, J. S. Lau, R. A. Wilcox. D. B. Flies, D. Liu, H. Dong. G. L. Sica, G. Zhu, K. Tamada, and L. Chen. 2001. B7-H3: a costimulatory molecule for T cell activation and IFN-gamma production. *Nat. Immunol.* 2: 269-274.
12. Prasad, D. V., S. Richards. X. M. Mai, and C. Dong. 2003. B7S1, a novel B7 family member that negatively regulates T cell activation. *Immunity* 18: 863-873.
13. Sica, G. L., I. H. Choi, G. Zhu, K. Tamada, S. D. Wang, H. Tamura, A. I. Chapoval, D. B. Flies, J. Bajorath, and L. Chen. 2003. B7-H4, a molecule of the B7 family, negatively regulates T cell immunity. *Immunity* 18: 849-861.
14. Zang, X., P. Loke, J. Kim, K. Murphy, R. Waitz, and J. P. Allison. 2003. B7x: a widely expressed B7 family member that inhibits T cell activation. *Proceedings of the National Academy of Sciences of the United States of America* 100: 10388-10392.
15. Zhao, R., J. M. Chinai, S. Buhl, L. Scandiuzzi, A. Ray, H. Jeon, K. C. Ohaegbulam, K. Ghosh, A. Zhao, M. D. Scharff and X. Zang. 2013. HHLA2 is a member of the B7 family and inhibits human CD4 and CD8 T-cell function. *Proceedings of the National Academy of Sciences of the United States of America* 110:9879-9884.
16. Zhu, Y., S. Yao, B. P. Iliopoulou, X. Han, M. M. Augustine, H. Xu, R. T. Phennicie, S. J. Flies, M. Broadwater, W. Ruff, J. M. Taube, L. Zheng, L. Luo, G. Zhu, J. Chen, and L. Chen. 2013. B7-H5 costimulates human T cells via CD28H. *Nature communications* 4: 2043.
17. Brandt, C. S., M. Baratin, E. C. Yi, J. Kennedy, Z. Gao, B. Fox, B. Haldeman, C. D. Ostrander, T. Kaifu, C. Chabannon, A. Moretta, R. West, W. Xu, E. Vivier, and S. D. Levin. 2009. The B7 family member B7-H6 is a tumor cell ligand for the activating natural killer cell receptor NKp30 in humans. *J. Exp. Med.* 206:1495-1503.
18. Abeler-Dorner, L., M. Swamy, G. Williams, A. C. Hayday, and A. Bas. 2012. Butyrophilins: an emerging family of immune regulators. *Trends Immunol.* 33: 34-41.
19. Afrache, H., P. Gouret, S. Ainouche, P. Pontarotti, and D. Olive. 2012. The butyrophilin (BTN) gene family: from milk fat to the regulation of the immune response. *Immunogenetics* 64: 781-794.
20. Arnett, H. A., and J. L. Viney. 2014. Immune modulation by butyrophilins. *Nat. Rev. Immunol.* 14: 559-569.
21. Guo, Y., and A. Y. Wang. 2015. Novel Immune Check-Point Regulators in Tolerance Maintenance. *Front Immunol* 6: 421.
22. Rhodes, D. A., W. Reith, and J. Trowsdale. 2016. Regulation of Immunity by Butyrophilins. *Annu. Rev. Immunol.* 34: 151-172.
23. Chapoval, A. I., G. Smithson, L. Brunick, M. Mesri, F. L. Boldog, D. Andrew, N. V. Khramtsov, E. A. Feshchenko, G. C. Starling, and P. S. Mezes. 2013. BTNL8, a butyrophilin-like molecule that costimulates the primary immune response. *Mol. Immunol.* 56: 819-828.
24. Nguyen, T., X. K. Liu, Y. Zhang, and C. Dong. 2006. BTNL2, a butyrophilin-like molecule that functions to inhibit T cell activation. *J. Immunol.* 176:7354-7360.
25. Arnett, H. A., S. S. Escobar, E. Gonzalez-Suarez, A. L. Budelsky, L. A. Steffen, N. Boiani, M. Zhang, G. Siu, A. W. Brewer, and J. L. Viney. 2007. BTNL2, a butyrophilin/B7-like molecule, is a negative costimulatory molecule modulated in intestinal inflammation. *J. Immunol.* 178: 1523-1533.
26. Yamazaki, T. I. Goya, D. Graf, S. Craig, N. Martin-Orozco, and C. Dong. 2010. A butyrophilin family member critically inhibits T cell activation. *J Immunol.* 185: 5907-5914.
27. Ammann, J. U., A. Cooke, and J. Trowsdale. 2013. Butyrophilin Btn2a2 inhibits TCR activation and phosphatidylinositol 3-kinase/Akt pathway signaling and induces Foxp3 expression in T lymphocytes. *J. Immunol.* 190: 5030-5036.
28. Swanson, R. M., M. A. Gavin, S. S. Escobar, J. B. Rottman, B. P. Lipsky, S. Dube, L. Li, J. Bigler, M. Wolfson, H. A. Arnett. and J. L. Viney. 2013. Butyrophilin-like 2 modulates B7 costimulation to induce Foxp3 expression and regulatory T cell development in mature T cells. *J. Immunol.* 190: 2027-2035.
29. Smith, I. A., B. R. Knezevic, J. U. Ammann, D. A. Rhodes, D. Aw, D. B. Palmer, I. H. Mather, and J. Trowsdale. 2010. BTN1A1, the mammary gland butyrophilin, and BTN2A2 are both inhibitors of T cell activation. *Journal of immunology* (Baltimore. Md.: 1950) 184: 3514-3525.
30. Cubillos-Ruiz, J. R., D. Martinez, U. K. Scarlett, M. R. Rutkowski, Y. C. Nesbeth, A. L. Camposeco-Jacobs, and J. R. Conejo-Garcia. 2010. CD277 is a negative co-stimulatory molecule universally expressed by ovarian cancer microenvironmental cells. *Oncotarget* 1: 329-338.
31. Compte, E., P. Pontarotti, Y. Collette, M. Lopez, and D. Olive. 2004. Frontline: Characterization of BT3 molecules belonging to the B7 family expressed on immune cells. *European journal of immunology* 34: 2089-2099.
32. Yamashiro, H., S. Yoshizaki, T. Tadaki, K. Egawa, and N. Seo. 2010. Stimulation of human butyrophilin 3 molecules results in negative regulation of cellular immunity. *J Leukoc Biol* 88: 757-767.
33. Palakodeti, A., A. Sandstrom, L. Sundaresan, C. Harly, S. Nedellec, D. Olive, E. Scotet, M. Bonneville, and E. J. Adams. 2012. The molecular basis for modulation of human Vgamma9Vdelta2 T cell responses by CD277/butyrophilin-3 (BTN3A)-specific antibodies. *J. Biol. Chem.* 287: 32780-32790.
34. Linsley, P. S., R. Peach, P. Gladstone. and J. Bajorath. 1994. Extending the B7 (CD80) gene family. *Protein Sci.* 3: 1341-1343.
35. Yang, Y., X. K. Liu, T. Nguyen, C. Bishop, D. Graf, and C. Dong. 2007. Characterization of B7S3 as a novel negative regulator of T cells. *Journal of immunology* (Baltimore, Md.: 1950) 178: 3661-3667.
36. Boyden, L. M., J. M. Lewis, S. D. Barbee, A. Bas, M. Girardi, A. C. Hayday, R. E. Tigelaar, and R. P. Lifton. 2008. Skint1, the prototype of a newly identified immunoglobulin superfamily gene cluster, positively selects epidermal gammadelta T cells. *Nat. Genet.* 40: 656-662.
37. Yan, Y., M. Su, Y. Song, Y. Tang, C. Tian, D. Rood, and L. Lai. 2014. Tbx1 Modulates Endodermal and Mesodermal Differentiation from Mouse Induced Pluripotent Stem cells. *Stem cells and development*.
38. Jin, J., I. Goldschneider, and L. Lai. 2011. In vivo administration of the recombinant IL-7/hepatocyte growth factor beta hybrid cytokine efficiently restores thymopoiesis and naive T cell generation in lethally irradiated mice after syngeneic bone marrow transplantation. *Journal of immunology* (Baltimore, Md.: 1950) 186:1915-1922.
39. Lai, L., M. Zhang, and I. Goldschneider. 2012. Recombinant IL-7/HGFbeta efficiently induces transplantable murine hematopoietic stem cells. *J. Clin. Invest.* 122: 3552-3562.
40. Lai, L., M. Zhang, Y. Song, and D. Rood. 2013. Recombinant IL-7/HGFbeta Hybrid Cytokine Enhances T Cell Recovery in Mice Following Allogeneic Bone Marrow Transplantation. *PloS one* 8: e82998.
41. Song, Y., M. Su, P. Panchatsharam, D. Rood, and L. Lai. 2015. c-Met signalling is required for efficient postnatal thymic regeneration and repair. *Immunology* 144: 245-253.

Example 4. BTN5

In this example, we identify BTN5, previously called erythroid membrane-associated protein (ERMAP), as a novel T cell inhibitory molecule. BTN5 protein is expressed on the cell surface of resting and activated antigen presenting cells (APCs), and in tumor tissues. The BTN5 putative receptor is expressed on activated CD4 and CD8 T cells, and macrophages. Both mouse and human BTN5-IgG2a Fc (BTN5-Ig) fusion proteins inhibit T cell proliferation, activation, and/or cytokine production in vitro. Administration of BTN5-Ig protein ameliorates autoimmune diseases including experimental autoimmune encephalomyelitis (EAE) and type I diabetes (TID) in mice. BTN5 also affects macrophage function because anti-BTN5 blocking antibody enhances macrophage phagocytosis of cancer cells in vitro. Furthermore, administration of the anti-BTN5 antibody inhibits tumor growth in mice, likely by blocking the inhibitory effects of BTN5 on T cells and macrophages. These results demonstrate that therapeutic interaction of the BTN5 inhibitory pathway represents a novel strategy for treating patients with autoimmune disease or cancer.

Results:
BTN5 Shares Sequence and Structural Similarity to Existing B7 Family Members in the Extracellular Region B7-H3 is a B7 family member whose putative receptor is expressed on activated T cells. B7-H3 has been shown to have either a stimulatory or an inhibitory effect on T cells. By a series of genome-wide database searches, we found that the extracellular region of mouse BTN5 (mBTN5) shares a strong similarity with that of B7-H3 with 25% identity and 15% similarity, including a conserved pattern of 4 cysteines in identical positions. mBTN5 also has a significant homology with other B7 family members, sharing 20%, 17%, 24%, 20%, 22% and 22% identity in the extracellular region with mouse PD-L1, PD-L2, B7-1, B7-2, B7-H2, B7-H4, respectively (data not shown). These levels of identity are similarly observed among the known B7 family members, suggesting that BTN5 is a new B7 family member or B7-related molecule. BTN5 is highly conserved among vertebrates, and human BTN5 (hBTN5) shares a striking homology with mBTN5 (73% identity and 14% similarity; data not shown). Both mBTN5 and hBTN5 proteins contain an extracellular region, a transmembrane domain, and an intracellular region. The extracellular region in mBTN5 contains an IgV domain and an IgC domain, whereas hBTN5 has an IgV domain, but no IgC domain [37, 38, 41]. BTN5 also shares a significant homology across its entire length to other BTN molecules [37]. Phylogenic tree analysis shows that the extracellular region of mBTN5 is closer to that of B7-H3, B7-H4. PD-L1 and PD-L2 than that of B7.1 and B7.2.

BTN5 is Expressed on APCs, and Some Cancer Tissues and Tumor Cell Lines

We evaluated the expression of mBTN5 mRNA in various tissues by using RT-PCR analysis. mBTN5 mRNA was detected in the lymph node, thymus and lung. mBTN5 mRNA was also weakly expressed in other organs including the spleen, pancreas, blood, liver, heart, and kidney.

It has been reported that BTN5 protein was predominately located on cell surfaces of BTN5 gene transfected cells [37, 38, 41]. We analyzed the expression of mBTN protein on the cell surface of immune cells by flow cytometry. As shown in FIG. 19A, mBTN5 protein was not expressed on the cell surface of resting $CD19^+$ or $B220^+$ B cells. $CD11b^+$ monocytes, F4/80 macrophages, and $CD11c^+$ dendritic cells (DCs), but was induced upon activation by LPS. (FIG. 19A). mBTN5 protein was also expressed weakly on resting $CD4^+$ and $CD8^+$ T cells, and the expression levels were upregulated upon activation by anti-CD3 and CD28 antibodies (FIG. 19A). These results suggest that endogenous mBTN5 is an integral cell surface protein that is expressed on activated APCs, resting and activated T cells.

We then determined the expression of hBTN5 protein in normal and cancer human tissues by immunohistochemistry. As shown in FIGS. 19B and C, control isotype antibody did not stain any normal or cancer tissues. In contrast, an anti-hBTN5 antibody detected hBTN5 protein expression in normal breast, lung, liver, colon, and prostate tissues at low levels (FIG. 19B). hBTN5 protein was also detected in cancer tissues, and the expression levels of hBTN5 in breast, lung, liver, colon, and prostate tumor tissues were higher than those of the respective normal tissues (FIG. 19C vs 19B). hBTN5 protein was largely confined to the plasma membrane or cytoplasm of epithelial cells.

We also examined BTN5 protein expression on some tumor cell lines by flow cytometry. As shown in FIG. 19D, BTN5 protein was expressed highly on the cell surface of murine neuro-2a neuroblastoma cells, Lewis lung carcinoma, P388 leukemia, and human erythroleukemia line K562. BTN5 protein was weakly or not expressed on murine CT-26 colon cancer cells and B16F10 melanoma cells.

The Expression of the Putative BTN5 Receptor

To determine the expression pattern of the putative BTN5 receptor, we constructed an mBTN5-Ig fusion protein that contains the IgV domain of mBTN5 and the constant region of mouse IgG2a. Purified mBTN5-Ig fusion protein and control mouse IgG2a Fc (control Ig) were biotinylated. Splenocytes from C57BL/6 mice were stained with the biotinylated proteins, followed by Streptavidin-PE. The binding of mBTN5-Ig or control Ig to immune cells was analyzed by flow cytometry. As shown in FIGS. 20A and B. mBTN5 scarcely bound to resting $CD4^+$ and $CD8^+$ T cells, but bound significantly to anti-CD3 and anti-CD28 antibody-activated CD4 and $CD8^+$ T cells (FIG. 20A). The results indicate that activated CD4 and CD8 T cells express the putative BTN5 receptor.

We also analyzed the expression of the putative BTN5 receptor on other immune cells. We found that mBTN5 bound to a proportion of resting $B220^+$ B cells, $CD11c^+$ DCs, $CD11b^+$ monocytes, and $F4/80^+$ macrophages (FIG. 20A). After activation by LPS, the mBTN5 binding to B cells, DCs, monocytes and macrophages was increased (FIG. 20A). The data suggest that resting B cells, DCs, monocytes and macrophages also express the putative BTN5 receptor and the expression levels on these cells are upregulated upon activation.

To determine whether the putative BTN5 receptor is a known B7 member receptor, HEK-293 cells were transfected with an expression vector containing the murine PD-1, CD28, BTLA, CTLA-4, or ICOS gene. The expression of PD-1, CD28, BTLA, CTLA-4, or ICOS protein on the transfected cells was confirmed by flow cytometric analysis with the antibodies against the respective receptors (FIG. 20B). The binding of mBTN5 to the transfected cells was then analyzed. mBTN5 did not bind to the PD-, CD28, BTLA, CTLA-4, or ICOS transfected cells (FIG. 20C). The results suggest that mBTN5 binds to a receptor distinct from PD-1. CD28, BTLA, CTLA-4, or ICOS.

mBTN-Ig Fusion Protein Inhibits T Cell Proliferation and Activation In Vitro

The data that mBTN5 protein is expressed on APCs and its putative receptor is expressed on activated T cells suggest a potential function of mBTN5 on T cells. We therefore investigated the effect of mBTN5-Ig on T cell proliferation in vitro. $CD3^+$ T cells were purified from splenocytes of C57BL/c mice, and cultured on plates pre-coated with or without anti-CD3 antibody in the presence of graded doses of mBTN5-Ig or control Ig for 3 days. T cell proliferation was measured by [$^3$H] thymidine incorporation. mBTN5-Ig in the absence of anti-CD3 antibody did not affect the proliferation of T cells (data not shown). However, mBTN5-Ig inhibited anti-CD3-induced T cell proliferation in a dose-dependent manner, with ~22%, 52% and 79% inhibition in the presence of 1434, 2868, and 5736 ng/ml mBTN5-Ig, respectively, as compared to respective amounts of control Ig (FIG. 21A).

To confirm the T cell inhibitory effect and to determine whether mBTN5 inhibits CD4 and/or CD8 T cells, splenocytes were labelled with carboxyfluorescein diacetate succinimidyl ester (CFSE), and cultured with anti-CD3 antibody and graded doses of mBTN5-Ig or control Ig. T cell proliferation was analyzed for CFSE fluorescent intensity in $CD4^+$ or $CD8^+$ T cells by flow cytometry. Consistent with the results from the [$^3$H] thymidine incorporation assay, mBTN5-Ig inhibited anti-CD3-activated proliferation of $CD4^+$ and $CD8^+$ T cells in a dose-dependent manner (FIG. 21B-D).

We then determined whether mBTN5-Ig affects T cell activation in vitro. Splenocytes were cultured with anti-CD3 antibody and mBTN5-Ig or control Ig. Since CD69 is an early marker of T cell activation, the expression of CD69 was analyzed after 24 hours. As shown in FIGS. 21E and F, the expression levels of CD69 on both CD4 and CD8 T cells were significantly reduced in the presence of mBTN5-Ig. The results suggest that mBTN5-Ig inhibits the activation of CD4 and CD8 T cells.

T cells can be divided into naïve and effective memory T cells based on the expression levels of CD44 and CD62L. We next analyzed the effect of mBTN5-Ig on these T cell subsets. We found that the percentages of $CD44^{lo}CD62L^{hi}$ CD4 and CD8 T naïve cells were significantly higher in the presence of mBTN5-Ig than those in the control group (FIG. 21G-I). In contrast, the percentages of $CD44^{hi}CD62L^{lo}$ CD4 and CD8 effective memory T cells were significantly lower in the presence of mBTN5-Ig (FIG. 21, G, J, K). The results further suggest that mBTN5-Ig inhibits the activation of CD4 and CD8 T cells. Taken together, our results suggest that mBTN5-Ig inhibits TCR-mediated proliferation and activation of both CD4 and CD8 T cells in vitro.

hBTN5-Ig Fusion Protein Inhibits T Cell Proliferation and Cytokine Production In Vitro Having demonstrated that mBTN5-Ig protein inhibits the proliferation and activation of murine T cells in vitro, we wished to know whether hBTN5 has similar effects. Like mBTN5-Ig, we cloned and expressed hBTN5-Ig fusion protein containing the IgV domain of hBTN5 and the constant region of mouse IgG2a. hBTN5-Ig protein was then purified from the expression system until a relatively high purity, as determined by Coomassie blue-stained SDS-PAGE. The identity of the fusion protein was verified by Western blot using anti-IgG2a antibody. [$^3$H] thymidine incorporation assay showed that hBTN5-Ig also inhibited the proliferation of murine T cells in a dose-dependent manner, with ~15%, 61% and 85% inhibition in the presence of 1434, 2868, and 5736 ng/m hBTN5-Ig, respectively (FIG. 22A). CFSE dilution assay showed that hBTN5-Ig inhibited the proliferation of both $CD4^+$ and $CD8^+$ T cells (FIG. 22B-D).

We also determined whether hBTN5-Ig inhibits the proliferation of human T cells. Purified human T cells were cultured with anti-human CD3 antibody in the presence of hBTN5-Ig or control Ig, and T cell proliferation was measured by [3H] thymidine incorporation. As shown in FIG. 22E, hBTN5-Ig significantly inhibited the proliferation of human T cells. Collectively, hBTN5 inhibits the proliferation of both mouse and human primary T cells, suggesting that its binding partner and its conferred function on T cells may be conserved across species.

We next examined whether hBTN5-Ig affects cytokine production from T cells in vitro. Purified T cells were stimulated with anti-CD3 antibody in the presence of hBTN5-Ig or control Ig protein for 3 days. The cytokines in the supernatants were measured by ELISA. As shown in FIG. 22F, hBTN5-Ig inhibited the production of IFNγ, TNFα, IL-2, and IL-10 from T cells. Taken together, the results suggest that hBTN5-Ig can inhibit TCR-mediated proliferation and/or cytokine production from mouse and human T cells in vitro Anti-hBTN5 Antibody Enhances Macrophage Phagocytosis of Cancer Cells In Vitro and Inhibits Tumor Growth In Vivo.

It has been reported that CD47 is expressed on erythroid cells and cancer cells, and represents a "don't eat me" signal that protects these cells from phagocytosis by macrophages [42, 43]. Conversely, anti-CD47 blocking antibodies enhance macrophage phagocytosis of cancer cells [43]. Since BTN5 is also expressed on erythroid cells and cancer cells, we determined whether BTN5 could affect macrophage phagocytosis of cancer cells. We made anti-hBTN5 polyclonal antibody by immunizing hBTN5-Ig in mice. K562 cancer cells that express hBTN5 were labelled with CFSE. BM-derived macrophages were incubated with the K562 cells in the presence of the anti-hBTN5 or control antibody for 2 hours. The cells were then harvested, washed, and analyzed for the percentages of $CFSE^+$ cells, which represents phagocytosis of the cancer cells by macrophages. As shown in FIGS. 23A and B, macrophage-mediated phagocytosis of cancer cells was significantly augmented in the presence of the anti-BTN5 antibody.

Macrophages are composed of distinct subsets, including the classically activated M and alternatively activated M2 macrophages. M1 macrophages are proinflammatory, whereas M2 macrophages are anti-inflammatory or protumor. We investigated whether BTN5-Ig protein affects the differentiation of M1 or M2 in vitro. BM cells were first induced to generate proliferative nonactivated macrophages (also named M0 macrophages) in vitro according to published protocols [44]. The M0 macrophages were then induced to differentiate into M1 or M2 as described [44] in the presence of hBTN5-Ig or control Ig protein. We found that hBTN-Ig significantly increased the generation of $CD206^{hi}MHC\ II^{lo}$ M2 macrophages (FIG. 23C, D), but did not affect the generation of $MHC\ II^{hi}CD206^{lo}$ M1 macrophages (data not shown).

Having observed that BTN5-Ig fusion protein inhibits T cell proliferation, activation, and cytokine production in vitro, and that anti-hBTN5 blocking antibody enhances macrophage phagocytosis of cancer cells, we hypothesized that administration of anti-hBTN5 antibody could block the inhibitory effects of BTN5 on T cells and macrophages, resulting in enhanced antitumor immunity and the inhibition of tumor growth in vivo. We transfected murine CT-26 colon cancer cells with an expression vector containing the full-length hBTN5 gene and screened for the cancer cells that stably expressed BTN5. As shown in FIG. 23E, transfected CT-26 cells expressed hBTN5 protein on the cell surface. We then injected the hBTN5-expressing CT-26 cells s.c. into syngeneic BALB/c mice. When the tumors were palpable, the mice were injected at the tumor site with same amounts of mouse anti-hBTN5 or control polyclonal antibody. As shown in FIG. 23F, the anti-hBTN5 antibody significantly inhibited the growth of CT-26 cancer cells, as compared to control antibody treatment. Analysis of tumor-infiltrating immune cells shows that there were significantly higher percentages of (FIG. 23G) CD4 and CD8 T cells, and lower percentages of (FIG. 23H) M2 macrophages in hBTN5-Ig-treated tumors.

Taken together, our results suggest that hBTN5 protein induces the production of M2 macrophages that may promote tumor growth. Conversely, anti-hBTN5 blocking antibody enhances macrophage phagocytosis of cancer cells in vitro, and inhibits the growth of BTN5 expressing cancer cells in vivo. The in vivo antitumor activity is likely due to the anti-BTN5 antibody blocking the inhibitory effects of BTN5 on T cells and macrophages.

Administration of hBTN5-Ig Fusion Protein Ameliorates EAE in Mice

Since BTN5-Ig fusion protein inhibits T cell proliferation, activation and cytokine production in vitro, we set out to investigate whether in vivo administration of BTN5-Ig could ameliorate autoimmune diseases that are caused by an overactive immune system. Multiple sclerosis (MS) is an autoimmune disease of the central nervous system, and EAE is a common animal model for MS. To determine whether BTN5 attenuates EAE, C57BL/6 mice were immunized with pMOG peptide to induce EAE development. The mice were then treated with hBTN5-Ig or control Ig protein. As shown in FIG. 24A, hBTN5-Ig treatment delayed EAE onset, and reduced the mean clinical scores throughout the entire 42 day time course. In addition, the percentage of disease-free mice in hBTN5-Ig-treated group was increased (FIG. 24B). Furthermore, histological evaluation showed a significant reduction in inflammatory lesions, with little or no demyelination and/or axonal damage or loss in hBTN5-Ig-treated group (FIG. 24C). Consequently, the histological scores were significantly reduced in the hBTN5-Ig-treated mice, as compared to those in the control group (FIG. 24D).

We then analyzed T cell subsets in the spleen of the EAE mice. As shown in FIG. 246E-H, the percentages of $CD44^{lo}CD62L^{hi}$ naïve CD4 and CD8 T cells were increased, while the percentages of $CD44^{hi}CD62L^{b}$ effective memory CD4 and CD8 T cells were decreased in hBTN5-Ig-treated mice, although the percentages of $CD44^{hi}CD62L^{hi}$ CD4 and CD8 central memory T cells were not significantly different between the hBTN5-Ig and control groups. The results are in agreement with our in vitro data that BTN5-Ig protein inhibits T cell activation.

Since Tregs are involved in immune tolerance induction and $CD4^+CD25^+FoxP3^+$ cells are the most profoundly characterized Tregs [45], we evaluated $CD4^+CD25^+FoxP3^+$ Tregs. We found that hBTN5-Ig treatment increased the percentage of Tregs in the spleen (FIG. 24I, J). Furthermore, the percentages of arginase$^+$ and $CD206^{hi}MHC^{lo}$ M2 macrophages were increased, while the percentage of $MHC^{hi}CD206^{lo}$ M1 macrophages was not altered in hBTN5-Ig-treated mice (FIG. 24K, L).

We next investigated T cell proliferation and cytokine production after MOG stimulation in vitro. As shown in FIGS. 24M and N, the proliferation of CD4 T cells from hBTN5-Ig-treated mice was reduced in response to $pMOG_{35-55}$ stimulation, although the proliferation of CD8 T cells was not significantly different between control- and hBTN5-Ig-groups. hBTN5-Ig treatment also reduced the production of Th1 cytokines IFNγ and TNFα, as well as Th17 cytokine, but increased the production of Th2-type cytokine IL-10 from CD4 T cells (FIG. 24 O, P).

Administration of hBTN5-Ig Fusion Protein Attenuates T1D in Mice

Type 1 diabetes (T1D) is an autoimmune disease caused by the destruction of insulin-secreting islet β-cells by autoreactive T cells. The NOD mouse is the most commonly used animal model for human TD [46]. We also investigated whether hBTN5-Ig could attenuate T1D. Female 22 week-old NOD mice were divided into two groups and 33% of the mice in each group had T1D. The mice were injected with 30 μg hBTN5-Ig or control Ig protein at 2-day intervals for 3 weeks. At 30 weeks 67% control Ig-treated mice had T1D, while none of hBTN5-Ig-treated mice had TID. Histological analysis showed that inflammation and loss of islets in BTN5-Ig-treated mice were significantly lower than control Ig-treated group (FIG. 25A). We then examined T cells and macrophages in the spleen. Like the EAE mice, hBTN5-Ig treatment resulted in increased percentages of naïve CD4 and CD8 naïve T cells, although the percentages of $CD44^{hi}CD62L^{lo}$ effective memory and $CD44^{hi}CD62L^{hi}$ central memory CD4 and CD8 T cells were not significantly different between hBTN5-Ig and control groups (FIG. 25B-E). Furthermore, the percentage of M2 macrophages was increased, and that of M1 macrophages were decreased in hBTN5-Ig-treated NOD mice (FIG. 25F, G). Taken together, our results suggest that hBTN5-Ig treatment ameliorates EAE and T1D, probably by inhibiting the proliferation and activation of autoreactive T cells, as well as increasing the number of M2 macrophages.

Generation of Anti-hBTN5-Ig Monoclonal Antibodies (mAbs)

To generate anti-hBTN5 mAbs, BALB/c mice (8-10 weeks of age) were immunized with 100 μg hBTN5-Ig protein in complete Freund's adjuvant (CFA) on day 0 and boosted on day 14 and day 21 in the same protein quantity in incomplete Freund's adjuvant (IFA). The mice were boosted with 100 μg hBTN5-Ig (no adjuvant, add 100 ml 1×PBS instead) three times three days in a row (days 28, 29, 30). The spleens were harvested from the mice on day 31. Single-cell suspension of the splenocytes were fused to X63-Ag8.653 myeloma cells to produce hybridomas. ELISA was performed to identify the hybridomas that could produce anti-hBTN5 mAbs but not with control Ig protein. These hybridoma clones were further subcloned. A total of 9 hybridoma lines that can produce anti-hBTN5 mAbs have been generated.

We then determined whether the anti-hBTN5 mAbs could enhance macrophage-mediated phagocytosis of cancer cells. BM-derived macrophages were incubated with the K562 cells that had been labelled with CFSE as in FIG. 23A. The anti-hBTN5 mAbs were added to the cultures for 2 hours. The cells were then analyzed for the percentages of CFSE+ cells. As shown in FIG. 26, macrophage-mediated phagocytosis of cancer cells was significantly augmented by two anti-hBTN5 mAbs (clones D4 and D16). We are investigating the ability of the mAbs to treat tumors in several tumor animal models.

Discussion

The present study identifies BTN5 as a novel inhibitory molecule for T cells and macrophages. BTN5 shares significant sequence and structural homolog with existing B7 family members in the extracellular region. Like B7 family molecules, the extracellular region in mBTN5 contains an IgV-like and an IgC-like domain. Although hBTN5 are highly homologous to mBTN5, hBTN5 contains only an IgV-like domain, and no IgC-like domain. However, the absence of the IgC-like domain in hBTN5 seems not to affect its functions. We have shown that hBNT5-Ig protein inhibits T cell proliferation and cytokine production in vitro and ameliorates autoimmune diseases in vivo. The mBTN5-Ig protein that we produced contains the IgV-like domain only, but also significantly inhibits T cell proliferation and activation in vitro.

By using flow cytometric analysis, we show that mBTN5 protein was expressed on the cell surface of activated APCs including DCs, monocytes, macrophages and B cells, as well as resting and activated T cells. The expression of BTN5 protein on the cell surface of APCs is also in accordance with its functions in regulating T cell proliferation and/or activation.

BTN5-Ig protein binds to activated CD4 and CD8 T cells, but not to resting T cells, suggesting that the putative BTN5 receptor is expressed on activated T cells. BTN5 joins ICOS, PDL1/2, B7-H3, B7-H4, BTN1A1, BTN2A2, BTNL2, BTNL1 and BTN3, to recognize receptors induced after T cell activation [24, 26, 29, 31]. However, BTN5 protein did not bind the CD28, CTLA-4, PD-, BTLA or ICOS transfected cells. Therefore, the putative BTN5 receptor appears distinct from CD28, PD-1, CTLA-4, BTLA, or ICOS.

In addition to inhibiting T cell functions, BTN5 also affects macrophages. We have shown that anti-BTN5 antibody enhances macrophage-mediated phagocytosis of BTN5 expressing cancer cells. The IgV domain in both mBTN5 and hBTN5 contains a C1q recognition sequence that is a macrophage membrane protein. The interaction between macrophages and BTN5 expressing cancer cells may be mediated by the C1q recognition sequence.

Our immunohistochemical analyses show that hBTN5 protein was expressed in breast, colon, lung, liver and prostate tumor tissues at medium to high levels, whereas only low levels of hBTN5 protein was detected in the respective normal tissues. Furthermore, we detected the expression of BTN5 protein on the cell surface of several cancer cell lines. The expression pattern indicates that BTN5 is involved in immune evasion of cancer cells. Indeed, we have demonstrated that in vivo administration of anti-BTN5 polyclonal antibody inhibits the growth of BTN5 expressing colon cancer cells in mice.

We have also demonstrated that in vivo administration of BTN5-Ig protein ameliorates EAE. We have shown that T cells from BTN5-treated EAE mice have a reduced proliferation in response to in vitro MOG stimulation. Furthermore, splenocytes from BTN5-treated EAE mice secreted decreased amounts of the Th1 cytokines TNFα, IFNγ, and IL-2 in response to MOG, but increased amount of the Th2 cytokine IL-10. Interestingly. BTN5 increased IL-10 amounts in the serum of EAE mice, but inhibited IL-10 production in vitro.

In addition to inhibition of T cell proliferation and activation, BTN5-induced production of Tregs and M2 macrophages is involved in the beneficial effects of BTN5 in autoimmune diseases BTN5-Ig protein treatment also attenuates T1D in NOD mice. Although the mechanisms by which BTN5-Ig inhibits EAE and T1D are similar, there are also some differences. For examples, BTN5-Ig not only increased the percentages of naïve T cells, but also decreased the percentages of effective memory cells in the EAE model, whereas BTN5-Ig only increased the percentages of naïve T cells in the T1D model. In addition, BTN5-Ig increased the percentages of M2 macrophage and decreased the percentages of inflammatory M1 macrophages in the T1D model, but only increased the percentages of M2 macrophages in the EAE model. These differences are probably due to the different animal models and/or different doses and duration of hBTN5-Ig used.

In summary, we have identified BTN5 as a novel inhibitory molecule for T cells and macrophages. BTN5 protein is expressed on APCs, and some tumor tissues and cancer cells. The BTN5 putative receptor is expressed on activated T cells, and resting and activated macrophages. BTN5-Ig fusion protein inhibits the proliferation, activation, and cytokine production of T cells, and increases the generation of anti-inflammatory M2 macrophages in vitro. In vivo administration of hBTN5-Ig attenuates autoimmune diseases including EAE and T1D. Conversely, anti-BTN5 antibody enhances macrophage-mediated phagocytosis of cancer cells in vitro, and administration of the antibody inhibits tumor growth in vivo. Therefore, targeting the BTN5 pathway is an innovative approach for the treatment of autoimmune diseases, cancer and infections.

Materials and Methods

Bioinformatics Analysis of BTN5.

Sequence alignments of the extracellular domains of mBTN5 and existing B7 family members, as well as the full sequences of mBTN5 and hBTN5 proteins were analyzed via the Clustal W program in MacVector 16.0.5 (MacVector, Inc.). Phylogenic tree analysis was also performed via the Clustal W program in MacVector. The transmembrane, and Ig-like domain were predicted with TMHMM server version 2.0, and InterPro.

Cloning and Purification of mBTN5 and hBTN5

The extracellular domains of mBTN5 (aa48-156) and hBTN5 (aa30-145) were cloned and fused into a pCMV6-AC-FC-S expression vector containing the constant region of mouse IgG2a (ORIGENE, Rockville, Md.). The vectors were transfected into HEK-293 cells. The fusion proteins were purified for the supernatant using Protein G Sepharose 4 Fast Flow according to the manufacturer's instructions (GE Healthcare). Purified proteins were verified by SDS-PAGE, Coomassie Staining and Western blot. Protein was quantified using the Pierce™ BCA Protein Assay Kit (Pierce, Rockford, Ill.). Control Ig (recombinant mouse IgG2a Fc protein) was purchased from BXCell (West Lebanon, NH). The endotoxin levels of the recombinant proteins were less than 0.01 EU/ml of 1 µg of purified protein.

Mice

BALB/c, C57BL/6 and NOD/LtJ NOD mice were purchased from Jackson Laboratory. The mice were used in accordance with protocols approved by the Institutional Animal Care and Use Committee of the University of Connecticut.

Flow Cytometry Analysis

Single cell suspensions of organs and tumors were stained with the fluorochrome-conjugated antibodies protein as described [53-56]. For intracellular staining, the cells were first permeabilized with a BD Cytofix/Cytoperm solution for 20 minutes at 4° C. Direct or indirect staining of fluorochrome-conjugated antibodies included: CD4, CD8, CD19, B220, CD11c, CD11b, F4/80, CD44, CD62L, CD69, FoxP3, CD206, MHC II, IFN$\gamma$, TNF$\alpha$, IL-17A, IL-10, CTLA-4, CD28, PD-1, BTLA, and ICOS (BioLegend, or BD Biosciences, San Jose, Calif., San Diego, Calif.). Anti-arginase 1 antibody, anti-hBTN5 monoclonal antibody were purchased from R&D System (Minneapolis, Minn.). mBTN5-Ig was biotinylated with sulfo-NHS-LC-Biotin (ThermFisher, Grand Island, N.Y.). The samples were analyzed on a FACSCalibur or LSRFortessa X-20 Cell Analyzer (BD Biosciences). Data analysis was done using FlowJo software (Ashland, Oreg.).

ELISA

The concentration of cytokines IFN$\gamma$, TNF$\alpha$, IL-2, and IL-10 was determined respectively by ELISA Kit (Biolegend) according to the manufacturer's instructions.

Histopathology

Spinal cords and pancreata were removed from mice and fixed with 10% formaldehyde for 24 hours. Segments of the tissues were embedded in paraffin, and sections were prepared. The sections were stained with hematoxylin-eosin (H&E). The sections of spinal cords were also stained with Luxol fast blue (LFB) and Bielschowski silver impregnation (BSI) to assess demyelination, and axonal damage, respectively. The histological stained sections were semiquantitatively scored blind as described [57].

Human Multiple Normal and Tumor Tissue Arrays were purchased from BioChain (Newark, Calif.). The tissues were subjected to antigen unmasking, and then incubated with anti-hBTN5 monoclonal antibody (R&D system), followed by ImmPRESS VR Polymer HRP anti-mouse IgG reagent, and developed with peroxidase substrate solution (Vector Laboratories) according to the manufacturer's instructions.

In Vitro T Cell Assays

Normal human peripheral blood CD3$^+$ Pan T Cells that were negatively isolated from mononuclear cells using an indirect immunomagnetic Pan-T labeling system were purchased from ALLCELLS, LLC (Alameda, Calif.). Murine CD3$^+$ T cells were purified from C57BL/6 mice by an immunomagnetic system (Miltenyi, Auburn, Calif.), and the purity of the cells was usually >95%. T cells were stimulated with anti-CD3 and/or anti-CD28 (Biolegend) in the presence of BTN5-Ig or control Ig. Proliferative response was assessed by pulsing the culture with [$^3$H] thymidine (1 $\mu$Ci/well) (PerkinElmer, Inc., Downers Grove, Ill.) 12 hours before harvest. Incorporation of [$^3$H] thymidine was measured by liquid scintillation spectroscopy (PerkinElmer, Inc.). For carboxyfluorescein diacetate succinimidyl ester (CFSE) assay, splenocytes were labeled with CFSE (ThermoFisher Scientific) and stimulated with anti-CD3 in the presence of BTN5-Ig or control Ig. The cells were analyzed by flow cytometry.

Reverse Transcription Polymerase Chain Reaction (RT-PCR)

Total RNA from cells was isolated from tissues and cDNA was synthesized as described [58]. Equal amounts of cDNAs were used for RT-PCR. PCR products were viewed by agarose gel.

Culturing of BM-Derived Macrophages

BM was harvested from C57BL/6 mice and cultured in medium containing M-CSF for 7 days to differentiate into M0 macrophages [44]. The M0 macrophages were induced to differentiate into M1 and M2 as described [44] in the presence of mBTN5-Ig or control Ig.

For the macrophage phagocytosis assay, cancer cells were labeled with CFSE, and cultured with M0 macrophages in the presence of anti-hBTN5 antibody or isotype antibody for 2 hours. Phagocytosis was measured by flow cytometric analysis of CFSE$^+$ cells.

Generation of Anti-hBTN5 Polyclonal and Monoclonal Antibodies

BALB/c mice were immunized with 100 $\mu$g hBTN5-Ig protein emulsified in complete Freund's adjuvant (CFA) on day 0 and boosted on day 14 and day 21 in the same protein quantity in incomplete Freund's adjuvant (IFA). The mice were boosted with 100 $\mu$g hBTN5-Ig without IFA 3 times (days 28, 29, and 30). On day 31, the serum that contain anti-hBTN5 polyclonal antibody was harvested.

To make anti-hBTN5 monoclonal antibody, the spleens were also harvested from the immunized mice on day 31. Single-cell suspension of the splenocytes were fused to X63-Ag8.653 myeloma cells to produce hybridomas. ELISA was performed to identify the hybridomas that could produce anti-hBTN5 mAbs but not with control Ig protein. These hybridoma clones were further subcloned by limiting dilution.

Evaluation of Local Tumor Growth

Murine CT-26 colon cancer cells were obtained from the ATCC. The cancer cells that had been transfected with a vector containing the hBTN5 gene were injected subcutaneously (s.c.) into the flank of syngeneic BALB/c mice. Mouse anti-hBTN5 or control polyclonal antibody were then injected into the tumor injection site. Tumor size (volume) was determined every other day by caliper measurements of the shortest (A) and longest (B) diameter, using the formula $V=(A2B)/2$.

Induction and Assessment of EAE

Mouse MOG$_{35-55}$ (GL Biochem, Shanghai. China) was emulsified in complete Freud's adjuvant (Sigma-Aldrich, St Louis, Mo., USA) supplemented with *Mycobacterium tuberculosis* H37Ra (Difco Laboratories, Detroit, Mich.). Mice were injected s.c. with the MOG at 4 points in the dorsal flank on day 0. The mice were also injected i.p. with 500 ng of purified *Bordetella pertussis* toxin (Sigma-Aldrich). The mice were then observed for clinical scores based on the following scale: 0, normal; 0.5, partially limp tail; 1, paralyzed tail; 2, loss in coordinated movement, hind limb paresis: 2.5, one hind limb paralyzed; 3, both hind limbs paralyzed; 3.5, hind limbs paralyzed, weakness in forelimbs; 4, forelimbs paralyzed; 5, moribund or dead. As required by animal ethics, mice were euthanized beyond a clinical score of 4.

Assessment of T1D

Female NOD mice were injected i.p. with hBTNL5-Ig, or control Ig protein. The blood glucose levels of mice were determined by test strips (Advanced glucose meter, CVS health, USA). Mice with a blood glucose measurement of greater than 250 mg/dL on two consecutive readings were considered diabetic.

Statistical Analysis

P-values were based on the two-sided Student's t test. A confidence level above 95% (p<0.05) was determined to be significant.

REFERENCES

[1] Freeman G J, Gray G S, Gimmi C D, Lombard D B, Zhou L J, White M et al. Structure, expression, and T cell costimulatory activity of the murine homologue of the human B lymphocyte activation antigen B7. J Exp Med, 1991:174:625-31.
[2] Freeman G J, Gribben J G, Boussiotis V A, Ng J W, Restivo V A, Jr., Lombard L A et a. Cloning of B7-2: a CTLA-4 counter-receptor that costimulates human T cell proliferation. Science (New York, N.Y.), 1993; 262:909-11.
[3] Dong H. Zhu G, Tamada K, Chen L. B7-H1, a third member of the B7 family, co-stimulates T-cell proliferation and interleukin-10 secretion. Nat Med, 1999:5:1365-9.
[4] Freeman G J, Long A J, Iwai Y, Bourque K, Chemova T, Nishimura H et a. Engagement of the PD-1 immunoinhibitory receptor by a novel B7 family member leads to negative regulation of lymphocyte activation. J Exp Med, 2000:192:1027-34.
[5] Latchman Y, Wood C R, Chemova T, Chaudhary D. Borde M, Chemova I et a. P D-L2 is a second ligand for PD-1 and inhibits T cell activation. Nat Immunol, 2001; 2:261-8.
[6] Tseng S Y, Otsuji M, Gorski K, Huang X, Slansky J E, Pai S I et al. B7-D C, a new dendritic cell molecule with potent costimulatory properties for T cells. J Exp Med, 2001; 193:839-46.
[7] Wang S, Zhu G, Chapoval A I, Dong H, Tamada K, Ni J et al. Costimulation of T cells by B7-H2, a B7-like molecule that binds ICOS. Blood, 2000; 96:2808-13.
[8] Ling V. Wu P W, Finnerty H F, Bean K M, Spaulding V. Fouser L A et al. Cutting edge: identification of GL50, a novel B7-like protein that functionally binds to ICOS receptor. Journal of immunology (Baltimore, Md.: 1950), 2000; 164:1653-7.
[9] Swallow M M, Wallin J J, Sha W C. B7h, a novel costimulatory homolog of B7.1 and B7.2, is induced by TNFalpha. Immunity, 1999:11:423-32.
[10] Yoshinaga S K, Whoriskey J S, Khare S D, Sarmiento U, Guo J, Horan T et al. T-cell co-stimulation through B7RP-1 and ICOS. Nature, 1999; 402:827-32.
[11] Chapoval A I. Ni J, Lau J S, Wilcox R A, Flies D B, Liu D et al. B7-H3: a costimulatory molecule for T cell activation and IFN-gamma production. Nat Immunol, 2001; 2:269-74.
[12] Prasad D V, Richards S. Mai X M, Dong C. B7S1, a novel B7 family member that negatively regulates T cell activation. Immunity. 2003; 18:863-73.
[13] Sica G L, Choi I H, Zhu G, Tamada K, Wang S D, Tamura H et al. B7-H4, a molecule of the B7 family, negatively regulates T cell immunity. Immunity, 2003; 18:849-61.
[14] Zang X, Loke P, Kim J, Murphy K. Waitz R, Allison J P. B7x: a widely expressed B7 family member that inhibits T cell activation. Proceedings of the National Academy of Sciences of the United States of America, 2003; 100:10388-92.
[15] Zhao R, Chinai J M, Buhl S, Scandiuzzi L, Ray A, Jeon H et al. HHLA2 is a member of the B7 family and inhibits human CD4 and CD8 T-cell function. Proceedings of the National Academy of Sciences of the United States of America, 2013; 110:9879-84.
[16] Zhu Y, Yao S, Iliopoulou B P, Han X, Augustine M M, Xu H et al. B7-H5 costimulates human T cells via CD28H. Nature communications, 2013; 4:2043.
[17] Brandt C S, Baratin M, Yi E C, Kennedy J, Gao Z, Fox B et al. The B7 family member B7-H6 is a tumor cell ligand for the activating natural killer cell receptor NKp30 in humans. J Exp Med, 2009:206:1495-503.
[18] Abeler-Dorner L, Swamy M, Williams G, Hayday A C, Bas A. Butyrophilins: an emerging family of immune regulators. Trends Immunol, 2012; 33:34-41.
[19] Afrache H, Gouret P. Ainouche S, Pontarotti P, Olive D. The butyrophilin (BTN) gene family: from milk fat to the regulation of the immune response. Immunogenetics, 2012; 64:781-94.
[20] Arnett H A, Viney J L. Immune modulation by butyrophilins. Nat Rev Immunol, 2014; 14:559-69.
[21] Guo Y. Wang A Y. Novel Immune Check-Point Regulators in Tolerance Maintenance. Front Immunol, 2015; 6:421.
[22] Rhodes D A, Reith W, Trowsdale J. Regulation of Immunity by Butyrophilins. Annu Rev Immunol, 2016; 34:151-72.
[23] Chapoval A I, Smithson G, Brunick L, Mesri M, Boldog F L, Andrew D et al. BTNL8, a butyrophilin-like molecule that costimulates the primary immune response. Mol Immunol, 2013; 56:819-28.
[24] Nguyen T, Liu X K, Zhang Y, Dong C. BTNL2, a butyrophilin-like molecule that functions to inhibit T cell activation. J Immunol, 2006; 176:7354-60.
[25] Arnett H A, Escobar S S, Gonzalez-Suarez E, Budelsky A L, Steffen L A, Boiani N et al. BTNL2, a butyrophilin/B7-like molecule, is a negative costimulatory molecule modulated in intestinal inflammation. J Immunol, 2007; 178:1523-33.
[26] Yamazaki T, Goyal, Graf D, Craig S Martin-Orozco N, Dong C. A butyrophilin family member critically inhibits T cell activation. J Immunol, 2010:185:5907-14.
[27] Ammann J U, Cooke A, Trowsdale J. Butyrophilin Btn2a2 inhibits TCR activation and phosphatidylinositol 3-kinase/Akt pathway signaling and induces Foxp3 expression in T lymphocytes. J Immunol, 2013; 190: 5030-6.
[28] Swanson R M, Gavin M A, Escobar S S, Rottman J B, Lipsky B P, Dube S et al. Butyrophilin-like 2 modulates B7 costimulation to induce Foxp3 expression and regulatory T cell development in mature T cells. J Immunol, 2013:190:2027-35.
[29] Smith I A, Knezevic B R, Ammann J U, Rhodes D A, Aw D, Palmer D B et al. BTN1A1, the mammary gland butyrophilin, and BTN2A2 are both inhibitors of T cell activation. Journal of immunology (Baltimore. Md.: 1950), 2010; 184:3514-25.
[30] Cubillos-Ruiz J R, Martinez D, Scarlett U K, Rutkowski M R, Nesbeth Y C, Camposeco-Jacobs A L et al. CD277 is a negative co-stimulatory molecule universally expressed by ovarian cancer microenvironmental cells. Oncotarget, 2010; 1:329-38.
[31] Compte E, Pontarotti P, Collette Y, Lopez M, Olive D. Frontline: Characterization of BT3 molecules belonging to the B7 family expressed on immune cells. European journal of immunology, 2004; 34:2089-99.
[32] Yamashiro H, Yoshizaki S. Tadaki T, Egawa K, Seo N. Stimulation of human butyrophilin 3 molecules results in negative regulation of cellular immunity. J Leukoc Biol, 2010; 88:757-67.
[33] Palakodeti A, Sandstrom A, Sundaresan L, Harly C, Nedellec S, Olive D et al. The molecular basis for modulation of human Vgamma9Vdelta2 T cell responses by CD277/butyrophilin-3 (BTN3A)-specific antibodies. J Biol Chem, 2012; 287:32780-90.
[34] Linsley P S, Peach R, Gladstone P, Bajorath J. Extending the B7 (CD80) gene family. Protein Sci, 1994; 3:1341-3.

[35] Yang Y, Liu X K, Nguyen T. Bishop C, Graf D, Dong C. Characterization of B7S3 as a novel negative regulator of T cells. Journal of immunology (Baltimore, Md.: 1950), 2007:178:3661-7.

[36] Arnett H A, Escobar S S, Viney J L. Regulation of costimulation in the era of butyrophilins. Cytokine, 2009: 46:370-5.

[37] Su Y Y, Gordon C T, Ye T Z, Perkins A C, Chui D H. Human ERMAP: an erythroid adhesion/receptor transmembrane protein. Blood cells, molecules & diseases, 2001; 27:938-49.

[38] Xu H, Foltz L, Sha Y, Madlansacay M R, Cain C. Lindemann G et al. Cloning and characterization of human erythroid membrane-associated protein, human ERMAP. Genomics, 2001; 76:2-4.

[39] Hofmeyer K A, Ray A, Zang X. The contrasting role of B7-H3. Proceedings of the National Academy of Sciences of the United States of America, 2008; 105:10277-8.

[40] Prasad DVR, Nguyen T, Li Z, Yang Y, Duong J, Wang Y et al. Murine B7-H3 Is a Negative Regulator of T Cells. The Journal of Immunology, 2004; 173:2500-6.

[41] Ye T Z, Gordon C T, Lai Y H, Fujiwara Y, Peters L L, Perkins A C et al. Ermap, a gene coding for a novel erythroid specific adhesion/receptor membrane protein. Gene, 2000:242:337-45.

[42] Oldenborg P A, Zheleznyak A, Fang Y F, Lagenaur C F, Gresham H D, Lindberg F P. Role of CD47 as a marker of self on red blood cells. Science (New York, N.Y.), 2000; 288:2051-4.

[43] Weiskopf K, Weissman I L. Macrophages are critical effectors of antibody therapies for cancer. mAbs, 2015; 7:303-10.

[44] Pineda-Torra I, Gage M, de Juan A, Pello O M. Isolation, Culture, and Polarization of Murine Bone Marrow-Derived and Peritoneal Macrophages. Methods in molecular biology (Clifton, N.J.), 2015; 1339:101-9.

[45] Sakaguchi S. Yamaguchi T, Nomura T, Ono M. Regulatory T cells and immune tolerance. Cell, 2008; 133:775-87.

[46] Anderson M S, Bluestone J A. The NOD mouse: a model of immune dysregulation. Annu Rev Immunol, 2005; 23:447-85.

[47] Zhang X, Schwartz J C, Almo S C, Nathenson S G. Crystal structure of the receptor-binding domain of human B7-2: insights into organization and signaling. Proceedings of the National Academy of Sciences of the United States of America, 2003; 100:2586-91.

[48] Brown E J, Frazier W A. Integrin-associated protein (CD47) and its ligands. Trends Cell Biol, 2001; 11:130-5.

[49] Gordon S R, Maute R L, Dulken B W, Hutter G, George B M, McCracken M N et al. PD-1 expression by tumour-associated macrophages inhibits phagocytosis and tumour immunity. Nature, 2017:545:495-9.

[50] Mana P, Goodyear M, Bernard C, Tomioka R, Freire-Garabal M, Linares D. Tolerance induction by molecular mimicry: prevention and suppression of experimental autoimmune encephalomyelitis with the milk protein butyrophilin. Int Immunol, 2004:16:489-99.

[51] Stefferl A. Schubart A, Storch M. Amini A. Mather I, Lassmann H et al. Butyrophilin, a milk protein, modulates the encephalitogenic T cell response to myelin oligodendrocyte glycoprotein in experimental autoimmune encephalomyelitis. Journal of immunology (Baltimore, Md.: 1950), 2000; 165:2859-65.

[52] Podojil J R, Liu L N, Marshall S A, Chiang M Y, Goings G E, Chen L et al. B7-H4Ig inhibits mouse and human T-cell function and treats EAE via IL-10/Treg-dependent mechanisms. J Autoimmun, 2013; 44:71-81.

[53] Jin J, Goldschneider I, Lai L. In vivo administration of the recombinant IL-7/hepatocyte growth factor beta hybrid cytokine efficiently restores thymopoiesis and naive T cell generation in lethally irradiated mice after syngeneic bone marrow transplantation. Journal of immunology (Baltimore, Md.: 1950), 2011; 186:1915-22.

[54] Lai L, Zhang M, Goldschneider I. Recombinant IL-7/HGFbeta efficiently induces transplantable murine hematopoietic stem cells. J Clin Invest. 2012; 122:3552-62.

[55] Lai L, Zhang M, Song Y, Rood D. Recombinant IL-7/HGFbeta Hybrid Cytokine Enhances T Cell Recovery in Mice Following Allogeneic Bone Marrow Transplantation. PloS one, 2013; 8:e82998.

[56] Song Y. Su M, Panchatsharam P, Rood D, Lai L. c-Met signalling is required for efficient postnatal thymic regeneration and repair. Immunology, 2015; 144:245-53.

[57] Su M, Song Y. He Z, Hu R, Rood D, Lai L. Administration of embryonic stem cell-derived thymic epithelial progenitors expressing MOG induces antigen-specific tolerance and ameliorates experimental autoimmune encephalomyelitis. J Autoimmun, 2015; 58:3647.

[58] Yan Y, Su M, Song Y, Tang Y, Tian C, Rood D et al. Tbx1 Modulates Endodermal and Mesodermal Differentiation from Mouse Induced Pluripotent Stem cells. Stem cells and development, 2014.

Example 5. CD300f

We have demonstrated that both mouse and human CD300c-Fc fusion proteins significantly inhibit T cell functions in vitro. Administration of CD300c-Fc protein attenuates graft-versus-host disease (GVHD) and autoimmune diseases including experimental autoimmune encephalomyelitis (EAE) and collagen-induced arthritis (CIA), murine models for human multiple sclerosis (MS) and rheumatoid arthritis (RA). Furthermore, anti-CD300c antibodies inhibit tumor growth in mouse tumor models.

Since CD300 family contains other members, we have cloned and expressed CD300f-Fc fusion protein. The extracellular domain of human CD300f (aa22-125) was cloned and fused into a pCMV6-AC-FC-S expression vector containing the constant region of mouse IgG2a (ORIGENE). The vector was transfected into HEK293F cells. The fusion protein was purified for supernatant using Protein G Sepharose 4 Fast Flow according to the manufacturer's instructions (GE Healthcare). Purified protein was verified by SDS-PAGE, Coomassie Staining and Western blot. Protein was quantified using the Pierce™ BCA Protein Assay Kit (Pierce, Rockford, Ill.).

After we obtained purified CD300f-Fc fusion protein, we determined whether CD300f-Ig protein affected lymphocyte and T cell proliferation. Splenocytes from C57BL/c mice were cultured on plates pre-coated with anti-CD3 antibody in the presence of graded doses of CD300f-Ig (800, 1600, and 3200 ng/ml) for 3 days. Since the molecular weight of CD300-Ig fusionprotein is ~1.5-fold higher than that of control Ig protein, we used equimolar amounts of the control Ig (533, 1066, and 2133 ng/ml) as a control. T cell proliferation was measured by [$^3$H] thymidine incorporation. As shown in FIG. 27, CD300f-Ig inhibited anti-CD3-activated T cell proliferation in a dose-responsive manner, as compared to equimolar amounts of control Ig. We also determined whether CD300f could inhibit anti-CD3 and anti-CD28 antibody-activated T cell proliferation. Similarly, CD300f-Ig reduced anti-CD3 and anti-CD28-activated T cell proliferation (data not shown).

To confirm the effect on T cell proliferation and to determine whether CD300f affects CD4 and/or CD8 T cells, we performed a carboxyfluorescein diacetate succinimidyl ester (CFSE) dilution assay. Murine splenocytes were labelled with CFSE, and then cultured with anti-CD3 antibody in the presence of graded doses of CD300f-Ig or control Ig as in FIG. 27. T cell proliferation was measured by CFSE fluorescent dilution in CD4 and CD8 T cells. As shown in FIG. 28, CD300f-g inhibited anti-CD3-activated proliferation of both CD4 and CD8 T cells in a dose-dependent manner.

We next determined whether CD300f-Ig affects the activation of T cells in vitro. CD69 is an early activation marker. After splenocytes were cultured with anti-CD3 antibody or anti-CD3 plus anti-CD28 antibodies in the presence of graded doses of CD300f-Ig or control Ig. The expression of the CD69 on CD4 and CD8 T cells was analyzed 24 hours later. As shown in FIG. 29, CD300f-Ig reduced the expression of CD69 on both CD4 and CD8 T cells in a dose-responsive manner. The results suggest that CD300f also inhibits the activation of CD4 and CD8 T cells.

To further confirm that CD300f2-Ig inhibits T cell activation, we analyzed the expression of CD44 and CD62L by CD4$^+$ and CD8$^+$ T cells. It has been reported that naïve T cells are CD44$^{low}$CD62L$^{hi}$, while effective memory T cells are CD44$^{hi}$CD62L$^{low}$. We found that CD300f-Ig significantly increased the percentages of CD44$^{low}$CD62L$^{hi}$ naïve cells in anti-CD3-activated CD4$^+$ and CD8$^+$ T cells, but decreased the percentages of CD44$^{hi}$CD62L$^{low}$ effector memory T cells (data not shown).

Collectively, our results indicate that CD300f-Ig inhibits both TCR-mediated proliferation and activation of both CD4 and CD8 T cells in vitro. Like CD300c, therapeutic interaction with the CD300f inhibitory pathway has the potential to be used in the treatment of GVHD and autoimmune disease, as well as cancer.

I claim:

1. An isolated anti-human CD300c antibody, or fragment thereof, comprising each of the following complementarity determining regions (CDRs):
Heavy chain CDR1 (H-CDR1) comprising the amino acid sequence IYGMN (SEQ ID NO: 10);
Heavy chain CDR2 (H-CDR2) comprising the amino acid sequence WINTYT (SEQ ID NO: 11);
Heavy chain CDR3 (H-CDR3) comprising the amino acid sequence ARSRFAY (SEQ ID NO: 12);
Light chain CDR1 (L-CDR1) comprising the amino acid sequence KASQNVGTNVA (SEQ ID NO: 13);
Light chain CDR2 (L-CDR2) comprising the amino acid sequence SASYRYS (SEQ ID NO:14); and
Light chain CDR3 (L-CDR3) comprising the amino acid sequence QQYNSYPLT (SEQ ID NO:15).

2. The isolated anti-human CD300c antibody, or fragment thereof, of claim 1, comprising:
(a) a heavy chain comprising an amino acid sequence having at least 60% identity to the amino acid sequence of SEQ ID NO:16; and
(b) a light chain comprising an amino acid sequence having at least 60% identity to the amino acid sequence of SEQ ID NO:17.

3. The isolated anti-human CD300c antibody, or fragment thereof, of claim 1, comprising
(a) a heavy chain comprising an amino acid sequence having at least 75% identity to the amino acid sequence of SEQ ID NO:16;
and
(b) a light chain comprising an amino acid sequence having at least 75% identity to the amino acid sequence of SEQ ID NO:17.

4. The isolated anti-human CD300c antibody, or fragment thereof, of claim 1, comprising
(a) a heavy chain comprising the amino acid sequence having at least 90% identity to the amino acid sequence of SEQ ID NO:16;
and
(b) a light chain comprising the amino acid sequence having at least 90% identity to the amino acid sequence of SEQ ID NO:17.

5. The isolated antibody or fragment thereof of claim 1, wherein the antibody comprises a monoclonal antibody, or fragment thereof.

6. The isolated antibody or fragment thereof of claim 1, comprising:
(a) a heavy chain comprising the amino acid sequence of SEQ ID NO:16; and
(b) a light chain comprising the amino acid sequence of SEQ ID NO:17.

7. A nucleic acid encoding the isolated antibody or fragment thereof of claim 1.

8. A vector comprising the recombinant nucleic acid of claim 7 operatively linked to a suitable control sequence.

9. A host cell comprising the nucleic acid of claim 7.

10. A method for treating colon cancer or a melanoma, comprising administering to a subject in need thereof an antibody that selectively binds to an extracellular domain (ECD) of human CD300c, in an amount effective to treat the colon cancer or melanoma, wherein the antibody comprises each of the following complementarity determining regions (CDRs):
Heavy chain CDR1 (H-CDR1) comprising the amino acid sequence IYGMN (SEQ ID NO: 10);
Heavy chain CDR2 (H-CDR2) comprising the amino acid sequence WINTYT (SEQ ID NO: 11);
Heavy chain CDR3 (H-CDR3) comprising the amino acid sequence ARSRFAY (SEQ ID NO: 12);
Light chain CDR1 (L-CDR1) comprising the amino acid sequence KASQNVGTNVA (SEQ ID NO: 13);
Light chain CDR2 (L-CDR2) comprising the amino acid sequence SASYRYS (SEQ ID NO:14); and
Light chain CDR3 (L-CDR3) comprising the amino acid sequence QQYNSYPLT (SEQ ID NO:15).

11. The method of claim 10, wherein the cancer is colon cancer.

12. The method of claim 10, wherein the antibody is a monoclonal antibody.

13. The method of claim 10, wherein the antibody selectively binds to an extracellular domain (ECD) of CD300c within amino acid residues 21-138 of SEQ ID NO: 2, and/or to an IgV domain of CD300c within amino acid residues 20-135 of SEQ ID NO:2.

14. The method of claim 10, wherein the cancer is a melanoma.

15. The method of claim 10, wherein the antibody, or fragment thereof, comprises:
(a) a heavy chain comprising an amino acid sequence having at least 60% identity to the amino acid sequence of SEQ ID NO: 16;
and
(b) a light chain comprising an amino acid sequence having at least 60% identity to the amino acid sequence of SEQ ID NO: 17.

16. The method of claim 10, wherein the antibody, or fragment thereof, comprises:
(a) a heavy chain comprising an amino acid sequence having at least 75% identity to the amino acid sequence of SEQ ID NO: 16;
and
(b) a light chain comprising an amino acid sequence having at least 75% identity to the amino acid sequence of SEQ ID NO: 17.

17. The method of claim 10, wherein the antibody, or fragment thereof, comprises:
- (a) a heavy chain comprising an amino acid sequence having at least 90% identity to the amino acid sequence of SEQ ID NO: 16;

and
- (b) a light chain comprising an amino acid sequence having at least 90% identity to the amino acid sequence of SEQ ID NO: 17.

18. The method of claim 10, wherein the antibody, or fragment thereof, comprises:
- (a) a heavy chain comprising the amino acid sequence of SEQ ID NO:16; and
- (b) a light chain comprising the amino acid sequence of SEQ ID NO: 17.

19. The method of claim 10, wherein the antibody comprises a monoclonal antibody, or fragment thereof.

* * * * *